(12) United States Patent
Wrasidlo et al.

(10) Patent No.: US 10,975,066 B2
(45) Date of Patent: *Apr. 13, 2021

(54) BIS-HETEROARYL DERIVATIVES AS MODULATORS OF PROTEIN AGGREGATION

(71) Applicant: UCB Biopharma SRL, Brussels (BE)

(72) Inventors: Wolfgang Wrasidlo, La Jolla, CA (US); Emily M. Stocking, Encinitas, CA (US); Adrian Hall, Brussels (BE); Malcolm Maccoss, Seabrook Island, SC (US)

(73) Assignee: UCB Biopharma SRL, Brussels (BE)

( * ) Notice: Subject to any disclaimer, the term of this patent is extended or adjusted under 35 U.S.C. 154(b) by 54 days.

This patent is subject to a terminal disclaimer.

(21) Appl. No.: 15/748,154

(22) PCT Filed: Jul. 29, 2016

(86) PCT No.: PCT/US2016/044871
§ 371 (c)(1),
(2) Date: Jan. 26, 2018

(87) PCT Pub. No.: WO2017/020010
PCT Pub. Date: Feb. 2, 2017

(65) Prior Publication Data
US 2018/0222899 A1 Aug. 9, 2018

Related U.S. Application Data

(60) Provisional application No. 62/198,515, filed on Jul. 29, 2015.

(51) Int. Cl.
| C07D 417/12 | (2006.01) |
| C07D 417/14 | (2006.01) |
| C07D 487/08 | (2006.01) |
| C07D 403/12 | (2006.01) |
| C07D 403/14 | (2006.01) |
| C07D 413/12 | (2006.01) |
| C07D 413/14 | (2006.01) |
| A61P 25/28 | (2006.01) |

(52) U.S. Cl.
CPC ............ *C07D 417/12* (2013.01); *A61P 25/28* (2018.01); *C07D 403/12* (2013.01); *C07D 403/14* (2013.01); *C07D 413/12* (2013.01); *C07D 413/14* (2013.01); *C07D 417/14* (2013.01); *C07D 487/08* (2013.01)

(58) Field of Classification Search
None
See application file for complete search history.

(56) References Cited

U.S. PATENT DOCUMENTS

| 8,846,682 B2 | 9/2014 | Masliah et al. |
| 9,284,309 B2 | 3/2016 | Wrasidlo |
| 2013/0274260 A1 | 10/2013 | Griffioen et al. |
| 2015/0183776 A1 | 7/2015 | Wrasidlo |
| 2016/0207912 A1 | 7/2016 | Wrasidlo |
| 2019/0367502 A1 | 12/2019 | Hall |
| 2019/0367513 A1 | 12/2019 | Hall |

FOREIGN PATENT DOCUMENTS

| WO | WO-2010/142801 | 12/2010 | |
| WO | WO-2011/084642 | 7/2011 | |
| WO | WO-2013/134371 | 9/2013 | |
| WO | WO-2013/148365 | 10/2013 | |
| WO | WO2014/014937 | * 1/2014 | ........... A61K 31/496 |
| WO | WO-2014/014937 | 1/2014 | |
| WO | WO-2015/116663 | 8/2015 | |
| WO | WO-2017/020010 A1 | 2/2017 | |

OTHER PUBLICATIONS

Bagshawe, "Antibody-directed enzyme prodrug therapy: A review," Drug Dev. Res. 1995, 34, 220-230.
Berge, et al., "Pharmaceutical Salts," J. Pharm. Sci., 1977, 66, 1-19.
Bertolini et al., "A New Rational Hypothesis for the Pharmacophore of the Active Metabolite of Leflunomide, a Potent Immunosuppressive Drug," J. Med. Chem. 1997, 40, 2011-2016.
Bodner et al., "Differential Phospholipid Binding of α-Synuclein Variants Implicated in Parkinson's Disease Revealed by Solution NMR Spectroscopy," Biochemistry 2010, 49, 862-871.
Bodor, Adv. Drug Res. 1984, 13, 255-331.
Brooks, D.J., "Positron Emission Tomography and Single-Photon Emission Computed Tomography in Central Nervous System Drug Development," NeuroRx 2005, 2(2), 226-236.
Delaglio et al., "NMRPipe: a multidimensional spectral processing system based on UNIX pipes," J Biomol NMR 1995, 6, 277-293.
Masliah et al., "Dopaminergic Loss and Inclusion Body Formation in α-Synuclein Mice: Implications for Neurodegenerative Disorders," Science, 2000, 287(5456): 1265-9.
Pan et al., "The Role of Alpha-Synuclein in Melanin Synthesis in Melanoma and Dopaminergic Neuronal Cells," PLOS One 7(9):e45183.
Rao et al., "Effect of pseudorepeat rearrangement on alpha-synuclein misfolding, vesicle binding, and micelle binding," J Mol Biol 2009, 390, 516-529.

(Continued)

*Primary Examiner* — Jeffrey S Lundgren
*Assistant Examiner* — Michael J Schmitt
(74) *Attorney, Agent, or Firm* — Morrison & Foerster LLP

(57) ABSTRACT

The present invention relates to certain bis-heteroaryl compounds, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, Parkinson's disease with dementia, fronto-temporal dementia, Huntington's Disease, amyotrophic lateral sclerosis, and multiple system atrophy, and cancer including melanoma.

21 Claims, No Drawings

(56) References Cited

OTHER PUBLICATIONS

Schanda, "SOFAST-HMQC experiments for recording two-dimensional heteronuclear correlation spectra of proteins within a few seconds," J Biomol NMR 2005, 33, 199-211.
Shan et al., "Prodrug strategies based on intramolecular cyclization reactions," J. Pharm. Sci. 1997, 86 (7), 765-767.
Non-Final Office Action for U.S. Appl. No. 15/666,503, dated Jul. 27, 2018, 7 pages.
Awad, R.A. "Neurogenic Bowel Dysfunction in Patients with Spinal Cord Injury, Myelomeningocele, Multiple Sclerosis, and Parkinson's Disease," World J. Gastroenterol. 2011, 17(46), 5035-5048.
Bodis-Wollner, I. et al., "Fovea and Foveation in Parkinson's Disease," Behav. Neurosci. 2013, 127(2), 139-150.
Bodis-Wollner, I., "Foveal Vision Is Impaired in Parkinson's Disease," Parkinsonism Relat. Disord. 2013, 19(1), 1-14.
Bodis-Wollner, I. et al., "α-Synuclein in the Inner Retina in Parkinson Disease," Ann. Neurol. 2014, 75(6), 964-966.
Botha, H. and J. Carr, "Attention and Visual Dysfunction in Parkinson's Disease," Parkinsonism Relat. Disord. 2012, 18(6), 742-747.
Cannon, J.G. in: Burger's Medicinal Chemistry and Drug Discovery, Fifth Edition, vol. 1: Principles and Practice, Wiley-Interscience (1995) Ch. 19, pp. 783-802.
Fleming, S.M., "Cardiovascular Autonomic Dysfunction in Animal Models of Parkinson's Disease," J. Parkinsons Dis. 2011, 1(4), 321-327.
International Preliminary Report on Patentability for PCT/US2015/013263, dated Jan. 7, 2016, 18 pages.
International Search Report and Written Opinion for International Application No. PCT/US2015/013263, dated Apr. 23, 2015, 9 pages.
International Search Report and Written Opinion for PCT/US16/44871, dated Oct. 18, 2016, 8 pages.
International Search Report and Written Opinion for PCT/EP2018/051579, dated May 16, 2018, 9 pages.
International Search Report and Written Opinion for PCT/EP2018/051580, dated Mar. 12, 2018, 13 pages.
International Search Report and Written Opinion for PCT/EP2018/051584, dated Mar. 21, 2018, 12 pages.
Jain, S. and D.S. Goldstein, "Cardiovascular Dysautonomia in Parkinson Disease: From Pathophysiology to Pathogenesis," Neurobiol. Dis. 2012, 46(3), 572-580.
Javaid, M.A. et al., "Cortical Control of Voluntary Saccades in Parkinson's Disease and Pre-emptive Perception," Parkinsonism Relat. Disord. 2012, 18(Suppl. 1), S100-3.
Jellinger, K.A., "Synuclein Deposition and Non-motor Symptoms in Parkinson Disease," J. Neurol. Sci. 2011, 310(1-2), 107-111.
Kaufmann, H. and D.S. Goldstein, "Chapter 21—Autonomic Dysfunction in Parkinson Disease," Handbook Clin. Neurol. 2013, 117, 259-278.
Kim, J.S. et al., "Anorectal Dysfunctions in Parkinson's Disease," J. Neurol. Sci. 2011, 310(1-2), 144-151.
Loudon, G.M., Organic Chemistry, $4^{th}$ Edition, New York: Oxford University Press, 2002, pp. 360-361, 1084-1085.
Post, K.K. et al., "Cardiac Denervation and Dysautonomia in Parkinson's Disease: A Review of Screening Techniques," Parkinsonism Relat. Disord. 2008, 14(7), 524-531.
Pubchem: "MolPort-010-919-232 | $C_{21}H_{29}N_5O_3S$—Pubchem," Jun. 21, 2011, 9 pages, retrieved from the Internet: URL:http://pubchem.ncbi.nlm.nih.gov/compound/53161072#section=Chemical-Vendors [retrieved on Mar. 14, 2017].
Pubchem: "MolPort-010-919-196 | $C_{21}H_{29}N_5O_3S$—PubChem," Jun. 21, 2011, 9 pages, retrieved from the Internet: URL:http://pubchem.ncbi.nlm.nih.gov/compound/53161036#section=Top [retrieved on Mar. 14, 2017].
Pubchem: "MolPort-010-919-1631 | $C_{20}H_{27}N_5O_2S$—PubChem," Jun. 21, 2011, 9 pages, retrieved from the Internet: URL:http://pubchem.ncbi.nlm.nih.gov/compound/53161003#section=Top [retrieved on Mar. 14, 2017].
Pubchem: "MolPort-028-860-176 | $C_{20}H_{26}FN_5O_2S$—PubChem," Nov. 29, 2013, 9 pages, retrieved from the Internet: URL: http://pubchem.ncbi.nlm.nih.gov/compound/71840278#section=Substrances-by-Category [retrieved on Mar. 14, 2017].
Pubchem: "MolPort-028-860-061 | $C_{20}H_{26}FN_5OS$—PubChem," Nov. 29, 2013, 9 pages, retrieved from the Internet: URL:http://pubchem.ncbi.nlm.nih.gov/compound/71840292#section=Information-Sources [retrieved on Mar. 14, 2017].
Pubchem: "MolPort-028-860-051 | $C_{22}H_{31}N_5O_2S$—PubChem," Nov. 29, 2013, 9 pages, retrieved from the Internet: URL:http://pubchem.ncbi.nlm.nih.gov/compound/71840396#section=Chemical-Vendors [retrieved on Mar. 14, 2017].
Pubchem: "SR-01000649247 | $C_{19}H_{26}N_6O_2S$—PubChem," Feb. 21, 2016, 9 pages, retrieved from the Internet: URL:http://pubchem.ncbi.nlm.nih.gov/compound/117082374#section=Top [retrieved on Mar. 14, 2017].
Pubchem: "SR-01000647965 | $C_{19}H_{26}N_6O_2S$—PubChem," Feb. 11, 2016, 9 pages, retrieved from the Internet: URL:http://pubchem.ncbi.nlm.nih.gov/compound/117080913#section=Top [retrieved on Mar. 14, 2017.
Rockenstein, E. et al., "Retinal Scanning Evaluations of Alpha-Synuclein-eGFP Deposition in a Transgenic Mouse Model of PD/DLB," Society for Neurosciences, Annual Meeting, Nov. 11, 2013, Abstract No. 329.06.
Rockenstein, E. et al., "Lysosomal Pathology Associated with a-Synuclein Accumulation in Transgenic Models Using an eGFP Fusion Protein," J. Neurosci. Res. 2005, 80, 247-259.
Senard, J.M. and A. Pathak, "Neurogenic Orthostatic Hypotension of Parkinson's Diseas: What Exploration for What Treatment?" Rev. Neurol. (Paris) 2010, 166(10), 779-784.
Wang, L. et al. "Mice Overexpressing Wild-Type Human Alpha-Synuclein Display Alterations in Colonic Myenteric Ganglia and Defecation," Neurogastroenterol. Motil. 2012, 24(9), e425-436.
Yu, J.G. et al., "Retinal Nerve Fiber Layer Thickness Changes in Parkinson Disease: A Meta-Analysis," PLoS One 2014, 9(1), e85718.
Dermer, "Another Anniversary for the War on Cancer," Bio/Technology (1994) 12:320.
Freshney, Culture of Animal Cells, a Manual of Basic Technique, Alan R. Liss, Inc., 1983, New York, p. 4.
Layzer, "Degenerative Diseases of the Nervous System," in: Cecil Textbook of Medicine, Bennet and Plum (eds.), 20th Edition, W.B. Saunders Co. (1996) vol. 2, pp. 2050-2057.

* cited by examiner

BIS-HETEROARYL DERIVATIVES AS MODULATORS OF PROTEIN AGGREGATION

CROSS-REFERENCE TO RELATED APPLICATIONS

This application is a U.S. National Phase of International Patent Application No. PCT/US2016/044871, filed Jul. 29, 2016, which claims priority to U.S. Provisional Application No. 62/198,515, filed Jul. 29, 2015. The contents of these applications are incorporated herein by reference in their entirety.

TECHNICAL FIELD

The present invention relates to certain bis-heteroaryl derivatives, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, Parkinson's disease with dementia, fronto-temporal dementia, Huntington's Disease, amyotrophic lateral sclerosis, and multiple system atrophy, and cancer including melanoma.

BACKGROUND

Neurodegenerative disorders of the aging population such as Alzheimer's disease (AD), Parkinson's disease (PD), and fronto-temporal dementia (FTD), affect over 20 million people in the United States and European Union alone and rank among the top causes of death for the elderly. A common feature among these neurological disorders is the chronic accumulation of proteins into neurotoxic aggregates. Each disease is characterized by the specific neuronal populations that are affected, the particular protein aggregates that are involved, and the clinical features that result from the neuronal degeneration.

Studies suggest that the initial stages of protein aggregation involve mutation or post-translational modification (e.g., nitrosilation, oxidation) of the target protein, which then adopts an abnormal conformation that facilitates interactions with similarly misfolded proteins. The abnormal proteins then aggregate to form dimers, trimers, and higher-order multimers, also termed "soluble oligomers," which may disrupt synaptic function. Additionally, the aggregates may then anchor in the cell membrane and form globular oligomers (which in turn can form pores in the membrane) and/or protofibrils or fibrils. These larger, insoluble fibrils may function as reservoirs of the bioactive oligomers.

Diverse lines of evidence support the notion that the progressive accumulation of protein aggregates is causally involved in the pathogenesis of neurodegenerative diseases. A number of other proteins may accumulate in the brains of patients with neurodegeneration, such as α-synuclein, Aβ protein, Tau, and TDP43. The cognitive impairment of these patients is closely associated with synaptic loss in the neocortex and limbic systems, and increasing levels of protein aggregates may contribute to this synaptic loss. Much research is focused on detailing the mechanisms through which accumulation of α-synuclein and other amyloid precursor protein (APP) metabolites contributes to synaptic damage and neurodegeneration. Many studies support the hypothesis that formation of small aggregates, also known as oligomers, plays a major role in neurotoxicity. These peptide oligomers can organize into dimers, trimers, tetramers, pentamers, and other higher order arrays that can form annular structures. High levels of such oligomers are predictive of dementia and synaptic loss in patients. Because evidence indicates the oligomers rather than smaller precursor fibrils are the toxic species, compounds that target these early aggregation processes in a specific manner would be useful as potential new therapies for PD, AD and related conditions.

Various neurodegenerative diseases involve the accumulation of neurotoxic protein-based aggregates. In idiopathic Parkinson's disease (IPD), dementia with Lewy bodies (LBD), Parkinson's disease with dementia (PDD), and multiple system atrophy (MSA), the neurotoxic aggregates are composed of α-synuclein (SYN), which is a synaptic protein that is intracellular under normal conditions. In FTD and amyotrophic lateral sclerosis (ALS), neurotoxic aggregates originate from other intracellular proteins such as tau, TDP-43, or SOD1. For certain diseases, such as AD, SYN aggregates with the primary protein (e.g., Aβ protein). In Huntington's Disease, aggregates form from the cleavage products of Htt proteins.

Accumulation of α-synuclein has also been implicated in cancer, in particular, in melanoma cancer cells. Pan et al., PLoS One 2012, 7(9), e45183. Thus, compounds that inhibit such accumulation may prove useful in treatment of various cancers, including melanoma.

Two mechanisms are implicated in these protein aggregation processes. In the first, the misfolded and/or aggregated proteins anchor to the various cell membrane structures. Binding of the misfolded or aggregated molecules to the plasma membrane or the membranes of organelles (e.g., mitochondria or lysosomes) may interfere with protein transcription, autophagy, mitochondrial function, and pore formation. By way of example, neurotoxic SYN aggregates and interacts with lipids in cell membranes by a specific portion of the c-terminal region of the synuclein protein. Compounds that bind to this region can inhibit protein-protein or protein-lipid interactions and can therefore be used to block neurotoxic oligomerization of SYN or other proteins and their interactions with membranes. In the second process, aggregated protein is released from the anchored subunit and propagates to adjacent cells. This cell-to-cell propagation of toxic protein aggregates may then underlie the anatomic progression of neurodegeneration and worsening of symptoms. Small molecule drugs that interact with the target proteins may limit release and/or propagation, and therefore reduce the neurotoxic effects of aggregated proteins.

Compounds that are inhibitors of protein aggregation are described in PCT Publ. Nos. WO2011/084642, WO2013/148365, WO2013/134371, WO2014/014937, and WO2015/116663, and in U.S. Pat. No. 9,284,309. Additional compounds are described in U.S. Pat. No. 8,846,682. Indole amide derivatives are described in PCT Publ. No. WO2010/142801.

There remains a need for inhibitors of protein aggregation with desirable pharmaceutical properties. Certain bis-heteroaryl compounds have been found in the context of this invention to have protein aggregation modulating activity.

SUMMARY OF THE INVENTION

In one aspect, the invention relates to a chemical entity of the following Formula (IA):

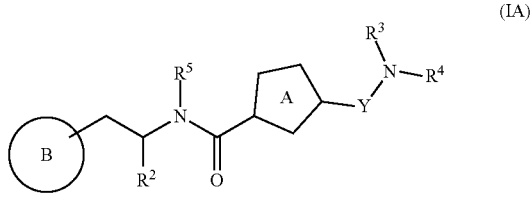

(IA)

wherein
B is a 9- or 10-membered heteroaryl, or a 5- or 6-membered heterocycloalkyl, each unsubstituted or substituted with —$(R^1)_m$;
wherein m is 0, 1, or 2; and
each $R^1$ is independently $C_{1-4}$alkyl (optionally substituted with one or more halo or —$OC_{1-4}$alkyl groups), halo, —OH, or —$OC_{1-4}$alkyl;
$R^2$ is H, $C_{1-5}$alkyl (unsubstituted or substituted with one or more halo substituents), —$OC_{1-4}$alkyl, or —$SC_{1-4}$alkyl, or an aryl, monocyclic cycloalkyl, or —$C_{1-4}$alkyl-(monocyclic cycloalkyl) group, wherein each aryl or cycloalkyl is unsubstituted or substituted with halo, $C_{1-4}$alkyl, or halo-$C_{1-4}$alkyl;
A is a 5-membered heteroaryl ring;
Y is absent or is $C_{1-4}$alkylene; and
when Y is absent or is $C_{1-4}$alkylene, $R^3$ and $R^4$ taken together with the nitrogen to which they are attached form a monocyclic or bicyclic heterocycloalkyl or

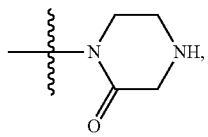

each unsubstituted or substituted with one or more $R^g$ substituents;
wherein each $R^g$ substituent is independently $C_{1-4}$alkyl (unsubstituted or substituted with one or more $C_{1-4}$alkoxy, halo-$C_{1-4}$alkoxy, or halo groups), $C_{3-7}$cycloalkyl, $C_{1-4}$alkoxy, halo-$C_{1-4}$alkoxy, or halo;
or, when Y is $C_{1-4}$alkylene, $R^3$ and Y taken together with the nitrogen to which $R^3$ is attached form a monocyclic or bicyclic heterocycloalkyl ring, which ring is unsubstituted or substituted with $C_{1-4}$alkyl or halo; and $R^4$ is H or $C_{1-4}$alkyl; and
$R^5$ is H or $C_{1-4}$alkyl;
or a pharmaceutically acceptable salt thereof.

In one aspect, the invention relates to a chemical entity of the following Formula (I):

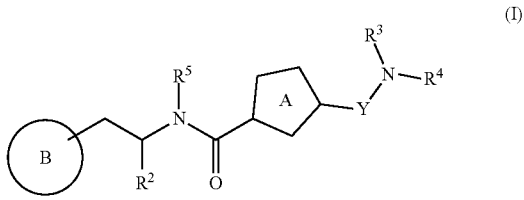

(I)

wherein
B is a 9- or 10-membered heteroaryl, or a 5- or 6-membered heterocycloalkyl, each unsubstituted or substituted with —$(R^1)_m$;
wherein m is 0, 1, or 2; and
each $R^1$ is independently $C_{1-4}$alkyl (optionally substituted with one or more halo or —$OC_{1-4}$alkyl groups), halo, —OH, or —$OC_{1-4}$alkyl;
$R^2$ is H, $C_{1-5}$alkyl (unsubstituted or substituted with one or more halo substituents), —$OC_{1-4}$alkyl, or —$SC_{1-4}$alkyl, or an aryl, monocyclic cycloalkyl, or —$C_{1-4}$alkyl-(monocyclic cycloalkyl) group, wherein each aryl or cycloalkyl is unsubstituted or substituted with halo, $C_{1-4}$alkyl, or halo-$C_{1-4}$alkyl;
A is a 5-membered heteroaryl ring;
Y is absent or is $C_{1-4}$alkylene; and
when Y is absent or is $C_{1-4}$alkylene, $R^3$ and $R^4$ taken together with the nitrogen to which they are attached form a monocyclic or bicyclic heterocycloalkyl, unsubstituted or substituted with one or more $R^g$ substituents;
wherein each $R^g$ substituent is independently $C_{1-4}$alkyl (unsubstituted or substituted with one or more $C_{1-4}$alkoxy, halo-$C_{1-4}$alkoxy, or halo groups), $C_{3-7}$cycloalkyl, $C_{1-4}$alkoxy, halo-$C_{1-4}$alkoxy, or halo;
or, when Y is $C_{1-4}$alkylene, $R^3$ and Y taken together with the nitrogen to which $R^3$ is attached form a monocyclic or bicyclic heterocycloalkyl ring, which ring is unsubstituted or substituted with $C_{1-4}$alkyl or halo; and $R^4$ is H or $C_{1-4}$alkyl; and
$R^5$ is H or $C_{1-4}$alkyl;
or a pharmaceutically acceptable salt thereof.

In certain embodiments, the compound of Formula (I) or (IA) is a compound selected from those species described or exemplified in the detailed description below.

In a further aspect, the invention relates to a pharmaceutical composition comprising at least one compound of Formula (I) or (IA) or a pharmaceutically acceptable salt thereof. Pharmaceutical compositions according to the invention may further comprise a pharmaceutically acceptable excipient. The invention is also a compound of Formula (I) or (IA) or a pharmaceutically acceptable salt thereof for use as a medicament.

In another aspect, the invention is directed to a method of treating a neurodegenerative disease or condition associated with protein or peptide aggregation, comprising administering to a subject in need of such treatment an effective amount of at least one compound of Formula (I) or (IA) or a pharmaceutically acceptable salt thereof. In another aspect, described herein is a compound or composition for use in treating a neurodegenerative disease or medical condition associated with protein or peptide aggregation.

In another aspect, the invention is directed to a method of treating a disease or medical condition associated with protein or peptide aggregation, comprising administering to a subject in need of such treatment an effective amount of at least one compound of Formula (I) or (IA) or a pharmaceutically acceptable salt thereof. The invention is also directed to the use of a compound of Formula (I) or (IA) or a pharmaceutically acceptable salt thereof for the treatment of, or for the preparation of a medicament for the treatment of, such diseases and medical conditions.

In yet another aspect, the invention relates to a method of interfering with the accumulation of protein or peptide aggregates in a cell, or modulating, preventing, slowing, reversing, or inhibiting protein or peptide aggregation in a cell, comprising contacting the cell with an effective amount of at least one compound of Formula (I) or (IA) or a salt thereof, and/or with at least one pharmaceutical composition of the invention, wherein the contacting is in vitro, ex vivo, or in vivo.

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION OF THE INVENTION

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available ChemBioDraw Ultra software, Version 14.0.0.117.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

REPRESENTATIVE EMBODIMENTS

In some embodiments of Formula (I) or (IA), all variables are as defined herein (including any of the particular definitions listed below), and one or more of the following limitations also applies:

(a1) m is 1 or 2; or (a2) m is 1 or 2, and $R^1$ is as defined herein, wherein at least one $R^1$ is $C_{1-4}$alkyl (substituted with one or two halo groups, or with —$OC_{1-4}$alkyl), $C_{1-4}$alkyl (substituted with —$CF_3$), —OH, or —$OC_{1-4}$alkyl;

(b) $R^2$ is $C_{1-5}$alkyl substituted with two halo groups, —$OC_{1-4}$alkyl, or —$SC_{1-4}$alkyl, or is monocyclic cycloalkyl substituted with halo, $C_{1-4}$alkyl, or halo-$C_{1-4}$alkyl, or is —$C_{1-4}$alkyl-(monocyclic cycloalkyl), wherein the cycloalkyl is unsubstituted or substituted with halo, $C_{1-4}$alkyl, or halo-$C_{1-4}$alkyl, or is aryl substituted with halo, $C_{1-4}$alkyl, or halo-$C_{1-4}$alkyl;

(c) when $R^3$ and $R^4$ taken together with the nitrogen to which they are attached form a monocyclic heterocycloalkyl, said heterocycloalkyl is substituted with one or more $R^g$ substituents and $R^g$ is as defined herein; and at least one $R^g$ substituent is $C_{1-4}$alkyl (substituted with one or more $C_{1-4}$alkoxy, halo-$C_{1-4}$alkoxy, or halo groups), $C_{1-4}$alkoxy, halo-$C_{1-4}$alkoxy, or halo.

In some embodiments of the formulae described herein, B is an optionally substituted 9-membered bicyclic heteroaryl. In other embodiments, B is optionally substituted indole, benzofuran, benzothiophene, indazole, benzimidazole, benzoxazole, benzisoxazole, imidazopyridine, or pyrrolopyridine. In other embodiments, B is benzothiophene, benzimidazole, benzisoxazole, imidazopyridine, or pyrrolopyridine (in which the pyridine nitrogen is not attached to the same carbon as the pyrrole nitrogen). In other embodiments, B is optionally substituted indole, benzofuran, benzothiophene, indazole, benzisoxazole, imidazopyridine, or pyrrolopyridine. In other embodiments, B is optionally substituted indole. In other embodiments, B is optionally substituted 3-indole. In other embodiments, B is substituted indole or substituted 3-indole. In other embodiments, B is an optionally substituted 10-membered bicyclic heteroaryl. In other embodiments, B is optionally substituted quinoline or isoquinoline. In other embodiments, B is an optionally substituted monocyclic 5- or 6-membered heterocycloalkyl. In other embodiments, B is optionally substituted pyrrolidine, piperidine, piperazine, or morpholine.

In some embodiments, m is 0. In other embodiments, m is 1. In other embodiments, m is 2.

In some embodiments, each $R^1$ substituent is independently —OH, or is fluoro, chloro, bromo, or iodo. In other embodiments, each $R^1$ is fluoro or bromo. In other embodiments, each $R^1$ substituent is independently methyl, ethyl, propyl, isopropyl, butyl, sec-butyl, isobutyl, tert-butyl, or is $C_{1-4}$alkyl (substituted with one or more fluoro, chloro, bromo, methoxy, ethoxy, propoxy, isopropoxy, or butoxy groups). In other embodiments, each $R^1$ is independently halo or $C_{1-4}$alkyl optionally substituted with one or more halo groups. In other embodiments, each $R^1$ is independently OMe, OCHF$_2$, OCF$_3$, OEt, OiPr, Me, CF$_3$, Cl, or CH$_2$F, CHF$_2$.

In some embodiments, $R^2$ is H. In other embodiments, $R^2$ is $C_{1-5}$alkyl (unsubstituted or substituted with one or more halo substituents). In other embodiments, $R^2$ is —OC$_{1-4}$alkyl or —SC$_{1-4}$alkyl. In other embodiments, $R^2$ is $C_{1-5}$alkyl (substituted with one or more halo substituents). In other embodiments, $R^2$ is unsubstituted $C_{1-5}$alkyl or is $C_{1-5}$alkyl substituted as described herein. In other embodiments, $R^2$ is unsubstituted $C_{3-5}$alkyl or is $C_{3-5}$alkyl substituted as described herein. In other embodiments, $R^2$ is methyl, ethyl, propyl, butyl, or isopentyl. In other embodiments, $R^2$ is 1,1-difluorobutyl, trifluoro-isopentyl, trifluorobutyl, 3,3-difluorobutyl, 2,2-difluorobutyl, or propoxy. In other embodiments, $R^2$ is monocyclic cycloalkyl or —C$_{1-4}$alkyl-(monocyclic cycloalkyl), wherein each cycloalkyl is unsubstituted or substituted with halo, $C_{1-4}$alkyl, or halo-$C_{1-4}$alkyl. In some embodiments, $R^2$ is cyclobutyl, cyclopentyl, cyclopentadienyl, cyclohexyl, or cycloheptyl, each optionally substituted with one or two substituents selected from the group consisting of methyl, halo, or trifluoromethyl. In some embodiments, $R^2$ is substituted monocyclic cycloalkyl or substituted —C$_{1-4}$alkyl-(monocyclic cycloalkyl). In some embodiments, $R^2$ is cyclopropylethyl, (3-methylcyclobutyl)methyl, or (3,3-difluorocyclobutyl)methyl. In other embodiments, $R^2$ is cyclobutylmethyl. In some embodiments, $R^2$ is substituted $C_{1-5}$alkyl, substituted monocyclic cycloalkyl, or substituted —C$_{1-4}$alkyl-(monocyclic cycloalkyl). In other embodiments, $R^2$ is optionally substituted aryl. In other embodiments, $R^2$ is optionally substituted phenyl. In other embodiments, $R^2$ is phenyl. In other embodiments, $R^2$ is substituted aryl or substituted phenyl. In some embodiments, $R^2$ is methyl, ethyl, propyl, or isobutyl.

In some embodiments, the carbon to which $R^2$ is attached is in the R configuration. In other embodiments, the carbon to which $R^2$ is attached is in the S configuration.

In some embodiments, A is pyrrole, furan, thiophene, pyrazole, imidazole, oxazole, isoxazole, thiazole, triazole, oxadiazole, thiadiazole, or tetrazole. In other embodiments, A is pyrrole, furan, thiophene, pyrazole, imidazole, oxazole, thiazole, triazole, oxadiazole, thiadiazole, or tetrazole. In other embodiments, A is imidazole, oxazole, or thiazole. In other embodiments, A is thiazole.

In some embodiments, Y is absent. In other embodiments, Y is —CH$_2$—, —CH$_2$CH$_2$—, —CH(CH$_3$)—, —(CH$_2$)$_3$—, —C(CH$_3$)$_2$—, —(CH$_2$)$_4$—, —CH((CH$_2$)$_2$CH$_3$)—, —CH(CH(CH$_3$)$_2$)—, —CH(CH$_2$CH$_3$)CH$_2$—, —CH(CH$_3$)CH(CH$_3$)—, —CH(CH$_3$)(CH$_2$)$_2$—, or —CH$_2$CH(CH$_3$)CH$_2$—. In other embodiments, Y is —CH$_2$—, —CH$_2$CH$_2$—, or —CH(CH$_3$)—. In still other embodiments, Y is —CH$_2$CH$_2$—.

In some embodiments, where Y is absent or is $C_{1-4}$alkylene, $R^3$ and $R^4$ taken together with the nitrogen to which they are attached form a monocyclic or bicyclic heterocycloalkyl ring, unsubstituted or substituted with one or more $R^g$ substituents. In other embodiments, $R^3$ and $R^4$ taken together with the nitrogen to which they are attached form azetidine, pyrrolidine, piperidine, piperazine, morpholine, thiomorpholine, 1,1-dioxo-thiomorpholine, azepine, or diazepine, each unsubstituted or substituted with one or more $R^g$ substituents. In other embodiments, $R^3$ and $R^4$ taken together with the nitrogen to which they are attached form piperidine, piperazine, or diazepine, each unsubstituted or substituted with one or more $R^g$ substituents. In other embodiments, $R^3$ and $R^4$ taken together with the nitrogen to which they are attached form piperazine substituted with one, two, or three $R^g$ substituents. In other embodiments, $R^3$ and $R^4$ taken together with the nitrogen to which they are attached form piperazine, unsubstituted or substituted with $C_{1-4}$alkyl. In still other embodiments, $R^3$ and $R^4$ taken together with the nitrogen to which they are attached form piperazine or 4-methylpiperazine. In some embodiments in which $R^3$ and $R^4$ taken together with the nitrogen to which they are attached form a monocyclic heterocycloalkyl ring, unsubstituted or substituted with one or more $R^g$ substituents, Y is absent, or Y is $C_{2-4}$alkylene.

In some embodiments, each $R^g$ substituent is independently methyl, ethyl, propyl, isopropyl, butyl, isobutyl, sec-butyl, tert-butyl, or is cyclopropyl, cyclobutyl, cyclopentyl, or cyclohexyl, or is methoxy, ethoxy, propoxy, or isopropoxy, or is trifluoromethoxy or trifluoroethoxy, or is bromo, chloro, or fluoro, each unsubstituted or substituted as described herein. In other embodiments, each $R^g$ substituent is independently ethyl, isopropyl, cyclopropyl, tert-butyl, isobutyl, 2-methoxyethyl, 2,2-difluoroethyl, trifluoroethyl, trifluoroethoxy-ethyl, trifluoromethyl, difluoromethyl, or fluoromethyl, or is fluoroethyl, methoxyethyl, trifluoromethoxyethyl, or trifluoromethyl.

In some embodiments, there are 0, 1, 2, or 3 $R^g$ substituents. In other embodiments, there is one, or there are two, or there are three $R^g$ substituents.

In some embodiments, where Y is $C_{1-4}$alkylene, $R^3$ and Y are taken together with the nitrogen to which $R^3$ is attached form a monocyclic heterocycloalkyl ring, which ring is unsubstituted or substituted with $C_{1-4}$alkyl or halo; and $R^4$ is H or $C_{1-4}$alkyl. In other embodiments, Y and $R^3$ taken together with the nitrogen to which $R^3$ is attached form pyrrolidine or piperidine, which ring is optionally substituted as described herein. In other embodiments, $R^4$ is H or methyl.

In some embodiments of Formula (I) or (IA), $R^3$ and $R^4$ taken together with the nitrogen to which they are attached form a monocyclic heterocycloalkyl ring, substituted with one or more $R^g$ substituents; wherein $R^g$ is as defined herein; and at least one $R^g$ substituent is $C_{1-4}$alkyl (substituted with one or more $C_{1-4}$alkoxy, halo-$C_{1-4}$alkoxy, or halo groups), $C_{1-4}$alkoxy, halo-$C_{1-4}$alkoxy, or halo. In some embodiments, $R^3$ and $R^4$ taken together with the nitrogen to which they are attached form

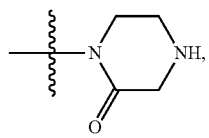 [SMILES: *N1CCNCC1=O]

optionally substituted with methyl, for example, as

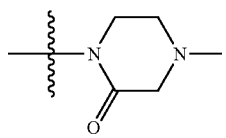

In some embodiments, $R^2$ is $C_{1-5}$alkyl (substituted with one or more halo substituents), —$OC_{1-4}$alkyl, or —$SC_{1-4}$alkyl, or a monocyclic cycloalkyl or —$C_{1-4}$alkyl-(monocyclic cycloalkyl), wherein each cycloalkyl is substituted with halo, $C_{1-4}$alkyl, or halo-$C_{1-4}$alkyl.

In some embodiments, $R^5$ is H. In other embodiments, $R^5$ is $C_{1-4}$alkyl. In other embodiments, $R^5$ is H or methyl.

In some embodiments, the compound of Formula (I) or (IA) is a compound of Formula (II):

(II)

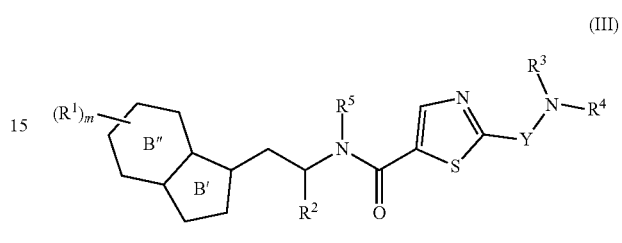

wherein

B' is a 5-membered heteroaryl;

B" is phenyl or a 6-membered heteroaryl; and $R^1$, $R^2$, $R^3$, $R^4$, $R^5$, m, A, and Y are as defined herein;

or a pharmaceutically acceptable salt thereof.

In some embodiments, the compound of Formula (I) or (IA) is a compound of Formula (III):

(III)

wherein

B' is a 5-membered heteroaryl;

B" is phenyl or a 6-membered heteroaryl; and $R^1$, $R^2$, $R^3$, $R^4$, $R^5$, m, and Y are as defined herein;

or a pharmaceutically acceptable salt thereof.

In some embodiments of the formulae described herein, B' and B" together form indole, benzofuran, benzothiophene, indazole, benzimidazole, benzoxazole, benzisoxazole, imidazopyridine, or pyrrolopyridine. In other embodiments, B' and B" together are optionally substituted indole, benzofuran, benzothiophene, indazole, benzisoxazole, imidazopyridine, or pyrrolopyridine. In other embodiments, B' and B" together are optionally substituted indole. In other embodiments, B' and B" together are optionally substituted 3-indole. In some embodiments, B' and B" together are substituted indole or substituted 3-indole. In some embodiments, m is 0. In other embodiments, m is 1. In other embodiments, m is 2.

In other embodiments, the compound of Formula (I) or (IA) is not a compound in Table X:

TABLE X

| Structure | Chemical Name |
| --- | --- |
| 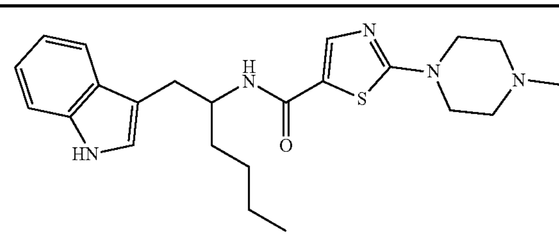 | N-(1-(1H-Indol-3-yl)-hexan-2-yl)-2-(4-methylpiperazin-1-yl)-thiazole-5-carboxamide |
| 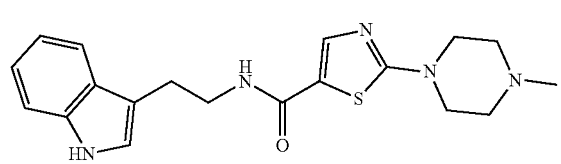 [SMILES: CN1CCN(c2ncc(C(=O)NCCc3c[nH]c4ccccc34)s2)CC1] | N-(2-(1H-Indol-3-yl)-ethyl)-2-(4-methyl-piperazin-1-yl)thiazole-5-carboxamide |

TABLE X-continued

| Structure | Chemical Name |
|---|---|
| 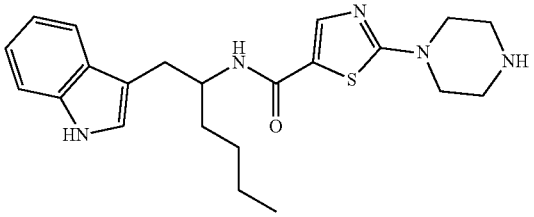 [SMILES: CCCCC(Cc1c[nH]c2ccccc12)NC(=O)c1cnc(N2CCNCC2)s1] | N-(1-(1H-Indol-3-yl)-hexan-2-yl)-2-(piperazin-1-yl)thiazole-5-carboxamide |
| 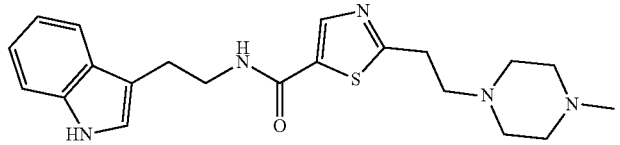 [SMILES: CN1CCN(CCc2ncc(C(=O)NCCc3c[nH]c4ccccc34)s2)CC1] | N-(2-(1H-Indol-3-yl)-ethyl)-2-(2-(4-methylpiperazin-1-yl)ethyl)thiazole-5-carboxamide |
| 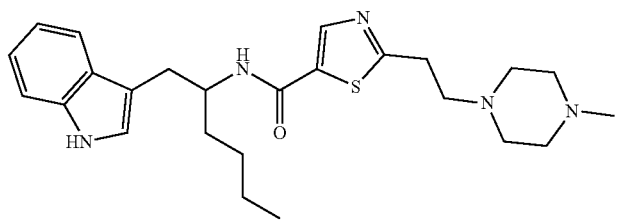 [SMILES: CCCCC(Cc1c[nH]c2ccccc12)NC(=O)c1cnc(CCN2CCN(C)CC2)s1] | N-(1-(1H-Indol-3-yl)-hexan-2-yl)-2-(2-(4-methylpiperazin-1-yl)ethyl)thiazole-5-carboxamide |
| 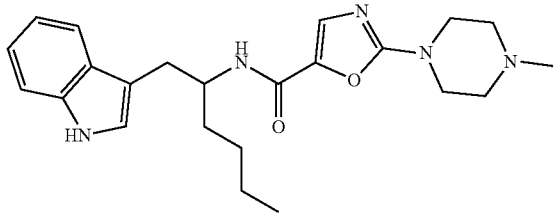 | N-(1-(1H-Indol-3-yl)-hexan-2-yl)-2-(4-methylpiperazin-1-yl)oxazole-5-carboxamide |
| 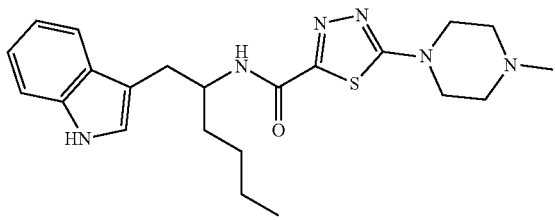 | N-(1-(1H-Indol-3-yl)-hexan-2-yl)-5-(4-methylpiperazin-1-yl)-1,3,4-thiadiazole-2-carboxamide |
| 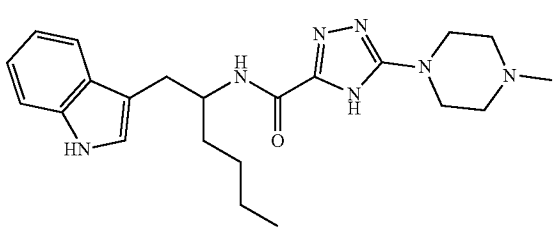 [SMILES: CCCCC(Cc1c[nH]c2ccccc12)NC(=O)c1nnc(N2CCN(C)CC2)[nH]1] | N-(1-(1H-Indol-3-yl)-hexan-2-yl)-5-(4-methylpiperazin-1-yl)-4H-1,2,4-triazole-3-carboxamide |
| 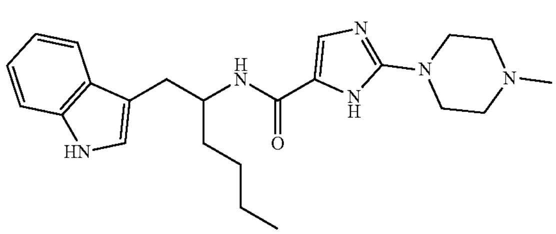 [SMILES: CCCCC(Cc1c[nH]c2ccccc12)NC(=O)c1cnc(N2CCN(C)CC2)[nH]1] | N-(1-(1H-Indol-3-yl)-hexan-2-yl)-2-(4-methylpiperazin-1-yl)-1H-imidazole-5-carboxamide |

TABLE X-continued

| Structure | Chemical Name |
|---|---|
| 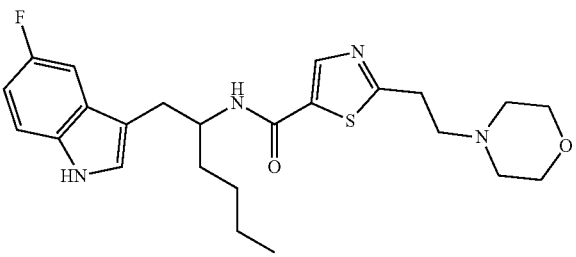 [SMILES: CCCCC(Cc1c[nH]c2ccc(F)cc12)NC(=O)c1cnc(CCN2CCOCC2)s1] | N-(1-(5-Fluoro-1H-indol-3-yl)hexan-2-yl)-2-(2-morpholinoethyl)-thiazole-5-carboxamide |
| 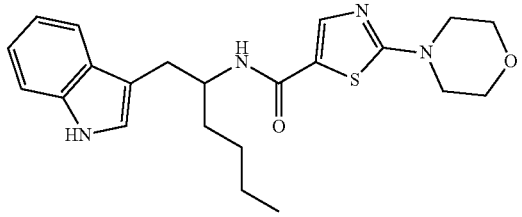 [SMILES: CCCCC(Cc1c[nH]c2ccccc12)NC(=O)c1cnc(N2CCOCC2)s1] | N-(1-(1H-Indol-3-yl)-hexan-2-yl)-2-morpholinothiazole-5-carboxamide |
| 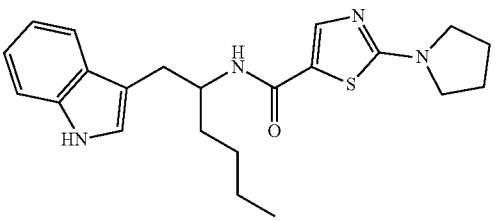 [SMILES: CCCCC(Cc1c[nH]c2ccccc12)NC(=O)c1cnc(N2CCCC2)s1] | N-(1-(1H-indol-3-yl)-hexan-2-yl)-2-(pyrrolidin-1-yl)thiazole-5-carboxamide |
| 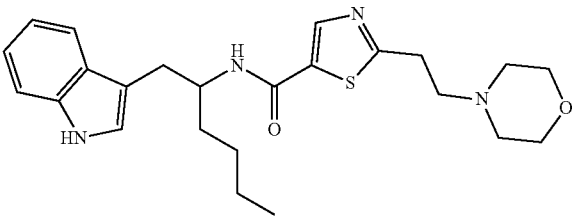 [SMILES: CCCCC(Cc1c[nH]c2ccccc12)NC(=O)c1cnc(CCN2CCOCC2)s1] | N-(1-(1H-indol-3-yl)-hexan-2-yl)-2-(2-morpholinoethyl)-thiazole-5-carboxamide |
| 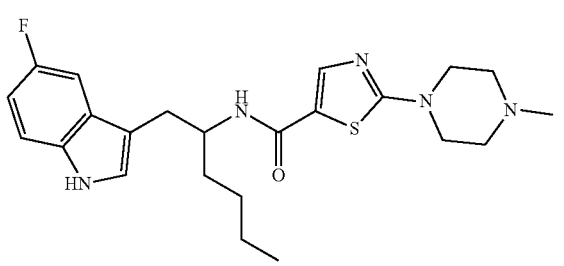 [SMILES: CCCCC(Cc1c[nH]c2ccc(F)cc12)NC(=O)c1cnc(N2CCN(C)CC2)s1] | N-(1-(5-fluoro-1H-indol-3-yl)hexan-2-yl)-2-(4-methyl-piperazin-1-yl)thiazole-5-carboxamide |
| 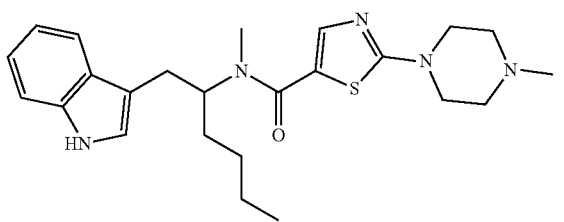 [SMILES: CCCCC(Cc1c[nH]c2ccccc12)N(C)C(=O)c1cnc(N2CCN(C)CC2)s1] | N-(1-(1H-indol-3-yl)hexan-2-yl)-N-methyl-2-(4-methyl-piperazin-1-yl)thiazole-5-carboxamide |

TABLE X-continued

| Structure | Chemical Name |
|---|---|
| 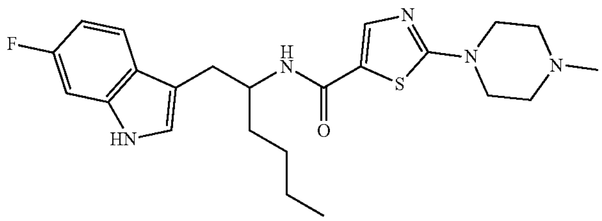 [SMILES: CCCCC(Cc1c[nH]c2cc(F)ccc12)NC(=O)c1cnc(N2CCN(C)CC2)s1] | N-(1-(6-fluoro-1H-indol-3-yl)hexan-2-yl)-2-(4-methyl-piperazin-1-yl)thiazole-5-carboxamide |
| 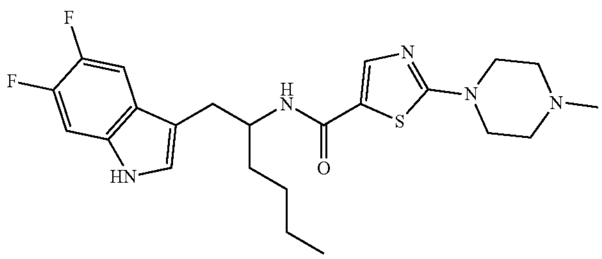 [SMILES: CCCCC(Cc1c[nH]c2cc(F)c(F)cc12)NC(=O)c1cnc(N2CCN(C)CC2)s1] | N-(1-(5,6-difluoro-1H-indol-3-yl)hexan-2-yl)-2-(4-methyl-piperazin-1-yl)thiazole-5-carboxamide |
| 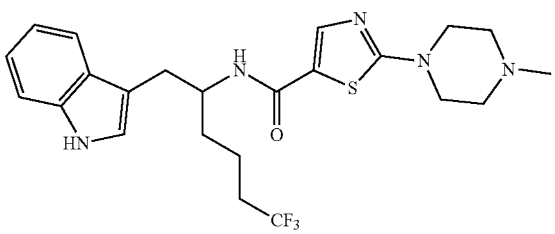 [SMILES: CN1CCN(c2ncc(C(=O)NC(CCCC(F)(F)F)Cc3c[nH]c4ccccc34)s2)CC1] | 2-(4-methylpiperazin-1-yl)-N-(6,6,6-trifluoro-1-(1H-indol-3-yl)-hexan-2-yl)thiazole-5-carboxamide |
| 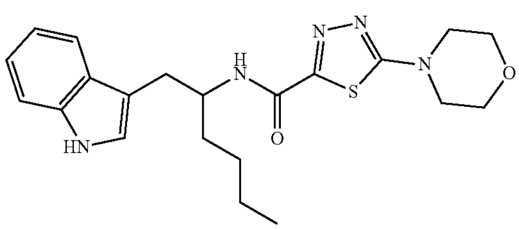 [SMILES: CCCCC(Cc1c[nH]c2ccccc12)NC(=O)c1nnc(N2CCOCC2)s1] | N-(1-(1H-indol-3-yl)-hexan-2-yl)-5-morpholino-1,3,4-thiadiazole-2-carboxamide |
| 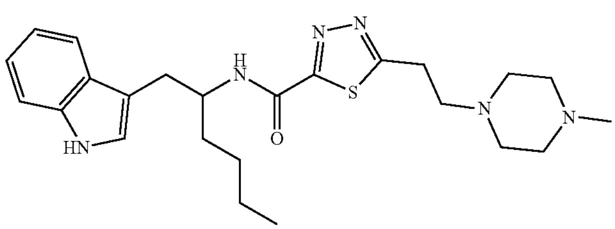 [SMILES: CCCCC(Cc1c[nH]c2ccccc12)NC(=O)c1nnc(CCN2CCN(C)CC2)s1] | N-(1-(1H-indol-3-yl)hexan-2-yl)-5-(2-(4-methylpiperazin-1-yl)ethyl)-1,3,4-thiadiazole-2-carboxamide |
| 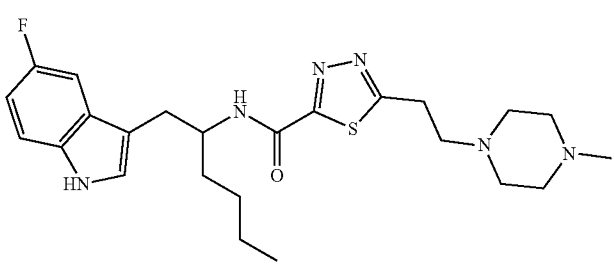 [SMILES: CCCCC(Cc1c[nH]c2ccc(F)cc12)NC(=O)c1nnc(CCN2CCN(C)CC2)s1] | N-(1-(5-fluoro-1H-indol-3-yl)hexan-2-yl)-5-(2-(4-methyl-piperazin-1-yl)ethyl)-1,3,4-thiadiazole-2-carboxamide |

TABLE X-continued

| Structure | Chemical Name |
|---|---|
| 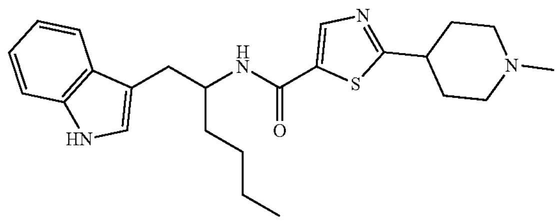 | N-(1-(1H-indol-3-yl)hexan-2-yl)-2-(1-methylpiperidin-4-yl)thiazole-5-carboxamide |
| 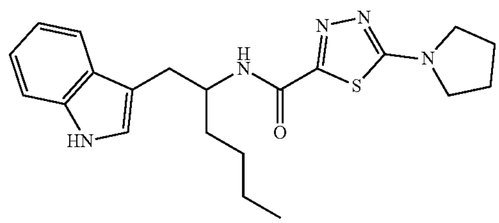 [SMILES: CCCCC(Cc1c[nH]c2ccccc12)NC(=O)c1nnc(N2CCCC2)s1] | N-(1-(1H-indol-3-yl)hexan-2-yl)-5-(pyrrolidin-1-yl)-1,3,4-thiadiazole-2-carboxamide |
| 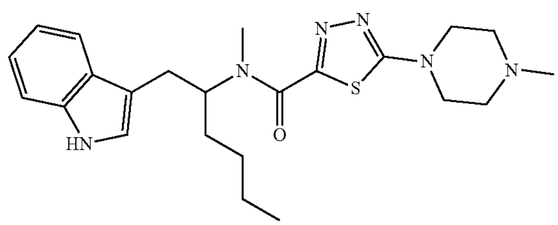 [SMILES: CCCCC(Cc1c[nH]c2ccccc12)N(C)C(=O)c1nnc(N2CCN(C)CC2)s1] | N-(1-(1H-indol-3-yl)hexan-2-yl)-N-methyl-5-(4-methylpiperazin-1-yl)-1,3,4-thiadiazole-2-carboxamide |
| 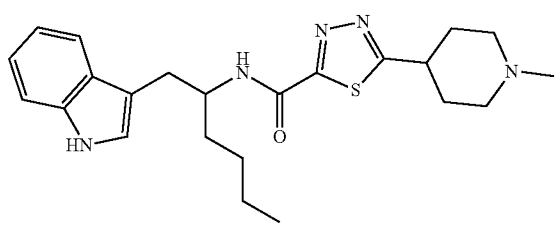 [SMILES: CCCCC(Cc1c[nH]c2ccccc12)NC(=O)c1nnc(C2CCN(C)CC2)s1] | N-(1-(1H-indol-3-yl)hexan-2-yl)-5-(1-methylpiperidin-4-yl)-1,3,4-thiadiazole-2-carboxamide |
| | N-(1-(1H-indol-3-yl)hexan-2-yl)-2-(4-methyl-1,4-diazepan-1-yl)thiazole-5-carboxamide | or a pharmaceutically acceptable salt thereof.

In other embodiments, the compound of Formula (I) or (IA) is selected from the group consisting of:

| Ex. | Structure | Chemical Name |
|---|---|---|
| 1 | 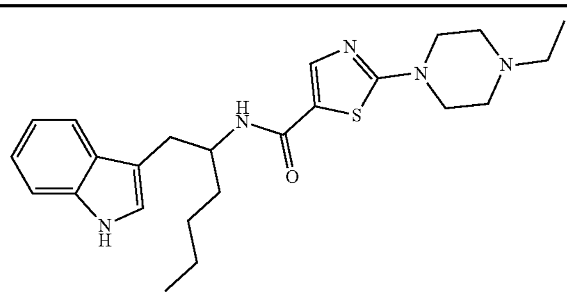 | N-(1-(1H-indol-3-yl)hexan-2-yl)-2-(4-ethylpiperazin-1-yl)thiazole-5-carboxamide |

-continued

| Ex. | Structure | Chemical Name |
|---|---|---|
| 2 | 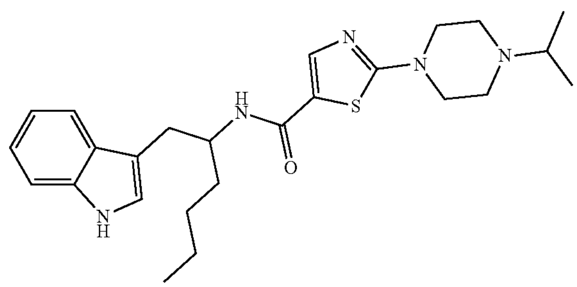 [SMILES: CCCCC(Cc1c[nH]c2ccccc12)NC(=O)c1cnc(N2CCN(C(C)C)CC2)s1] | N-(1-(1H-indol-3-yl)hexan-2-yl)-2-(4-isopropylpiperazin-1-yl)thiazole-5-carboxamide |
| 3 | 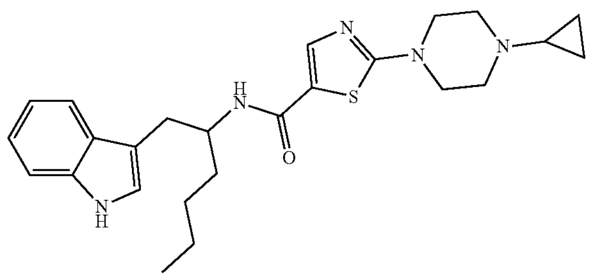 [SMILES: CCCCC(Cc1c[nH]c2ccccc12)NC(=O)c1cnc(N2CCN(C3CC3)CC2)s1] | N-(1-(1H-indol-3-yl)hexan-2-yl)-2-(4-cyclopropyl-piperazin-1-yl)-thiazole-5-carboxamide |
| 4 | 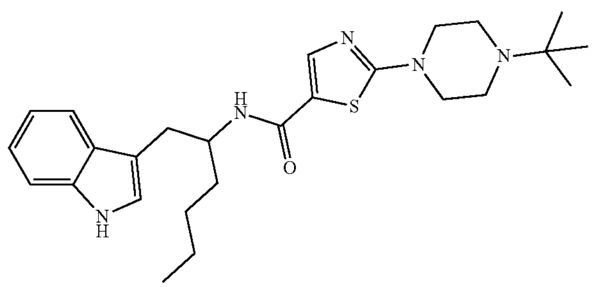 [SMILES: CCCCC(Cc1c[nH]c2ccccc12)NC(=O)c1cnc(N2CCN(C(C)(C)C)CC2)s1] | N-(1-(1H-indol-3-yl)hexan-2-yl)-2-(4-(tert-butyl)-piperazin-1-yl)-thiazole-5-carboxamide |
| 5 | 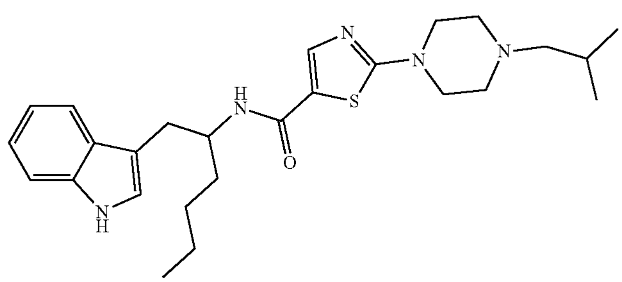 [SMILES: CCCCC(Cc1c[nH]c2ccccc12)NC(=O)c1cnc(N2CCN(CC(C)C)CC2)s1] | N-(1-(1H-indol-3-yl)hexan-2-yl)-2-(4-isobutyl-piperazin-1-yl)-thiazole-5-carboxamide |
| 6 | 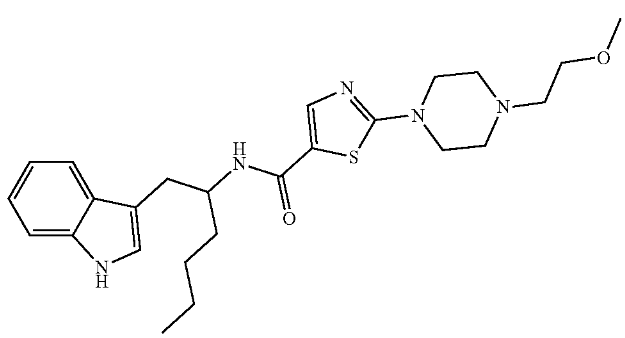 [SMILES: CCCCC(Cc1c[nH]c2ccccc12)NC(=O)c1cnc(N2CCN(CCOC)CC2)s1] | N-(1-(1H-indol-3-yl)hexan-2-yl)-2-(4-(2-methoxy-ethyl)piperazin-1-yl)thiazole-5-carboxamide |

-continued

| Ex. | Structure | Chemical Name |
|---|---|---|
| 7 | 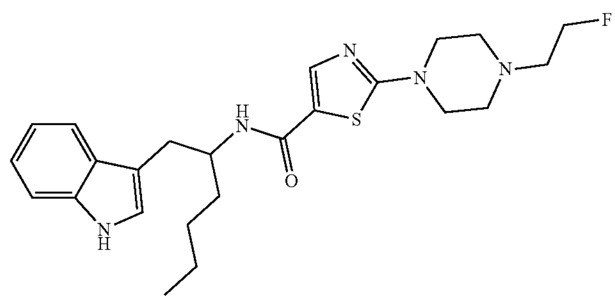 [SMILES: CCCCC(Cc1c[nH]c2ccccc12)NC(=O)c1cnc(N2CCN(CCF)CC2)s1] | N-(1-(1H-indol-3-yl)hexan-2-yl)-2-(4-(2-fluoroethyl)-piperazin-1-yl)-thiazole-5-carboxamide |
| 8 | 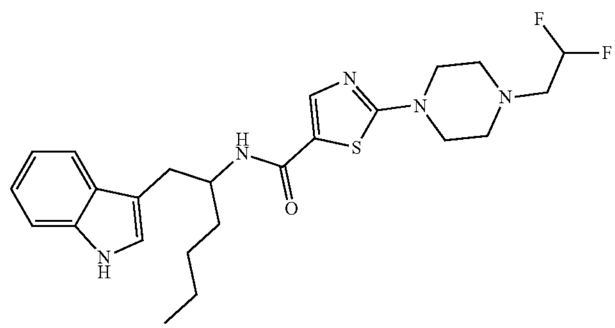 [SMILES: CCCCC(Cc1c[nH]c2ccccc12)NC(=O)c1cnc(N2CCN(CC(F)F)CC2)s1] | N-(1-(1H-indol-3-yl)hexan-2-yl)-2-(4-(2,2-difluoro-ethyl)piperazin-1-yl)thiazole-5-carboxamide |
| 9 | 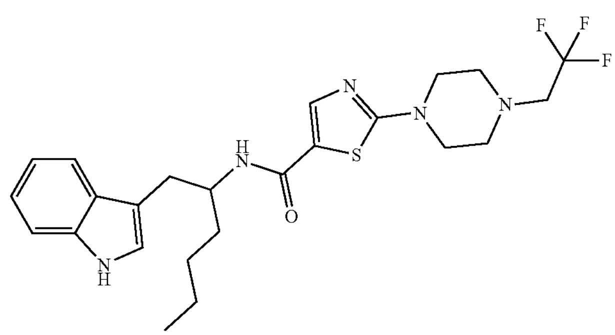 [SMILES: CCCCC(Cc1c[nH]c2ccccc12)NC(=O)c1cnc(N2CCN(CC(F)(F)F)CC2)s1] | N-(1-(1H-indol-3-yl)hexan-2-yl)-2-(4-(2,2,2-trifluoro-ethyl)piperazin-1-yl)thiazole-5-carboxamide |
| 10 | 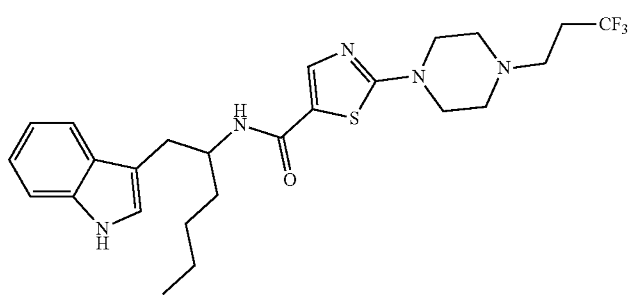 [SMILES: CCCCC(Cc1c[nH]c2ccccc12)NC(=O)c1cnc(N2CCN(CCC(F)(F)F)CC2)s1] | N-(1-(1H-indol-3-yl)hexan-2-yl)-2-(4-(3,3,3-trifluoro-propyl)piperazin-1-yl)thiazole-5-carboxamide |
| 11 | 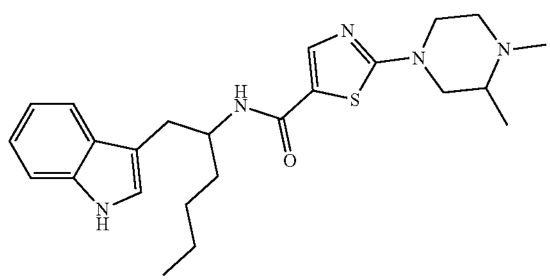 [SMILES: CCCCC(Cc1c[nH]c2ccccc12)NC(=O)c1cnc(N2CCN(C)C(C)C2)s1] | N-(1-(1H-indol-3-yl)hexan-2-yl)-2-(3,4-dimethyl-piperazin-1-yl)-thiazole-5-carboxamide |

-continued

| Ex. | Structure | Chemical Name |
|---|---|---|
| 12 | 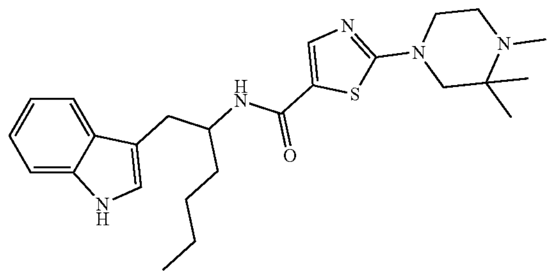 [SMILES: CCCCC(Cc1c[nH]c2ccccc12)NC(=O)c1cnc(N2CCN(C)C(C)(C)C2)s1] | N-(1-(1H-indol-3-yl)hexan-2-yl)-2-(3,3,4-trimethyl-piperazin-1-yl)-thiazole-5-carboxamide |
| 13 | 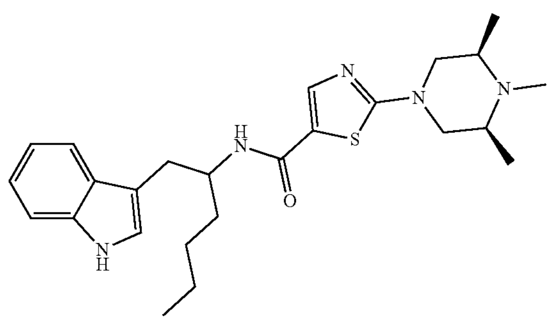 [SMILES: CCCCC(Cc1c[nH]c2ccccc12)NC(=O)c1cnc(N2C[C@@H](C)N(C)[C@@H](C)C2)s1] | N-(1-(1H-indol-3-yl)hexan-2-yl)-2-(cis-3,4,5-trimethylpiperazin-1-yl)thiazole-5-carboxamide |
| 14 | 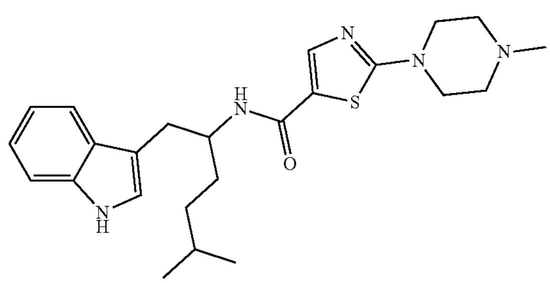 [SMILES: CC(C)CCC(Cc1c[nH]c2ccccc12)NC(=O)c1cnc(N2CCN(C)CC2)s1] | N-(1-(1H-indol-3-yl)-5-methyl-hexan-2-yl)-2-(4-methylpiperazin-1-yl)thiazole-5-carboxamide |
| 15 | 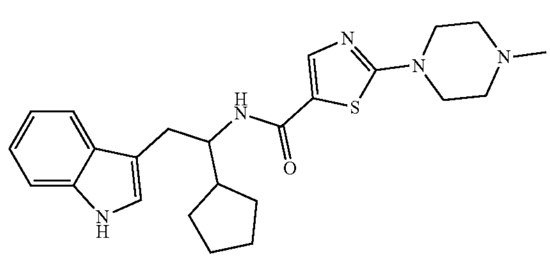 [SMILES: CN1CCN(c2ncc(C(=O)NC(Cc3c[nH]c4ccccc34)C3CCCC3)s2)CC1] | N-(1-cyclopentyl-2-(1H-indol-3-yl)ethyl)-2-(4-methylpiperazin-1-yl)thiazole-5-carboxamide |
| 16 | 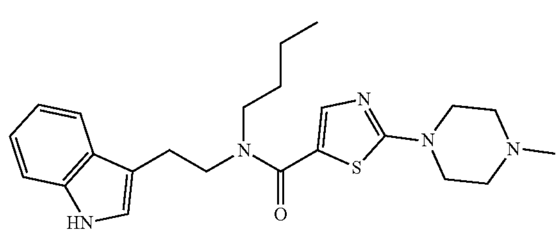 [SMILES: CCCCN(CCc1c[nH]c2ccccc12)C(=O)c1cnc(N2CCN(C)CC2)s1] | N-(2-(1H-indol-3-yl)ethyl)-N-butyl-2-(4-methyl-piperazin-1-yl)-thiazole-5-carboxamide |

-continued

| Ex. | Structure | Chemical Name |
|-----|-----------|---------------|
| 17 | 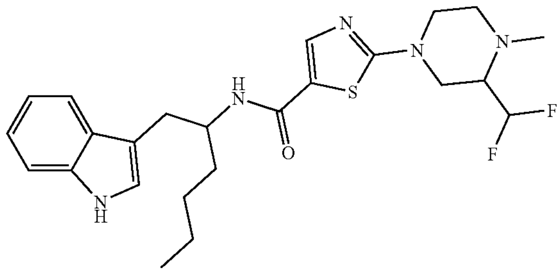 [SMILES: CCCCC(Cc1c[nH]c2ccccc12)NC(=O)c1cnc(N2CCN(C)C(C(F)F)C2)s1] | N-(1-(1H-indol-3-yl)hexan-2-yl)-2-(3-(difluoromethyl)-4-methylpiperazin-1-yl)thiazole-5-carboxamide |
| 18 | 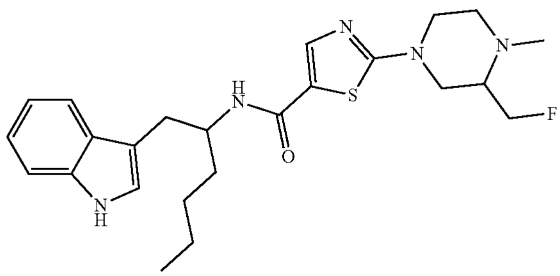 [SMILES: CCCCC(Cc1c[nH]c2ccccc12)NC(=O)c1cnc(N2CCN(C)C(CF)C2)s1] | N-(1-(1H-indol-3-yl)hexan-2-yl)-2-(3-(fluoromethyl)-4-methylpiperazin-1-yl)thiazole-5-carboxamide |
| 19 | 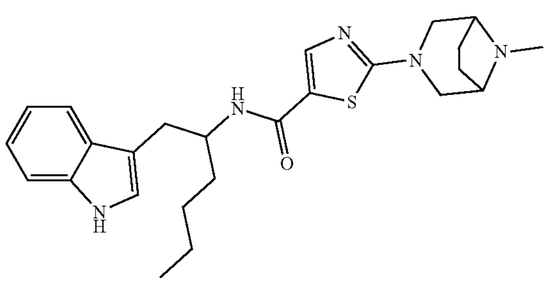 [SMILES: CCCCC(Cc1c[nH]c2ccccc12)NC(=O)c1cnc(N2CC3CCC(C2)N3C)s1] | N-(1-(1H-indol-3-yl)hexan-2-yl)-2-(8-methyl-3,8-diazabicyclo[3.2.1]-octan-3-yl)thiazole-5-carboxamide |
| 20 | 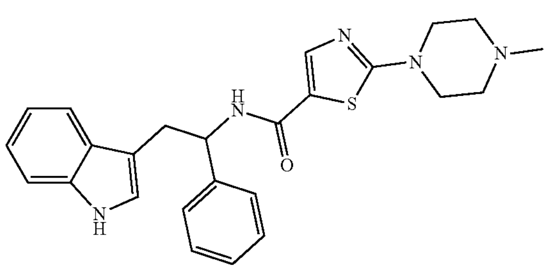 [SMILES: CN1CCN(c2ncc(C(=O)NC(Cc3c[nH]c4ccccc34)c3ccccc3)s2)CC1] | N-(2-(1H-indol-3-yl)-1-phenylethyl)-2-(4-methyl-piperazin-1-yl)-thiazole-5-carboxamide |

| Ex. | Structure | Chemical Name |
|---|---|---|
| 21 | | N-(2-(1H-indol-3-yl)ethyl)-N-methyl-2-(4-methylpiperazin-1-yl)thiazole-5-carboxamide | and pharmaceutically acceptable salts thereof.

In other embodiments, the compound of Formula (I) or (IA) is selected from the group consisting of:

| Ex. | Compound |
|---|---|
| 22 | |
| 23 | |
| 24 | (trans) |
| 25 | |

-continued
| Ex. | Compound |
|---|---|
| 26 | 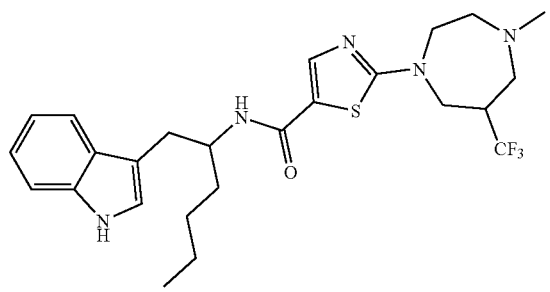 [SMILES: CCCCC(Cc1c[nH]c2ccccc12)NC(=O)c1cnc(N2CCN(C)CC(C(F)(F)F)C2)s1] |
| 27 | 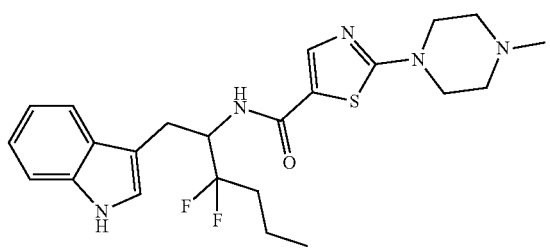 [SMILES: CCCC(F)(F)C(Cc1c[nH]c2ccccc12)NC(=O)c1cnc(N2CCN(C)CC2)s1] |
| 28 | 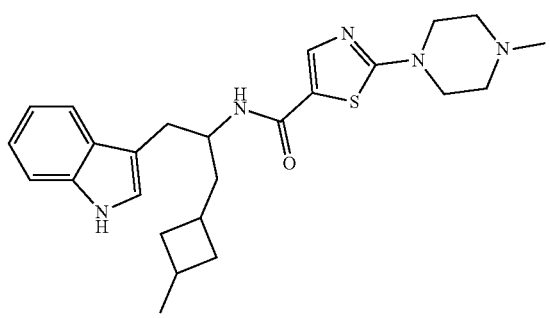 [SMILES: CC1CC(CC(Cc2c[nH]c3ccccc23)NC(=O)c2cnc(N3CCN(C)CC3)s2)C1] |
| 29 | 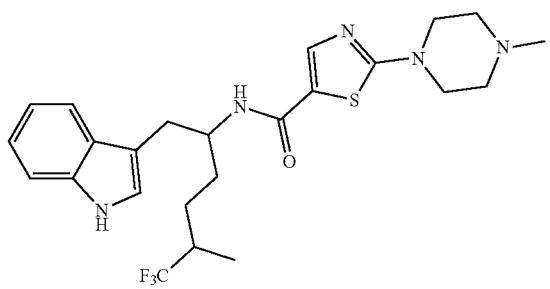 [SMILES: CC(CCC(Cc1c[nH]c2ccccc12)NC(=O)c1cnc(N2CCN(C)CC2)s1)C(F)(F)F] |
| 30 | 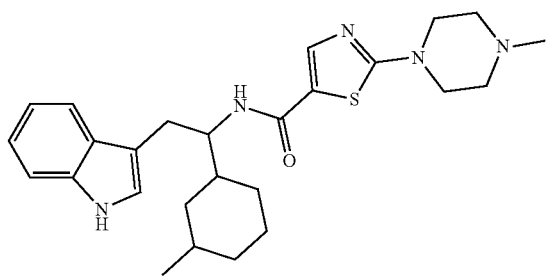 [SMILES: CC1CCCC(C(Cc2c[nH]c3ccccc23)NC(=O)c2cnc(N3CCN(C)CC3)s2)C1] |

-continued
| Ex. | Compound |
|---|---|
| 31 | 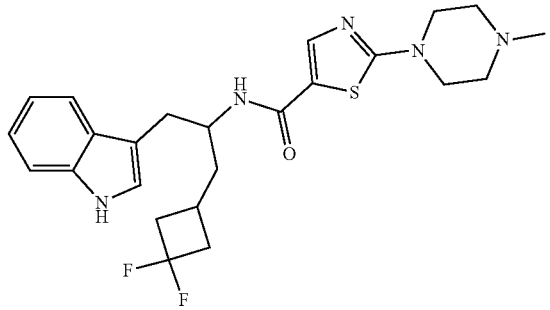 [SMILES: CN1CCN(c2ncc(C(=O)NC(Cc3c[nH]c4ccccc34)CC3CC(F)(F)C3)s2)CC1] |
| 32 | 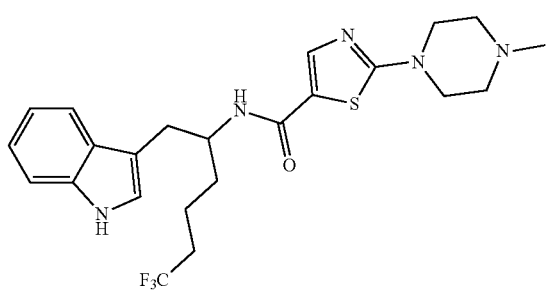 [SMILES: CN1CCN(c2ncc(C(=O)NC(CCCC(F)(F)F)Cc3c[nH]c4ccccc34)s2)CC1] |
| 33 | 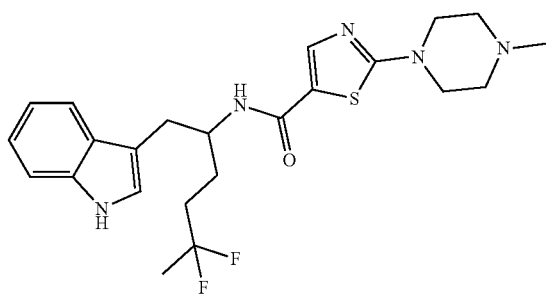 [SMILES: CN1CCN(c2ncc(C(=O)NC(CCC(C)(F)F)Cc3c[nH]c4ccccc34)s2)CC1] |
| 34 | 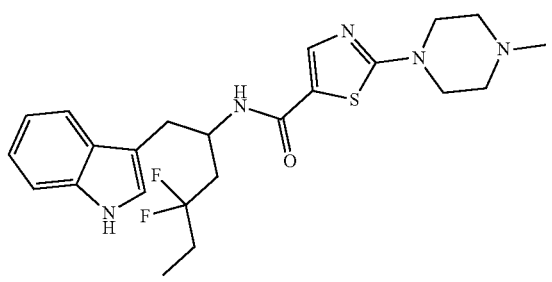 [SMILES: CCC(F)(F)CC(Cc1c[nH]c2ccccc12)NC(=O)c1cnc(N2CCN(C)CC2)s1] |
| 35 | 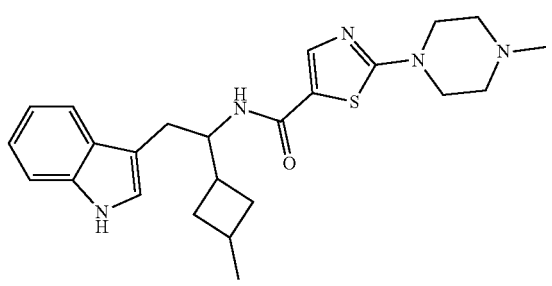 [SMILES: CC1CC(C(Cc2c[nH]c3ccccc23)NC(=O)c2cnc(N3CCN(C)CC3)s2)C1] |

-continued

| Ex. | Compound |
|---|---|
| 36 | |
| 37 | |
| 38 | |
| 39 | |
| 40 | |
| 41 | |

-continued
| Ex. | Compound |
|---|---|
| 42 | 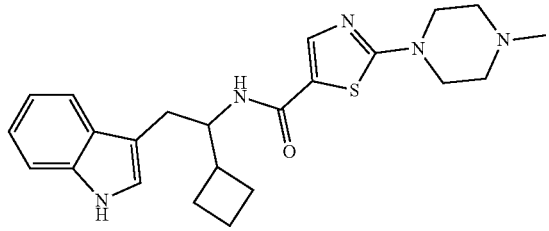 [SMILES: CN1CCN(c2ncc(C(=O)NC(Cc3c[nH]c4ccccc34)C3CCC3)s2)CC1] |
| 43 | 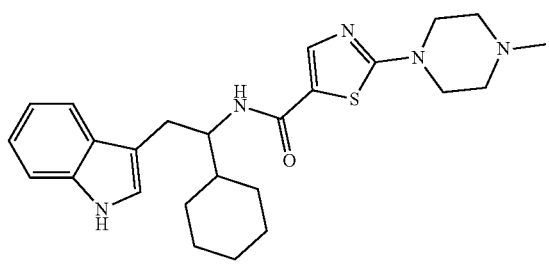 [SMILES: CN1CCN(c2ncc(C(=O)NC(Cc3c[nH]c4ccccc34)C3CCCCC3)s2)CC1] |
| 44 | 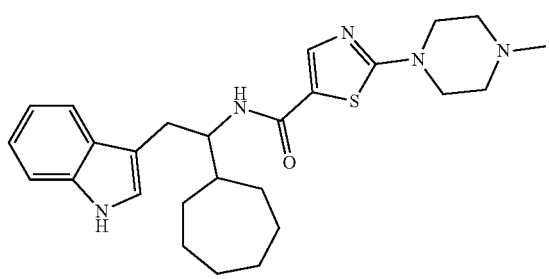 [SMILES: CN1CCN(c2ncc(C(=O)NC(Cc3c[nH]c4ccccc34)C3CCCCCC3)s2)CC1] |
| 45 | 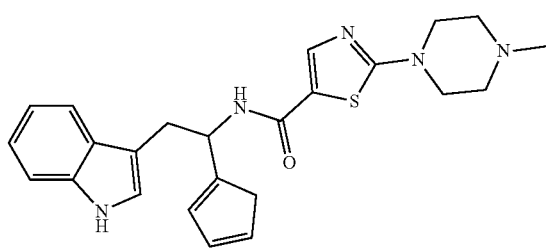 [SMILES: CN1CCN(c2ncc(C(=O)NC(Cc3c[nH]c4ccccc34)C3=CC=CC3)s2)CC1] |
| 46 | 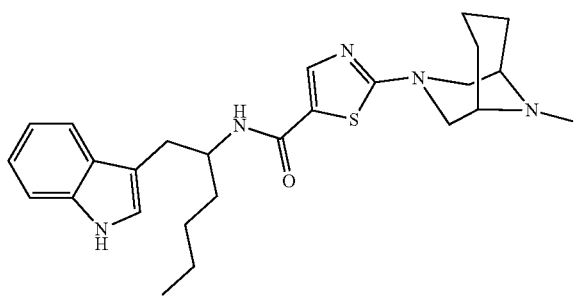 [SMILES: CCCCC(Cc1c[nH]c2ccccc12)NC(=O)c1cnc(N2CC3CCCC(C2)N3C)s1] |

| Ex. | Compound |
|---|---|
| 47 | 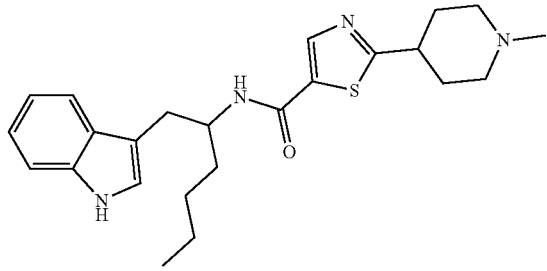 [SMILES: CCCCC(Cc1c[nH]c2ccccc12)NC(=O)c1cnc(C2CCN(C)CC2)s1] |
| 48 | 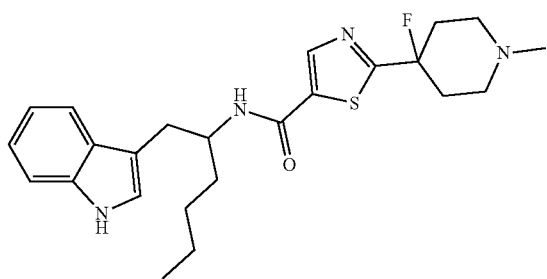 [SMILES: CCCCC(Cc1c[nH]c2ccccc12)NC(=O)c1cnc(C2(F)CCN(C)CC2)s1] |
| 49 | 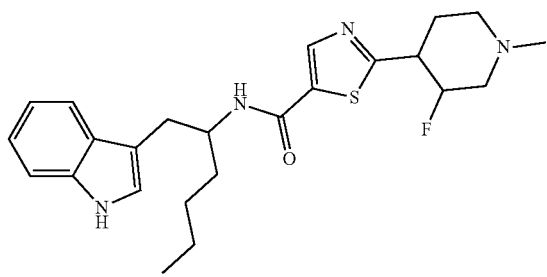 [SMILES: CCCCC(Cc1c[nH]c2ccccc12)NC(=O)c1cnc(C2CCN(C)CC2F)s1] |
| 50 | 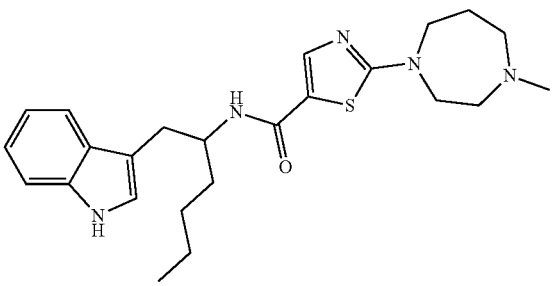 [SMILES: CCCCC(Cc1c[nH]c2ccccc12)NC(=O)c1cnc(N2CCCN(C)CC2)s1] |
| 51 | 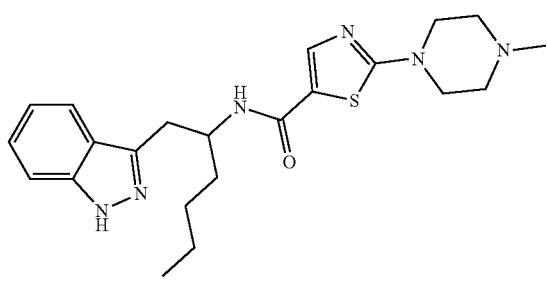 [SMILES: CCCCC(Cc1n[nH]c2ccccc12)NC(=O)c1cnc(N2CCN(C)CC2)s1] |

-continued
| Ex. | Compound |
|---|---|
| 52 | 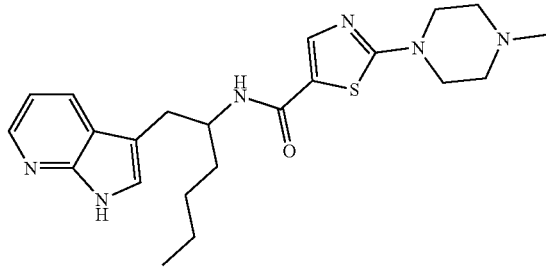 [SMILES: CCCCC(Cc1c[nH]c2ncccc12)NC(=O)c1cnc(N2CCN(C)CC2)s1] |
| 53 | 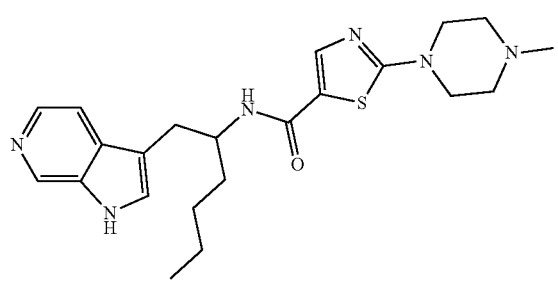 [SMILES: CCCCC(Cc1c[nH]c2cnccc12)NC(=O)c1cnc(N2CCN(C)CC2)s1] |
| 54 | 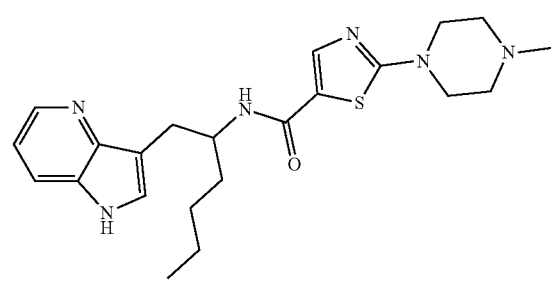 [SMILES: CCCCC(Cc1c[nH]c2cccnc12)NC(=O)c1cnc(N2CCN(C)CC2)s1] |
| 55 | 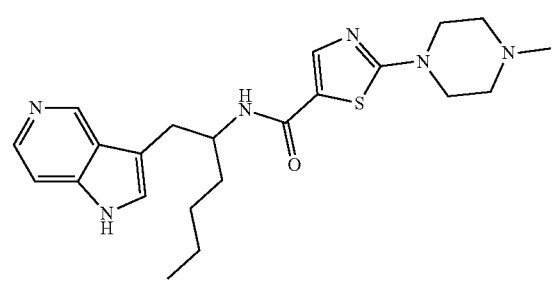 [SMILES: CCCCC(Cc1c[nH]c2ccncc12)NC(=O)c1cnc(N2CCN(C)CC2)s1] |
| 56 | 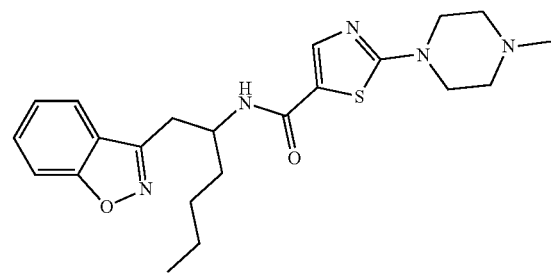 [SMILES: CCCCC(Cc1noc2ccccc12)NC(=O)c1cnc(N2CCN(C)CC2)s1] |

-continued
| Ex. | Compound |
|---|---|
| 57 | 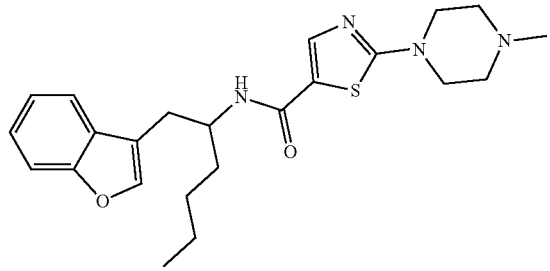 [SMILES: CCCCC(Cc1coc2ccccc12)NC(=O)c1cnc(N2CCN(C)CC2)s1] |
| 58 | 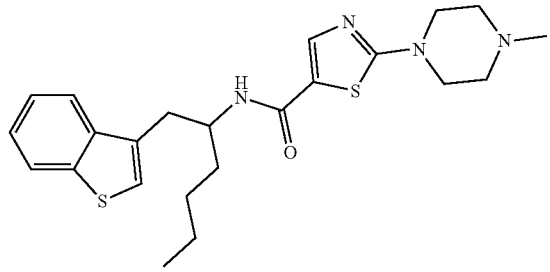 [SMILES: CCCCC(Cc1csc2ccccc12)NC(=O)c1cnc(N2CCN(C)CC2)s1] |
| 59 | 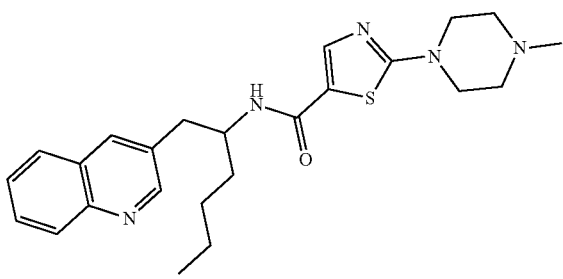 [SMILES: CCCCC(Cc1cnc2ccccc2c1)NC(=O)c1cnc(N2CCN(C)CC2)s1] |
| 60 | 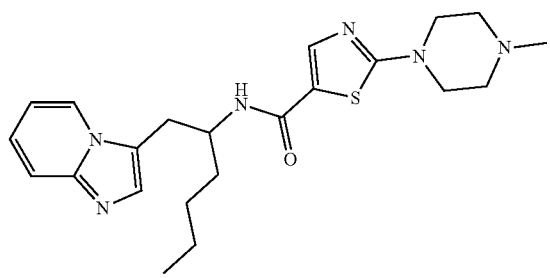 [SMILES: CCCCC(Cc1cnc2ccccn12)NC(=O)c1cnc(N2CCN(C)CC2)s1] |
| 61 | 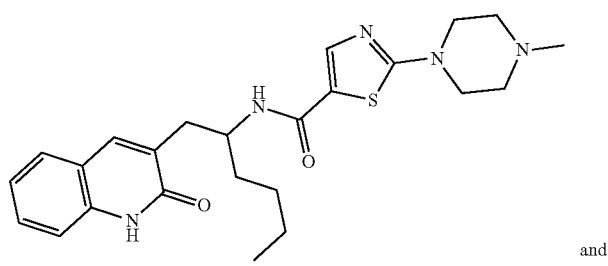 [SMILES: CCCCC(Cc1cc2ccccc2[nH]c1=O)NC(=O)c1cnc(N2CCN(C)CC2)s1] and |

| Ex. | Compound |
|---|---|
| 62 | 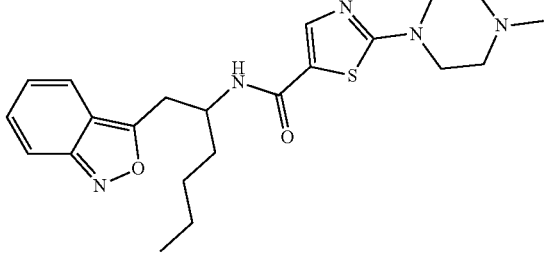 |
and pharmaceutically acceptable salts thereof.
In some embodiments, the compound of Formula (I) or (IA) is selected from the group consisting of Examples 1-62, and pharmaceutically acceptable salts thereof.
In still other embodiments, the compound of Formula (I) or (IA) is selected from the group consisting of:
| Ex. | Compound |
|---|---|
| 63 | 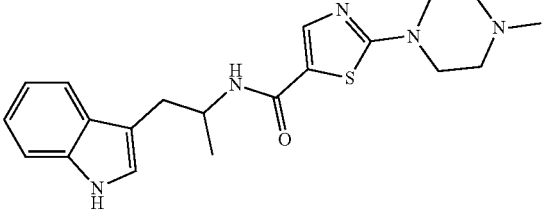 |
| 64 | 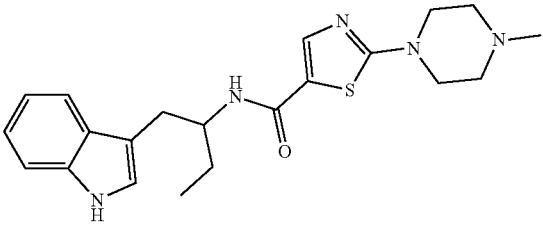 [SMILES: CCC(Cc1c[nH]c2ccccc12)NC(=O)c1cnc(N2CCN(C)CC2)s1] |
| 65 | 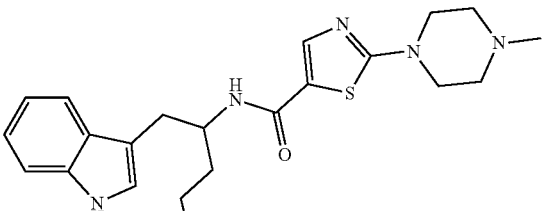 |
| 66 | 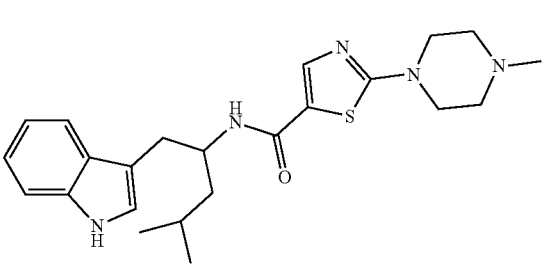 [SMILES: CC(C)CC(Cc1c[nH]c2ccccc12)NC(=O)c1cnc(N2CCN(C)CC2)s1] |

| Ex. | Compound |
|---|---|
| 67 | *(structure)* |
| 68 | *(structure)* |
| 69 | *(structure)* and |
| 70 | *(structure)* | and pharmaceutically acceptable salts thereof.

In other embodiments, the compound of Formula (I) or (IA) is selected from the group consisting of Examples 1-70, and pharmaceutically acceptable salts thereof.

In further embodiments, the compound is selected from the compounds in List 1 below, and pharmaceutically acceptable salts thereof.

List 1:
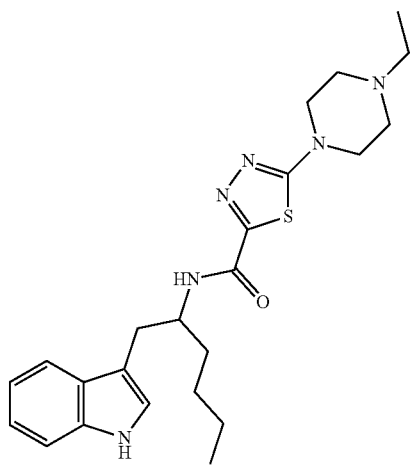
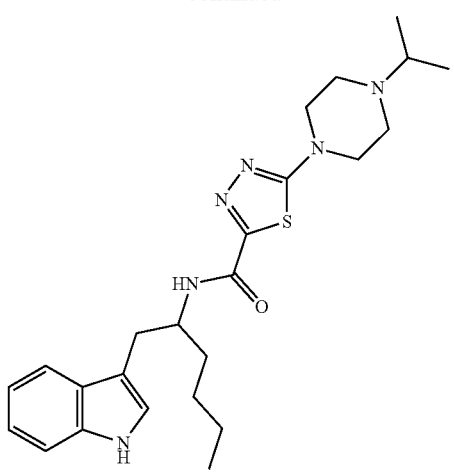
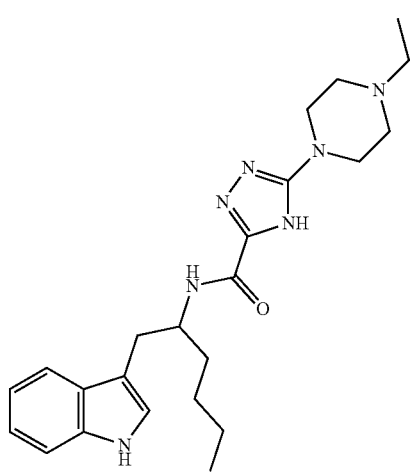
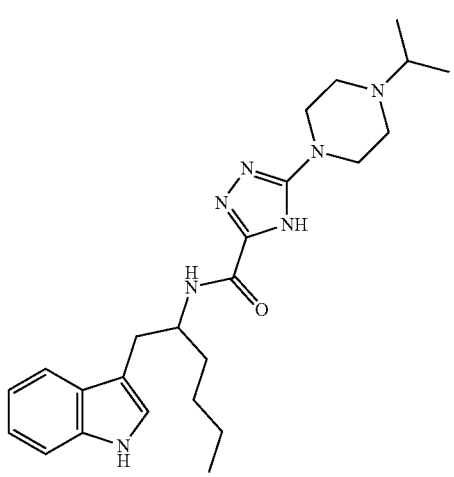
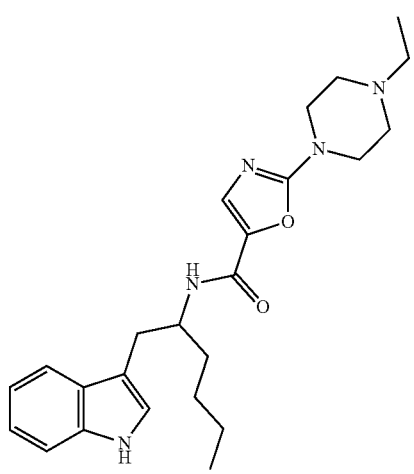
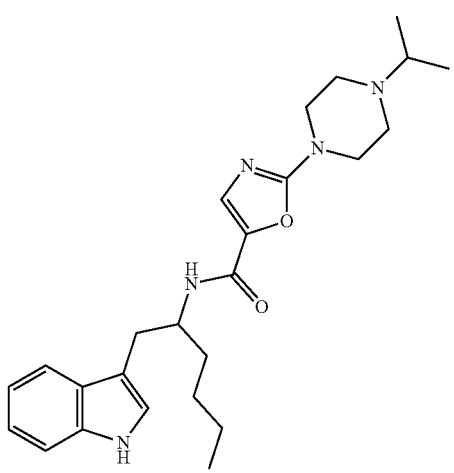

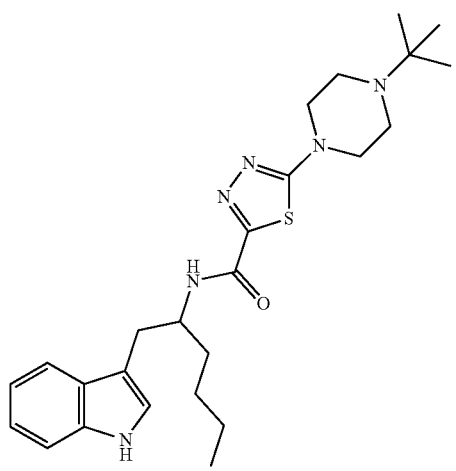
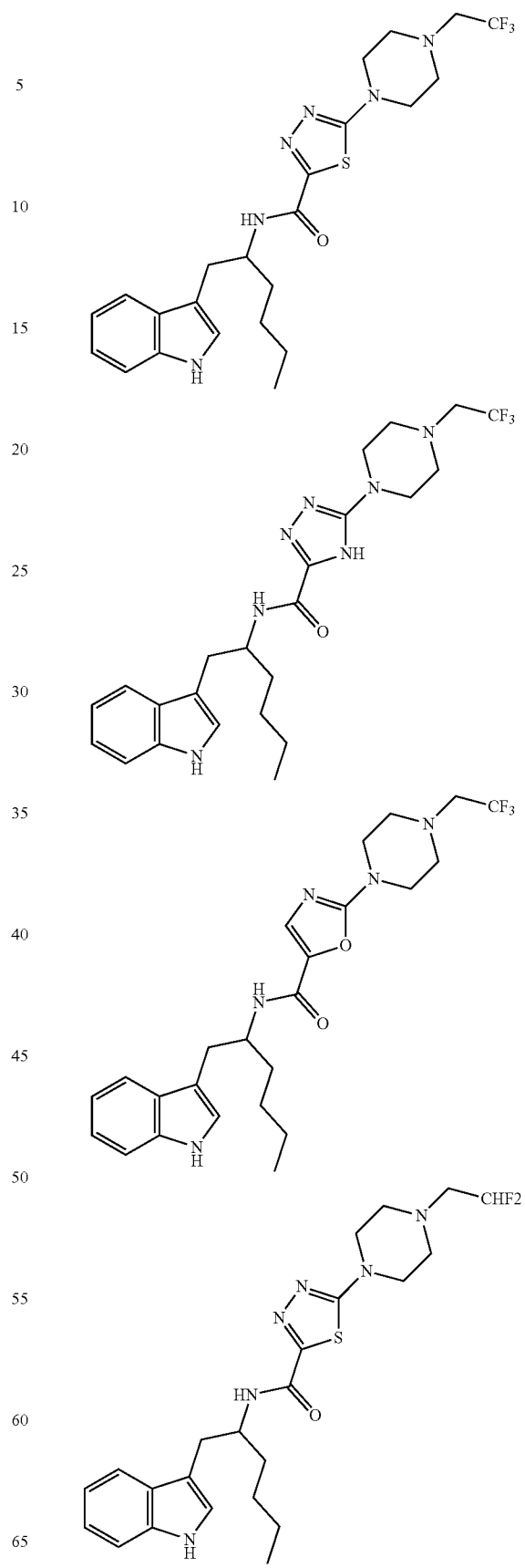

51
-continued
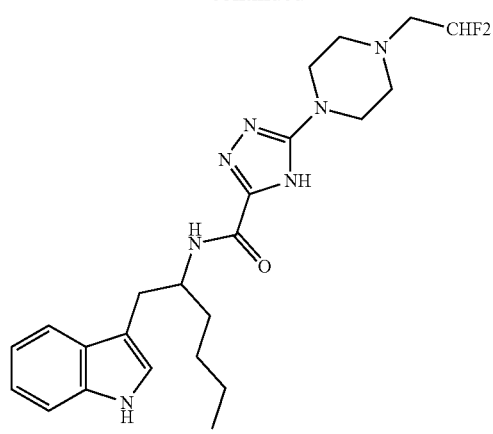
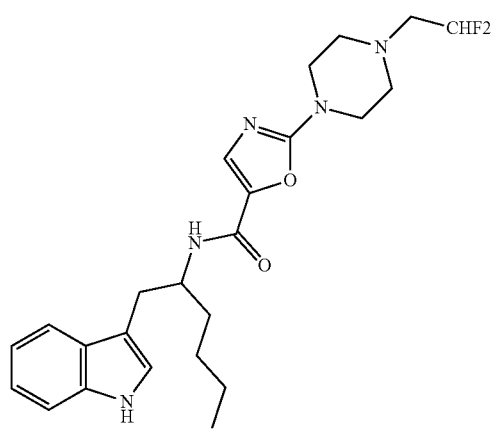
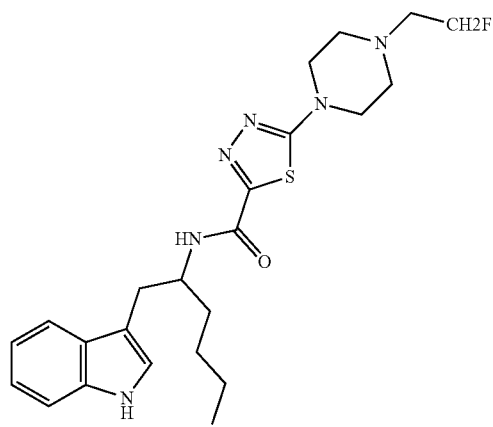
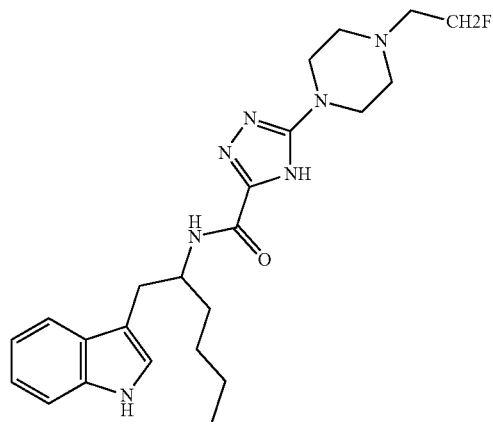
52
-continued
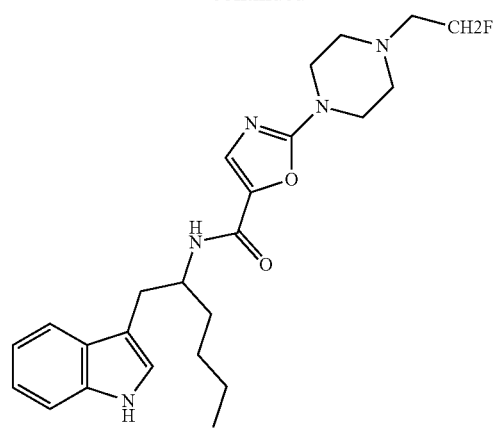
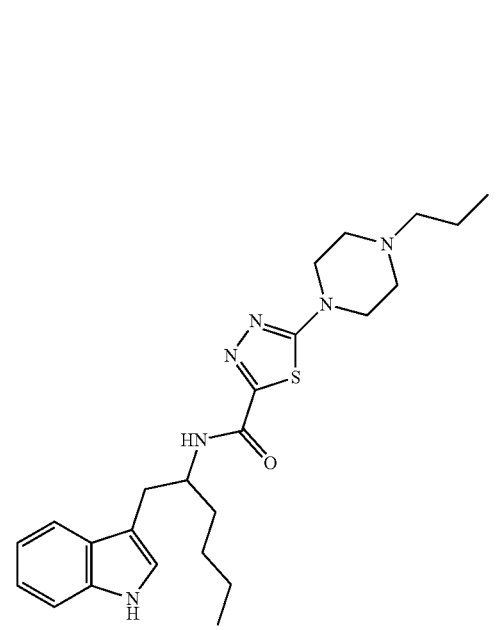
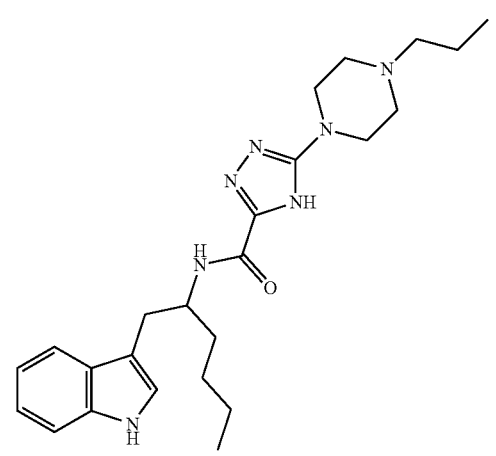

53
-continued
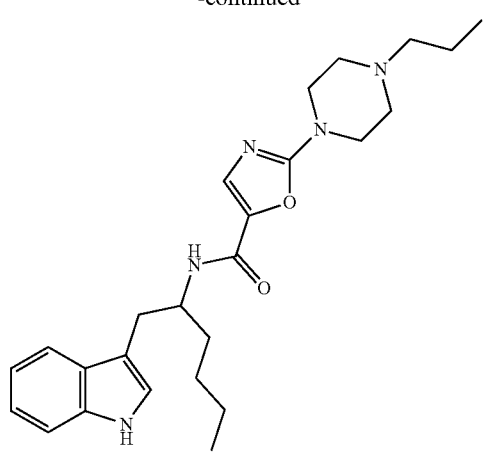
54
-continued
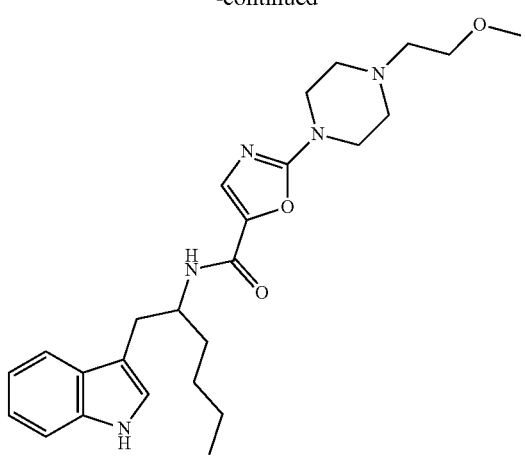
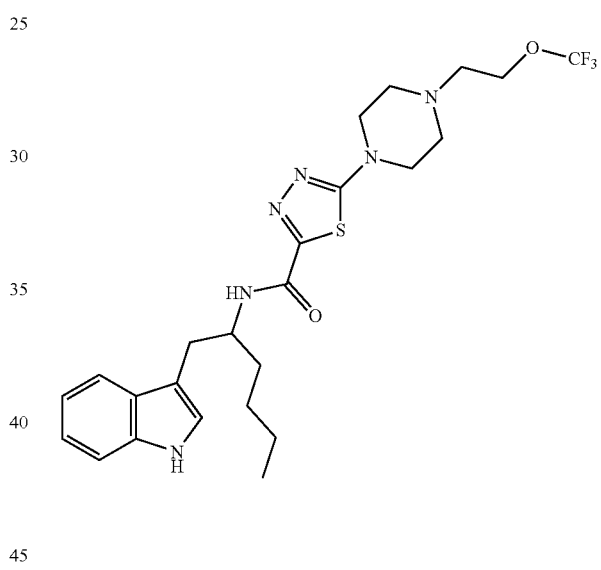
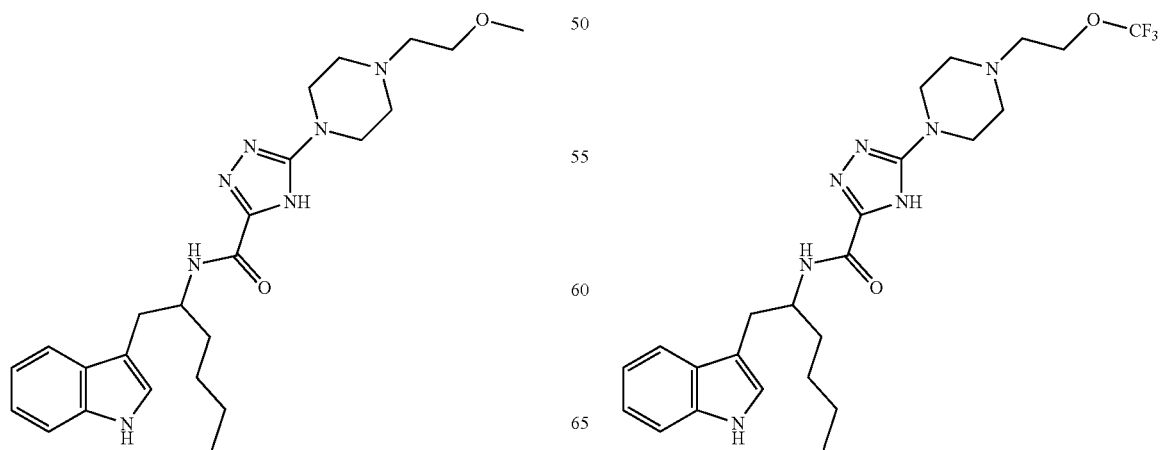

-continued
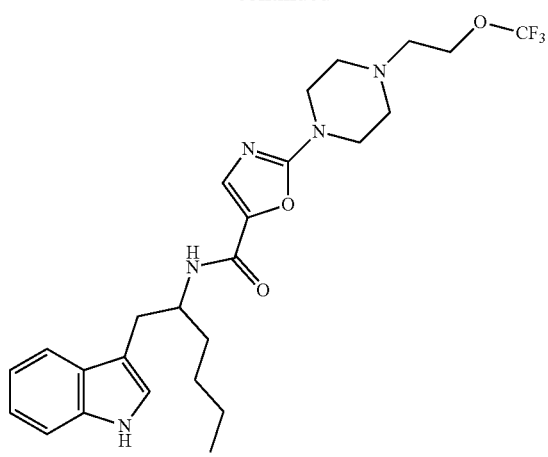
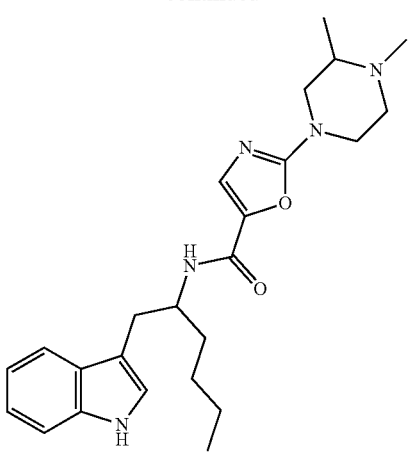
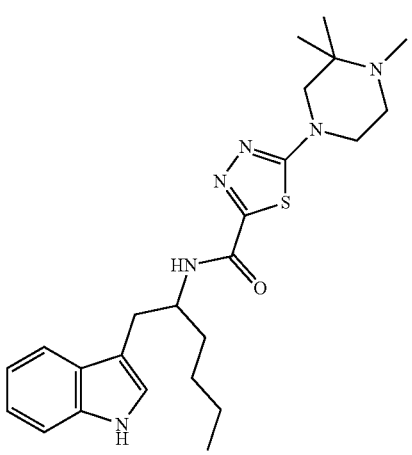
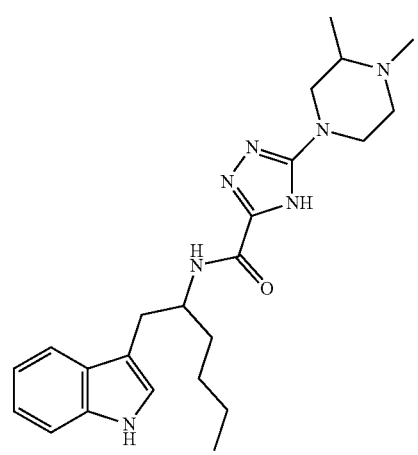

-continued
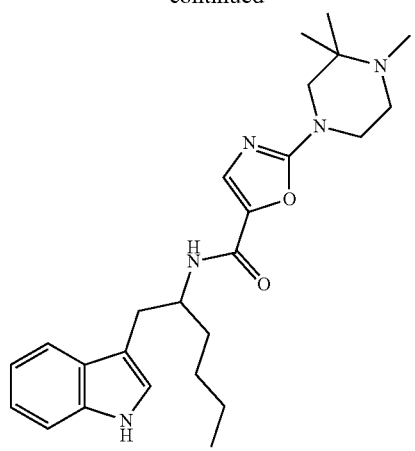
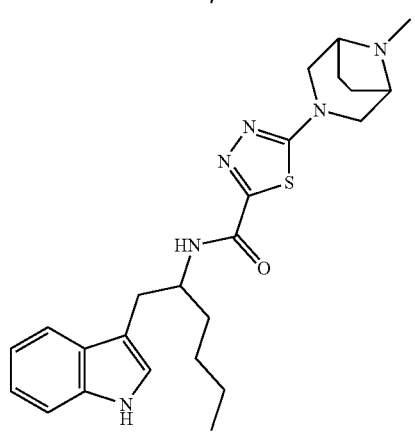
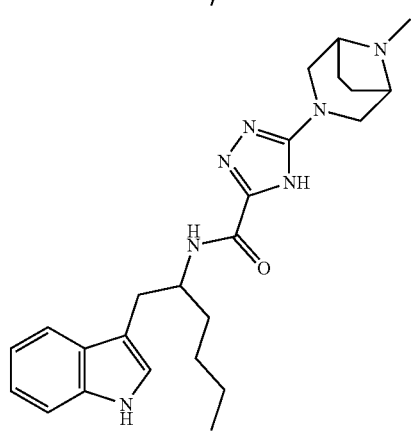
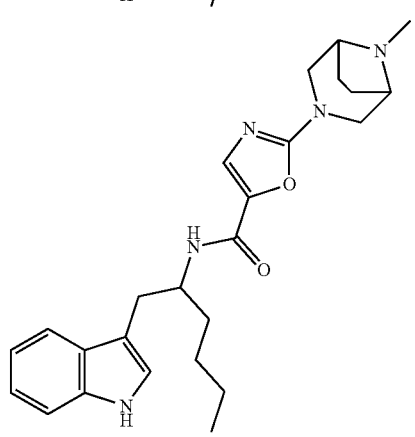
-continued
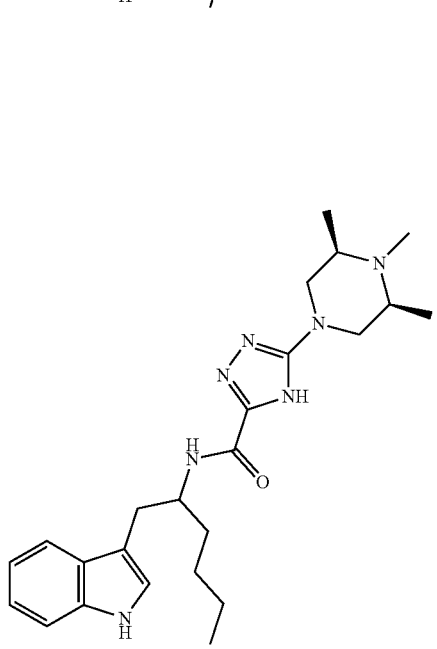
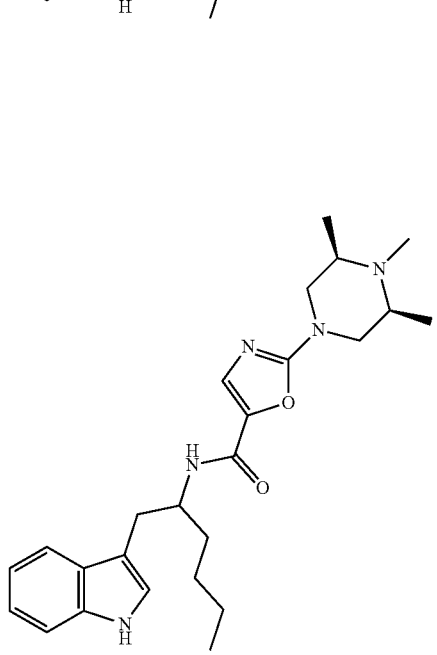

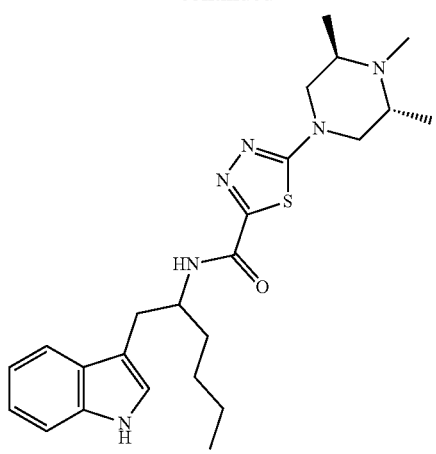
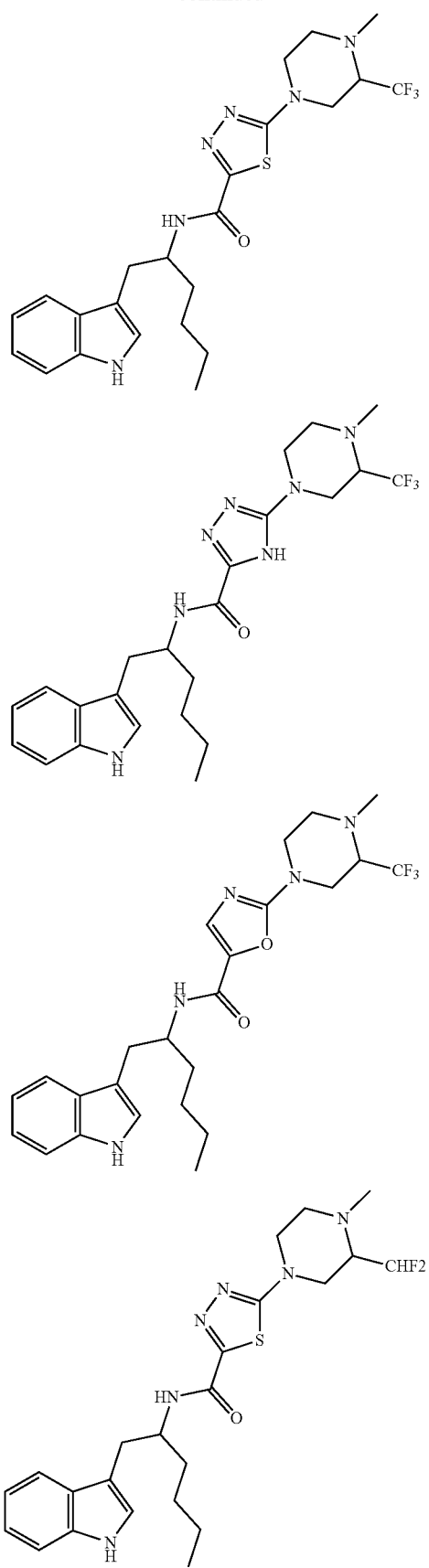

-continued
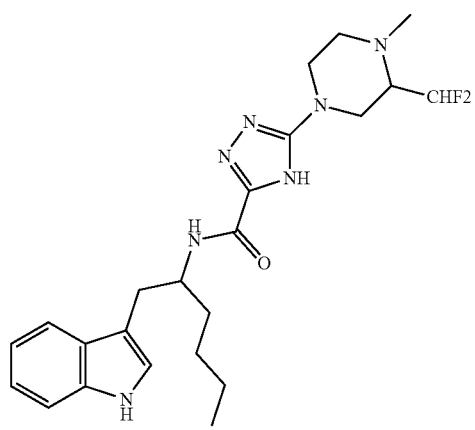
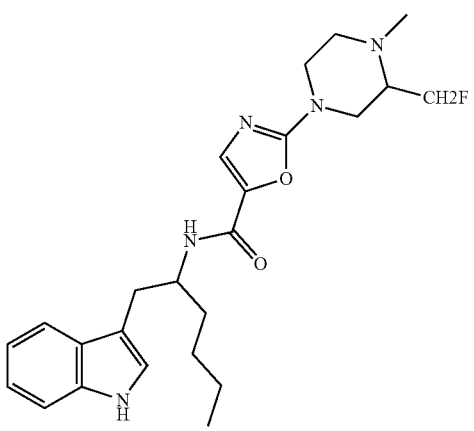
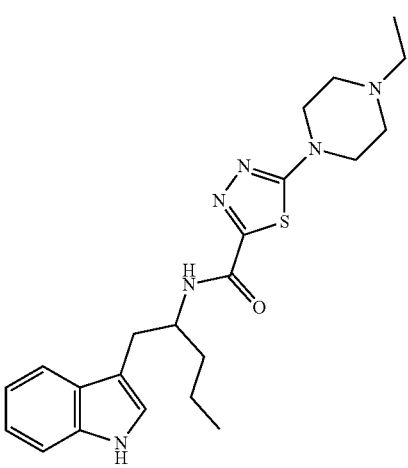
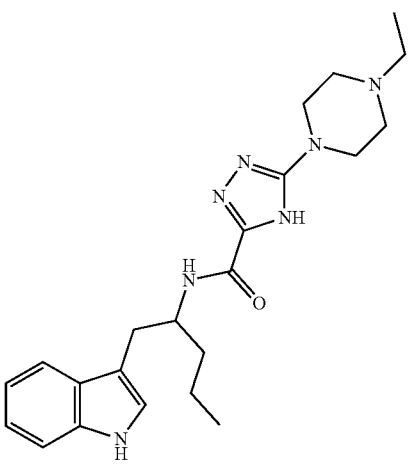

63
-continued
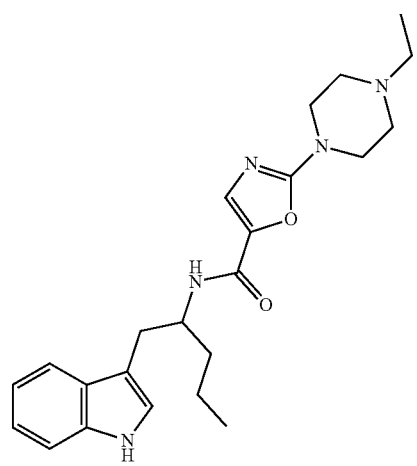
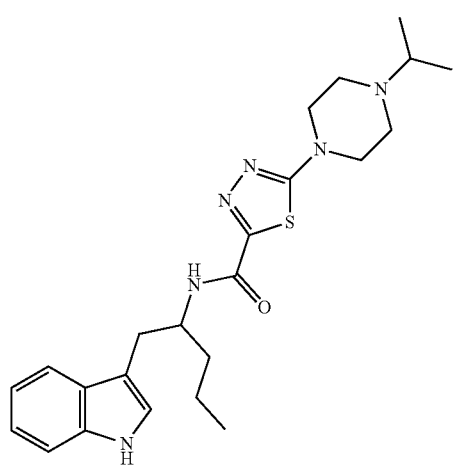
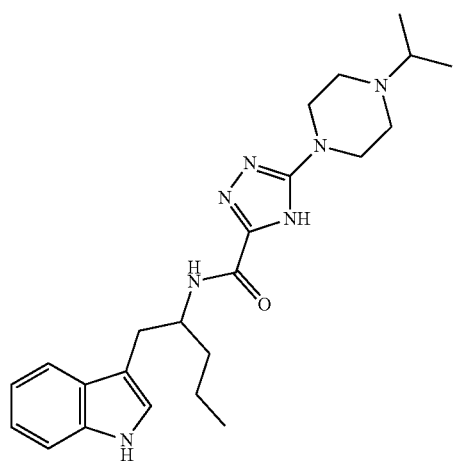
64
-continued
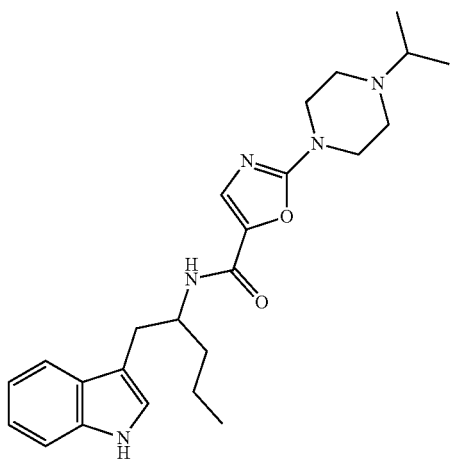
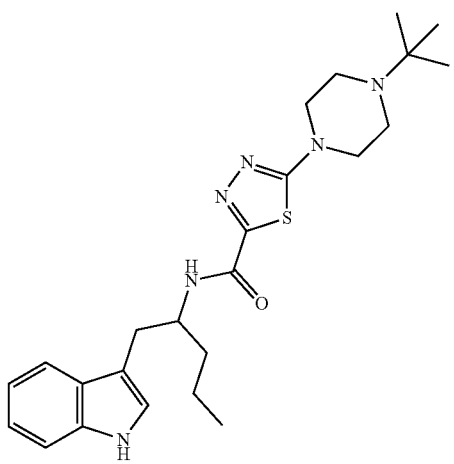
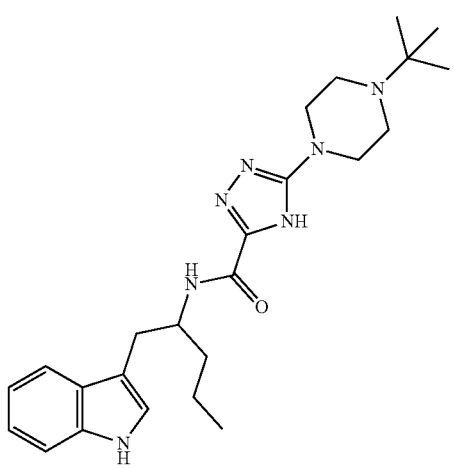

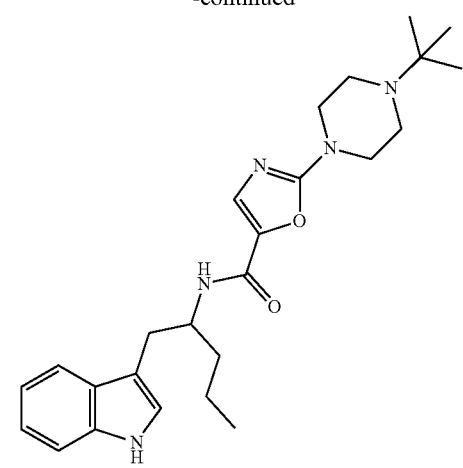
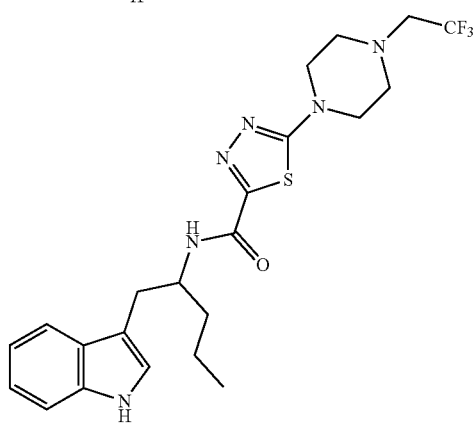
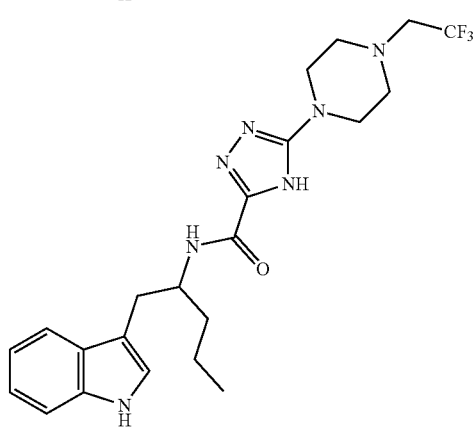

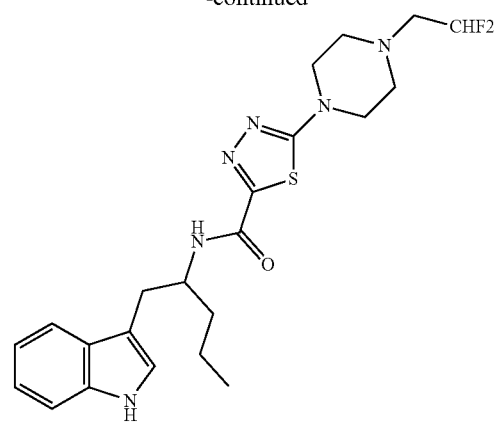
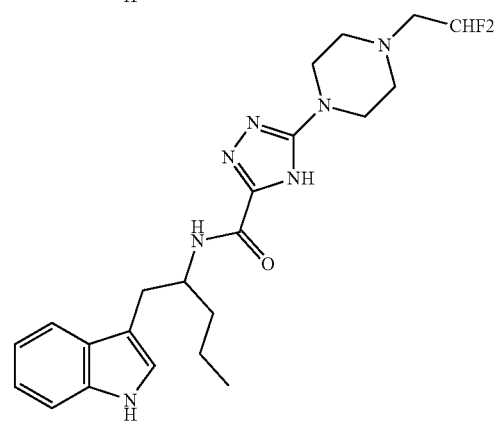
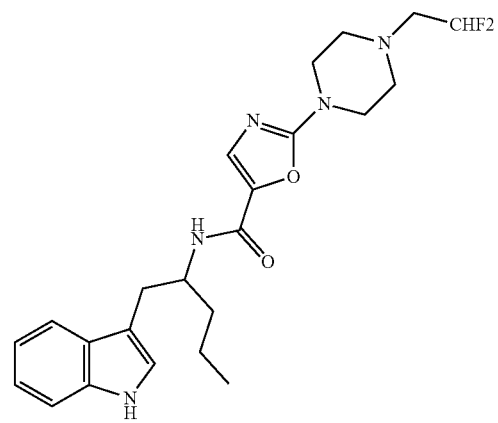
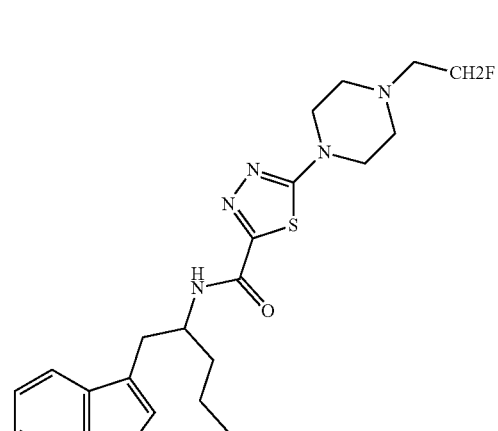

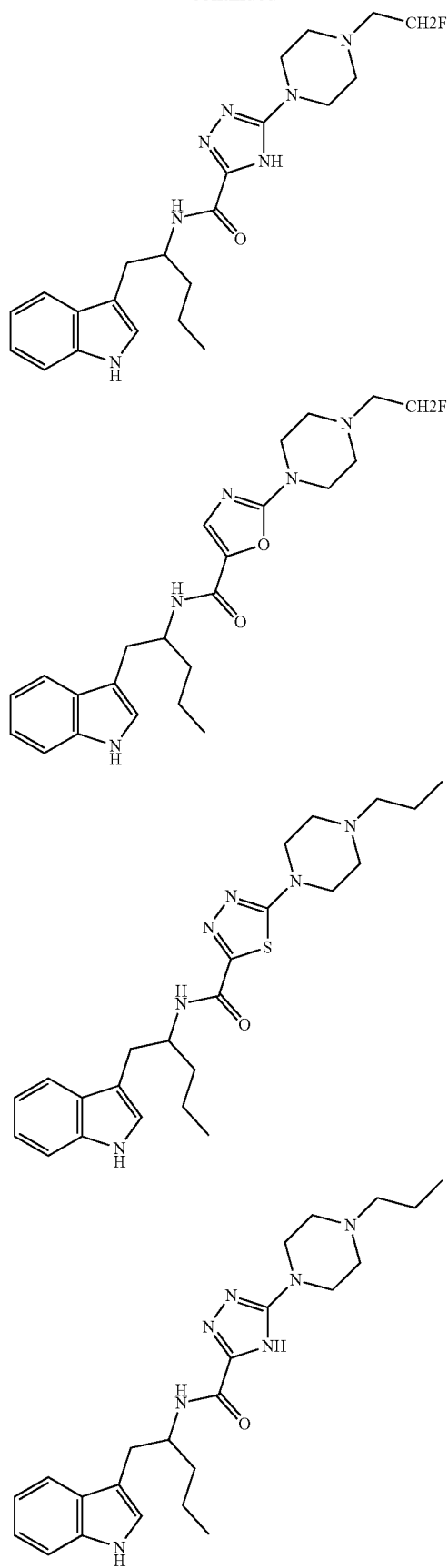
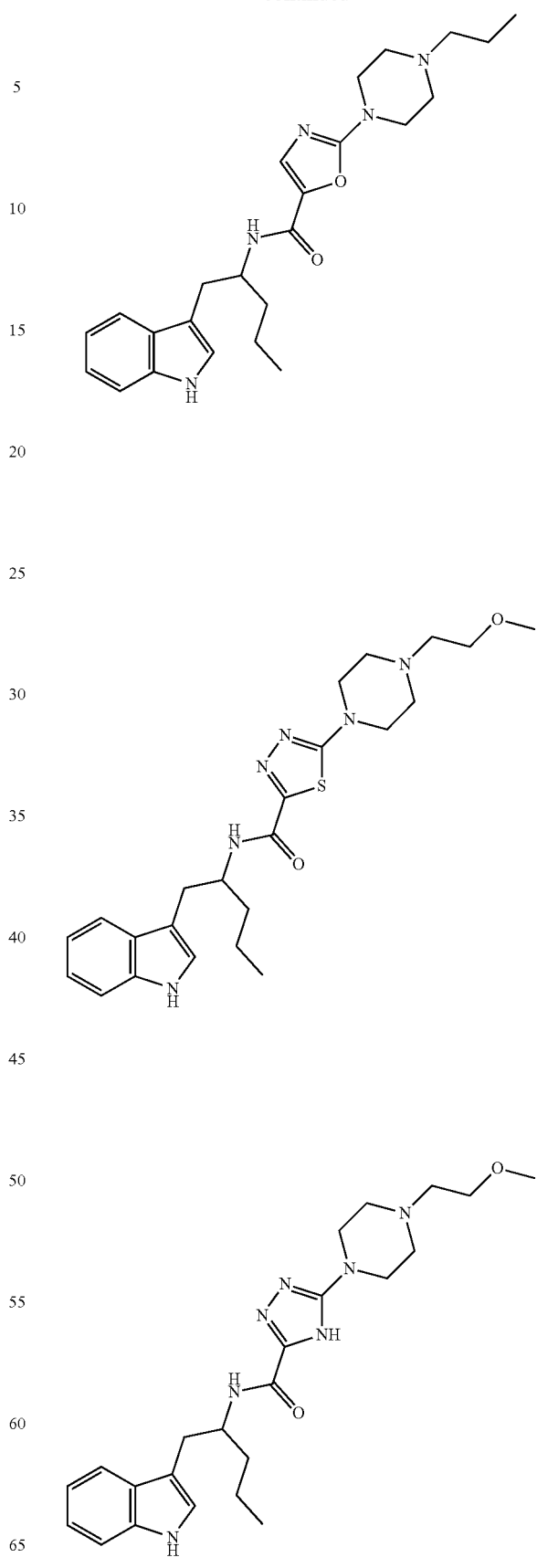

69 -continued
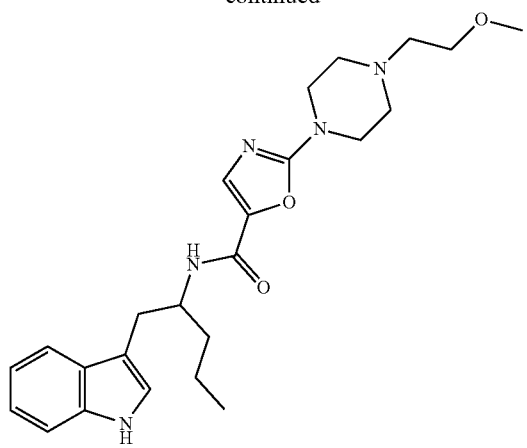
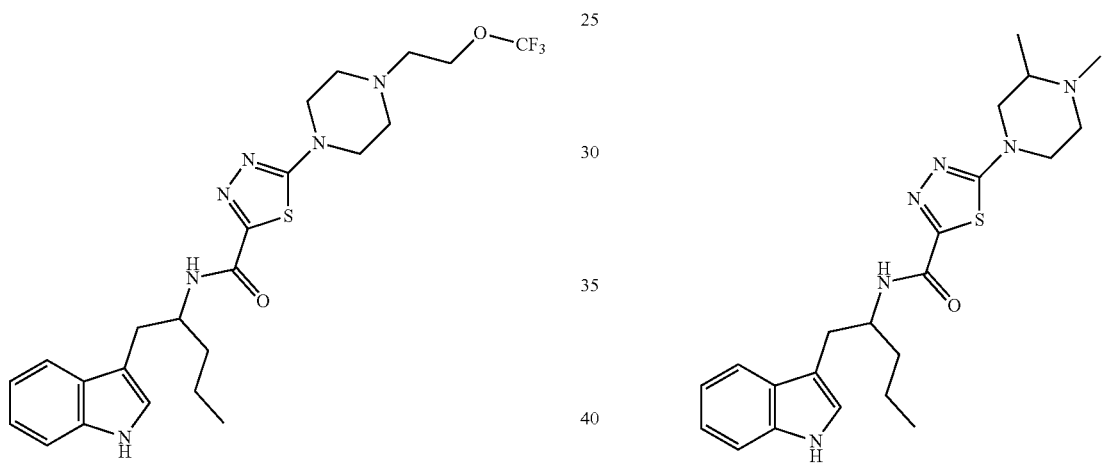
70 -continued
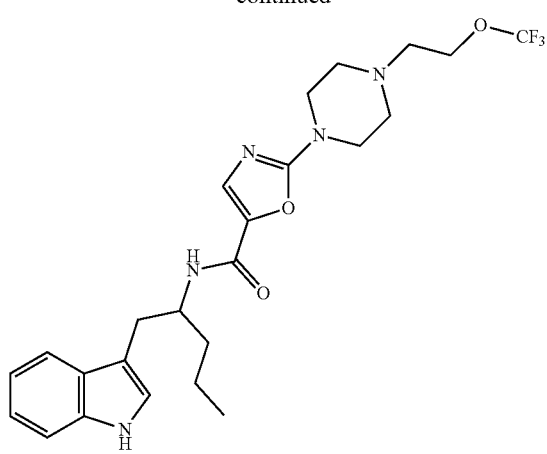
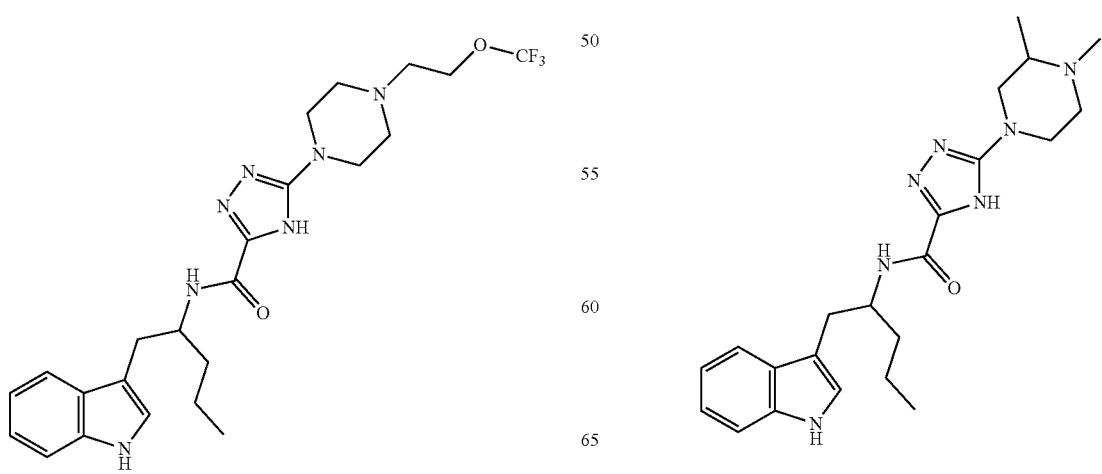

71
-continued
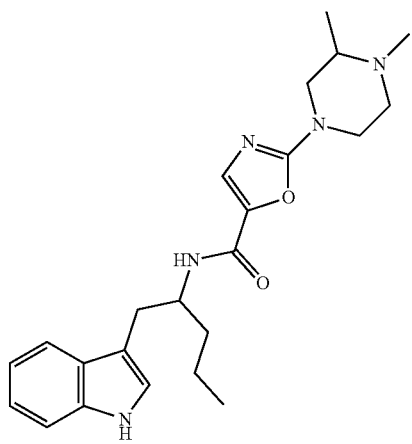
72
-continued
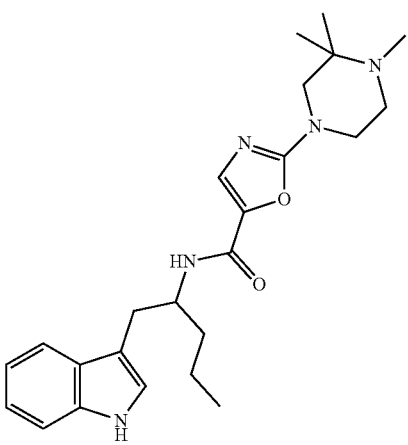

73
-continued
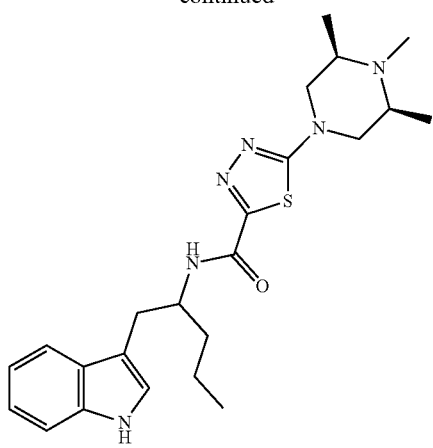
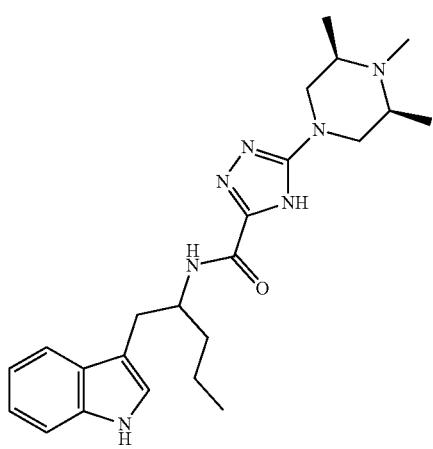
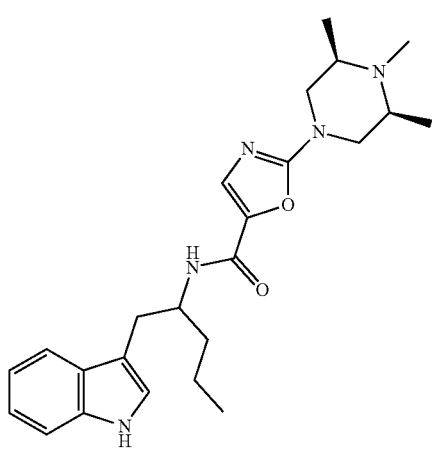
74
-continued
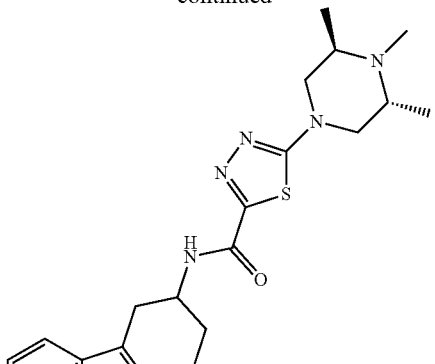
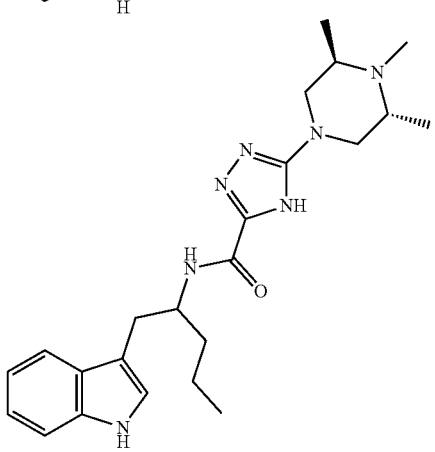
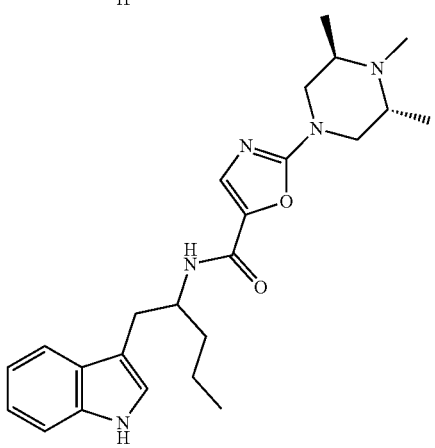
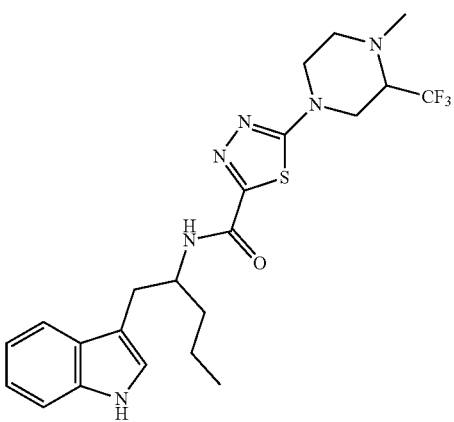

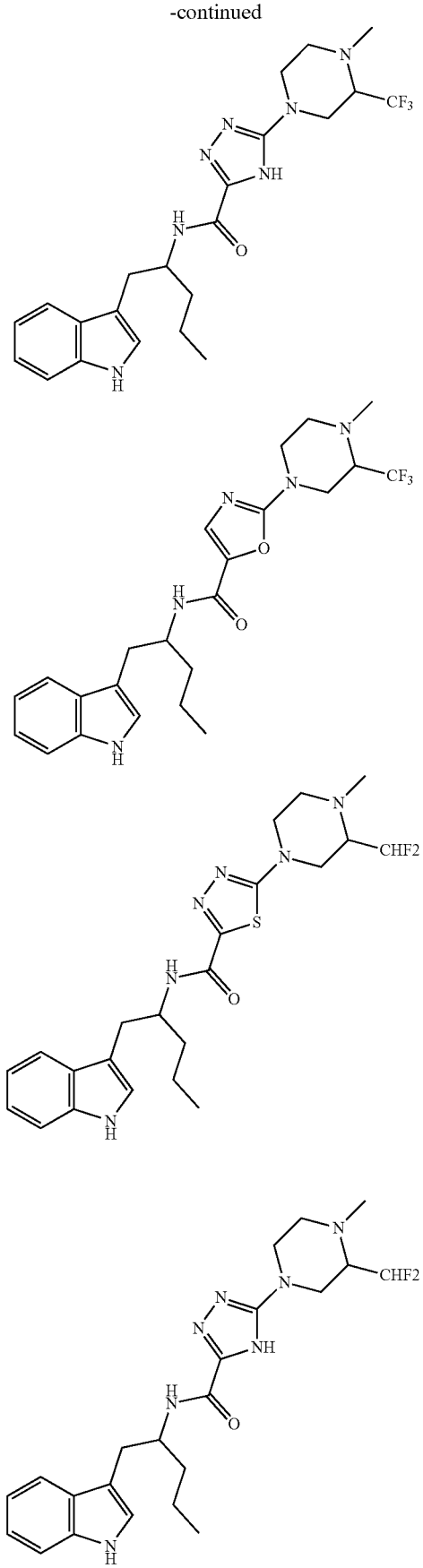
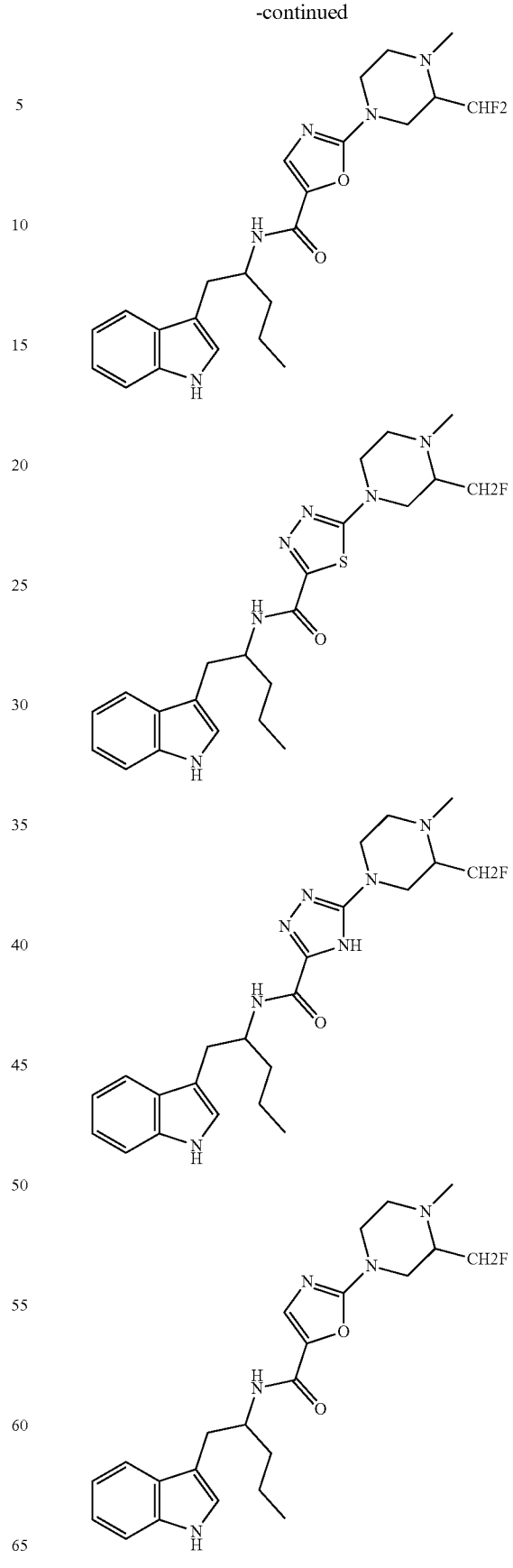

77
-continued
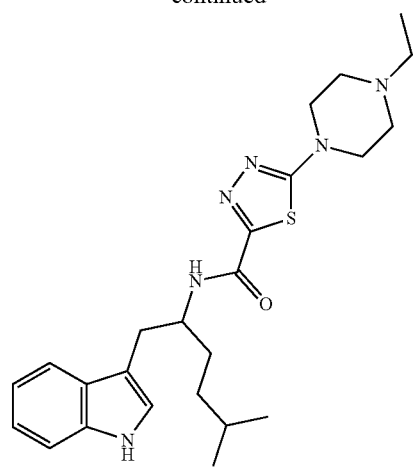
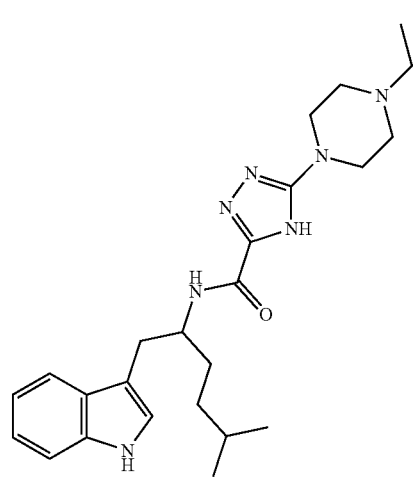
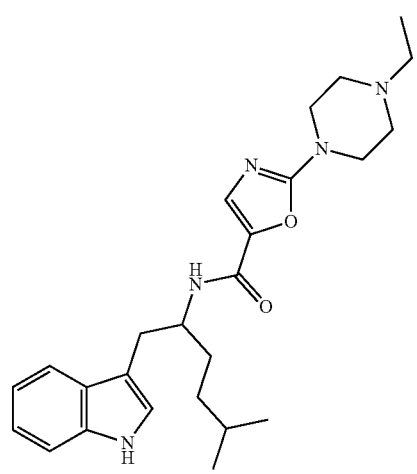
78
-continued
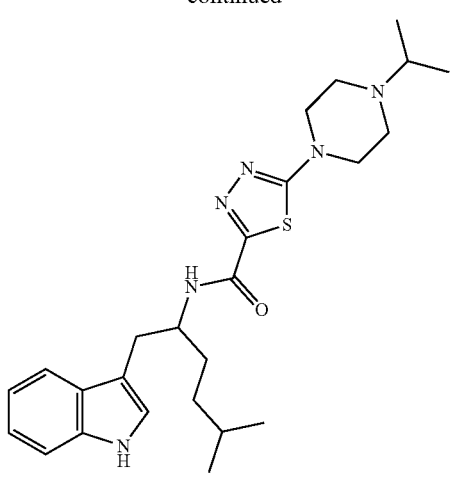
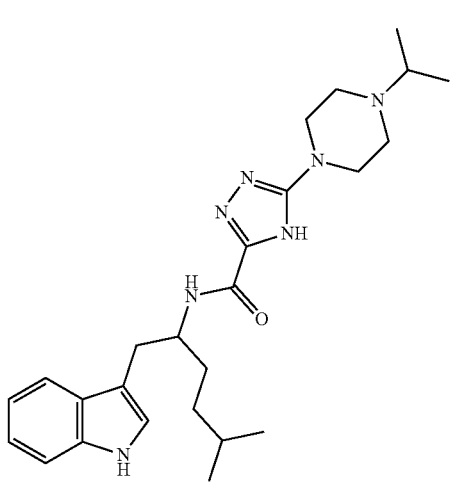
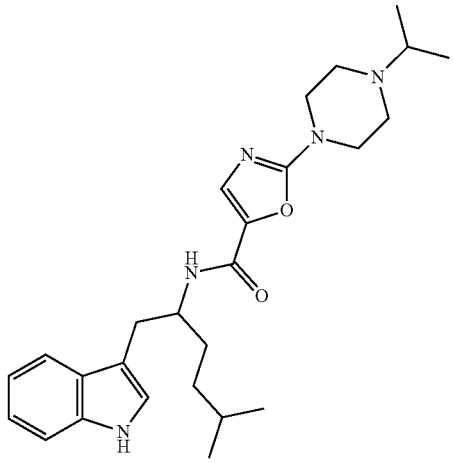

79
-continued
80
-continued
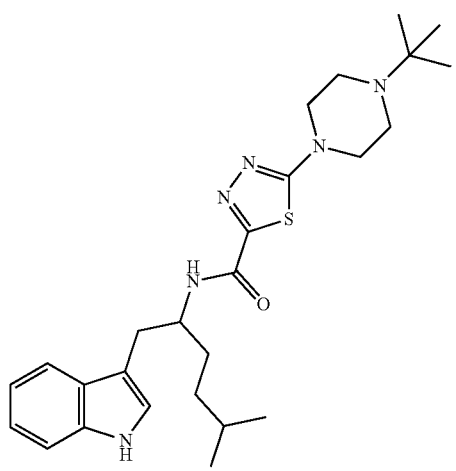
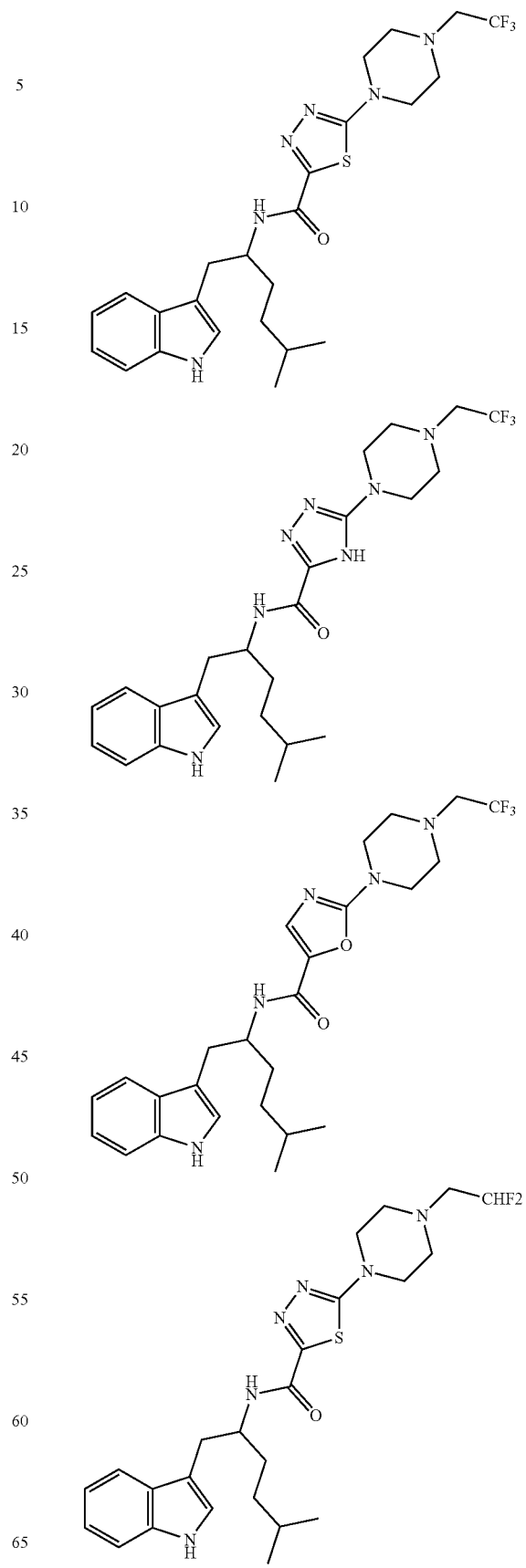

81
-continued
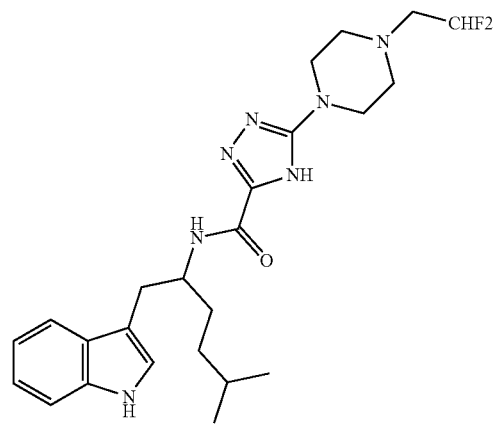
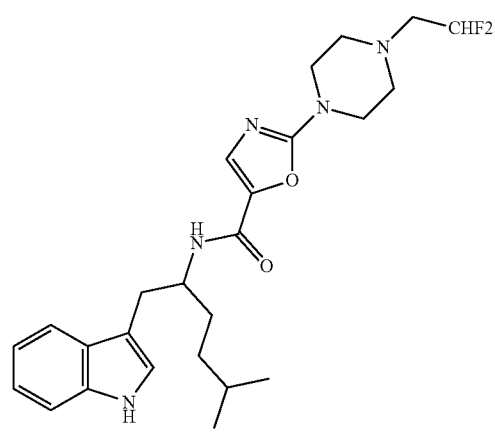
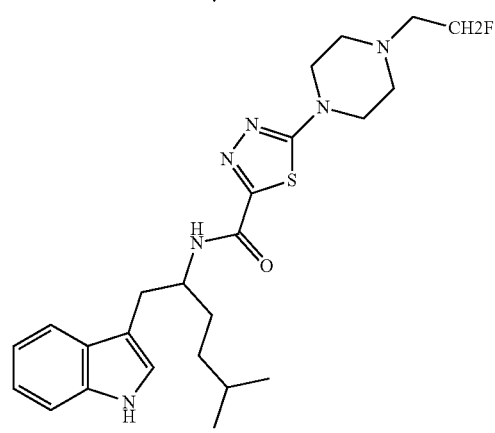
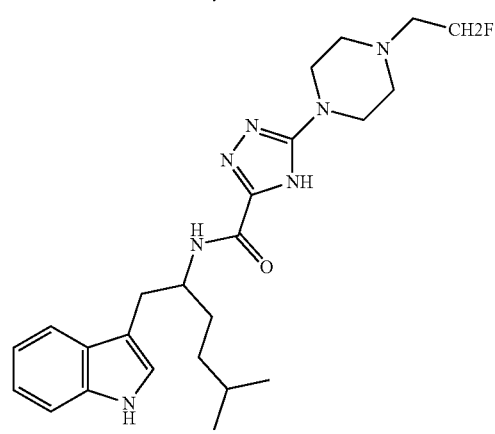
82
-continued
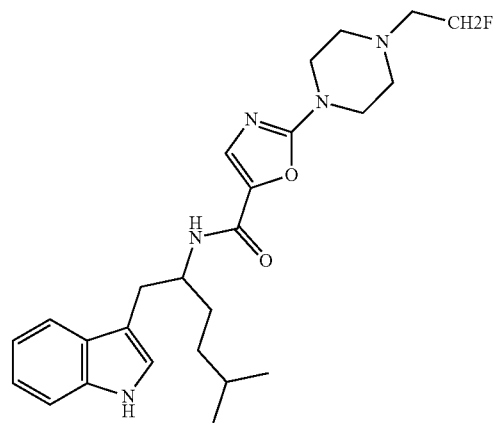
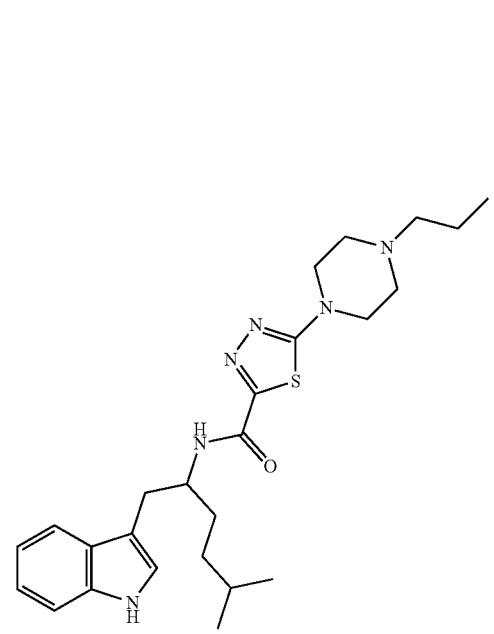
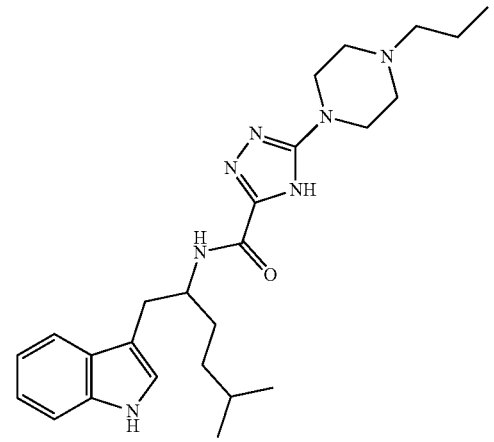

83
-continued
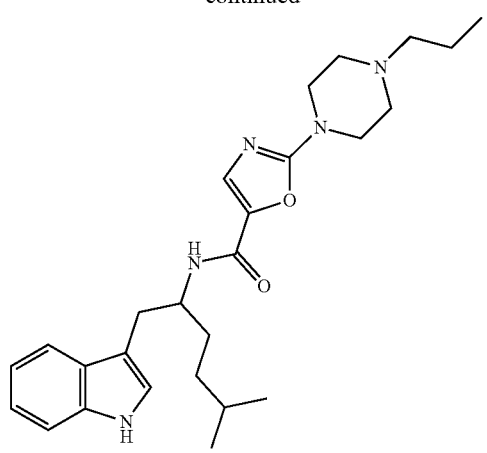
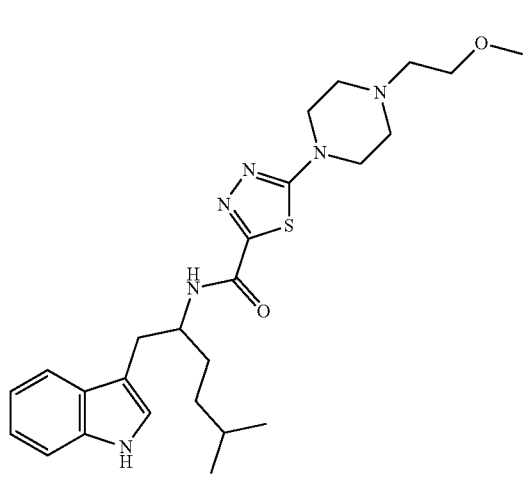
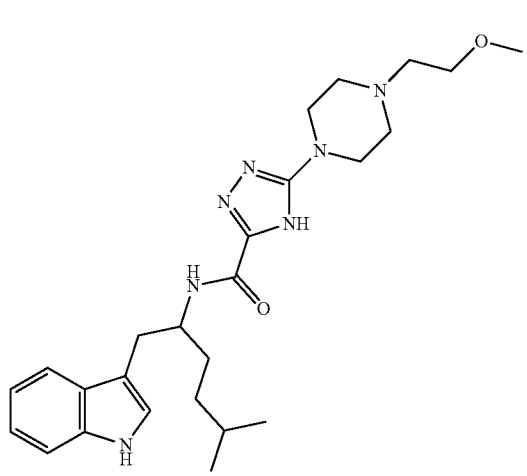
84
-continued
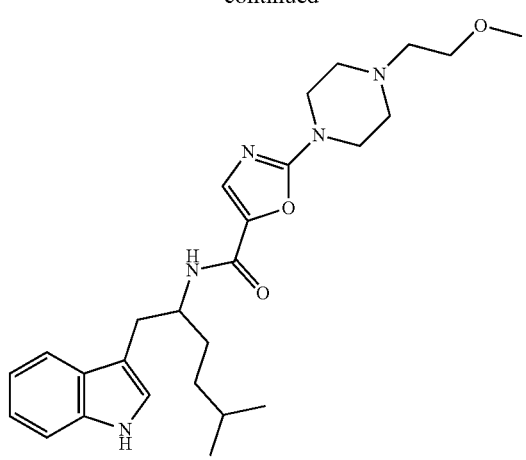
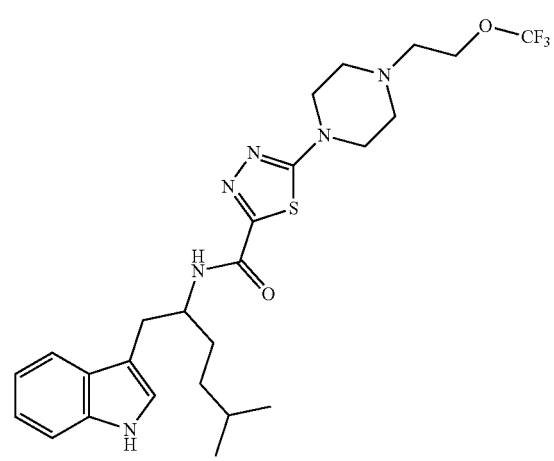
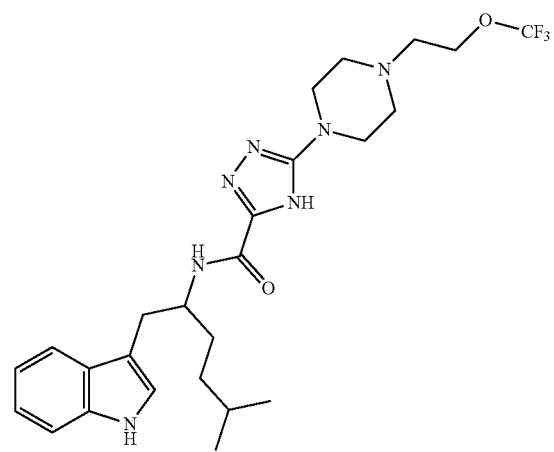

85
-continued
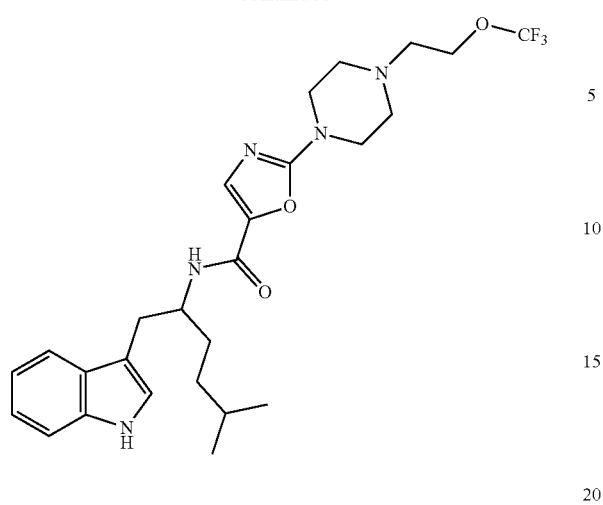
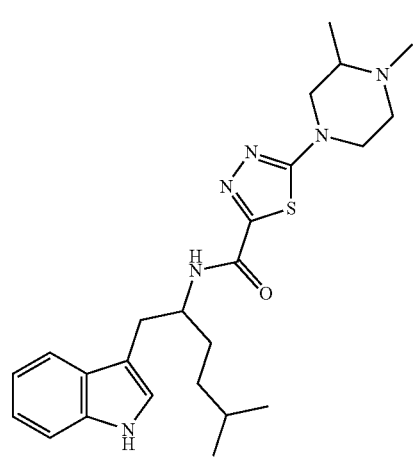
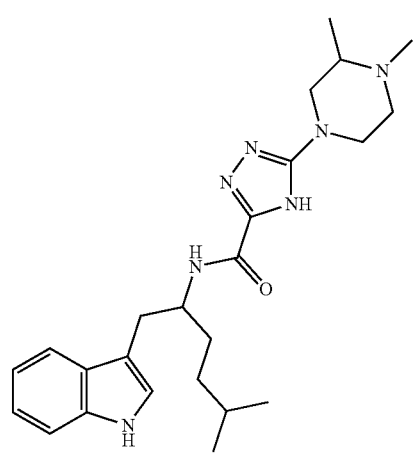
86
-continued
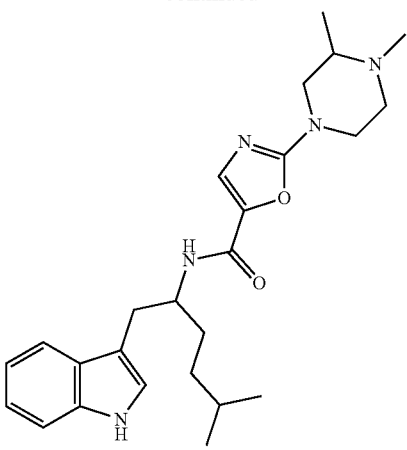
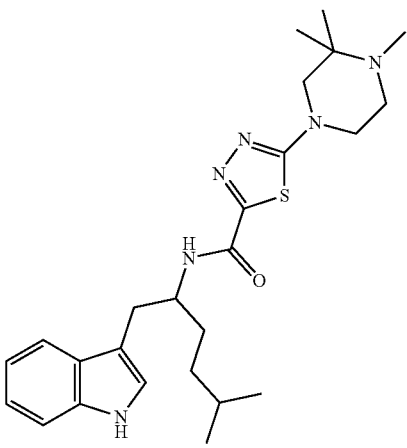
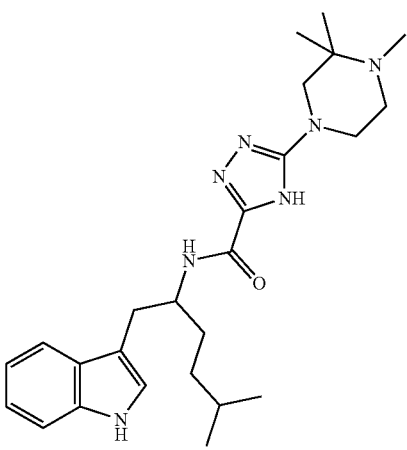

87
-continued
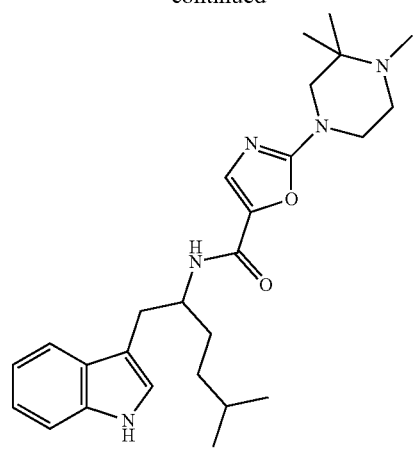
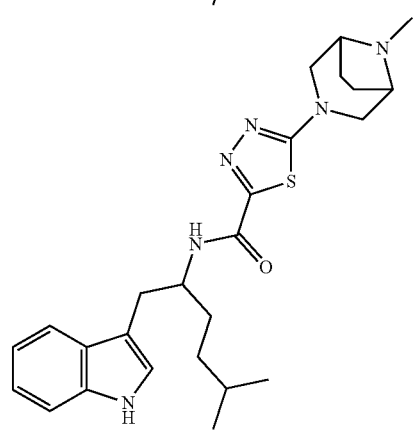
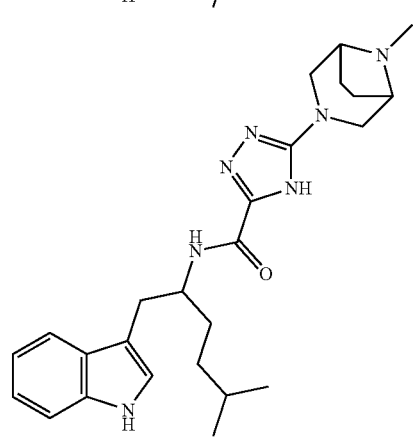
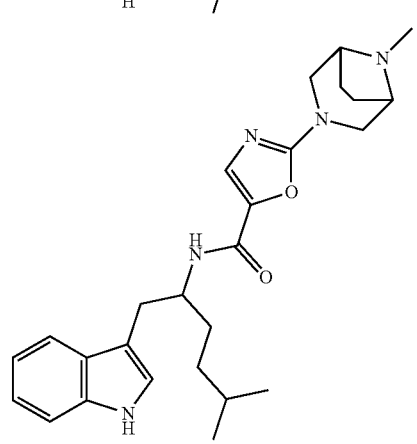
88
-continued
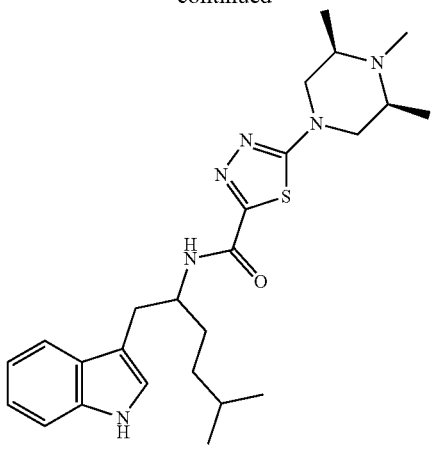
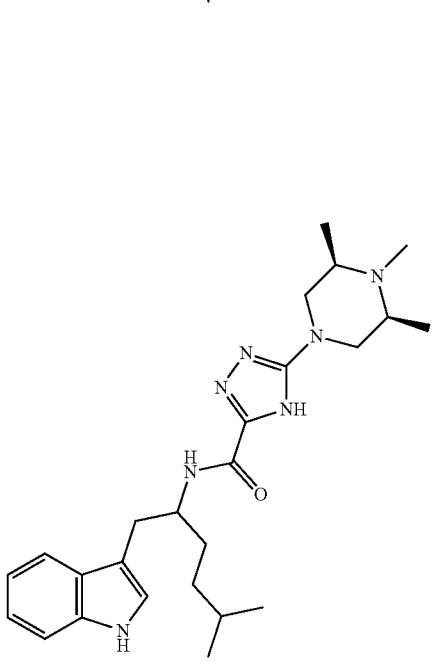
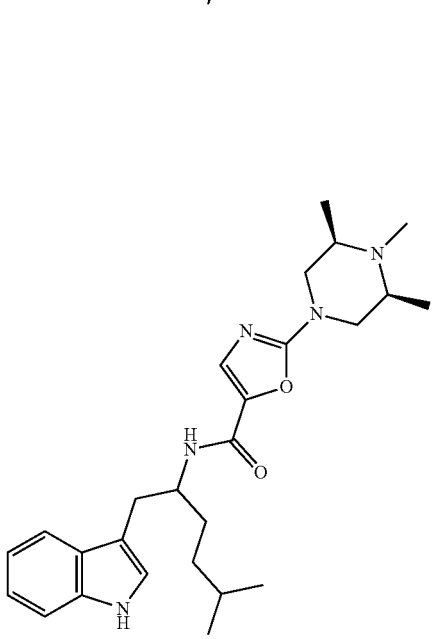

-continued
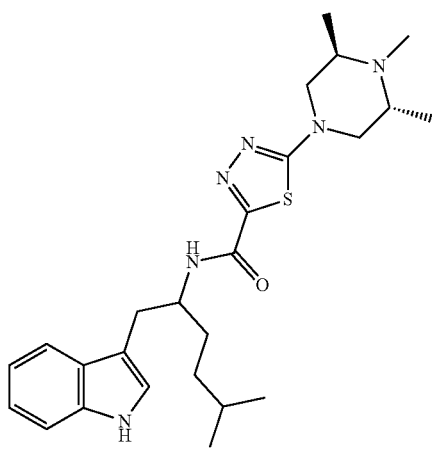
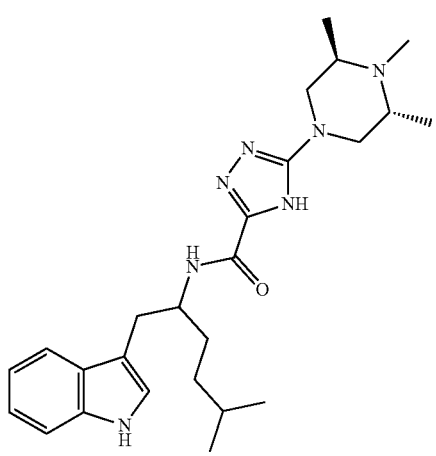
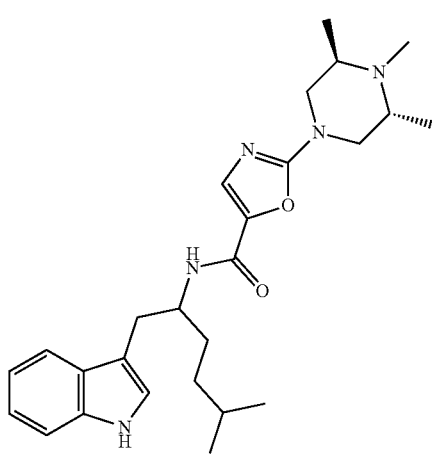
-continued
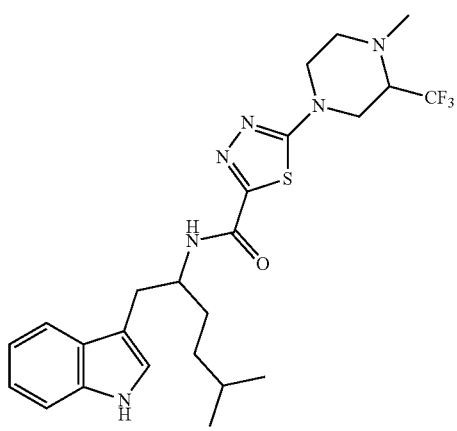
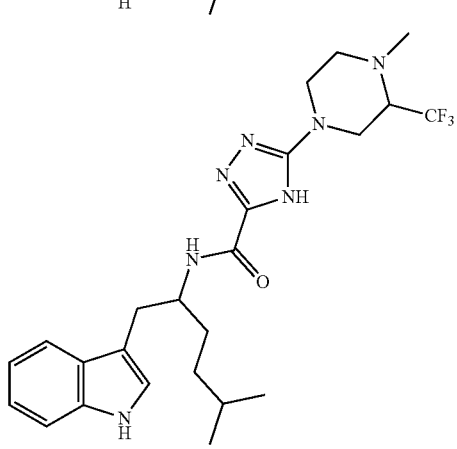
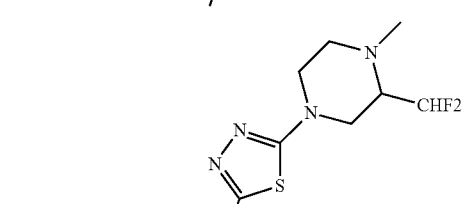
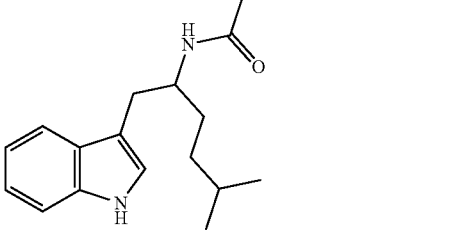

-continued
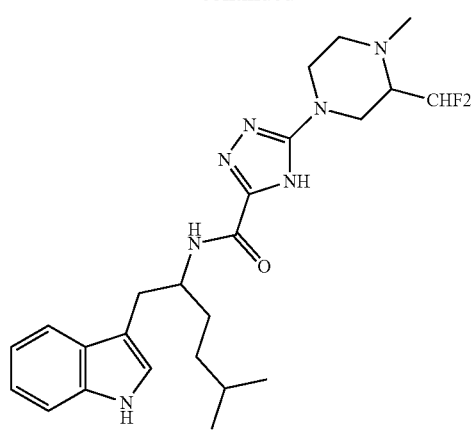
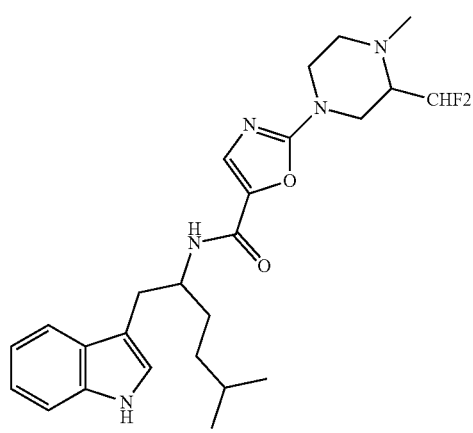
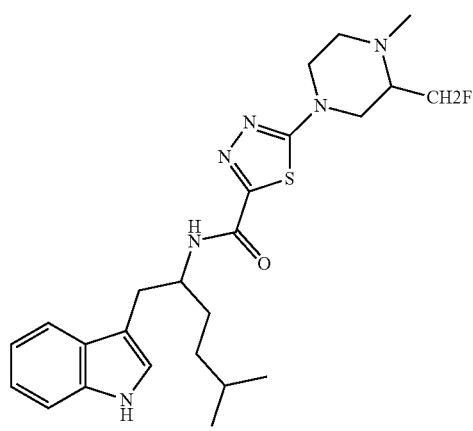
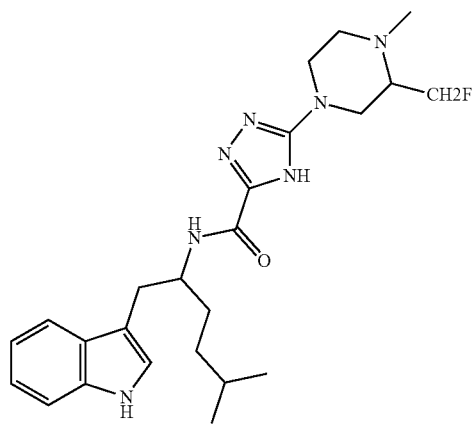
-continued
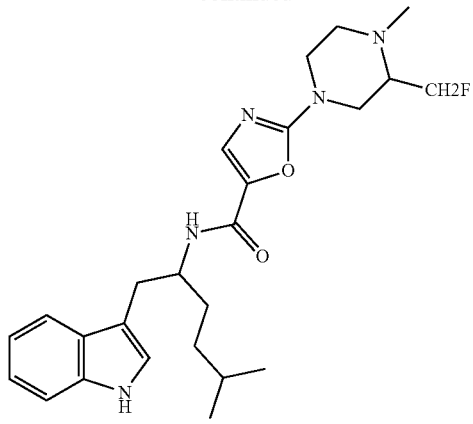
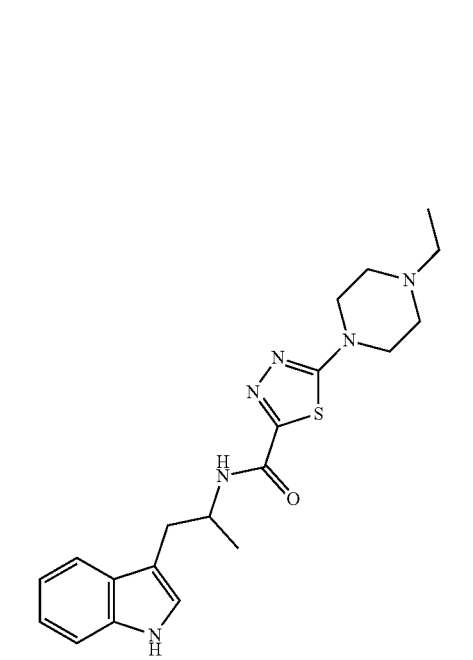
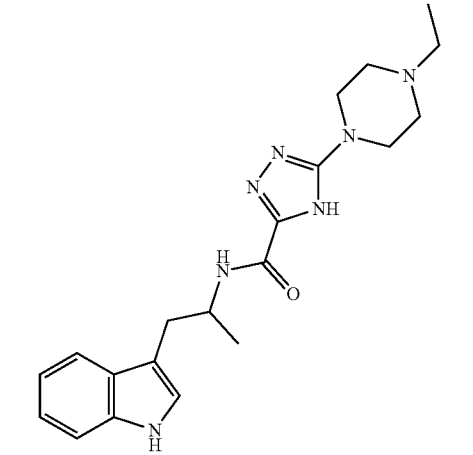

93
-continued
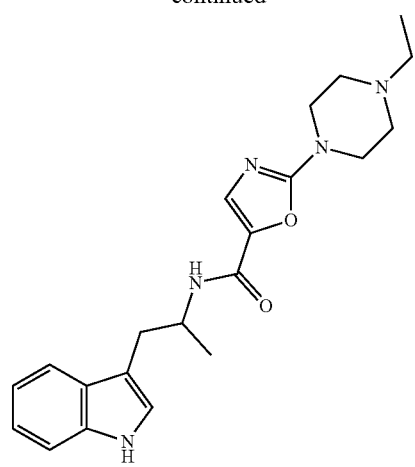
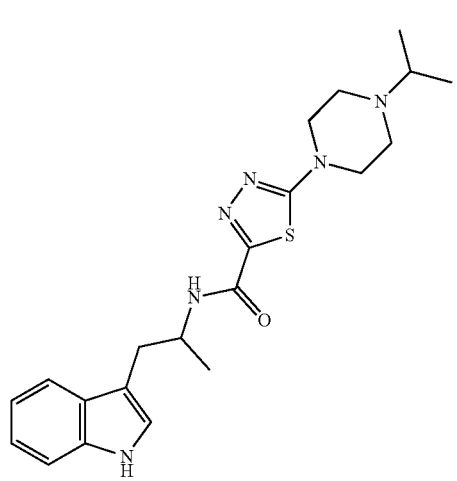
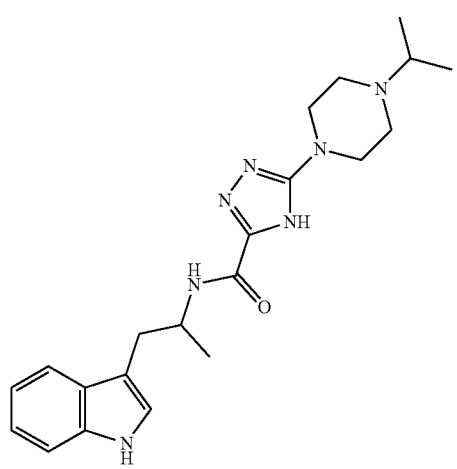
94
-continued
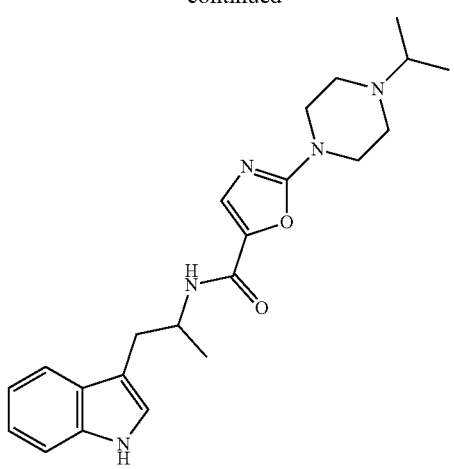
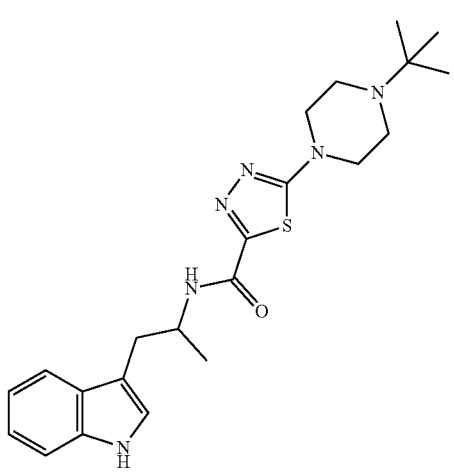
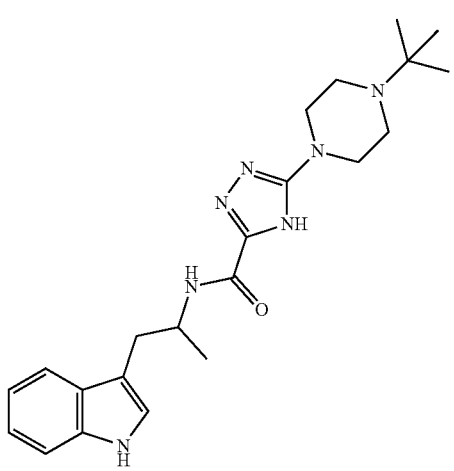

95
-continued
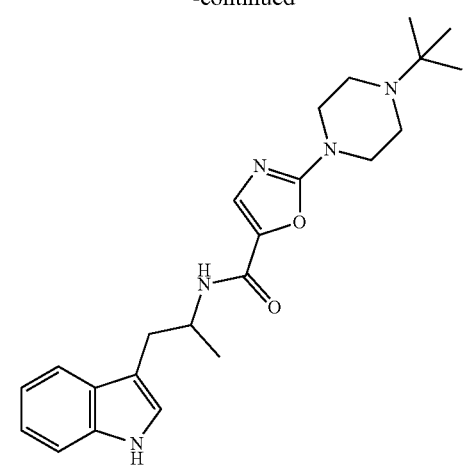
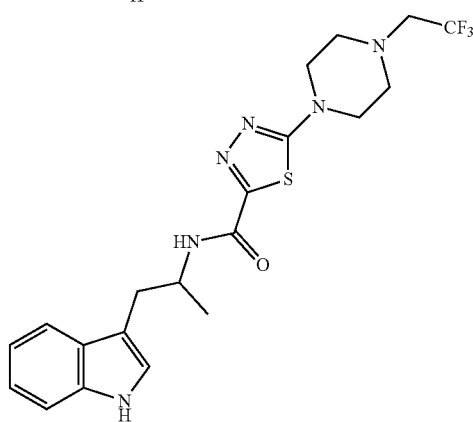
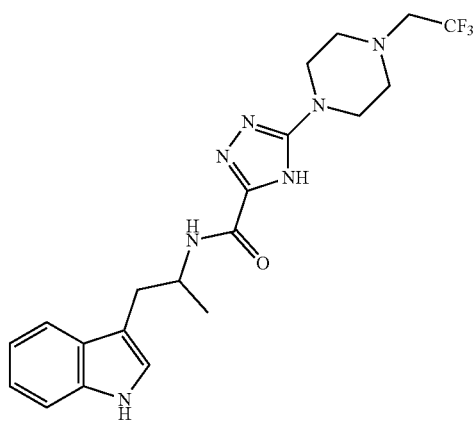
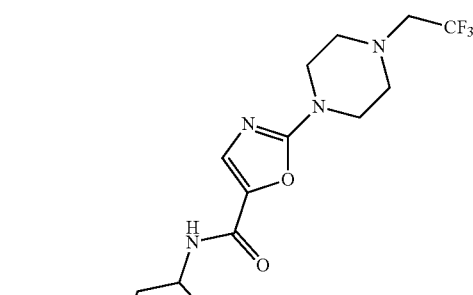
96
-continued
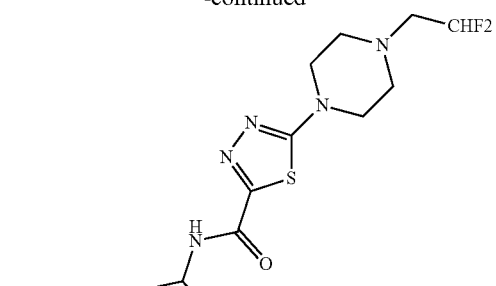
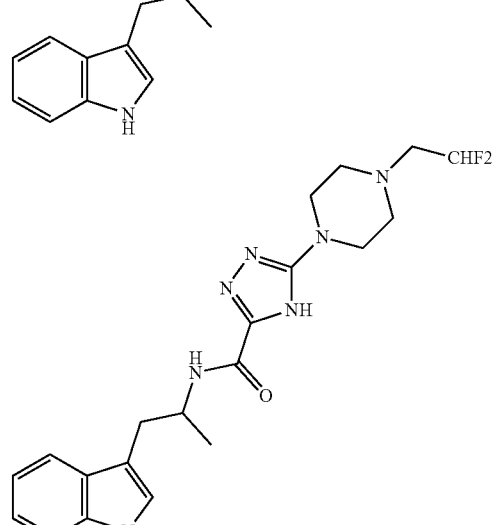
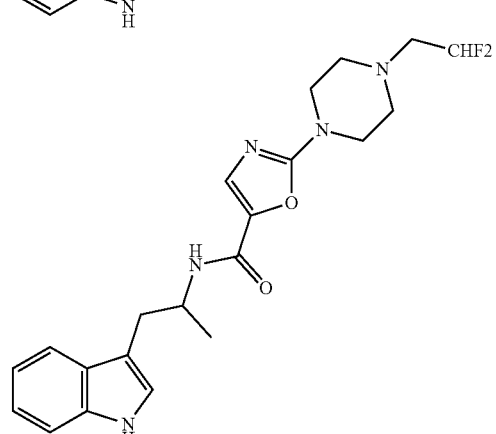
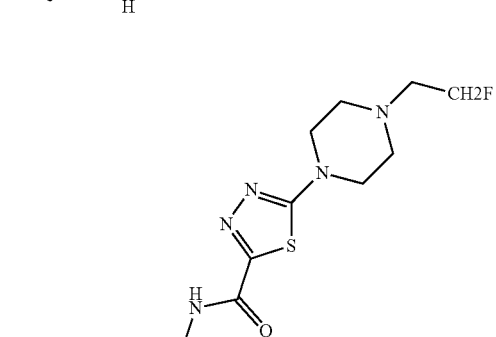

97
-continued
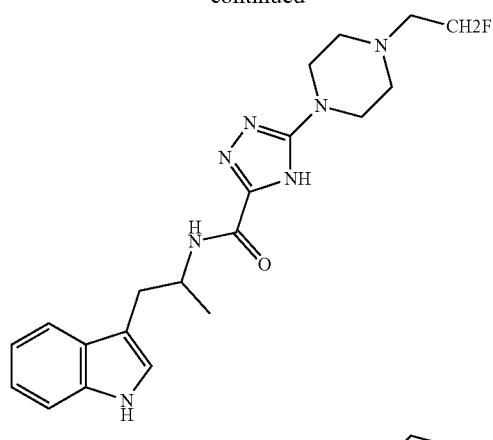
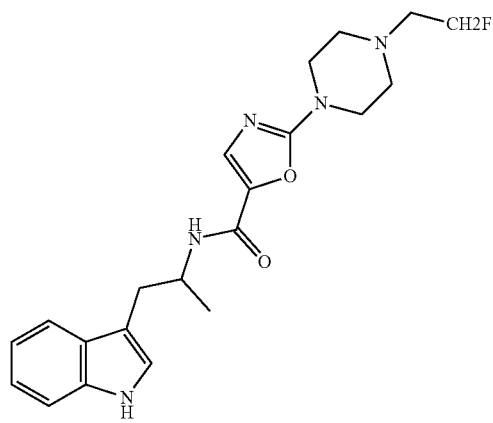
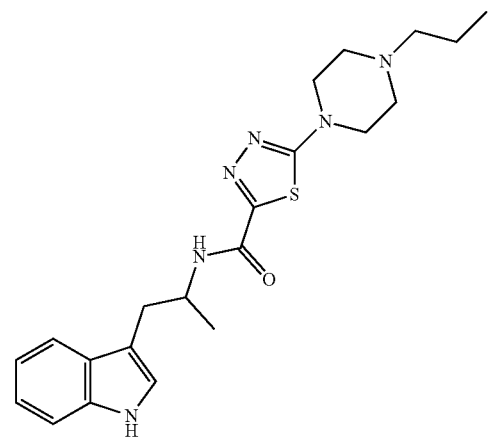
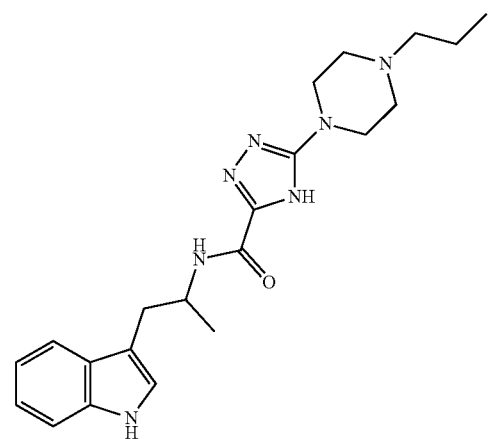
98
-continued
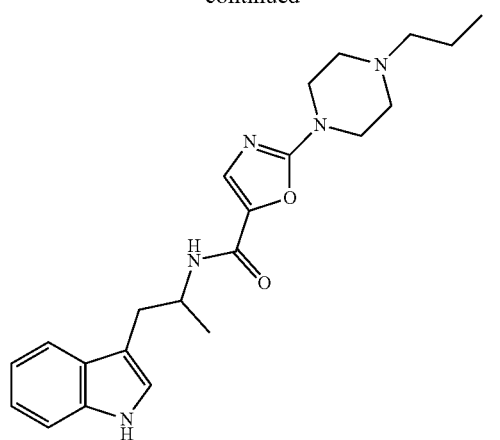
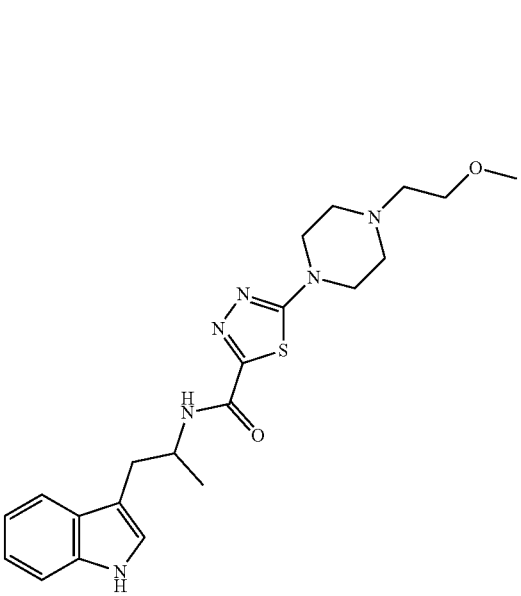
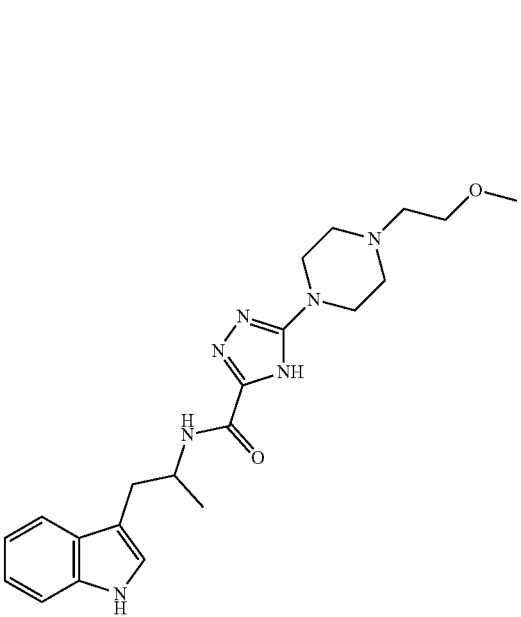

99
-continued
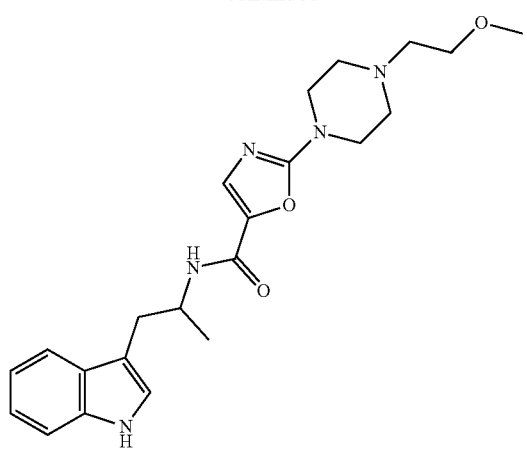
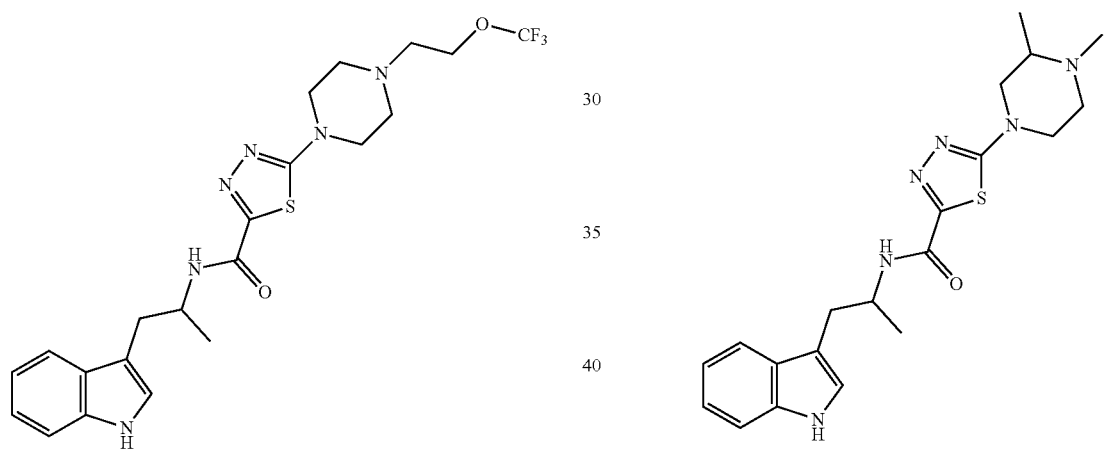
100
-continued
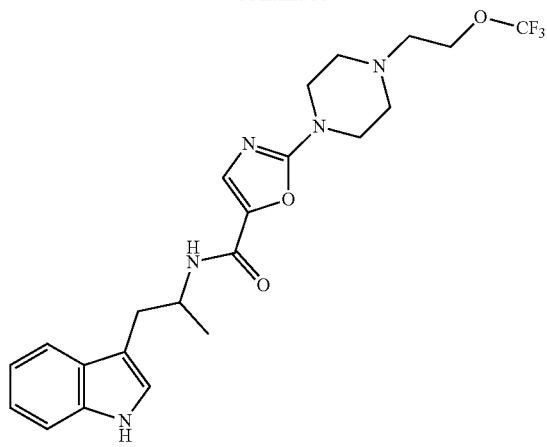
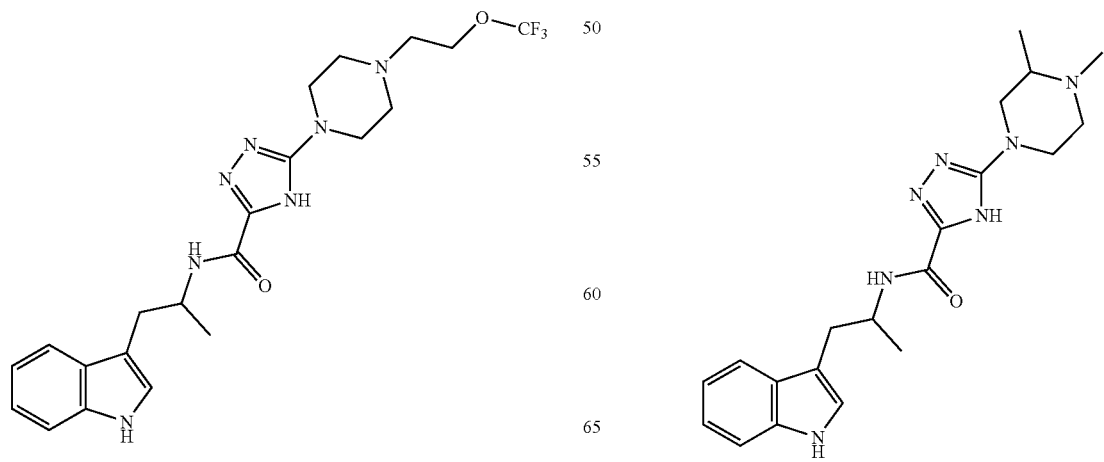

101
-continued
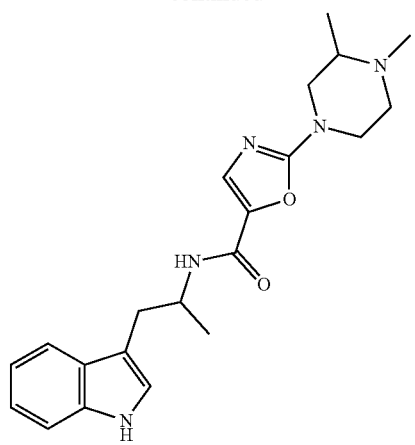
102
-continued
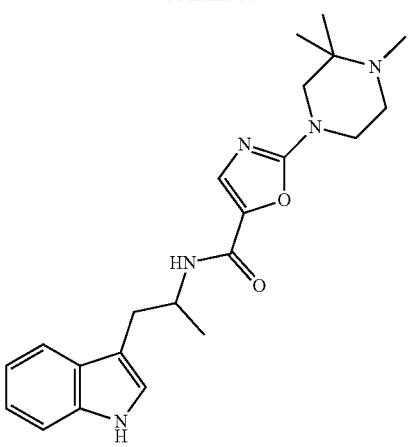
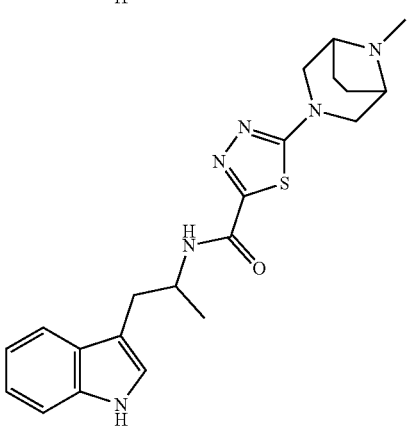
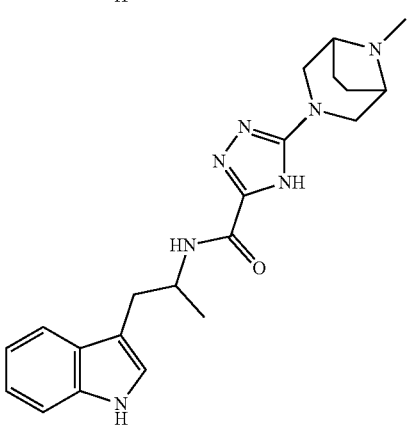
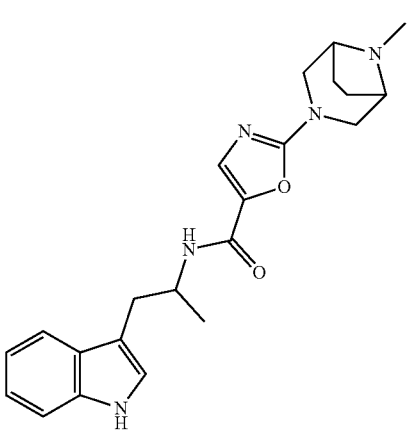

103
-continued
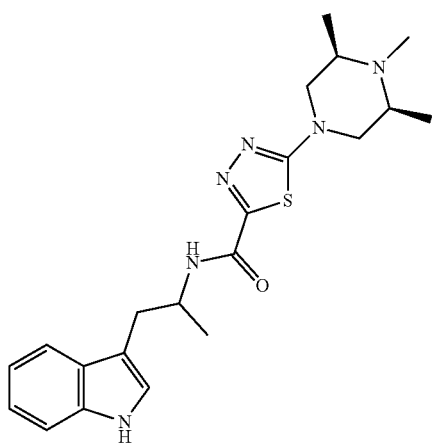
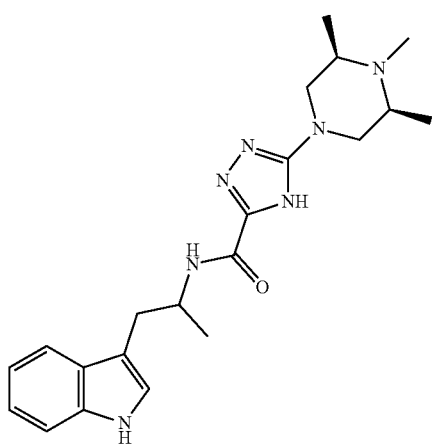
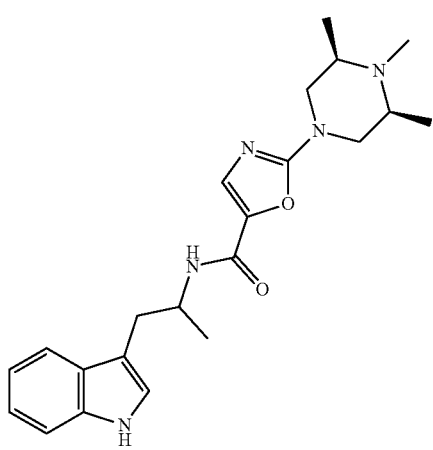
104
-continued
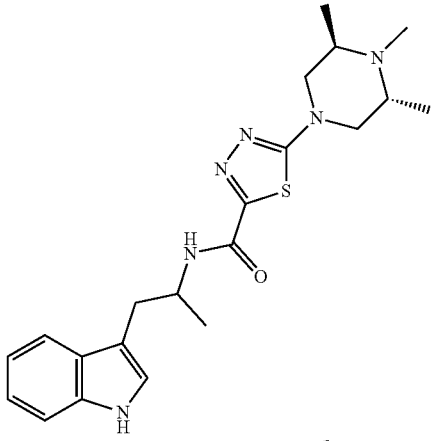
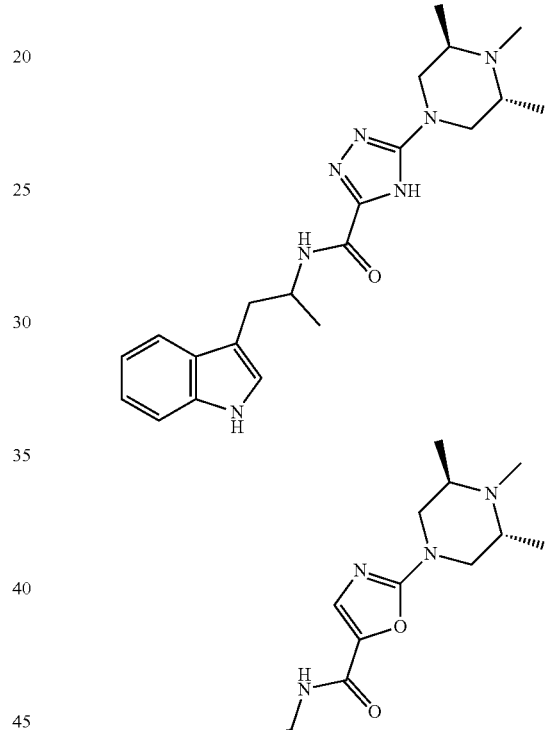
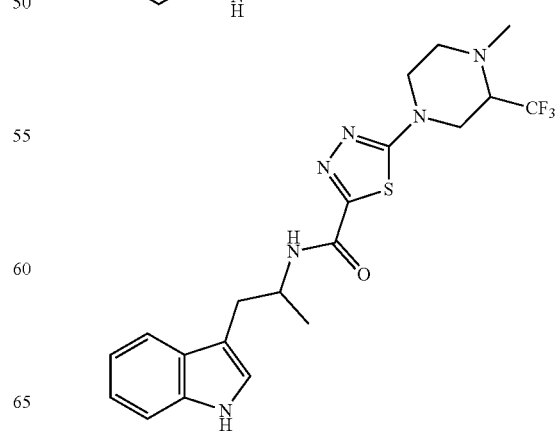

105
-continued
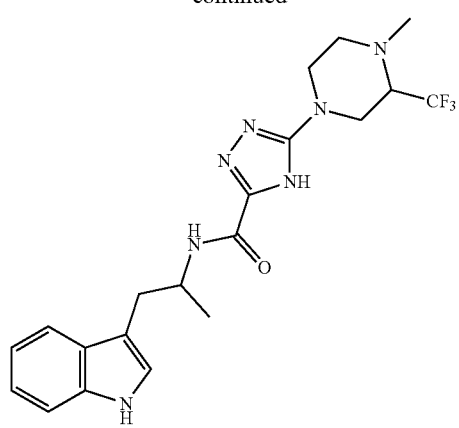
106
-continued
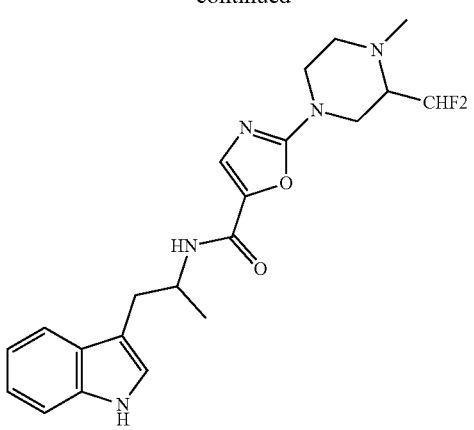

107
-continued
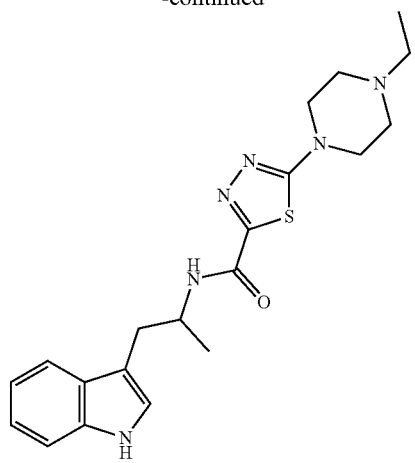
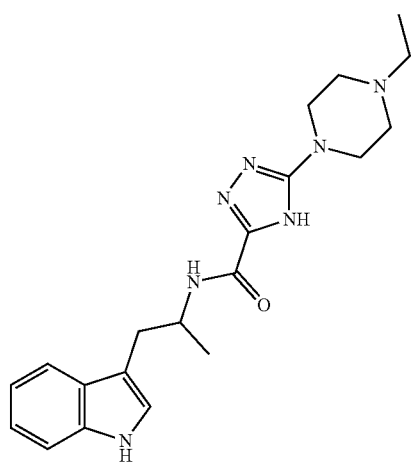
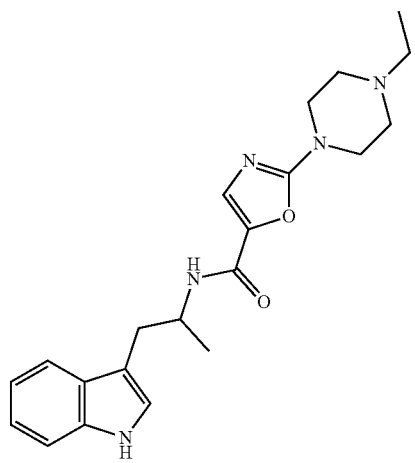
108
-continued
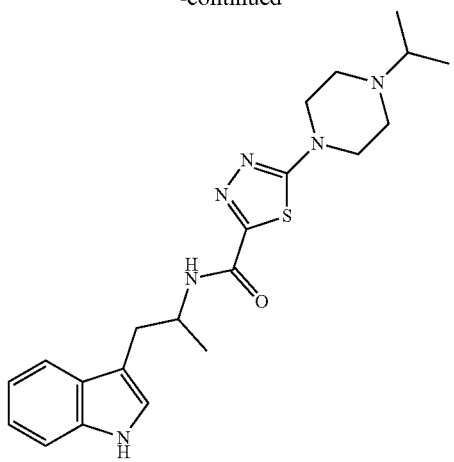
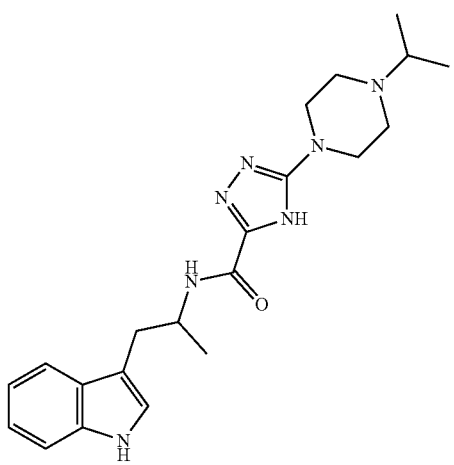
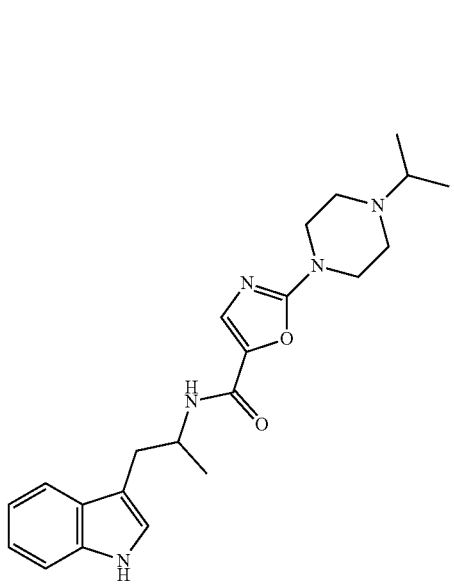

109
-continued
110
-continued
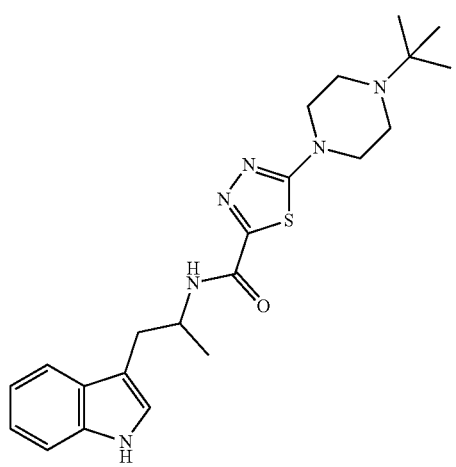
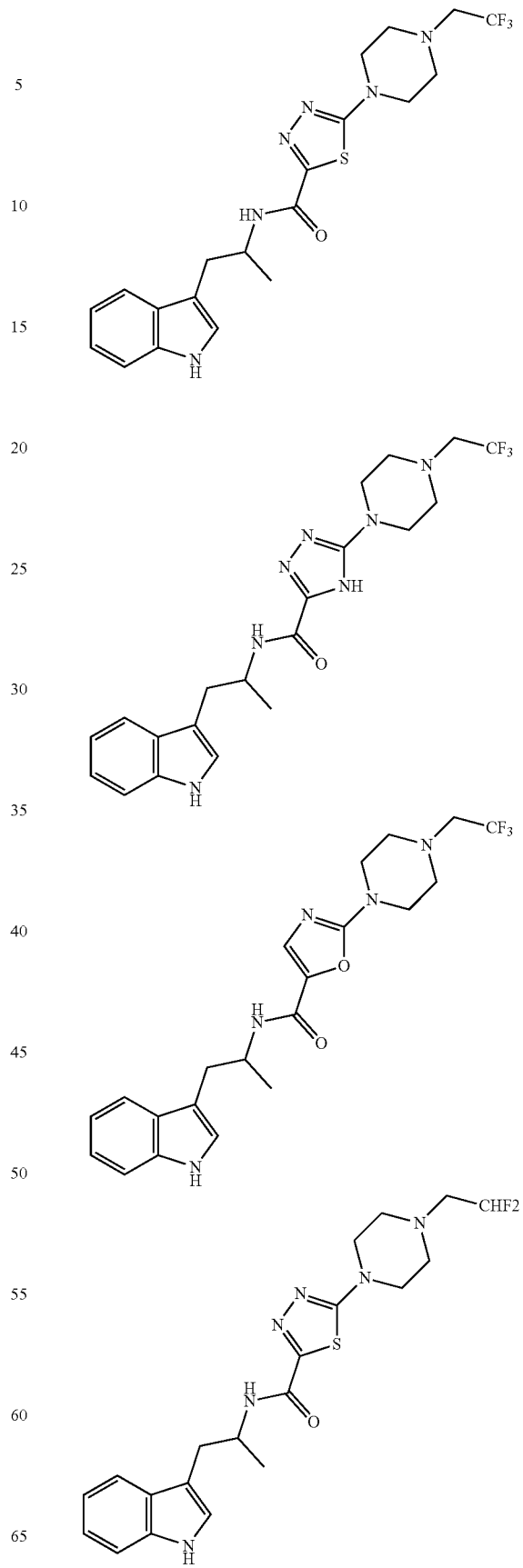

111
-continued
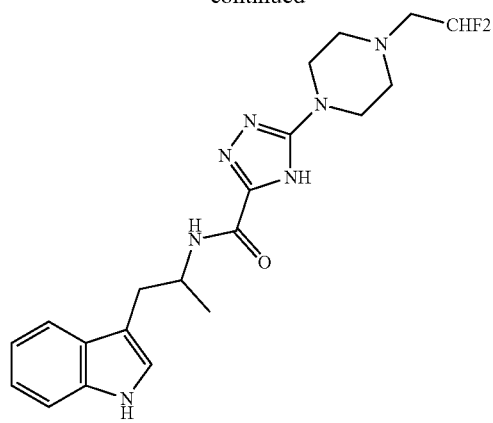
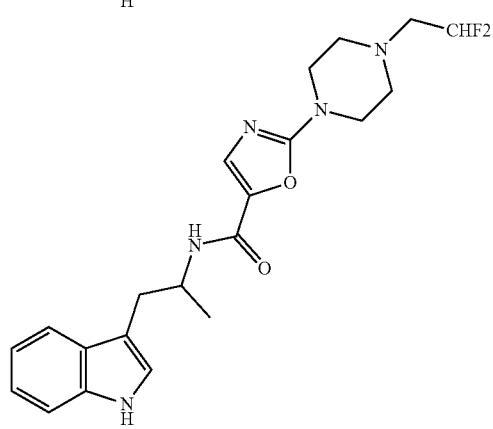
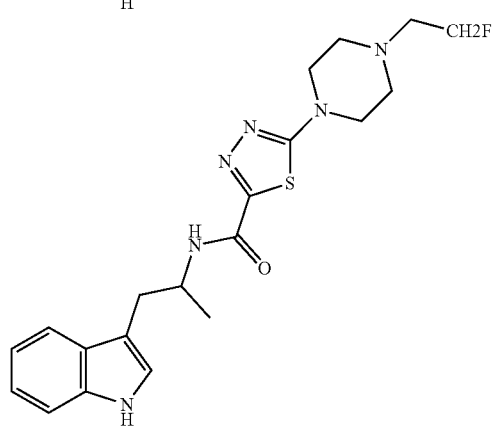
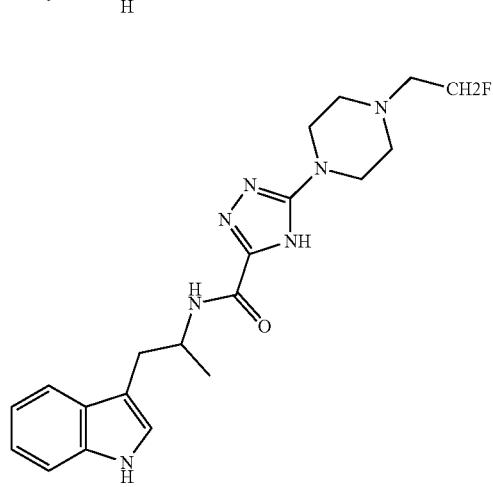
112
-continued
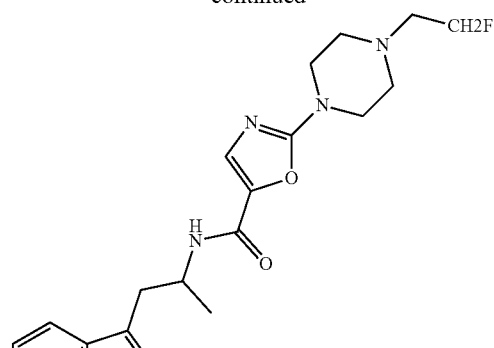
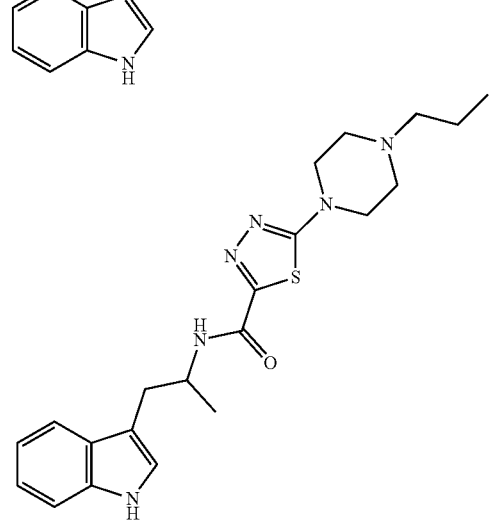
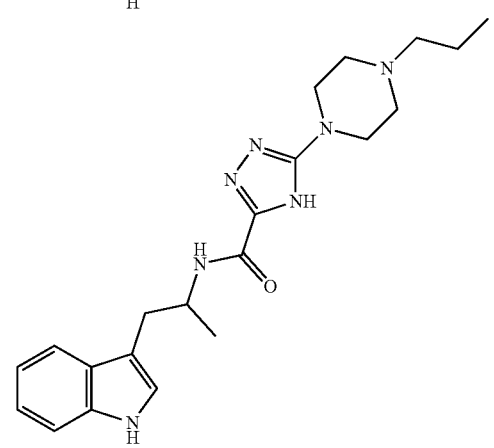
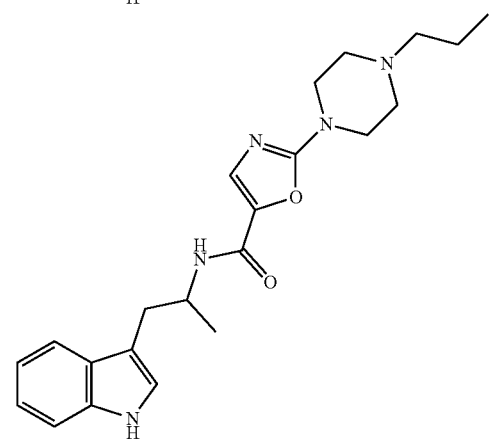

113
-continued
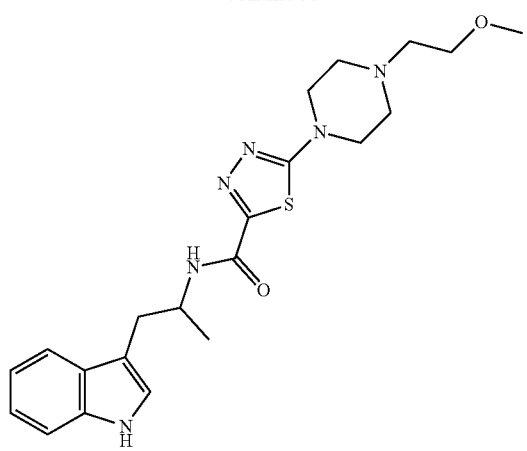
114
-continued
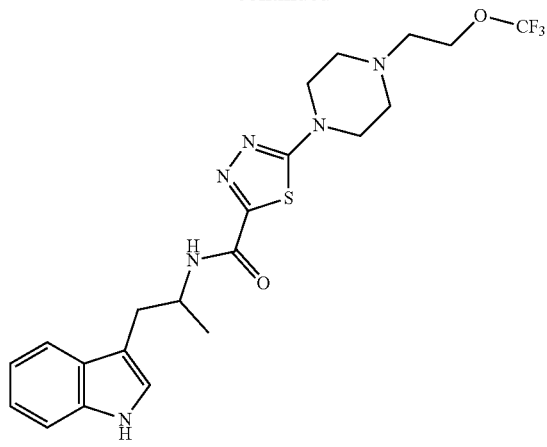

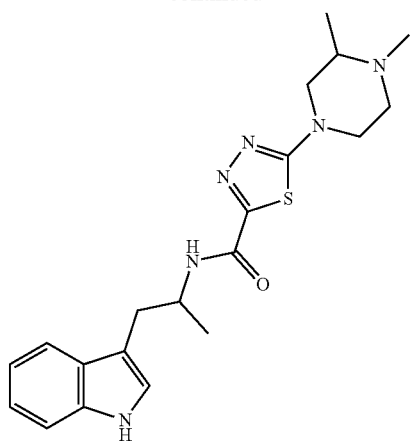
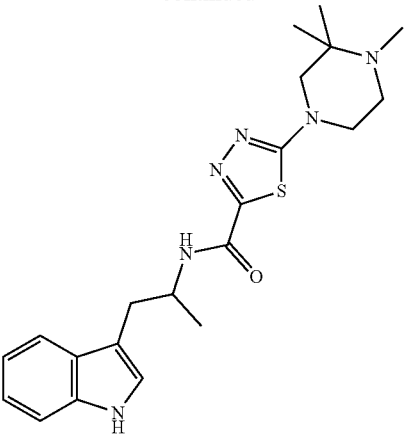

117
-continued
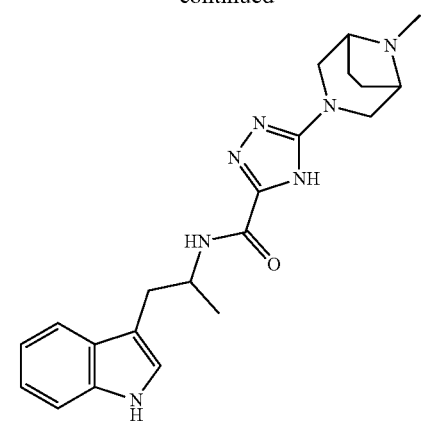
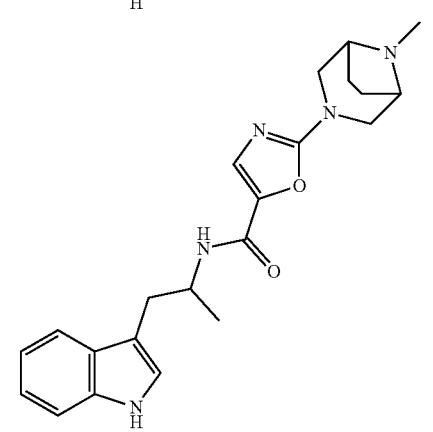
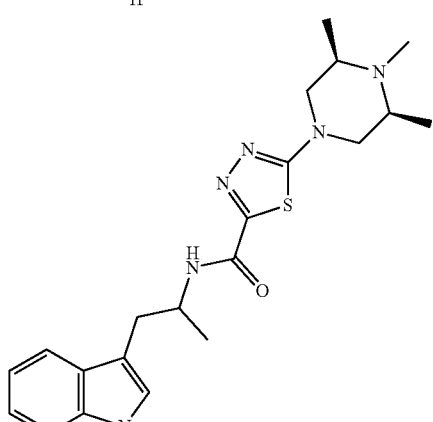
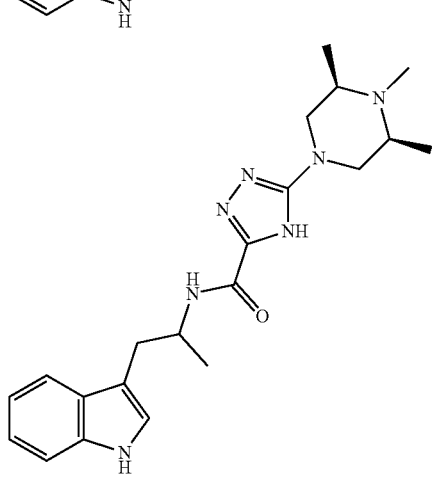
118
-continued
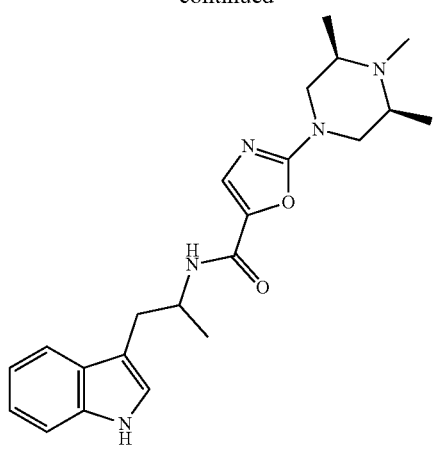
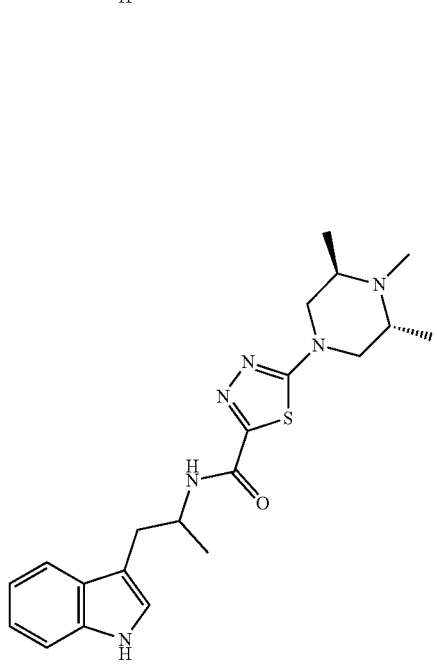
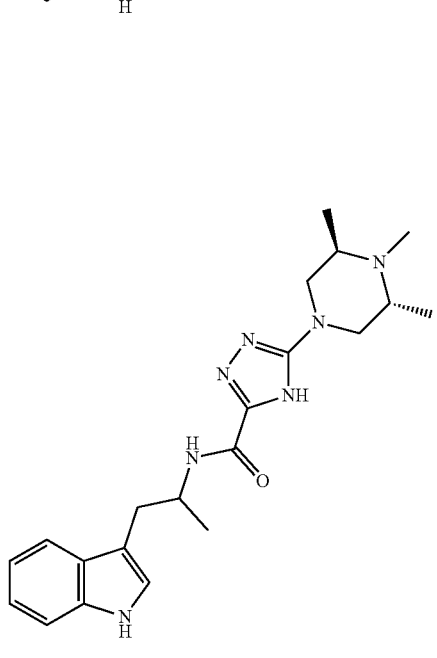

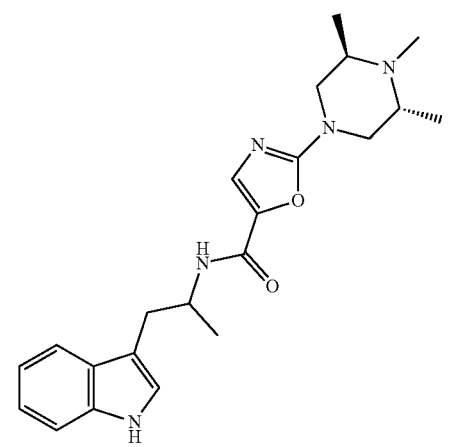
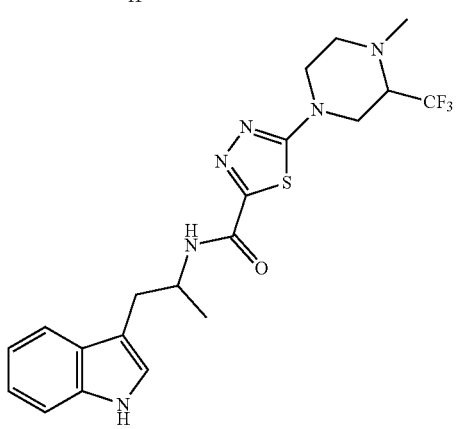
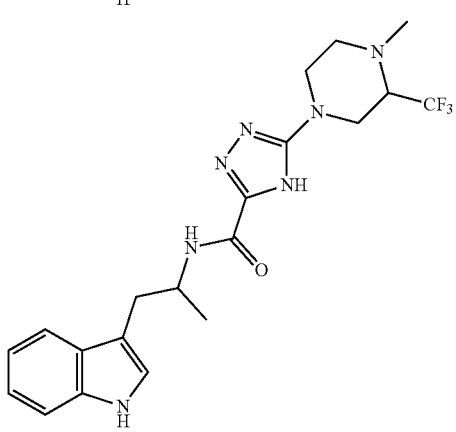
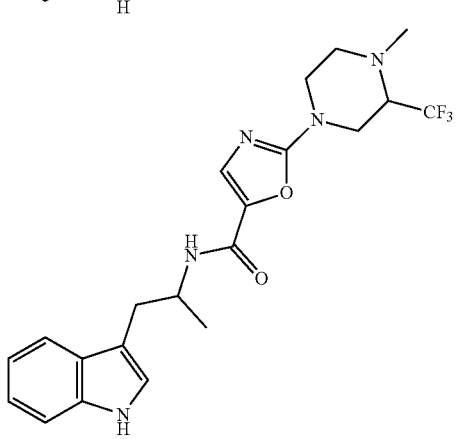
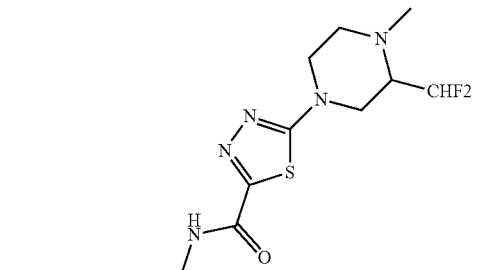
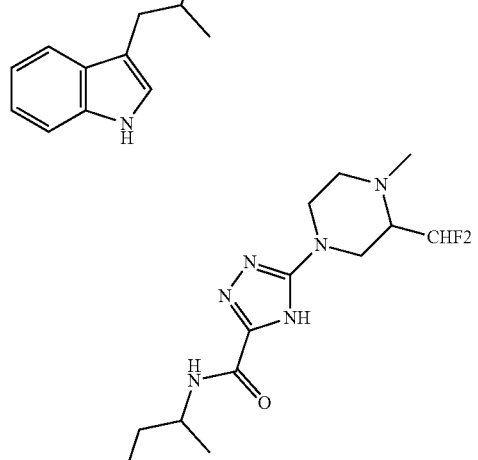
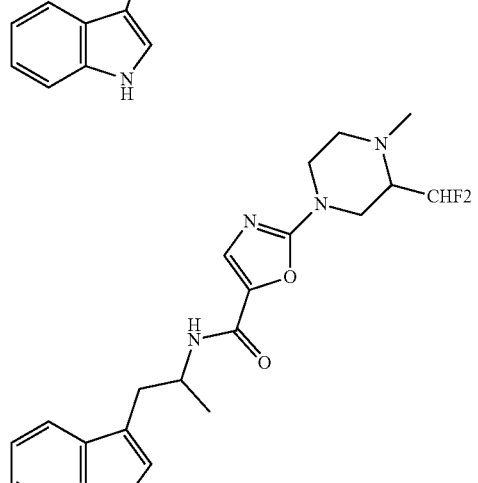
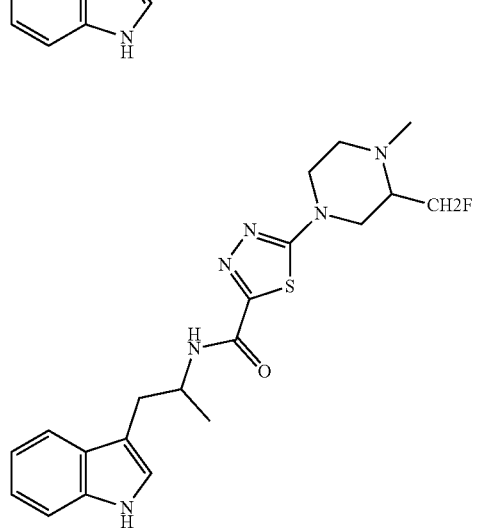

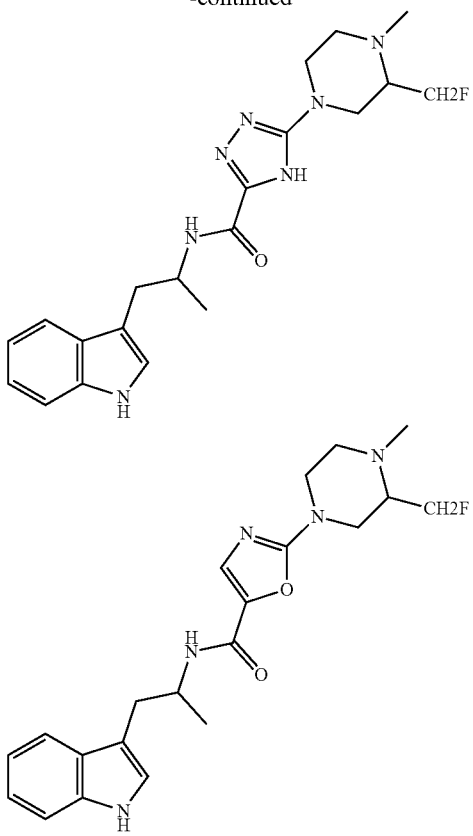

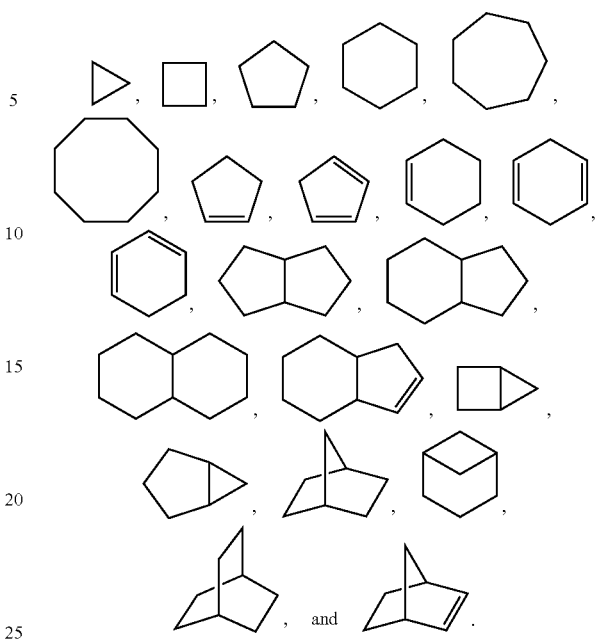

Chemical Definitions

The term "alkyl" refers to a straight- or branched-chain alkyl group having from 1 to 12 carbon atoms in the chain. "$C_{x-y}$alkyl" refers to alkyl groups with x to y carbon atoms. For example, "$C_{1-4}$alkyl" refers to alkyl groups with 1 to 4 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, and isohexyl.

The term "alkoxy" refers to an alkyl-O— group, where alkyl is as defined above. The alkoxy group is connected to the parent structure via the oxygen atom. "$C_{1-4}$alkoxy" refers to alkoxy groups in which an alkyl group with 1 to 4 carbon atoms is bonded to the oxygen.

The term "alkylene" refers to a divalent group that is a radical of an alkane. The alkylene can be a straight- or branched-chain divalent alkyl radical. "$C_{1-4}$ alkylene" refers to alkylene groups with 1 to 4 carbon atoms.

The term "aryl" refers to a monovalent aromatic carbocyclic group of from 6 to 14 carbon atoms having a single ring (a phenyl group) or a multiple condensed ring (such as napthyl, anthracenyl, or indanyl), in which condensed rings are optionally aromatic, provided that the point of attachment of the aryl group to the parent structure is through an atom of an aromatic ring.

The term "cycloalkyl" refers to a saturated or partially saturated, monocyclic, fused polycyclic, bridged polycyclic, or spiro polycyclic carbocycle having from 3 to 12 ring atoms per carbocycle. Illustrative examples of cycloalkyl groups include the following entities, in the form of properly bonded moieties:

The term "halogen" represents chlorine, fluorine, bromine, or iodine. The term "halo" represents chloro, fluoro, bromo, or iodo.

The term "halo-alkyl" refers to an alkyl group as described herein, wherein one or more hydrogen atoms on the alkyl group have been substituted with a halo group. Examples of such groups include, without limitation, fluoroalkyl groups, such as fluoromethyl, difluoromethyl, trifluoromethyl, fluoroethyl, trifluoroethyl, and the like.

The term "haloalkoxy" refers to the group alkyl-O— wherein one or more hydrogen atoms on the alkyl group have been replaced with a halo group and include, by way of examples, groups such as trifluoromethoxy, fluoroethoxy, and the like.

The term "heteroalkylene" refers to a divalent alkylene group in which one carbon chain atom is replaced by —S—, —O—, or —NR—, where R is H or $C_{1-4}$alkyl.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms. Bicyclic heteroaryl groups include bicyclic groups with one aromatic and one nonaromatic ring. Where a heteroaryl ring is substituted with —OH, one of ordinary skill would understand that the resulting ring system may be drawn as the corresponding oxo-substituted tautomer. Illustrative examples of heteroaryl groups include the following entities, in the form of properly bonded moieties:

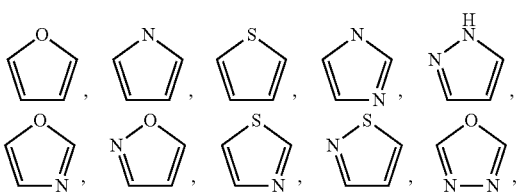

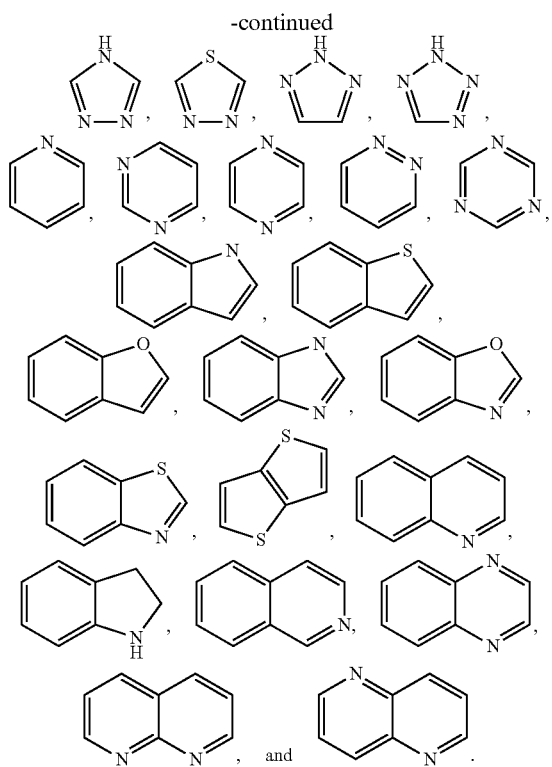

The term "heterocycloalkyl" refers to a saturated or partially unsaturated group having a single ring or multiple condensed rings, including fused, bridged, or spiro ring systems, and having from 3 to 20 ring atoms, including 1 to 10 heteroatoms. These ring atoms are selected from the group consisting of carbon, nitrogen, sulfur, or oxygen. In certain embodiments, the nitrogen and/or sulfur atom(s) of the heterocyclic group are optionally oxidized to provide for N-oxide, —S(O)—, or —SO$_2$— moieties. Illustrative examples of heterocyclic groups include the following entities, in the form of properly bonded moieties:

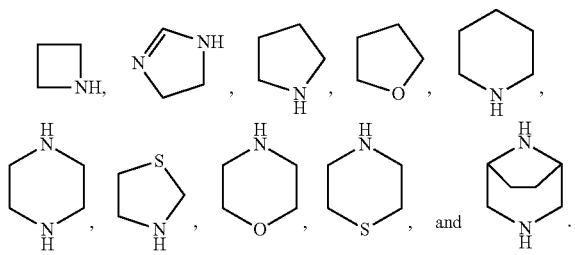

The term "oxo" represents a carbonyl oxygen. For example, a cyclopentyl substituted with oxo is cyclopentanone.

Those skilled in the art will recognize that the species listed or illustrated in the definitions provided herein are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

The invention also includes pharmaceutically acceptable salts of the compounds represented by Formula (I) or (IA), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (I) or (IA) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The invention also relates to pharmaceutically acceptable prodrugs of the compounds of Formula (I) or (IA), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or (IA)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present invention also relates to pharmaceutically active metabolites of compounds of Formula (I) or (IA), and uses of such metabolites in the methods of the invention. A "pharmaceutically active metabolite" means a pharmacologically active product of metabolism in the body of a compound of Formula (I) or (IA) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.01 to about 50 mg/kg daily, or from about 0.05 to about 20 mg/kg daily, or from about 0.1 to about 10 mg/kg daily. Additional dosages include from about 0.1 mg to 1 g daily, from about 1 mg to about 10 mg daily, from about 10 mg to about 50 mg daily, from about 50 mg to about 250 mg daily, or from about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary neurodegenerative diseases that are characterized by protein aggregation include Alzheimer's Disease, Parkinson's Disease, fronto-temporal Dementia, Dementia with Lewy Bodies (Lewy body disease), Parkinson's Disease with Dementia, Multiple System Atrophy, Amyotrophic Lateral Sclerosis, and Huntington's Disease, as well as cancers and inflammatory diseases such as Crohn's disease.

In one aspect, the compounds and pharmaceutical compositions of the invention specifically target α-synuclein, β-amyloid, and/or tau protein aggregates. Thus, these compounds and pharmaceutical compositions can be used to modulate, prevent, reverse, slow, or inhibit aggregation of α-synuclein, β-amyloid, and/or tau proteins, and are used in methods of the invention to treat degenerative neurological diseases related to or caused by aggregation, e.g., such as aggregation of α-synuclein, β-amyloid, and/or tau proteins. Preferably, the methods of the invention target neurodegenerative diseases associated with aggregation of α-synuclein, β-amyloid, and/or tau protein. In preferred embodiments, methods of treatment target Parkinson's disease, Alzheimer's disease, Lewy body disease, or multiple system atrophy. In other embodiments, the methods target cancer or melanoma. The compounds, compositions, and method of the present invention are also used to mitigate deleterious effects that are secondary to protein aggregation, such as neuronal cell death.

In some aspects, the compounds, compositions, and methods of the invention are used to target α-synuclein (SYN) aggregation. In alternative aspects, the compounds, compositions, and methods of the invention are used to target Aβ aggregation.

In the inhibitory methods of the invention, an "effective amount" means an amount sufficient to reduce, slow the progression of, or reverse protein or peptide aggregation. Measuring the amount of aggregation may be performed by routine analytical methods such as those described below. Such modulation is useful in a variety of settings, including in vitro assays. In such methods, the cell is preferably a nerve cell.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 µg to 2 mg of active agent per kilogram of subject's body weight per day, preferably about 0.05 to 100 mg/kg/day, or about 1 to 35 mg/kg/day, or about 0.1 to 10 mg/kg/day. In alternative embodiments an exemplary dose is in the range of about 1 mg to about 1 g per day, or about 1-500, 1-250, 1-100, 1-50, 50-500, or 250-500 mg per day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. Further additional active ingredients for cancer applications include other cancer therapeutics or agents that mitigate adverse effects of cancer chemotherapeutic agents. Such combinations may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Combination agents include additional active ingredients are those that are known or discovered to be effective in treating neurodegenerative disorders, including those active against another target associated with the disease, such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies); and c) drugs that act as neuroprotectants by complementary mechanisms (e.g., those targeting autophagy, those that are anti-oxidants, and those acting by other mechanisms such as adenosine A2A antagonists).

For example, compositions and formulations of the invention, as well as methods of treatment, can further comprise other drugs or pharmaceuticals, e.g., other active agents useful for treating or palliative for a degenerative neurological disease related to or caused by protein aggregation, e.g., synuclein, beta-amyloid and/or tau protein aggregation, e.g., Parkinson's disease, Alzheimer's Disease (AD), Lewy body disease (LBD) and multiple system atrophy (MSA), or related symptoms or conditions. For example, the pharmaceutical compositions of the invention may additionally comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods including dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, and gamma-secretase inhibitors. In particular embodiments, at least one compound of the present invention may be combined in a pharmaceutical composition or a method of treatment with one or more drugs selected from the group consisting of: tacrine (Cognex), donepezil (Aricept), rivastigmine (Exelon), galantamine (Reminyl), physostigmine, neostigmine, Icopezil (CP-118954, 5,7-dihydro-3-(2-(1-(2-fluorobenzyl)-4-piperidinyl)ethyl)-6H-pyrrolo(3,2,f)-1,2-benzisoxazol-6-one maleate), ER-127528 (4-[(5,6-dimethoxy-2-fluoro-1-indanon)-2-yl]methyl-1-(3-fluorobenzyl) piperidine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-α-[[2-(dimethylamino)ethoxy]methyl] benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methanamine), SDZ-220-581 ((S)-alpha-amino-5-(phosphonomethyl)-[1,1'-biphenyl]-3-propionic acid), memantine (Namenda/Exiba), 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethylphenyl)-1,2,3,6-tetrahydropyridine, Huperzine A, posatirelin, leuprolide or derivatives thereof, ispronicline, (3-aminopropyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate), and combinations thereof.

Potential combination agents for cancer therapies may include, for example, protein and lipid kinase inhibitors (e.g., PI3K, B-raf, BCR/ABL), radiation treatment enhancers, microtubule binders (e.g., taxol, vinblastine), cell metabolism inhibitors, DNA intercalators, topoisomerase inhibitors (e.g., doxorubicin), and DNA alkylating agents.

Assays

The compounds described herein can be used in research applications, including in in vitro, in vivo, or ex vivo experimental systems. Experimental systems can include, without limitation, cell samples, tissue samples, cell components or mixtures of cell components, whole or partial organs, or organisms. Research applications include, without limitation, use as assay reagents, elucidation of biochemical pathways, or evaluation of the effects of other agents on the experimental system in the presence or absence of one or more compounds described herein.

The compounds described herein can also be used in biochemical assays. In some embodiments, a compound described herein can be incubated with a tissue or cell sample from a subject to evaluate the subject's potential response to administration of the compound, or to determine which compound described herein produces the optimum effect in a specific subject or set of subjects. One such assay would involve (a) obtaining a cell sample or tissue sample from a subject in which modulation of one or more biomarkers can be assayed; (b) administering one or more compounds described herein to the cell sample or tissue sample; and (c) determining the amount of modulation of the one or more biomarkers after administration of the compound, compared to the status of the biomarker prior to administration of the compound. Optionally, following step (c), the assay would involve an additional step (d) selecting a compound for use in treating a disease or medical condition associated with protein aggregation based on the amount of modulation determined in step (c).

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I) or (IA). Isotopically labeled compounds as described herein are prepared according to the methods described below, using suitably labeled starting materials. Such materials are generally available from commercial suppliers of radiolabeled chemical reagents.

Scheme A

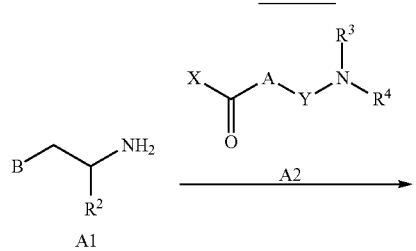

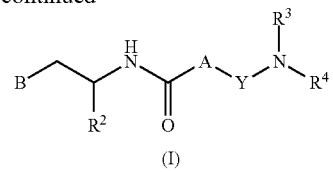

Certain compounds of Formula (I) or (IA) are prepared as shown in Scheme A. Substituted amino derivatives A1 are commercially available or are prepared according to known methods. Compounds A1 are coupled with activated acyl compounds A2, wherein X is, for example, —OH or —Cl, under standard amide formation conditions to produce compounds of Formula (I) or (IA). In alternative embodiments, A1 is coupled with X—C(O)-A-Hal, where Hal is, for example, bromo, and the bromo substituent is displaced in a separate step with $HNR^3R^4$.

Scheme B

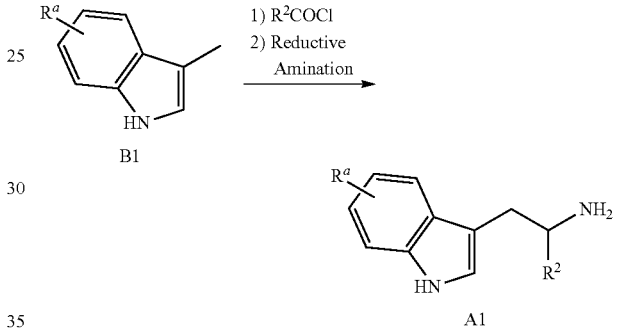

As shown in Scheme B, substituted indoles A1 are prepared from methyl-indoles B1 by acylation followed by reductive amination. These methods are also applicable to the preparation of derivatives where the $R^1$ ring is other than indole.

Scheme C

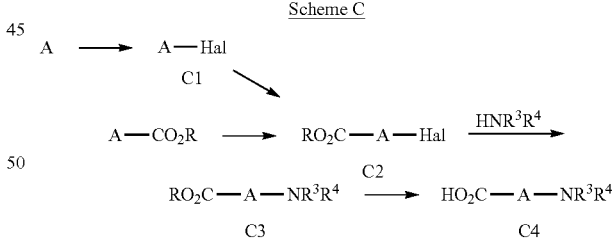

Heteroaryl compounds C4 are prepared according to Scheme C. Certain compounds A, C1, A-$CO_2$R (where R is H or $C_{1-4}$alkyl), and C2 are commercially available. In some embodiments, compounds A are halogenated to form halo compounds C1, and then are acylated to form bis-functionalized compounds C2. In other embodiments, compounds A-$CO_2$R are halogenated to form compounds C2. Coupling with amines $HNR^3R^4$ under standard amide coupling conditions provides compounds C3. Hydrolysis of esters C3 yields amino acids C4, which can be used in coupling reactions as shown in Scheme A. Suitable heterocyclic $HNR^3R^4$ intermediates such as piperazines are commercially available or are prepared, for example, by cyclization of a suitably protected diamine, or by alkylation or reductive amination of a benzyl-protected piperazine derivative.

Scheme D

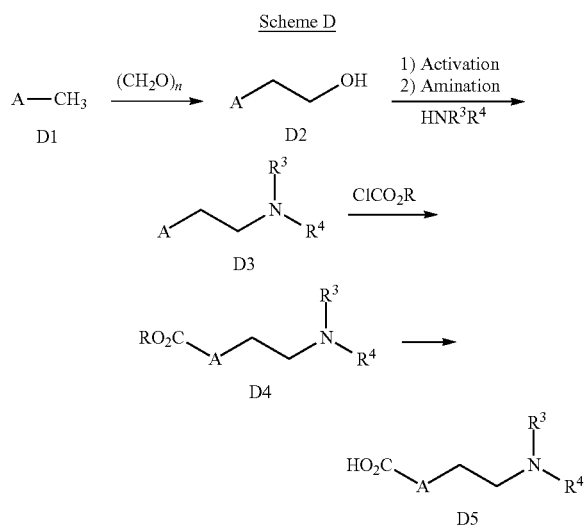

As shown in Scheme D, methyl-heterocyclic compounds D1 are homologated with, for example, paraformaldehyde, to provide hydroxyethyl compounds D2. Activation of the hydroxyl group as, for example, a halide or tosylate, and displacement with $HNR^3R^4$, yields amino compounds D3. Acylation of the heterocyclic ring gives esters D4, and hydrolysis generates amino acids D5.

Scheme E

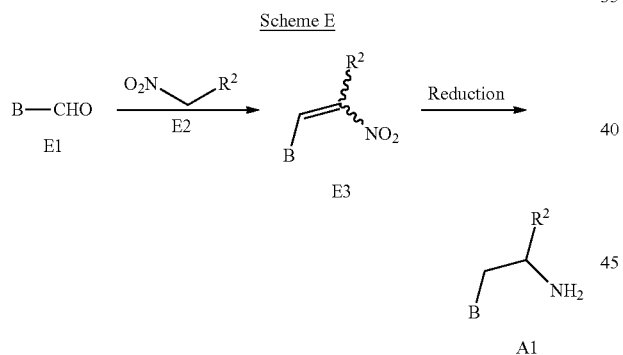

As shown in Scheme E, intermediates A1 may also be prepared using a Henry reaction to couple a heterocyclic aldehyde E1 with a suitable nitroalkane E2. Reduction of both the double bond and nitro groups (in one or two steps) provides amines A1.

Scheme F

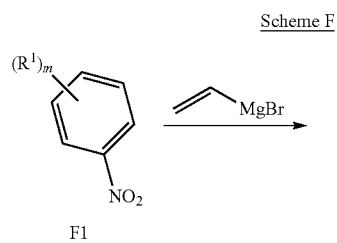

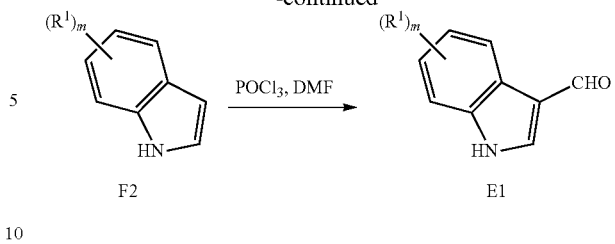

As shown in Scheme F, substituted intermediates E1 may also be prepared by cyclization of a nitrophenyl derivative F1 with vinylmagnesium bromide to form substituted indoles F2. Installation of a carbaldehyde substituent at the 3-position of the indole may be accomplished, for example, through a Vilsmaier-Haack reaction to give aldehydes E1.

EXAMPLES

The following examples are offered to illustrate but not to limit the invention One of skill in the art will recognize that the following synthetic reactions and schemes may be modified by choice of suitable starting materials and reagents in order to access other compounds of Formula (I) or (IA).

Example 1: N-(1-(1H-Indol-3-yl)hexan-2-yl)-2-(4-ethylpiperazin-1-yl)thiazole-5-carboxamide

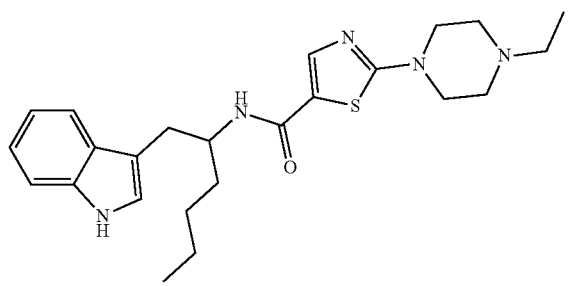 [SMILES: CCCCC(Cc1c[nH]c2ccccc12)NC(=O)c1cnc(N2CCN(CC)CC2)s1]

Step 1. Synthesis of 1-(1H-indol-3-yl)hexan-2-one

To a solution of 3-methylindole (12.0 g, 91.6 mmol) in N-(3-dimethylaminopropyl)-N'-ethylcarbodiimide hydrochloride (EDC) (160 mL) was added $AlCl_3$ (36.4 g, 274 mmol) at 0° C. The reaction mixture was stirred at room temperature for 30 min. The reaction mixture was cooled to 0° C. followed by dropwise addition of pentanoyl chloride (8.00 g, 124 mmol). The reaction mixture was stirred at room temperature for 16 h. The reaction mixture was quenched with ice and extracted with dichloromethane (4×400 mL). The organic layer was separated, washed with brine (200 mL), dried over anhydrous $Na_2SO_4$ and concentrated in vacuo. The crude obtained was purified by column chromatography (silica 100-200 mesh, 10 to 30% EtOAc in hexanes) to afford 1-(1H-indol-3-yl)hexan-2-one (9.00 g, 50%) as a brown liquid. $^1$H NMR (400 MHz, DMSO-$d_6$) δ 0.79 (t, J=7.3 Hz, 3H), 1.13-1.22 (m, 2H), 1.41 (m, 2H), 2.44-2.47 (m, 2H), 3.77 (s, 2H), 6.94-7.01 (m, 1H), 7.07 (t, J=7.6 Hz, 1H), 7.23 (d, J=2.0 Hz, 1H), 7.35 (d, J=7.8 Hz, 1H), 7.42 (d, J=7.8 Hz, 1H), 10.93 (brs, 1H).

Step 2. Synthesis of 1-(1H-Indol-3-Yl)Hexan-2-Amine Hydrochloride

To a solution of 1-(1H-indol-3-yl)hexan-2-one (12.0 g, 55.8 mmol) in methanol (600 mL) was added NH₄OAc (36.3 g, 474 mmol) and the reaction mixture was stirred at 50° C. for 10 min. NaBH₃CN (4.20 g, 66.9 mmol) was added portion-wise and the reaction mixture was heated at reflux for 12 h. The reaction mixture was acidified to pH 4 with 1 N HCl (50 mL) and concentrated in vacuo. The residue was diluted with H₂O (60 mL) and filtered. The crude obtained was washed with hexane (3×20 mL) and dried in vacuo to afford 1-(1H-indol-3-yl)hexan-2-amine hydrochloride (10.5 g, 75%) as a light yellow solid. LC/MS (ESI) m/e [M+H]⁺/RT (min)/%: 216.95/4.8/96.6%. ¹H NMR (400 MHz, DMSO-d₆) δ 0.82 (t, J=7.1 Hz, 3H), 1.12-1.34 (m, 4H), 1.41 (m, 1H), 1.54 (d, J=6.4 Hz, 2H), 2.86-2.98 (m, 1H), 3.02-3.11 (m, 1H), 6.95-7.03 (m, 1H), 7.04-7.13 (m, 1H), 7.26 (s, 1H), 7.37 (d, J=7.8 Hz, 1H), 7.58 (d, J=7.8 Hz, 1H), 8.07 (brs, 3H), 11.05 (brs, 1H).

Step 3. Synthesis of N-(1-(1H-indol-3-yl)hexan-2-yl)-2-bromothiazole-5-carboxamide To a solution of 1-(1H-indol-3-yl)hexan-2-amine hydrochloride (4.35 g, 17.2 mmol) and 2-bromothiazole-5-carboxylic acid (3.59 g, 17.2 mmol) in N,N-dimethylformamide (DMF; 87 mL) was added 2-chloro-1methylpyridinium iodide (Mukaiyama reagent; 7.45 g, 29.2 mmol) followed by addition of N,N-diisopropylethylamine (DIPEA; 11.0 g, 86.0 mmol). The reaction mixture was stirred at room temperature for 16 h. The reaction mixture was diluted with H₂O (50 mL) and extracted with dichloromethane (DCM; 3×50 mL). The organic layer was separated, dried over anhydrous Na₂SO₄ and concentrated in vacuo. The crude obtained was purified by column chromatography (silica 230-400 mesh, 5 to 30% EtOAc in hexanes) and triturating with petroleum ether and (10 mL) and pentane (25 mL) to afford N-(1-(1H-indol-3-yl)hexan-2-yl)-2-bromothiazole-5-carboxamide (3.30 g, 47%) as an off-white solid. MS (ESI) m/e [M+H]⁺/RT (min)/%: 405.70/3.56/99.7%. ¹H NMR (400 MHz, DMSO-d₆) δ 0.81 (t, J=6.9 Hz, 3H), 1.14-1.37 (m, 4H), 1.42-1.67 (m, 2H), 2.82-2.98 (m, 2H), 4.12 (d, J=4.1 Hz, 1H), 6.91-6.99 (m, 1H), 7.04 (t, J=7.4 Hz, 1H), 7.11 (d, J=1.8 Hz, 1H), 7.31 (d, J=8.3 Hz, 1H), 7.57 (d, J=7.8 Hz, 1H), 8.22 (s, 1H), 8.51 (d, J=8.3 Hz, 1H), 10.77 (brs, 1H).

Step 4

To a solution of N-(1-(1H-indol-3-yl)hexan-2-yl)-2-bromothiazole-5-carboxamide (0.15 g, 0.36 mmol) and 1-ethylpiperazine (0.05 g, 0.42 mmol) in CH₃CN (7.5 mL) was added K₂CO₃ (0.15 g, 0.11 mmol), and the reaction mixture was heated in a sealed tube at 80° C. for 16 h. The reaction mixture was concentrated in vacuo. The residue was diluted with H₂O (10 mL) and extracted with 10% MeOH in DCM (10 mL). The organic layer was separated, dried over anhydrous Na₂SO₄ and concentrated in vacuo. The crude obtained was purified by triturating with Et₂O (10 mL), pentane (25 mL) and DCM (5 mL) to afford N-(1-(1H-indol-3-yl)hexan-2-yl)-2-(4-ethylpiperazin-1-yl)thiazole-5-carboxamide (0.10 g, 62%) as a light yellow solid. HPLC Purity: 99.3%. MS (ESI) m/e [M+H]⁺/RT (min)/%: 440.00/2.74/99.2%. ¹H NMR (400 MHz, DMSO-d₆) δ 0.81 (t, J=6.9 Hz, 3H), 1.02 (t, J=7.1 Hz, 3H), 1.15-1.36 (m, 4H), 1.42-1.58 (s, 2H), 2.37 (q, J=7.3 Hz, 2H), 2.46 (d, J=4.4 Hz, 4H), 2.77-2.94 (m, 2H), 3.42-3.48 (m, 4H), 4.08-4.18 (m, 1H), 6.93-6.98 (m, 1H), 7.04 (t, J=7.3 Hz, 1H), 7.09 (s, 1H), 7.31 (d, J=8.3 Hz, 1H), 7.57 (d, J=7.3 Hz, 1H), 7.80 (s, 1H), 7.94 (d, J=8.3 Hz, 1H), 10.75 (brs, 1H).

Example 2: N-(1-(1H-Indol-3-yl)hexan-2-yl)-2-(4-isopropylpiperazin-1-yl)thiazole-5-carboxamide

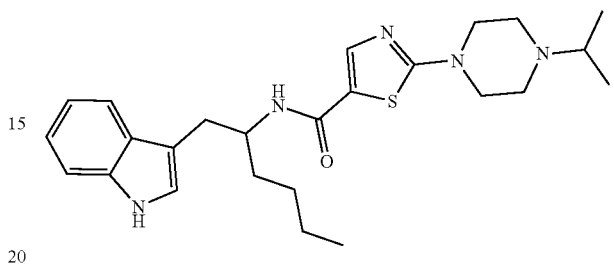

To a solution of N-(1-(1H-indol-3-yl)hexan-2-yl)-2-bromothiazole-5-carboxamide (0.20 g, 0.49 mmol) and 1-isopropylpiperazine (0.07 g, 0.54 mmol) in CH₃CN (4.5 mL) was added K₂CO₃ (0.20 g, 1.47 mmol) and the reaction mixture was heated at 80° C. for 16 h. The reaction mixture was concentrated in vacuo. The residue was diluted with H₂O (10 mL) and extracted with 10% MeOH in DCM (10 mL). The organic layer was separated, dried over anhydrous Na₂SO₄ and concentrated in vacuo. The crude obtained was purified by column chromatography (silica 230-400 mesh, 0 to 10% MeOH in DCM) and then triturating with petroleum ether (6 mL), pentane (10 mL), and DCM (2 mL) to afford N-(1-(1H-indol-3-yl)hexan-2-yl)-2-(4-isopropylpiperazin-1-yl)thiazole-5-carboxamide (0.16 g, 42%) as an off-white solid. HPLC Purity: 98.3%. LC/MS (ESI) m/e [M+H]⁺/RT (min)/%: 454.00/2.89/98.2.2%. ¹H NMR (400 MHz, DMSO-d₆) δ 0.81 (t, J=6.9 Hz, 3H), 0.98 (d, J=6.4 Hz, 6H), 1.13-1.37 (m, 4H), 1.42-1.60 (m, 2H), 2.66-2.75 (m, 1H), 2.76-2.95 (m, 2H), 3.40-3.48 (m, 4H), 4.08-4.18 (m, 1H), 6.91-6.99 (m, 1H), 7.04 (t, J=7.3 Hz, 1H), 7.09 (brs, 1H), 7.31 (d, J=8.3 Hz, 1H), 7.57 (d, J=7.8 Hz, 1H), 7.80 (s, 1H), 7.93 (d, J=8.3 Hz, 1H), 10.75 (brs, 1H) (4H's merged in solvent peak).

Example 3: N-(1-(1H-Indol-3-yl)hexan-2-yl)-2-(4-cyclopropylpiperazin-1-yl)thiazole-5-carboxamide

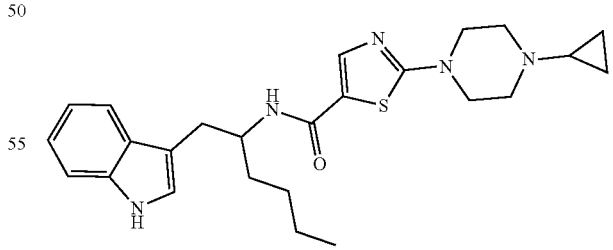

To a solution of N-(1-(1H-indol-3-yl)hexan-2-yl)-2-bromothiazole-5-carboxamide (0.20 g, 0.49 mmol) and 1-cyclopropylpiperazine (0.07 g, 0.54 mmol) in CH₃CN (4.5 mL) was added K₂CO₃ (0.20 g, 1.47 mmol) and the reaction mixture was heated at 80° C. for 16 h. The reaction mixture was concentrated in vacuo. The residue was diluted with H₂O (10 mL) and extracted with 10% MeOH in DCM (10 mL). The organic layer was separated, dried over anhydrous Na$_2$SO$_4$ and concentrated in vacuo. The crude obtained was purified by column chromatography (silica 230-400 mesh, 0 to 10% MeOH in DCM) and then triturating with petroleum ether (6 mL), pentane (10 mL) and DCM (2 mL) to afford N-(1-(1H-indol-3-yl)hexan-2-yl)-2-(4-cyclopropylpiperazin-1-yl)thiazole-5-carboxamide (0.14 g, 63%) as an off-white solid. HPLC Purity: 99.0%. LC/MS (ESI) m/e [M+H]$^+$/RT (min)/%: 452.00/2.91/98.8%. $^1$H NMR (400 MHz, DMSO-d$_6$) δ 0.35-0.44 (m, 4H), 0.82 (t, J=6.9 Hz, 3H), 1.16-1.37 (m, 4H), 1.40-1.60 (m, 2H), 1.62-1.68 (m, 1H), 2.60-2.68 (m, 4H), 2.73-2.98 (m, 2H), 3.40-3.48 (m, 4H), 4.04-4.18 (m, 1H), 6.92-6.99 (m, 1H), 7.04 (t, J=7.6 Hz, 1H), 7.09 (s, 1H), 7.31 (d, J=8.3 Hz, 1H), 7.57 (d, J=7.8 Hz, 1H), 7.80 (s, 1H), 7.94 (d, J=8.8 Hz, 1H), 10.75 (brs, 1H).

Example 4: N-(1-(1H-Indol-3-yl)hexan-2-yl)-2-(4-(tert-butyl)piperazin-1-yl)thiazole-5-carboxamide

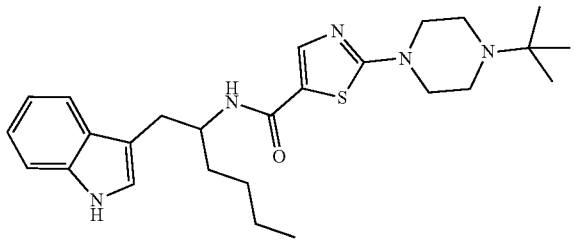 [SMILES: CCCCC(Cc1c[nH]c2ccccc12)NC(=O)c1cnc(N2CCN(C(C)(C)C)CC2)s1]

To a solution of N-(1-(1H-indol-3-yl)hexan-2-yl)-2-bromothiazole-5-carboxamide (0.20 g, 0.49 mmol) and 1-tert-butyl-piperazine (0.05 g, 0.54 mmol) in CH$_3$CN (4.5 mL) was added K$_2$CO$_3$ (0.20 g, 1.47 mmol) and the reaction mixture was heated at 80° C. for 16 h. The reaction mixture was concentrated in vacuo. The residue was diluted with H$_2$O (10 mL) and extracted with 10% MeOH in DCM (10 mL). The organic layer was separated, dried over anhydrous Na$_2$SO$_4$ and concentrated in vacuo. The crude obtained was purified by column chromatography (silica 230-400 mesh, 0 to 10% MeOH in DCM) and then triturating with petroleum ether (6 mL), pentane (10 mL) and DCM (2 mL) to afford N-(1-(1H-indol-3-yl)hexan-2-yl)-2-(4-(tert-butyl)piperazin-1-yl)thiazole-5-carboxamide (0.15 g, 65%) as an off-white solid. HPLC Purity: 99.1%. LC/MS (ESI) m/e [M+H]$^+$/RT (min)/%: 468.00/3.01/99.6%. $^1$H NMR (400 MHz, DMSO-d$_6$) δ 0.81 (t, J=6.8 Hz, 3H), 1.02 (s, 9H), 1.17-1.33 (m, 4H), 1.43-1.60 (m, 2H), 2.59 (d, J=4.4 Hz, 4H), 2.74-2.97 (m, 2H), 3.37-3.44 (m, 4H), 4.04-4.16 (m, 1H), 6.91-6.99 (m, 1H), 7.04 (t, J=7.6 Hz, 1H), 7.09 (d, J=1.5 Hz, 1H), 7.31 (d, J=8.3 Hz, 1H), 7.57 (d, J=7.8 Hz, 1H), 7.80 (s, 1H), 7.93 (d, J=8.3 Hz, 1H), 10.75 (brs, 1H).

Example 5: N-(1-(1H-Indol-3-yl)hexan-2-yl)-2-(4-isobutylpiperazin-1-yl)thiazole-5-carboxamide

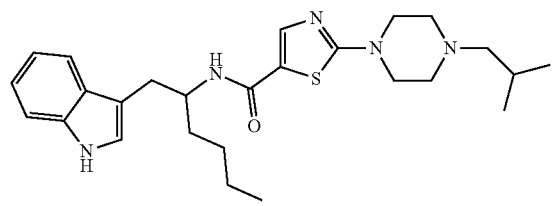 [SMILES: CCCCC(Cc1c[nH]c2ccccc12)NC(=O)c1cnc(N2CCN(CC(C)C)CC2)s1]

To a solution of N-(1-(1H-indol-3-yl)hexan-2-yl)-2-bromothiazole-5-carboxamide (0.20 g, 0.49 mmol) and 1-isobutylpiperazine (0.05 g, 0.54 mmol) in CH$_3$CN (4.5 mL) was added K$_2$CO$_3$ (0.20 g, 1.47 mmol) and the reaction mixture was heated at 80° C. for 16 h. The reaction mixture was concentrated in vacuo. The residue was diluted with H$_2$O (10 mL) and extracted with 10% MeOH in DCM (10 mL). The organic layer was separated, dried over anhydrous Na$_2$SO$_4$ and concentrated in vacuo. The crude obtained was purified by column chromatography (silica 230-400 mesh, 0 to 10% MeOH in DCM) and then triturating with petroleum ether (6 mL), pentane (10 mL) and DCM (2 mL) to afford N-(1-(1H-indol-3-yl)hexan-2-yl)-2-(4-isobutylpiperazin-1-yl)thiazole-5-carboxamide (0.16 g, 69%) as an off-white solid. HPLC Purity: 97.4%. LC/MS (ESI) m/e [M+H]$^+$/RT (min)/%: 468.00/3.33/99.52%. $^1$H NMR (400 MHz, DMSO-d$_6$) δ 0.81 (t, J=6.8 Hz, 3H), 0.87 (d, J=6.4 Hz, 6H), 1.13-1.37 (m, 4H), 1.42-1.58 (m, 2H), 1.76-1.82 (m, 1H), 2.08 (d, J=6.8 Hz, 2H), 2.40-2.48 (m, 4H), 2.73-2.95 (m, 2H), 3.42-3.48 (m, 4H), 4.10-4.18 (m, 1H), 6.92-6.99 (m, 1H), 7.04 (t, J=7.3 Hz, 1H), 7.09 (brs, 1H), 7.31 (d, J=8.3 Hz, 1H), 7.57 (d, J=7.3 Hz, 1H), 7.80 (s, 1H), 7.94 (d, J=8.8 Hz, 1H), 10.75 (brs, 1H).

Example 6: N-(1-(1H-Indol-3-yl)hexan-2-yl)-2-(4-(2-methoxyethyl)piperazin-1-yl)thiazole-5-carboxamide

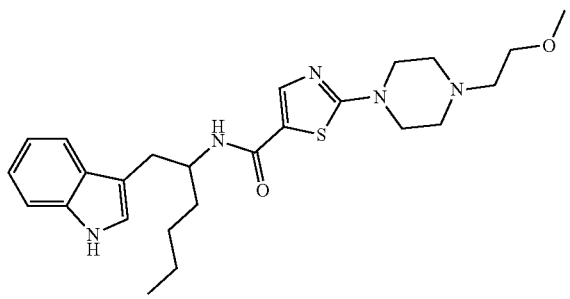 [SMILES: CCCCC(Cc1c[nH]c2ccccc12)NC(=O)c1cnc(N2CCN(CCOC)CC2)s1]

Step 1: Synthesis of 1-(2-methoxyethyl)piperazine hydrochloride

To a solution of tert-butyl piperazine-1-carboxylate (5.00 g, 26.8 mmol) in CH$_3$CN (50 mL) was added K$_2$CO$_3$ (3.70 g, 26.8 mmol) and KI (4.40 g, 26.8 mmol) in sealed tube, followed by addition of 1-bromo-2-methoxyethane (4.10 g, 29.5 mmol). The reaction mixture was heated at 80° C. for 16 h. The reaction mixture was diluted with EtOAc (100 mL) and washed with H$_2$O (2×25 mL). The organic layer was separated, washed with brine (50 mL), dried over anhydrous Na$_2$SO$_4$ and concentrated in vacuo. The residue was triturated with pentane (20 mL) and dissolved in dioxane (25 mL). Dioxane*HCl (20 mL) was added at 0° C., and the reaction mixture was stirred at room temperature for 16 h. The reaction mixture was cooled to 10° C. and filtered. The residue was washed with DCM (5 mL) and dried in vacuo to afford 1-(2-methoxyethyl)piperazine hydrochloride (3.00 g, 79%) as a white solid. LC/MS (ESI) m/e [M+H]$^+$/RT (min)/%: 145.00/1.39/97.4%. $^1$H NMR (400 MHz, DMSO-d$_6$) δ 3.28 (s, 3H), 3.43-3.63 (m, 10H), 3.73 (t, J=4.4 Hz, 2H), 9.99 (brs, 1H), 11.94 (brs, 1H).

Step 2

The title compound was prepared from 0.20 g (0.49 mmol) of N-(1-(1H-indol-3-yl)hexan-2-yl)-2-bromothiazole-5-carboxamide and 0.10 g (0.54 mmol) of 1-(2-methoxyethyl)piperazine hydrochloride using the method described for Example 1. The product N-(1-(1H-indol-3-yl)hexan-2-yl)-2-(4-(2-methoxyethyl)piperazin-1-yl)thiazole-5-carboxamide was obtained as an off-white solid (0.16 g, 69%). HPLC Purity: 99.5%. LC/MS (ESI) m/e [M+H]+/RT (min)/%: 470.00/3.33/99.5%. $^1$H NMR (400 MHz, DMSO-$d_6$) δ 0.81 (t, J=6.8 Hz, 3H), 1.16-1.60 (m, 6H), 2.80-2.94 (m, 2H), 3.24 (s, 3H), 3.38-3.53 (m, 6H), 4.06-1.16 (m, 1H), 6.97 (d, J=7.3 Hz, 1H), 7.05 (t, J=7.1 Hz, 1H), 7.10 (brs, 1H), 7.31 (d, J=7.8 Hz, 1H), 7.58 (d, J=7.3 Hz, 1H), 7.81 (brs, 1H), 7.94 (d, J=7.8 Hz, 1H), 10.76 (brs, 1H) (6H's merged in solvent peak).

Example 7: N-(1-(1H-Indol-3-yl)hexan-2-yl)-2-(4-(2-fluoroethyl)piperazin-1-yl)thiazole-5-carboxamide

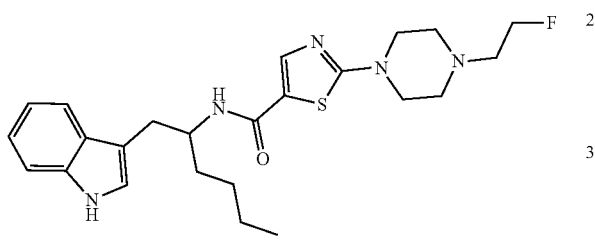

Step 1: Synthesis of 1-(2-fluoroethyl)piperazine hydrochloride

To a solution of tert-butyl piperazine-1-carboxlate (2.50 g, 13.4 mmol) in CH$_3$CN (45 mL) was added K$_2$CO$_3$ (4.62 g, 33.0 mmol) in sealed tube followed by addition of 1-fluoro-2-iodoethane (2.53 g, 20.1 mmol). The reaction mixture was heated at 80° C. for 14 h. The reaction mixture was diluted with EtOAc (200 mL) and washed with H$_2$O (100 mL). The organic layer was separated, washed with brine (20 mL), dried over anhydrous Na$_2$SO$_4$ and concentrated in vacuo. To the residue was added dioxane*HCl (100 mL) dropwise at 10° C. and the reaction mixture was stirred at room temperature for 4 h. The reaction mixture was cooled to 10° C. and filtered. The residue was washed with hexane (2×10 mL) and dried in vacuo to afford 1-(2-fluoroethyl)piperazine hydrochloride (1.75 g, 77%) as a white solid. MS (ESI) m/e [M+H]+/RT (min)/%: 133.00/2.69/99.6%. $^1$H NMR (400 MHz, DMSO-$d_6$) δ 3.46-3.63 (m, 8H), 4.84 (t, J=4.4 Hz, 2H), 4.96 (t, J=4.0 Hz, 2H), 10.02 (brs, 1H), 12.37 (brs, 1H).

Step 2

The title compound was prepared from N-(1-(1H-indol-3-yl)hexan-2-yl)-2-bromothiazole-5-carboxamide and 1-(2-fluoroethyl)piperazine using the method described for Example 1. The crude obtained was purified by column chromatography (silica 230-400 mesh, 0.5 to 3.5% MeOH in DCM) and then triturating with pentane (10 mL) to afford N-(1-(1H-indol-3-yl)hexan-2-yl)-2-(4-(2-fluoroethyl)piperazin-1-yl)thiazole-5-carboxamide (0.12 g, 53%) as a white solid. HPLC Purity: 99.4%. MS (ESI) m/e [M+H]+/RT (min)/%: 58.00/2.80/99.3%. $^1$H NMR (400 MHz, DMSO-$d_6$) δ 0.80 (t, J=6.8 Hz, 3H), 1.13-1.32 (m, 4H), 1.39-1.63 (m, 2H), 2.53-2.59 (m, 4H), 2.64 (t, J=4.9 Hz, 1H), 2.71 (t, J=4.9 Hz, 1H), 2.77-2.92 (m, 2H), 3.41-3.52 (m, 4H), 4.08-4.16 (m, 1H), 4.50 (t, J=4.9 Hz, 1H), 4.62 (t, J=4.9 Hz, 1H), 6.91-6.99 (m, 1H), 7.04 (t, J=7.1 Hz, 1H), 7.09 (d, J=2.0 Hz, 1H), 7.31 (d, J=8.3 Hz, 1H), 7.57 (d, J=7.8 Hz, 1H), 7.81 (s, 1H), 7.95 (d, J=8.3 Hz, 1H), 10.76 (s, 1H).

Example 8: N-(1-(1H-Indol-3-yl)hexan-2-yl)-2-(4-(2,2-difluoroethyl)piperazin-1-yl)thiazole-5-carboxamide

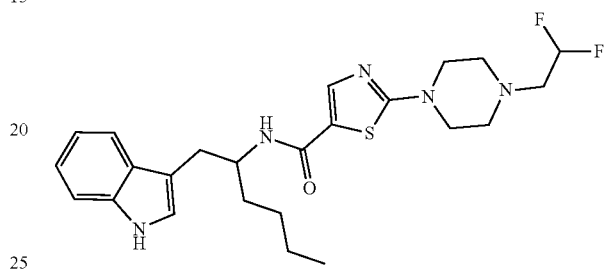

Step 1: Synthesis of 1-(2,2-difluoroethyl)piperazine

To a solution of 2,2-difluoroethan-1-ol (0.53 g, 6.40 mmol) in DCM (10 mL) was added a solution of triethylamine (0.98 g, 9.60 mmol) and O(SO$_2$CF$_3$)$_2$ (2.10 g, 7.50 mmol) at 0° C. and stirred at same temperature for 30 min. A solution of tert-butyl piperazine-1-carboxylate (1.00 g, 5.37 mmol) in DCM (16 mL) was added at 0° C. and the reaction mixture was stirred at room temperature for 16 h. The reaction mixture was diluted with H$_2$O (30 mL). The organic layer was separated, washed with brine (50 mL), dried over anhydrous Na$_2$SO$_4$ and concentrated in vacuo. The residue was dissolved in dioxane (15 mL) followed by addition of dioxane*HCl (15 mL) at 0° C. and the reaction mixture was stirred at room temperature for 5 h. The reaction mixture was cooled to 0° C. and filtered. The residue was washed with pentane (20 mL) and dried in vacuo to afford 1-(2,2-difluoroethyl)piperazine (0.70 g, 69%) as a white solid. $^1$H NMR (400 MHz, DMSO-$d_6$) δ 3.20-3.40 (m, 10H), 6.27-6.55 (m, 1H), 9.66 (brs, 1H).

Step 2

To a solution of N-(1-(1H-indol-3-yl)hexan-2-yl)-2-bromothiazole-5-carboxamide (0.20 g, 0.49 mmol) and 1-(2,2-difluoroethyl)piperazine (0.11 g, 0.58 mmol) in CH$_3$CN (4.5 mL) was added K$_2$CO$_3$ (0.20 g, 1.47 mmol) and the reaction mixture was heated at 80° C. for 16 h. The reaction mixture was concentrated in vacuo. The residue was diluted with H$_2$O (10 mL) and extracted with 10% MeOH in DCM (3×20 mL). The organic layer was separated, dried over anhydrous Na$_2$SO$_4$ and concentrated in vacuo. The crude obtained was purified by column chromatography (silica 230-400 mesh, 0.5 to 5% MeOH in DCM) and triturated with pentane (3×5 mL) to afford N-(1-(1H-indol-3-yl)hexan-2-yl)-2-(4-(2,2-difluoroethyl)piperazin-1-yl)thiazole-5-carboxamide (0.135 g, 58%) as an off-white solid. HPLC Purity: 99.5%. MS (ESI) m/e [M+H]+/RT (min)/%: 476.00/2.89/99.2%. $^1$H NMR (400 MHz, DMSO-$d_6$) δ 0.81 (t, J=6.8 Hz, 3H), 1.16-1.32 (m, 4H), 1.44-1.60 (m, 2H), 2.58-2.67 (m, 4H), 2.73-2.96 (m, 4H), 3.40-3.50 (m, 4H), 4.04-4.18 (m, 1H), 5.95-6.37 (m, 1H), 6.92-6.98 (m, 1H), 7.04 (t, J=7.1 Hz, 1H), 7.09 (d, J=2.0 Hz, 1H), 7.31 (d, J=7.8 Hz, 1H), 7.57 (d, J=7.8 Hz, 1H), 7.81 (s, 1H), 7.95 (d, J=8.3 Hz, 1H), 10.75 (brs, 1H).

Example 9: N-(1-(1H-Indol-3-yl)hexan-2-yl)-2-(4-(2,2,2-trifluoroethyl)piperazin-1-yl)thiazole-5-carboxamide

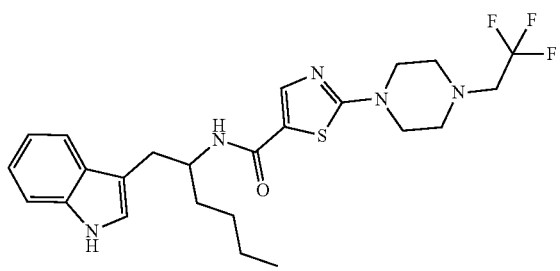 [SMILES: CCCCC(Cc1c[nH]c2ccccc12)NC(=O)c1cnc(N2CCN(CC(F)(F)F)CC2)s1]

Step 1: Synthesis of tert-butyl 4-(2,2,2-trifluoroethyl)piperazine-1-carboxylate To a solution of trifluoroethanol (0.32 g, 3.22 mmol) in DCM (10 mL) was added a solution of triethylamine (0.65 g, 4.82 mmol) and trifluoromethanesulfonic anhydride (1.05 g, 3.75 mmol) at 0° C. and stirred at same temperature for 30 min. A solution of tert-butyl piperazine-1-carboxylate (0.50 g, 2.68 mmol) in DCM (10 mL) was added and the reaction mixture was stirred at room temperature for 16 h. The reaction mixture was diluted with $H_2O$ (20 mL). The organic layer was separated, washed with $H_2O$ (20 mL), dried over anhydrous $Na_2SO_4$ and concentrated in vacuo. The crude obtained was purified by column chromatography (silica 100-200 mesh, 0.5 to 2% MeOH in DCM) to afford tert-butyl 4-(2,2,2-trifluoroethyl)piperazine-1-carboxylate (0.40 g, 55%) as a white solid. $^1$H NMR (400 MHz, DMSO-$d_6$) δ 1.46 (s, 9H), 2.64-2.58 (m, 4H), 2.92-3.04 (m, 2H), 3.48-3.36 (m, 4H).

Step 2: Synthesis of 1-(2,2,2-trifluoroethyl)piperazine

To a solution of tert-butyl 4-(2,2,2-trifluoroethyl)piperazine-1-carboxylate (0.40 g, 1.49 mmol) in dioxane (9 mL) was added 4 N HCl in dioxane (10 mL) at 0° C. and the reaction mixture was stirred at room temperature for 4 h. The reaction mixture was cooled to 0 to 5° C., filtered, and washed with hexane (20 mL). The crude obtained was purified by triturating with pentane (20 mL) to afford 1-(2,2,2-trifluoroethyl)piperazine (0.15 g, 60%) as a grey semi-solid. $^1$H NMR (400 MHz, DMSO-$d_6$) δ 2.88-2.81 (m, 4H), 3.02-3.12 (m, 4H), 3.24-3.38 (m, 2H), 9.15 (s, 1H).

Step 3

To a solution of N-(1-(1H-indol-3-yl)hexan-2-yl)-2-bromothiazole-5-carboxamide (0.20 g, 0.49 mmol) and 1-(2,2,2-trifluoroethyl)piperazine (0.11 g, 0.54 mmol) in $CH_3CN$ (4.5 mL) was added $K_2CO_3$ (0.20 g, 1.47 mmol) and the reaction mixture was heated at 80° C. for 16 h. The reaction mixture was concentrated in vacuo. The residue was diluted with $H_2O$ (10 mL) and extracted with 10% MeOH in DCM (10 mL). The organic layer was separated, dried over anhydrous $Na_2SO_4$ and concentrated in vacuo. The crude obtained was purified by column chromatography (silica 230-400 mesh, 0.5 to 3.5% MeOH in DCM) and then triturating pentane (10 mL) to afford N-(1-(1H-indol-3-yl)hexan-2-yl)-2-(4-(2,2,2-trifluoroethyl)piperazin-1-yl)thiazole-5-carboxamide (0.17 g, 70%) as an off-white solid. HPLC Purity: 97.9%. MS (ESI) m/e [M+H]$^+$/RT (min)/%: 494.00/3.09/98.2%. $^1$H NMR (400 MHz, DMSO-$d_6$) 0.81 (t, J=6.9 Hz, 3H), 1.12-1.37 (m, 4H), 1.44-1.62 (m, 2H), 2.64-2.74 (m, 4H), 2.78-2.97 (m, 2H), 3.30-3.20 (m, 2H), 3.44-3.52 (m, 4H), 4.06-4.18 (m, 1H), 6.92-6.99 (m, 1H), 7.04 (t, J=7.3 Hz, 1H), 7.09 (brs, 1H), 7.31 (d, J=7.8 Hz, 1H), 7.57 (d, J=7.8 Hz, 1H), 7.81 (s, 1H), 7.95 (d, J=8.3 Hz, 1H), 10.75 (brs, 1H).

Example 10: N-(1-(1H-Indol-3-yl)hexan-2-yl)-2-(4-(3,3,3-trifluoropropyl)piperazin-1-yl)thiazole-5-carboxamide

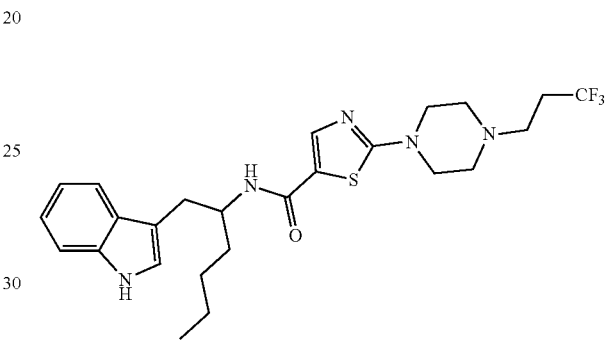

Step 1. Synthesis of 1-(3,3,3-trifluoropropyl)piperazine

To a solution of tert-butyl piperazine-1-carboxylate (0.50 g, 2.60 mmol) in $CH_3CN$ (20 mL) was added $K_2CO_3$ (0.92 g, 6.70 mmol) followed by addition of 1,1,1-trifluoro-3-iodopropane (0.90 g, 4.00 mmol). The reaction mixture was heated at 80° C. for 14 h. The reaction mixture was diluted with EtOAc (200 mL) and washed with $H_2O$ (100 mL). The organic layer was separated, washed with brine (10 mL), dried over anhydrous $Na_2SO_4$ and concentrated in vacuo. The residue was dissolved in dioxane (20 mL), and 4 M HCl in dioxane (20 mL) was added drop wise at 5° C. The reaction mixture was stirred at room temperature for 6 h. The reaction mixture was cooled to 0° C. and filtered. The residue was washed with pentane (20 mL) and dried in vacuo to afford 1-(3,3,3-trifluoropropyl)piperazine (0.40 g, 68%) as an off-white solid. MS (ESI) m/e [M+H]$^+$/RT (min)/%: 183.00/1.91/96.5%.

Step 2

To a solution of N-(1-(1H-indol-3-yl)hexan-2-yl)-2-bromothiazole-5-carboxamide (0.20 g, 0.49 mmol) and 1-(3,3,3-trifluoropropyl)piperazine (0.13 g, 0.58 mmol) in $CH_3CN$ (4.5 mL) was added $K_2CO_3$ (0.20 g, 1.47 mmol), and the reaction mixture was heated at 80° C. for 16 h. The reaction mixture was concentrated in vacuo. The residue was diluted with $H_2O$ (10 mL) and extracted with 10% MeOH in DCM (3×10 mL). The organic layer was separated, dried over anhydrous $Na_2SO_4$ and concentrated in vacuo. The crude obtained was purified by column chromatography (silica 230-400 mesh, 0.5 to 5% MeOH in DCM) and triturated with pentane (3×5 mL) to afford N-(1-(1H-indol-3-yl) hexan-2-yl)-2-(4-(3,3,3-trifluoropropyl)piperazin-1-yl)thiazole-5-carboxamide (0.10 g, 40%) as an off-white solid. HPLC Purity: 99.2%. MS (ESI) m/e [M+H]+/RT (min)/%: 508.00/3.28/98.1%. 1H NMR (400 MHz, DMSO-$d_6$) δ 0.81 (t, J=6.8 Hz, 3H), 1.16-1.30 (m, 4H), 1.46-1.57 (m, 2H), 2.56-2.61 (m, 2H), 2.77-2.93 (m, 2H), 3.39-3.48 (m, 4H), 4.06-4.18 (m, 1H), 6.92-6.98 (m, 1H), 7.04 (t, J=7.3 Hz, 1H), 7.09 (d, J=2.0 Hz, 1H), 7.31 (d, J=8.3 Hz, 1H), 7.57 (d, J=7.8 Hz, 1H), 7.81 (s, 1H), 7.95 (d, J=8.3 Hz, 1H), 10.76 (brs, 1H) (6H's merged in solvent peak).

Example 11: N-(1-(1H-Indol-3-yl)hexan-2-yl)-2-(3,4-dimethylpiperazin-1-yl)thiazole-5-carboxamide

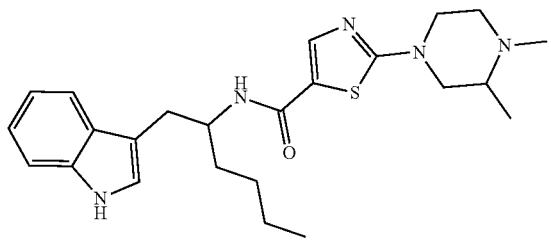 [SMILES: CCCCC(Cc1c[nH]c2ccccc12)NC(=O)c1cnc(N2CCN(C)C(C)C2)s1]

To a solution of N-(1-(1H-indol-3-yl)hexan-2-yl)-2-bromothiazole-5-carboxamide (0.20 g, 0.49 mmol) and 1,2-dimethylpiperazine (0.06 g, 0.54 mmol) in CH$_3$CN (4.5 mL) was added K$_2$CO$_3$ (0.20 g, 1.47 mmol) and the reaction mixture was heated at 80° C. for 16 h. The reaction mixture was concentrated in vacuo. The residue was diluted with H$_2$O (10 mL) and extracted with 10% MeOH in DCM (10 mL). The organic layer was separated, dried over anhydrous Na$_2$SO$_4$ and concentrated in vacuo. The crude obtained was purified by column chromatography (silica 230-400 mesh, 0.5 to 3.5% MeOH in DCM) and triturating with pentane (10 mL) to afford N-(1-(1H-indol-3-yl) hexan-2-yl)-2-(3,4-dimethylpiperazin-1-yl)thiazole-5-carboxamide (0.075 g, 34%) as a white solid. HPLC Purity: 99.2%. LC/MS (ESI) m/e [M+H]+/RT (min)/%: 440.00/2.76/99.8%. 1H NMR (400 MHz, DMSO-$d_6$) δ 0.81 (t, J=6.9 Hz, 3H), 1.02 (d, J=6.4 Hz, 3H), 1.18-1.31 (m, 4H), 1.40-1.60 (m, 2H), 2.06-2.18 (m, 2H), 2.20 (s, 3H), 2.69-2.91 (m, 4H), 3.10-3.22 (m, 1H), 3.64-3.77 (m, 2H), 4.11 (d, J=4.4 Hz, 1H), 6.91-6.99 (m, 1H), 7.04 (t, J=7.6 Hz, 1H), 7.09 (brs, 1H), 7.31 (d, J=7.8 Hz, 1H), 7.57 (d, J=7.8 Hz, 1H), 7.80 (s, 1H), 7.93 (d, J=8.3 Hz, 1H), 10.75 (brs, 1H).

Example 12: N-(1-(1H-Indol-3-yl)hexan-2-yl)-2-(3,3,4-trimethylpiperazin-1-yl)thiazole-5-carboxamide

Step 1: Synthesis of 3,3-dimethylpiperazin-2-one

To a solution of 1,2-diaminoethane (7.70 g, 128 mmol) in toluene (55 mL) was added a solution of ethyl 2-bromo-2-methylpropanoate (5.00 g, 25.6 mmol) in toluene (5 mL) dropwise at 0° C., and the reaction mixture was stirred at room temperature for 1 h and then at reflux for 16 h. The reaction mixture was extracted with toluene (30 mL). The organic layer was separated, dried over anhydrous Na$_2$SO$_4$ and concentrated in vacuo. The crude obtained was purified by column chromatography (silica 100-200 mesh, 2 to 10% methanolic NH$_3$ in DCM) to afford 3,3-dimethylpiperazin-2-one (2.81 g, 87%) as an off-white solid. LC/MS (ESI) m/e [M+H]+/RT (min)/%: 128.90/0.61/69.8%. 1H NMR (400 MHz, DMSO-$d_6$) δ 1.15 (s, 6H), 2.24 (s, 1H), 2.80-2.86 (m, 2H), 3.10-3.16 (m, 2H), 7.35 (s, 1H).

Step 2: Synthesis of 3,3,4-trimethylpiperazin-2-one

To a solution of 3,3-dimethylpiperazin-2-one (1.50 g, 11.7 mmol) in DCM (20 mL) was added a 37% HCHO solution (0.48 mL, 17.5 mmol) dropwise at 0° C. followed by portion-wise addition of Na(OAc)$_3$BH (3.22 g, 15.2 mmol). The reaction mixture was stirred at room temperature for 3 h. The reaction mixture was diluted with DCM (100 mL) and washed with satd. aq. NaHCO$_3$ (100 mL). The organic layer was separated, dried over anhydrous Na$_2$SO$_4$ and concentrated in vacuo to afford 3,3,4-trimethylpiperazin-2-one (0.85 g crude) as a white solid. This compound was used as such for the next reaction without further purification. LC/MS (ESI) m/e [M+H]+/RT (min)/%: 142.85/0.46/99.7%.

Step 3: Synthesis of 1,2,2-trimethylpiperazine

To a solution of 3,3,4-trimethylpiperazin-2-one (0.83 g, 5.84 mmol) in tetrahydrofuran (THF; 25 mL) was added lithium aluminum hydride (LAH) (0.17 g, 4.47 mmol) portion-wise at 0° C., and the reaction mixture was heated at reflux for 4.5 h. The reaction mixture was quenched with cold aq. NH$_4$Cl (20 mL) and extracted with DCM (3×25 mL). The organic layer was separated, dried over anhydrous Na$_2$SO$_4$ and concentrated in vacuo. The crude obtained was purified by triturating with pentane (10 mL) and Et$_2$O (3 mL) to afford 1,2,2-trimethylpiperazine (0.31 g crude) as a grey solid. LC/MS (ESI) m/e [M+H]+/RT (min)/%: 129.00/2.50/86.5%. 1H NMR (400 MHz, DMSO-$d_6$) δ 0.90 (s, 6H), 1.55 (s, 1H), 2.02 (s, 3H), 2.21-2.29 (m, 2H), 2.35 (s, 2H), 2.60-2.66 (m, 2H).

Step 4

To a solution of N-(1-(1H-indol-3-yl)hexan-2-yl)-2-bromothiazole-5-carboxamide (0.20 g, 0.49 mmol) and 1,2,2-trimethylpiperazine (0.07 g, 0.54 mmol) in CH$_3$CN (4.5 mL) was added K$_2$CO$_3$ (0.20 g, 1.47 mmol), and the reaction mixture was heated at 80° C. for 16 h. The reaction mixture was concentrated in vacuo. The residue was diluted with H$_2$O (3×10 mL) and extracted with 10% MeOH in DCM (3×20 mL). The organic layer was separated, dried over anhydrous Na$_2$SO$_4$ and concentrated in vacuo. The crude obtained was purified by column chromatography (silica 230-400 mesh, 0.5 to 5% MeOH in DCM) and triturated with pentane (3×5 mL) to afford N-(1-(1H-indol-3-yl) hexan-2-yl)-2-(3,3,4-trimethylpiperazin-1-yl)thiazole-5-carboxamide (0.09 g, 41%) as an off-white solid. HPLC Purity: 98.9%. LC/MS (ESI) m/e [M+H]+/RT (min)/%: 454.00/2.75/99.2%. 1H NMR (400 MHz, DMSO-$d_6$) δ 0.81

(t, J=6.9 Hz, 3H), 0.97 (s, 6H), 1.17-1.31 (m, 6H), 1.44-1.60 (m, 2H), 2.15 (s, 3H), 2.74-2.96 (m, 2H), 3.20 (s, 2H), 3.42-3.48 (m, 2H), 4.08-4.18 (m, 1H), 6.93-6.98 (m, 1H), 7.04 (t, J=7.3 Hz, 1H), 7.09 (s, 1H), 7.31 (d, J=7.8 Hz, 1H), 7.57 (d, J=7.8 Hz, 1H), 7.77 (s, 1H), 7.91 (d, J=8.3 Hz, 1H), 10.75 (brs, 1H).

Example 13: N-(1-(1H-Indol-3-yl)hexan-2-yl)-2-(cis-3,4,5-trimethylpiperazin-1-yl)thiazole-5-carboxamide

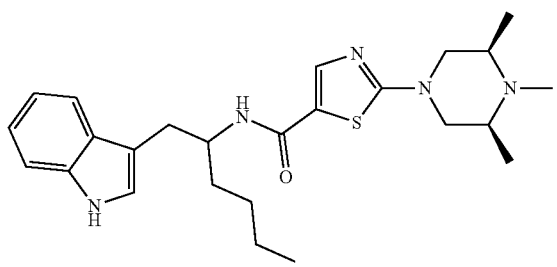 [SMILES: CCCCC(Cc1c[nH]c2ccccc12)NC(=O)c1cnc(N2C[C@@H](C)N(C)[C@@H](C)C2)s1]

Step 1: Synthesis of tert-butyl cis-3,5-dimethylpiperazine-1-carboxylate

To a solution of cis-2,6-dimethylpiperazine (1.00 g, 8.70 mmol) in CHCl$_3$ (20 mL) was added Boc anhydride (1.90 g, 8.70 mmol) drop-wise at 0° C., and the reaction mixture was stirred at room temperature for 16 h. The reaction mixture was diluted with DCM (30 mL) and washed with H$_2$O (30 mL). The organic layer was separated, washed with brine (10 mL), dried over anhydrous Na$_2$SO$_4$ and concentrated in vacuo to afford tert-butyl cis-3,5-dimethylpiperazine-1-carboxylate (1.82 g crude) as an off-white solid. This compound was used as such for the next reaction without further purification. LC/MS (ESI) m/e [M+H]$^+$/RT (min)/%: 215.00/2.52/83.4%. $^1$H NMR (400 MHz, DMSO-d$_6$) δ 1.05 (d, J=6.1 Hz, 6H), 1.20 (d, J=6.7 Hz, 1H), 1.46 (s, 9H), 2.32-2.40 (m, 2H), 2.72-2.82 (m, 2H), 3.80-4.02 (m, 2H).

Step 2: Synthesis of tert-butyl cis-3,4,5-trimethylpiperazine-1-carboxylate

To a solution of tert-butyl cis-3,5-dimethylpiperazine-1-carboxylate (1.80 g, 8.40 mmol) in DCM (20 mL) was added a 37% HCHO solution (0.34 mL, 12.0 mmol) dropwise at 0° C., followed by portion-wise addition of Na(OAc)$_3$BH (2.31 g, 10.9 mmol). The reaction mixture was stirred at room temperature for 4 h. The reaction mixture was diluted with DCM (30 mL) and washed with NaHCO$_3$ (20 mL) solution. The organic layer was separated, washed with brine (20 mL), dried over anhydrous Na$_2$SO$_4$ and concentrated in vacuo to afford tert-butyl cis-3,4,5-trimethylpiperazine-1-carboxylate (1.81 g crude) as a colorless liquid. This compound was used as such for the next reaction without further purification. LC/MS (ESI) m/e [M+H]$^+$/RT (min)/%: 228.90/4.29/88.5%. $^1$H NMR (400 MHz, CDCl$_3$) δ 1.08 (d, J=6.1 Hz, 6H), 1.48 (s, 9H), 2.04-2.18 (m, 2H), 2.26 (s, 3H), 2.56-2.62 (m, 2H), 3.78-3.98 (m, 2H).

Step 3: Synthesis of cis-1,2,6-trimethylpiperazine

To a solution of tert-butyl cis-3,4,5-trimethylpiperazine-1-carboxylate (1.80 g, 7.89 mmol) in dioxane (10 mL) was added 4 M HCl in dioxane (15 mL) at 0° C., and the reaction mixture was stirred at room temperature for 16 h. The reaction mixture was cooled to 0 to 10° C., filtered, washed with pentane (20 mL) and dried in vacuo to afford cis-1,2,6-trimethylpiperazine (1.40 g crude) as a colorless semi-solid. This compound was used as such for the next reaction without further purification. LC/MS (ESI) m/e [M+H]$^+$/RT (min)/%: 128.85/1.58/88.8%.

Step 4

To a solution of N-(1-(1H-indol-3-yl)hexan-2-yl)-2-bromothiazole-5-carboxamide (0.20 g, 0.49 mmol) and cis-1,2,6-trimethylpiperazine (0.09 g, 0.54 mmol) in CH$_3$CN (4.5 mL) was added K$_2$CO$_3$ (0.20 g, 1.47 mmol) and the reaction mixture was heated at 80° C. for 16 h. The reaction mixture was concentrated in vacuo. The residue was diluted with H$_2$O (10 mL) and extracted with 10% MeOH in DCM (3×10 mL). The organic layer was separated, dried over anhydrous Na$_2$SO$_4$ and concentrated in vacuo. The crude obtained was purified by column chromatography (silica 230-400 mesh, 0.5 to 5% MeOH in DCM) and triturated with pentane (3×5 mL) to afford N-(1-(1H-indol-3-yl)hexan-2-yl)-2-((3S,5R)-3,4,5-trimethylpiperazin-1-yl)thiazole-5-carboxamide (0.09 g, 41%) as an off-white solid. HPLC Purity: 99.8%. LC/MS (ESI) m/e [M+H]$^+$/RT (min)/%: 454.00/3.07/96.5%. $^1$H NMR (400 MHz, DMSO-d$_6$) δ 0.81 (t, J=6.8 Hz, 3H), 1.05 (d, J=5.9 Hz, 6H), 1.16-1.37 (m, 4H), 1.41-1.63 (m, 2H), 2.16 (s, 3H), 2.18-2.24 (m, 2H), 2.73-2.92 (m, 4H), 3.72 (d, J=11.2 Hz, 2H), 4.06-4.18 (m, 1H), 6.93-6.98 (m, 1H), 7.04 (t, J=7.3 Hz, 1H), 7.09 (d, J=2.0 Hz, 1H), 7.31 (d, J=8.3 Hz, 1H), 7.57 (d, J=7.8 Hz, 1H), 7.79 (s, 1H), 7.94 (d, J=8.8 Hz, 1H), 10.76 (brs, 1H).

Example 14: N-(1-(1H-Indol-3-yl)-5-methylhexan-2-yl)-(4-methylpiperazin-1-yl)thiazole-5-carboxamide

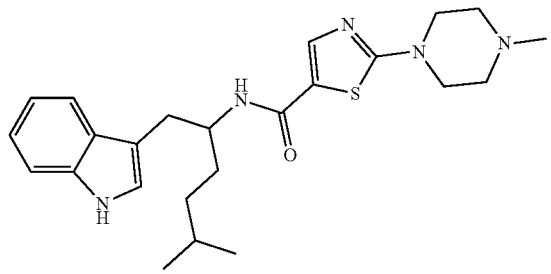 [SMILES: CC(C)CCC(Cc1c[nH]c2ccccc12)NC(=O)c1cnc(N2CCN(C)CC2)s1]

Step 1: Synthesis of 1-(1H-indol-3-yl)-5-methylhexan-2-one

To a solution of 3-methylindole (0.50 g, 3.80 mmol) in dichloroethane (20 mL) was added AlCl$_3$ (1.50 g, 11.2 mmol) at 0° C., and the reaction was stirred at 0° C. for 10 min and then at room temperature for 30 min. The reaction mixture was cooled to 0° C. followed by dropwise addition of 4-methylpentanoyl chloride (0.58 g, 4.32 mmol). The reaction mixture was stirred at room temperature for 16 h. The reaction mixture was quenched with ice H$_2$O (50 mL) and extracted with DCM (2×50 mL). The organic layer was separated, dried over anhydrous Na$_2$SO$_4$ and concentrated in vacuo. The crude obtained was purified by column chromatography (silica 100-200 mesh, 1 to 10% EtOAc in hexanes) to afford 1-(1H-indol-3-yl)-5-methylhexan-2-one (0.33 g, 38%) as a yellow liquid. MS (ESI) m/e [M+H]$^+$/RT (min)/%: 229.95/3.39/85.4%. $^1$H NMR (400 MHz, DMSO-d$_6$) δ 0.77 (d, J=6.5 Hz, 6H), 1.30-1.44 (m, 3H), 2.46 (t, J=7.5 Hz, 2H), 3.78 (s, 2H), 6.97 (t, J=7.3 Hz, 1H), 7.06 (t, J=7.3 Hz, 1H), 7.23 (d, J=2.0 Hz, 1H), 7.34 (d, J=8.1 Hz, 1H), 7.42 (d, J=7.8 Hz, 1H), 10.93 (s, 1H).

Step 2: Synthesis of
1-(1H-indol-3-yl)-5-methylhexan-2-amine
hydrochloride

To a solution of 1-(1H-indol-3-yl)-5-methylhexan-2-one (0.32 g, 1.40 mmol) in MeOH (25 mL) was added NH$_4$OAc (0.92 g, 11.9 mmol), and the reaction mixture was stirred at 50° C. for 10 min. NaBH$_3$CN (0.10 g, 1.68 mmol) was added portion-wise, and the reaction mixture was heated at reflux for 16 h. The reaction mixture was concentrated in vacuo. The residue was triturated with 3 N HCl (10 mL) and H$_2$O (5 mL). The crude obtained was washed with hexanes (20 mL) and pentane (10 mL) to afford 1-(1H-indol-3-yl)-5-methylhexan-2-amine hydrochloride (0.285 g, 75%) as a light yellow solid. MS (ESI) m/e [M+H]$^+$/RT (min)/%: 231.00/3.7/96.4%. $^1$H NMR (400 MHz, DMSO-d$_6$) δ 0.80 (d, J=6.5 Hz, 6H), 1.18-1.60 (m, 5H), 2.90-3.04 (m, 2H), 3.24-3.34 (m, 1H), 6.95 (t, J=7.4 Hz, 1H), 7.04 (t, J=7.4 Hz, 1H), 7.25 (s, 1H), 7.36 (d, J=8.0 Hz, 1H), 7.57 (d, J=7.7 Hz, 1H), 7.93 (brs, 2H), 11.00 (brs, 1H)

Step 3: Synthesis of N-(1-(1H-indol-3-yl)-5-methyl-
hexan-2-yl)-2-bromothiazole-5-carboxamide To a solution of 1-(1H-indol-3-yl)-5-methylhexan-2-amine hydrochloride (0.28 g, 1.04 mmol) and 2-bromothiazole-5-carboxylic acid (0.20 g, 1.25 mmol) in DMF (15 mL) was added Mukaiyama reagent (0.45 g, 1.77 mmol) followed by addition of DIPEA (0.68 g, 5.27 mmol). The reaction mixture was stirred at room temperature for 5 h. The reaction mixture was diluted with H$_2$O (60 mL) and extracted with DCM (3×20 mL). The organic layer was separated, dried over anhydrous Na$_2$SO$_4$ and concentrated in vacuo. The crude obtained was purified by column chromatography (silica 230-400 mesh, 5 to 25% EtOAc in hexanes) to afford N-(1-(1H-indol-3-yl)-5-methylhexan-2-yl)-2-bromothiazole-5-carboxamide (0.29 g, 66%) as a yellow semi solid. MS (ESI) m/e [M+H+1]$^+$/RT (min)/%: 422.00/3.7/95.9%. $^1$H NMR (400 MHz, DMSO-d$_6$) δ 0.80 (d, J=6.4 Hz, 6H), 1.14-1.24 (m, 2H), 1.42-1.61 (m, 3H), 2.89 (d, J=6.4 Hz, 2H), 4.06-4.14 (m, 1H), 6.95 (t, J=7.4 Hz, 1H), 7.04 (t, J=7.4 Hz, 1H), 7.12 (s, 1H), 7.31 (d, J=8.1 Hz, 1H), 7.56 (d, J=7.4 Hz, 1H), 8.21 (s, 1H), 8.50 (d, J=8.8 Hz, 1H), 10.77 (s, 1H).

Step 4

To a solution of N-(1-(1H-indol-3-yl)-5-methylhexan-2-yl)-2-bromothiazole-5-carboxamide (0.28 g, 0.66 mmol) and 1-methylpiperazine (0.10 g, 0.99 mmol) in CH$_3$CN (5 mL) was added K$_2$CO$_3$ (0.27 g, 1.90 mmol), and the reaction mixture was heated at 80° C. for 16 h. The reaction mixture was concentrated in vacuo. The residue was diluted with H$_2$O (20 mL) and extracted with 10% MeOH in DCM (3×20 mL). The organic layer was separated, dried over anhydrous Na$_2$SO$_4$ and concentrated in vacuo. The crude obtained was purified by column chromatography (silica 230-400 mesh, 2 to 10% MeOH in DCM) and triturated with pentane (2×10 mL) to afford N-(1-(1H-indol-3-yl)-5-methylhexan-2-yl)-2-(4-methylpiperazin-1-yl)thiazole-5-carboxamide (0.175 g, 60%) as a white solid. HPLC Purity: 99.8%. MS (ESI) m/e [M+H]$^+$/RT (min)/%: 440.00/2.25/99.7%. $^1$H NMR (400 MHz, DMSO-d$_6$) δ 0.80 (d, J=6.0 Hz, 6H), 1.26-1.15 (m, 2H), 1.57-1.40 (m, 3H), 2.22 (s, 3H), 2.40-2.48 (m, 4H), 2.94-2.77 (m, 2H), 3.42-3.42 (m, 4H), 4.02-4.16 (m, 1H), 6.95 (t, J=7.4 Hz, 1H), 7.04 (t, J=7.4 Hz, 1H), 7.12 (s, 1H), 7.31 (d, J=8.0 Hz, 1H), 7.57 (d, J=7.8 Hz, 1H), 7.80 (s, 1H), 7.94 (d, J=8.6 Hz, 1H), 10.75 (s, 1H).

Example 15: N-(1-Cyclopentyl-2-(1H-indol-3-yl)
ethyl)-2-(4-methylpiperazin-1-yl)thiazole-5-carbox-
amide

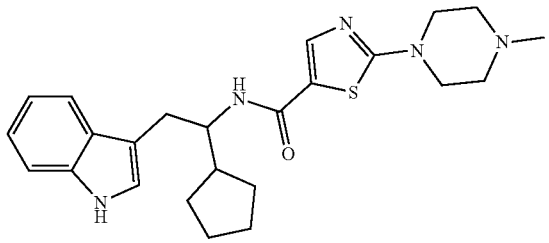 [SMILES: CN1CCN(c2ncc(C(=O)NC(Cc3c[nH]c4ccccc34)C3CCCC3)s2)CC1]

Step 1. Synthesis of
1-cyclopentyl-2-(1H-indol-3-yl)ethan-1-one

To a solution of 3-methylindole (0.20 g, 1.52 mmol) in dichloroethane (3 mL) was added AlCl$_3$ (0.95 g, 4.50 mmol) at 0° C. The reaction mixture was stirred at room temperature for 30 min. The reaction mixture was cooled to 0° C. followed by dropwise addition of cyclopentanecarbonyl chloride (0.27 g, 2.00 mmol). The reaction mixture was stirred at room temperature for 16 h. The reaction mixture was quenched with ice and extracted with DCM (3×25 mL). The organic layer was separated, dried over anhydrous Na$_2$SO$_4$ and concentrated in vacuo. The crude obtained was purified by column chromatography (silica 100-200 mesh, 1 to 10% EtOAc in hexanes) to afford 1-cyclopentyl-2-(1H-indol-3-yl)ethan-1-one (0.17 g, 50%) as a brown liquid. MS (ESI) m/e [M+H]$^+$/RT (min)/%: 228.00/3.4/89.9%. $^1$H NMR (400 MHz, DMSO-d6) δ 1.44-1.80 (m, 8H), 3.08-2.99 (m, 1H), 3.84 (s, 2H), 6.97 (t, J=7.0 Hz, 1H), 7.06 (t, J=7.0 Hz, 1H), 7.22 (s, 1H), 7.37 (d, J=7.8 Hz, 1H), 7.42 (d, J=7.8 Hz, 1H), 10.92 (s, 1H).

Step 2. Synthesis of
1-Cyclopentyl-2-(1H-Indol-3-Yl) Ethan-1-Amine
Hydrochloride To a solution of 1-cyclopentyl-2-(1H-indol-3-yl)ethan-1-one (0.17 g, 0.74 mmol) in MeOH (10 mL) was added NH$_4$OAc (0.49 g, 5.76 mmol), and the reaction mixture was stirred at 50° C. for 10 min. NaBH$_3$CN (0.06 g, 0.96 mmol) was added portion-wise, and the reaction mixture was heated to reflux for 16 h. The reaction mixture was quenched with 3 N HCl (10 mL) and filtered. The crude obtained was washed with hexanes (10 mL) and dried in vacuo to afford 1-cyclopentyl-2-(1H-indol-3-yl) ethan-1-amine hydrochloride (0.13 g, 77%) as an off-white solid. MS (ESI) m/e [M+H]$^+$/RT (min)/%: 229.00/3.7/84.0%. $^1$H NMR (400 MHz, DMSO-d$_6$) δ 1.24-1.82 (m, 8H), 1.98-2.06 (m, 1H), 3.09-2.92 (m, 2H), 3.34-3.28 (m, 1H), 6.94 (t, J=7.0 Hz, 1H), 7.01 (t, J=7.2 Hz, 1H), 7.28 (s, 1H), 7.36 (d, J=7.6 Hz, 1H), 7.57 (d, J=7.6 Hz, 1H), 7.81 (s, 2H), 11.03 (s, 1H).

Step 3. Synthesis of 2-bromo-N-(1-cyclopentyl-2-(1H-indol-3-yl)ethyl)thiazole-5-carboxamide To a solution of 1-cyclopentyl-2-(1H-indol-3-yl) ethan-1-amine hydrochloride (0.40 g, 2.43 mmol) and 2-bromothiazole-5-carboxylic acid (0.60 g, 2.91 mmol) in DMF (20 mL) was added Mukaiyama reagent (1.05 g, 4.13 mmol) followed by addition of DIPEA (1.56 g, 12.1 mmol). The reaction mixture was stirred at room temperature for 6 h. The reaction mixture was diluted with H$_2$O (100 mL) and extracted with DCM (3×25 mL). The organic layer was separated, dried over anhydrous Na$_2$SO$_4$ and concentrated in vacuo. The crude obtained was purified by column chromatography (silica 100-200 mesh, 1 to 10% MeOH in DCM) and triturated with Et$_2$O (5 mL) and pentane (5 mL) to afford 2-bromo-N-(1-cyclopentyl-2-(1H-indol-3-yl)ethyl)thiazole-5-carboxamide (0.155 g, 15%) as an off-white solid. MS (ESI) m/e [M+H]$^+$/RT (min)/%: 419.65/3.6/78.1%. $^1$H NMR (400 MHz, DMSO-d$_6$) δ 1.20-1.80 (m, 8H), 2.02-2.12 (m, 1H), 2.80-3.01 (m, 2H), 4.02-4.14 (m, 1H), 7.01 (t, J=7.2 Hz, 1H), 6.94 (t, J=7.0 Hz, 1H), 7.12 (s, 1H), 7.29 (d, J=7.7 Hz, 1H), 7.51 (d, J=7.8 Hz, 1H), 8.19 (s, 1H), 8.44 (d, J=8.6 Hz, 1H), 10.72 (s, 1H).

Step 4

To a solution of 2-bromo-N-(1-cyclopentyl-2-(1H-indol-3-yl)ethyl)thiazole-5-carboxamide (0.15 g, 0.35 mmol) and 1-methylpiperazine (0.04 g, 0.43 mmol) in CH$_3$CN (3 mL) was added K$_2$CO$_3$ (0.15 g, 1.07 mmol) and the reaction mixture was heated at 80° C. for 16 h. The reaction mixture was concentrated in vacuo. The residue was diluted with H$_2$O (10 mL) and extracted with 10% MeOH in DCM (3×10 mL). The organic layer was separated, dried over anhydrous Na$_2$SO$_4$ and concentrated in vacuo. The crude obtained was purified by column chromatography (silica 230-400 mesh, 2 to 4% MeOH in DCM) and dissolved in DCM (1 drop) and reprecipitated with pentane (10 mL) to afford N-(1-cyclopentyl-2-(1H-indol-3-yl)ethyl)-2-(4-methylpiperazin-1-yl)thiazole-5-carboxamide (0.07 g, 44%) as a white solid. HPLC Purity: 97.3%. MS (ESI) m/e [M+H]$^+$/RT (min)/%: 438.00/2.71/98.4%. $^1$H NMR (400 MHz, DMSO-d$_6$) δ 1.21-1.82 (m, 8H), 2.08-1.99 (m, 1H), 2.21 (s, 3H), 2.36-2.44 (m, 4H), 2.83-3.01 (m, 2H), 3.40-3.48 (m, 4H), 4.02-4.14 (m, 1H), 6.94 (t, J=7.4 Hz, 1H), 7.04 (t, J=7.4 Hz, 1H), 7.12 (s, 1H), 7.29 (d, J=8.1 Hz, 1H), 7.51 (d, J=7.8 Hz, 1H), 7.79 (s, 1H), 7.89 (d, J=8.8 Hz, 1H), 10.71 (s, 1H).

Example 16: N-(2-(1H-Indol-3-yl)ethyl)-N-butyl-2-(4-methylpiperazin-1-yl)thiazole-5-carboxamide

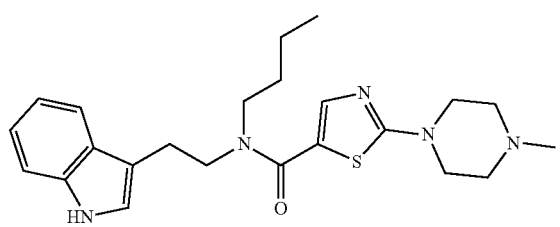 [SMILES: CCCCN(CCc1c[nH]c2ccccc12)C(=O)c1cnc(N2CCN(C)CC2)s1]

Step 1: Synthesis of 2-(1H-indol-3-yl)acetaldehyde

To a solution of 2-(1H-indol-3-yl)ethan-1-ol (1.00 g, 6.20 mmol) in CH$_3$CN (25 mL) was added 2-iodoxybenzoic acid (0.52 g, 18.0 mmol). The reaction mixture was heated at 80° C. for 3 h. The reaction mixture was filtered through a pad of diatomaceous earth, washing with CH$_3$CN (10 mL). The filtrate was concentrated in vacuo to afford 2-(1H-indol-3-yl) acetaldehyde (0.90 g, 91%) as a brown semi solid. This compound was used as such for the next reaction without further purification.

Step 2: Synthesis of N-(2-(1H-indol-3-yl)ethyl)butan-1-amine

To a solution of 2-(1H-indol-3-yl)acetaldehyde (0.90 g, 5.60 mmol) in MeOH (20 mL) was added nBuNH$_2$ (0.83 g, 11.0 mmol), and the reaction mixture was stirred at room temperature for 10 min. NaBH$_3$CN (0.70 g, 11.0 mmol) was added portion wise, and the reaction mixture was heated at reflux for 16 h. The reaction mixture was diluted with 3 N HCl (10 mL) and decanted. The crude product obtained was purified by triturating with hexanes (10 mL) and Et$_2$O (10 mL) to afford N-(2-(1H-indol-3-yl)ethyl)butan-1-amine (0.59 g, 48%) as an off-white solid. MS (ESI) m/e [M+]$^+$/RT (min)/%: 216.00/2.77/44.5%. $^1$H NMR (400 MHz, DMSO-d$_6$) δ 0.86 (t, J=7.2 Hz, 3H), 1.22-1.42 (m, 4H), 1.80 (brs, 1H), 2.55 (t, J=6.9 Hz, 2H), 2.76-2.84 (m, 4H), 6.96 (t, J=7.4 Hz, 1H), 7.05 (t, J=7.4 Hz, 1H), 7.12 (d, J=2.0 Hz, 1H), 7.32 (d, J=8.1 Hz, 1H), 7.50 (d, J=7.8 Hz, 1H), 10.77 (s, 1H).

Step 3: Synthesis of N-(2-(1H-indol-3-yl)ethyl)-2-bromo-N-butylthiazole-5-carboxamide To a solution of N-(2-(1H-indol-3-yl)ethyl)butan-1-amine (0.50 g, 2.31 mmol) and 2-bromothiazole-5-carboxylic acid (0.58 g, 2.77 mmol) in DMF (30 mL) was added Mukaiyama reagent (1.00 g, 3.93 mmol) followed by N,N-diisopropylethylamine (0.89 g, 6.94 mmol). The reaction mixture was stirred at room temperature for 16 h. The reaction mixture was diluted with H$_2$O (100 mL) and extracted with DCM (3×50 mL). The organic layer was separated, washed with brine (50 mL), dried over anhydrous Na$_2$SO$_4$ and concentrated in vacuo. The crude obtained was purified by column chromatography (silica 230-400 mesh, 1 to 10% MeOH in DCM) and triturating with Et$_2$O (10 mL) and pentane (10 mL) to afford N-(2-(1H-indol-3-yl)ethyl)-2-bromo-N-butylthiazole-5-carboxamide (0.60 g, 64%) as an off-white solid. MS (ESI) m/e [M+H+1]$^+$/RT (min)/%: 407.6/3.58/97.0%.

Step 4

To a solution of N-(2-(1H-indol-3-yl)ethyl)-2-bromo-N-butylthiazole-5-carboxamide (0.20 g, 0.49 mmol) and N-methylpiperazine (0.07 g, 0.73 mmol) in CH$_3$CN (4 mL) was added K$_2$CO$_3$ (0.20 g, 1.47 mmol), and the reaction mixture was heated at 80° C. for 16 h. The reaction mixture was concentrated in vacuo. The residue was diluted with H$_2$O (20 mL) and extracted with 10% MeOH in DCM (3×20 mL). The organic layer was separated, dried over anhydrous Na$_2$SO$_4$ and concentrated in vacuo. The crude obtained was purified by column chromatography (silica 230-400 mesh, 0.5 to 3.5% MeOH in DCM) and triturated with pentane (10 mL) to afford N-(2-(1H-indol-3-yl)ethyl)-N-butyl-2-(4-methylpiperazin-1-yl)thiazole-5-carboxamide (0.08 g, 38%) as an off-white solid. HPLC Purity: 99.6%. MS (ESI) m/e

[M+H]⁺/RT (min)/%: 426.00/2.66/99.2%. ¹H NMR (400 MHz, DMSO-d₆) δ 0.88 (t, J=7.3 Hz, 3H), 1.28 (m, 2H), 1.55 (m, 2H), 2.22 (s, 3H), 2.44-2.36 (m, 4H), 3.02-2.94 (m, 2H), 3.48-3.40 (m, 6H), 3.64-3.76 (m, 2H), 6.97 (t, J=7.4 Hz, 1H), 7.06 (t, J=7.5 Hz, 1H), 7.18 (d, J=1.9 Hz, 1H), 7.33 (d, J=8.1 Hz, 1H), 7.44 (s, 1H), 7.53 (d, J=7.7 Hz, 1H), 10.85 (s, 1H).

Example 17: N-(1-(1H-Indol-3-yl)hexan-2-yl)-2-(3-(difluoromethyl)-4-methylpiperazin-1-yl)thiazole-5-carboxamide

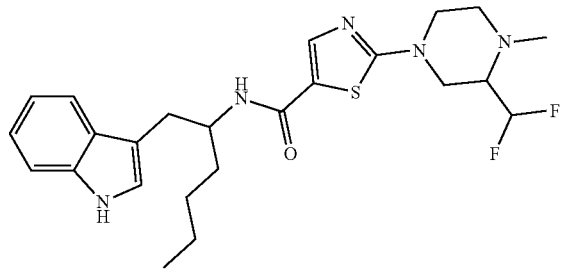 [SMILES: CCCCC(Cc1c[nH]c2ccccc12)NC(=O)c1cnc(N2CCN(C)C(C(F)F)C2)s1]

Step 1: Synthesis of 1-(tert-butyl) 3-methyl 4-methylpiperazine-1,3-dicarboxylate To a solution of KOH (24.0 g, 422 mmol) in H₂O (80 mL) was added Et₂O (200 mL) at 0° C. followed by addition of N-nitroso-N-methylurea (12.0 g, 116 mmol) portion-wise at 0° C. The reaction mixture was stirred at same temperature for 10 min. The separated Et₂O layer was added to a solution of 4-(tert-butoxycarbonyl)piperazine-2-carboxylic acid (4.00 g, 17.3 mmol) in Et₂O (200 mL) at 0° C. The reaction mixture was stirred at room temperature for 16 h. The reaction mixture was quenched with ice H₂O (25 mL) and extracted with Et₂O (3×50 mL). The organic layer was separated, dried over anhydrous Na₂SO₄ and concentrated in vacuo. The crude obtained was purified by column chromatography (silica 100-200 mesh, 5 to 40% EtOAc in hexanes) to afford 1-(tert-butyl) 3-methyl 4-methylpiperazine-1,3-dicarboxylate (2.50 g, 45%) as a yellow liquid. ¹H NMR (400 MHz, DMSO-d₆) δ 1.40 (s, 9H), 2.25 (s, 3H), 2.84-2.96 (m, 2H), 3.00-3.10 (m, 1H), 3.34-3.40 (m, 1H), 3.42-3.52 (m, 2H), 3.63 (s, 3H), 4.02-4.16 (m, 1H).

Step 2: Synthesis of tert-butyl 3-formyl-4-methylpiperazine-1-carboxylate

To a solution of 1-(tert-butyl) 3-methyl 4-methylpiperazine-1,3-dicarboxylate (1.30 g, 5.03 mmol) in toluene (25 mL) was added diisobutylaluminum hydride (12.6 mL, 12.6 mmol) dropwise over 30 min at −78° C. The reaction mixture was stirred at same temperature for 1 h. The reaction mixture was quenched with saturated NH₄Cl (15 mL) and extracted with 10% MeOH in DCM (3×30 mL). The organic layer was separated, dried over anhydrous sodium sulphate and concentrated in vacuo. The crude obtained was purified by column chromatography (basic alumina, 0.5% to 1% MeOH in DCM) to afford tert-butyl 3-formyl-4-methylpiperazine-1-carboxylate (0.68 g, 60%) as a brown liquid. ¹H NMR (400 MHz, Chloroform-d) δ 1.46 (s, 9H), 2.37 (s, 3H), 3.01-2.85 (m, 4H), 3.14-3.03 (m, 1H), 3.52-3.40 (m, 1H), 3.84-3.92 (m, 1H), 9.61 (s, 1H).

Step 3: Synthesis of tert-butyl 3-(difluoromethyl)-4-methylpiperazine-1-carboxylate To a solution of diethylaminosulfur trifluoride (1.14 g, 7.12 mmol) in DCM (20 mL) was added tert-butyl 3-formyl-4-methylpiperazine-1-carboxylate (0.65 g, 2.85 mmol) solution in DCM (20 mL) at −78° C. The reaction mixture was stirred at −78° C. for 1 h and at room temperature for 16 h. The reaction mixture was poured in to saturated NaHCO₃ (20 mL) solution and extracted with DCM (3×25 mL). The organic layer was separated, dried over anhydrous Na₂SO₄ and concentrated in vacuo. The crude obtained was purified by column chromatography (basic alumina, 1 to 2% MeOH in DCM) to afford tert-butyl 3-(difluoromethyl)-4-methylpiperazine-1-carboxylate (0.35 g, 49%) as a brown liquid. ¹H NMR (400 MHz, DMSO-d₆) δ 1.39 (s, 9H), 2.32 (s, 3H), 3.01-2.85 (m, 4H), 3.14-3.03 (m, 1H), 3.52-3.40 (m, 1H), 3.76-3.84 (m, 1H), 6.30 (t, J=54.0 Hz, 1H).

Step 4: Synthesis of 2-(difluoromethyl)-1-methylpiperazine

To a solution of tert-butyl 3-(difluoromethyl)-4-methylpiperazine-1-carboxylate (0.35 g, 1.40 mmol) in dioxane (10 mL) was added 4 M HCl in dioxane (20 mL) at 0° C. The reaction mixture was stirred at room temperature for 30 min. The reaction mixture was concentrated in vacuo. The crude obtained was purified by triturating with pentane (2×10 mL) at 0° C. to afford 2-(difluoromethyl)-1-methylpiperazine (0.20 g, 76%) as a brown solid.

Step 5

To a solution of N-(1-(1H-indol-3-yl)hexan-2-yl)-2-bromothiazole-5-carboxamide (0.20 g, 0.49 mmol) and 2-(difluoromethyl)-1-methylpiperazine (0.10 g, 0.58 mmol) in CH₃CN (4 mL) was added K₂CO₃ (0.27 g, 1.96 mmol) followed by addition of tetrabutylammonium bromide (0.002 g, 0.05 mmol). The reaction mixture was heated in sealed tube at 80° C. for 48 h. The reaction mixture was concentrated in vacuo. The residue was diluted with H₂O (5 mL) and extracted with DCM (3×10 mL). The organic layer was separated, dried over anhydrous Na₂SO₄ and concentrated in vacuo. The crude obtained was purified by preparative HPLC to afford N-(1-(1H-indol-3-yl)hexan-2-yl)-2-(3-(difluoromethyl)-4-methylpiperazin-1-yl)thiazole-5-carboxamide (0.05 g, 23%) as a white solid. HPLC Purity: 96.6%. MS (ESI) m/e [M+H]⁺/RT (min)/%: 476.00/2.58/98.8%. ¹H NMR (400 MHz, DMSO-d₆) δ 0.82 (t, J=7.3 Hz, 3H), 1.16-1.60 (m, 6H), 2.37 (s, 3H), 2.60-2.72 (m, 2H), 2.80-2.96 (m, 3H), 3.20-3.38 (m, 2H), 3.60-3.50 (m, 1H), 3.83 (d, J=12.4 Hz, 1H), 4.08-4.20 (m, 1H), 6.30 (t, J=54.0 Hz, 1H), 7.03-6.94 (m, 2H), 7.09 (s, 1H), 7.30 (d, J=7.8 Hz, 1H), 7.56 (d, J=7.3 Hz, 1H), 7.81 (s, 1H), 7.97 (d, J=7.8 Hz, 1H), 10.75 (s, 1H).

Example 18: N-(1-(1H-Indol-3-yl)hexan-2-yl)-2-(3-(fluoromethyl)-4-methylpiperazin-1-yl)thiazole-5-carboxamide

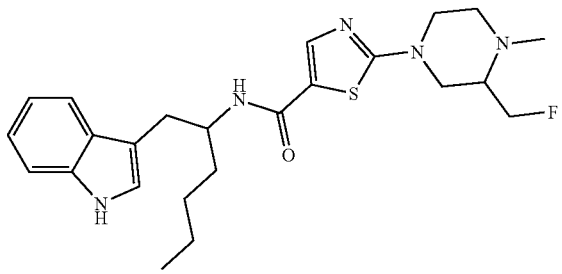 [SMILES: CCCCC(Cc1c[nH]c2ccccc12)NC(=O)c1cnc(N2CCN(C)C(CF)C2)s1]

Step 1: Synthesis of tert-butyl 3-(fluoromethyl)-4-methylpiperazine-1-carboxylate To a solution of tert-butyl 3-(hydroxymethyl)-4-methylpiperazine-1-carboxylate (0.70 g, 3.00 mmol) in DCM (25 mL) was added diethylaminosulfur trifluoride (0.59 g, 3.60 mmol) dropwise at 0° C. The reaction mixture was heated at 45° C. for 16 h. The reaction mixture was quenched with saturated NaHCO$_3$ (20 mL) solution. The organic layer was separated, washed with brine (20 mL), dried over anhydrous Na$_2$SO$_4$ and concentrated in vacuo. The crude obtained was purified by column chromatography (silica 100-200 mesh, 1-10% EtOAc in hexanes) to afford tert-butyl 3-(fluoromethyl)-4-methylpiperazine-1-carboxylate (0.50 g, 71%) as a white solid. This compound was used as such for the next reaction without further purification and analysis.

Step 2: Synthesis of 2-(fluoromethyl)-1-methylpiperazine

To a solution of tert-butyl 3-(fluoromethyl)-4-methylpiperazine-1-carboxylate (0.50 g, 2.15 mmol) in dioxane (10 mL) was added dioxane*HCl (15 mL) at 0° C. and the reaction mixture was stirred at room temperature for 16 h. The reaction mixture was cooled to 10° C. and filtered. The crude obtained was washed with DCM (10 mL) and dried in vacuo to afford 2-(fluoromethyl)-1-methylpiperazine (0.15 g, 38%) as an off-white semisolid. MS (ESI) m/e [M+H]$^+$/RT (min)/%: 132.90/1.3/73.6%.

Step 3

To a solution of 2-(fluoromethyl)-1-methylpiperazine (0.09 g, 0.53 mmol) and N-(1-(1H-indol-3-yl)hexan-2-yl)-2-bromothiazole-5-carboxamide (0.20 g, 0.49 mmol) in CH$_3$CN (4.5 mL) was added K$_2$CO$_3$ (0.20 g, 1.47 mmol) and the reaction mixture was heated at 80° C. for 16 h. The reaction mixture was concentrated in vacuo. The residue was diluted with H$_2$O (10 mL) and extracted with 10% MeOH in DCM (10 mL). The organic layer was separated, dried over anhydrous Na$_2$SO$_4$ and concentrated in vacuo. The crude obtained was purified by column chromatography (silica 230-400 mesh, 0.5 to 3.5% MeOH in DCM) and triturating with pentane (10 mL) to afford N-(1-(1H-indol-3-yl)hexan-2-yl)-2-(3-(fluoromethyl)-4-methylpiperazin-1-yl)thiazole-5-carboxamide (0.115 g, 51%) as a yellow solid. HPLC Purity: 98.7%. MS (ESI) m/e [M+H]$^+$/RT (min)/%: 458.00/2.76/99.4%. $^1$H NMR (400 MHz, DMSO-d$_6$) δ 0.81 (t, J=6.9 Hz, 3H), 1.18-1.50 (m, 6H), 2.30 (s, 3H), 2.32-2.40 (m, 2H), 2.75-2.91 (m, 3H), 3.01 (t, J=11.2 Hz, 1H), 3.17 (t, J=11.5 Hz, 1H), 3.69 (d, J=12.2 Hz, 1H), 3.85 (d, J=12.2 Hz, 1H), 4.11 (brs, 1H), 4.48-4.64 (m, 2H), 6.92-7.00 (m, 1H), 7.04 (t, J=7.1 Hz, 1H), 7.09 (brs, 1H), 7.31 (d, J=7.3 Hz, 1H), 7.57 (d, J=7.8 Hz, 1H), 7.81 (s, 1H), 7.96 (d, J=8.3 Hz, 1H), 10.75 (brs, 1H).

Example 19: N-(1-(1H-Indol-3-yl)hexan-2-yl)-2-(8-methyl-3,8-diazabicyclo[3.2.1]octan-3-yl)thiazole-5-carboxamide

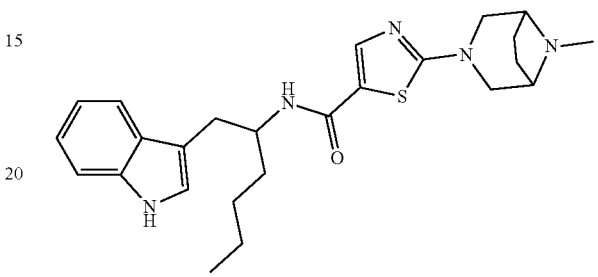

Step 1: Synthesis of methyl 5-oxopyrrolidine-2-carboxylate

To a solution of 5-oxopyrrolidine-2-carboxylic acid (9.00 g, 69.7 mmol) in MeOH (20 mL) was added SOCl$_2$ (6.60 mL, 90.6 mmol) at 0° C. The reaction mixture was stirred at room temperature for 16 h. The reaction mixture was concentrated in vacuo. The residue was diluted with H$_2$O (100 mL) and extracted with EtOAc (100 mL). The organic layer was separated, washed with H$_2$O (20 mL) and brine (50 mL), dried over anhydrous Na$_2$SO$_4$ and concentrated in vacuo to afford methyl 5-oxopyrrolidine-2-carboxylate (5.60 g, 58%) as a colorless liquid. This compound was used as such for the next reaction without further purification. MS (ESI) m/e [M+]/RT (min)/%: 144.00/1.33/68.6%. $^1$H NMR (400 MHz, DMSO-d$_6$) δ 2.04-2.18 (m, 2H), 3.56-3.62 (m, 2H), 3.70 (s, 3H), 4.16-4.22 (m, 1H), 7.97 (s, 1H).

Step 2: Synthesis of methyl 1-methyl-5-oxopyrrolidine-2-carboxylate

To a solution of methyl 5-oxopyrrolidine-2-carboxylate (4.50 g, 31.4 mmol) in 1,2-dimethoxyethane (40 mL) was added H$_2$O (0.21 mL, 11.0 mmol), triethylamine (0.44 mL, 3.10 mmol) and K$_2$CO$_3$ (7.80 g, 50.6 mmol) followed by addition of dimethyl sulfate (7.13 g, 56.6 mmol) at 20° C. The reaction mixture was stirred at room temperature for 16 h. The reaction mixture was filtered and washed with 1,2-dimethoxyethane (200 mL). The filtrate was concentrated in vacuo below 40° C. The crude obtained was purified by column chromatography (silica 230-400 mesh, 2% MeOH in DCM) to afford methyl 1-methyl-5-oxopyrrolidine-2-carboxylate (3.85 g, 71%) as a colorless liquid. MS (ESI) m/e [M+]$^+$/RT (min)/%: 158.00/1.49/85.0%. $^1$H NMR (400 MHz, DMSO-d$_6$) δ 2.18-2.38 (m, 4H), 2.49 (s, 3H), 3.76 (s, 3H), 4.28-4.20 (m, 1H).

Step 3: Synthesis of methyl 1-methyl-5-thioxopyrrolidine-2-carboxylate

To a solution of methyl 1-methyl-5-oxopyrrolidine-2-carboxylate (3.80 g, 24.2 mmol) in THF (40 mL) was added 2,4-bis(4-methoxyphenyl)-1,3,2,4-dithiadiphosphetane-2,4-disulfide (Lawesson's reagent; 7.30 g, 18.0 mmol). The reaction mixture was stirred at room temperature for 16 h. The reaction mixture was quenched with saturated NaHCO$_3$ (100 mL) and extracted with EtOAc (2×100 mL). The organic layer was separated, dried over anhydrous Na$_2$SO$_4$ and concentrated in vacuo below 40° C. The crude obtained was purified by column chromatography (silica 100-200 mesh, 1% MeOH in DCM) to afford methyl 1-methyl-5-thioxopyrrolidine-2-carboxylate (2.55 g, 61%) as a yellow solid. MS (ESI) m/e [M+H+1]$^+$/RT (min)/%: 174.00/2.01/99.9%. $^1$H NMR (400 MHz, DMSO-d$_6$) δ 2.00-2.12 (m, 1H), 2.45-2.32 (m, 1H), 2.82-2.96 (m, 2H), 3.14 (s, 3H), 3.76 (s, 3H), 4.75 (d, J=7.7 Hz, 1H).

Step 4: Synthesis of 5-mesityl-2-(methoxycarbonyl)-1-methyl-3,4-dihydro-2H-pyrrol-1-ium iodide To a solution of methyl 1-methyl-5-thioxopyrrolidine-2-carboxylate (2.50 g, 14.4 mmol) in toluene (10 mL) was added CH$_3$I (15 mL). The reaction mixture was stirred at room temperature for 16 h. The reaction mixture was concentrated in vacuo. The crude obtained was purified by triturating with toluene (10 mL) and pentane (10 mL) to afford 5-mesityl-2-(methoxycarbonyl)-1-methyl-3,4-dihydro-2H-pyrrol-1-ium iodide (3.20 g crude) as yellow semi solid. $^1$H NMR (400 MHz, DMSO-d$_6$) δ 2.32-2.40 (m, 1H), 2.44 (s, 3H), 2.58-2.64 (m, 1H), 2.89 (s, 3H), 3.51-3.60 (m, 2H), 3.77 (s, 3H), 5.23 (d, J=7.6 Hz, 1H).

Step 5: Synthesis of methyl (E)-1-methyl-5-(nitromethylene)pyrrolidine-2-carboxylate To a solution of 5-mesityl-2-(methoxycarbonyl)-1-methyl-3,4-dihydro-2H-pyrrol-1-ium iodide (3.18 g, 15.9 mmol) in DMF (30 mL) was added triethylamine (2.40 mL, 17.5 mmol) followed by dropwise addition of CH$_3$NO$_2$ (6.37 mL, 118 mmol). The reaction mixture was stirred at room temperature for 16 h. The reaction mixture was concentrated in vacuo. The crude obtained was purified by column chromatography (silica 100-200 mesh, 1% MeOH in DCM) to afford methyl (E)-1-methyl-5-(nitromethylene)pyrrolidine-2-carboxylate (0.70 g, 21%) as a light yellow solid. MS (ESI) m/e [M+H+1]$^+$/RT (min)/%: 200.8/1.97/97.6%. $^1$H NMR (400 MHz, Chloroform-d) δ 2.18-2.26 (m, 1H), 2.36-2.44 (m, 1H), 2.89 (s, 3H), 3.28-3.40 (m, 1H), 3.68-3.56 (m, 1H), 3.79 (s, 3H), 4.33-4.26 (m, 1H), 6.72 (s, 1H).

Step 6: Synthesis of 8-methyl-3,8-diazabicyclo[3.2.1]octan-2-one

To a solution of methyl (E)-1-methyl-5-(nitromethylene)pyrrolidine-2-carboxylate (0.70 g, 3.50 mmol) in MeOH (30 mL) was added Pd/C (0.70 g). The reaction mixture was stirred at room temperature under hydrogen pressure for 24 h. The reaction mixture was filtered through a pad of diatomaceous earth, washing with MeOH (10 mL). The filtrate was concentrated in vacuo to afford 8-methyl-3,8-diazabicyclo[3.2.1]octan-2-one (0.35 g crude) as a yellow liquid. This compound was used as such for the next reaction without further purification. MS (ESI) m/e [M+H+1]$^+$/RT (min)/%: 141.00/1.19/84.6%. $^1$H NMR (400 MHz, Chloroform-d) 1.69-1.86 (m, 2H), 2.16-2.24 (m, 2H), 2.49 (s, 3H), 2.97 (d, J=11.3 Hz, 3H), 3.32-3.40 (m, 2H), 3.74-3.63 (m, 1H), 5.63 (s, 1H).

Step 7: Synthesis of 8-methyl-3,8-diazabicyclo[3.2.1]octane

To a solution of 8-methyl-3,8-diazabicyclo[3.2.1]octan-2-one (0.35 g, 2.50 mmol) in THF (4 mL) was added 1 M lithium aluminum hydride solution in THF (4 mL) at 0° C. The reaction mixture was stirred at 0° C. for 1 h and then heated at 50° C. for 6 h. The reaction mixture was quenched with aqueous potassium sodium tartrate (4 mL) solution and filtered. The crude obtained washed with THF (4 mL) to afford 8-methyl-3,8-diazabicyclo[3.2.1]octane (0.18 g crude) as yellow liquid. MS (ESI) m/e [M+H+1]$^+$/RT (min)/%: 407.6/3.58/97.0%. $^1$H NMR (400 MHz, Chloroform-d) δ 1.74-1.63 (m, 4H), 2.24 (s, 3H), 2.60-2.64 (m, 2H), 2.98-3.04 (m, 4H).

Step 8

To a solution of N-(1-(1H-indol-3-yl)hexan-2-yl)-2-bromothiazole-5-carboxamide (0.20 g, 0.49 mmol) and 8-methyl-3,8-diazabicyclo[3.2.1]octane (0.07 g, 0.58 mmol) in CH$_3$CN (4 mL) was added K$_2$CO$_3$ (0.20 g, 1.47 mmol) and the reaction mixture was heated at 100° C. for 16 h. The reaction mixture was concentrated in vacuo. The residue was diluted with H$_2$O (10 mL) and extracted with DCM (3×10 mL). The organic layer was separated, dried over anhydrous Na$_2$SO$_4$ and concentrated in vacuo. The crude obtained was purified by column chromatography (silica 230-400 mesh, 0.5 to 3% MeOH in DCM) and triturating with pentane (10 mL) to afford N-(1-(1H-indol-3-yl)hexan-2-yl)-2-(8-methyl-3,8-diazabicyclo[3.2.1]octan-3-yl)thiazole-5-carboxamide (0.10 g, 45%) as an off-white solid. HPLC Purity: 99.0%. MS (ESI) m/e [M+H]$^+$/RT (min)/%: 452.00/2.62/99.0%. $^1$H NMR (400 MHz, DMSO-d$_6$) δ 0.82 (t, J=7.3 Hz, 3H), 1.16-1.40 (m, 4H), 1.42-1.60 (m, 4H), 1.92-1.98 (m, 2H), 2.23 (s, 3H), 2.80-2.92 (m, 2H), 3.12-3.22 (m, 4H), 3.46 (d, J=11.0 Hz, 2H), 4.06-4.16 (m, 1H), 6.96-7.04 (m, 2H), 7.11 (s, 1H), 7.31 (d, J=7.7 Hz, 1H), 7.57 (d, J=7.5 Hz, 1H), 7.79 (s, 1H), 7.90 (d, J=8.2 Hz, 1H), 10.74 (s, 1H).

Example 20: N-(2-(1H-Indol-3-yl)-1-phenylethyl)-2-(4-methylpiperazin-1-yl)thiazole-5-carboxamide

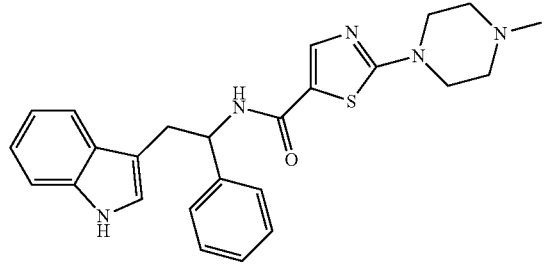 [SMILES: CN1CCN(c2ncc(C(=O)NC(Cc3c[nH]c4ccccc34)c3ccccc3)s2)CC1]

Step 1: Synthesis of 2-(1H-indol-3-yl)-N-methoxy-N-methylacetamide

To a solution of 2-(1H-indol-3-yl)acetic acid (9.00 g, 51.4 mmol) and N-methylmorpholine (5.19 g, 51.4 mmol) in THF (90 mL) was added isopropylchloroformate (56.4 mL, 56.5 mmol) solution in toluene drop wise at −20° C. and stirred at same temperature for 30 min. A suspension of N,O-dimethylhydroxylamine hydrochloride (7.38 g, 77.1 mmol) and triethylamine (6.00 g, 61.7 mmol) in DMF (5 mL) was added at 0° C., and the reaction mixture was stirred at 0° C. for 1 h. The reaction mixture was quenched with H₂O (20 mL) and extracted with EtOAc (2×150 mL). The organic layer was separated, dried over anhydrous Na₂SO₄ and concentrated in vacuo. The crude obtained was purified by column chromatography (silica 100-200 mesh, 1 to 2% MeOH in DCM) to afford 2-(1H-indol-3-yl)-N-methoxy-N-methylacetamide (8.00 g, 64%) as a brown solid. ¹H NMR (400 MHz, DMSO-d₆) δ 3.11 (s, 3H), 3.32 (s, 3H), 3.79 (s, 2H), 6.96 (t, J=7.1 Hz, 1H), 7.06 (t, J=7.1 Hz, 1H), 7.34 (d, J=8.1 Hz, 1H), 7.51 (d, J=7.9 Hz, 1H), 7.95 (s, 1H), 10.88 (s, 1H).

Step 2: Synthesis of N-methoxy-N-methyl-2-(1-(tetrahydro-2H-pyran-2-yl)-1H-indol-3-yl)acetamide To a solution of 2-(1H-indol-3-yl)-N-methoxy-N-methylacetamide (8.00 g, 36.8 mmol) in DCM (50 mL) was added 3,4-dihydro-2H-pyran (3.71 g, 44.2 mmol) at 0° C., and the reaction mixture was stirred at same temperature for 15 min. p-Toluenesulfonic acid (0.63 g, 3.68 mmol) was added, and the reaction mixture was stirred at room temperature for 16 h. The reaction mixture was extracted with DCM (3×20 mL). The organic layer was separated, dried over anhydrous Na₂SO₄ and concentrated in vacuo. The crude obtained was purified by column chromatography (silica 100-200 mesh, 0.5 to 2% MeOH in DCM) to afford N-methoxy-N-methyl-2-(1-(tetrahydro-2H-pyran-2-yl)-1H-indol-3-yl) acetamide (6.00 g, 54%) as a brown solid. ¹H NMR (400 MHz, Chloroform-d) δ 1.40-2.20 (m, 6H), 3.21 (s, 3H), 3.50-3.58 (m, 1H), 3.74 (t, J=10.8 Hz, 1H), 3.90 (s, 3H), 4.10 (s, 2H), 5.48 (d, J=9.9 Hz, 1H), 7.10-7.30 (m, 2H), 7.33 (s, 1H), 7.43 (d, J=7.8 Hz, 1H), 7.64 (d, J=7.5 Hz, 1H).

Step 3: Synthesis of 1-phenyl-2-(1-(tetrahydro-2H-pyran-2-yl)-1H-indol-3-yl)ethan-1-one To a solution of N-methoxy-N-methyl-2-(1-(tetrahydro-2H-pyran-2-yl)-1H-indol-3-yl)acetamide (6.00 g, 19.8 mmol) in THF (60 mL) was added PhMgBr (4.80 g, 39.6 mmol) dropwise at 0° C. The reaction mixture was stirred at room temperature for 16 h. The reaction mixture was quenched with saturated NH₄Cl (30 mL) and extracted with EtOAc (3×150 mL). The organic layer was separated, dried over anhydrous Na₂SO₄ and concentrated in vacuo. The crude obtained was purified by column chromatography (silica 100-200 mesh, 0 to 3% MeOH in DCM) to afford 1-phenyl-2-(1-(tetrahydro-2H-pyran-2-yl)-1H-indol-3-yl) ethan-1-one (5.00 g, 79%) as a light yellow liquid. ¹H NMR (400 MHz, Chloroform-d) δ 1.66-2.20 (m, 6H), 3.73 (t, J=10.8 Hz, 1H), 4.09 (d, J=11.0 Hz, 1H), 4.39 (s, 2H), 5.46 (d, J=9.9 Hz, 1H), 6.84 (d, J=7.3 Hz, 1H), 7.20-7.30 (m, 3H), 7.36-7.47 (m, 4H), 7.57 (dd, J=25.4, 7.1 Hz, 1H), 8.06 (d, J=7.2 Hz, 1H).

Step 4: Synthesis of 1-phenyl-2-(1-(tetrahydro-2H-pyran-2-yl)-1H-indol-3-yl)ethan-1-amine To a solution of 1-phenyl-2-(1-(tetrahydro-2H-pyran-2-yl)-1H-indol-3-yl)ethan-1-one (1.00 g, 3.13 mmol) in MeOH (10 mL) was added NH₄OAc (1.96 g, 31.3 mmol) and the reaction mixture was stirred at 0° C. for 10 min. NaBH₃CN (0.06 g, 0.96 mmol) was added portion-wise and the reaction mixture was heated at 60° C. for 5 h. The reaction mixture was quenched with H₂O (10 mL) and extracted with 10% MeOH in DCM. The organic layer was separated, dried over anhydrous Na₂SO₄ and concentrated in vacuo. The crude obtained was purified by column chromatography (silica 100-200 mesh, 1 to 3% MeOH in DCM) to afford 1-phenyl-2-(1-(tetrahydro-2H-pyran-2-yl)-1H-indol-3-yl)ethan-1-amine (0.60 g, 60%) as a brown liquid. MS (ESI) m/e [M+H]⁺/RT (min)/%: 321.00/3.3/59.1%.

Step 5: Synthesis of 2-bromo-N-(1-phenyl-2-(1-(tetrahydro-2H-pyran-2-yl)-1H-indol-3-yl)ethyl) thiazole-5-carboxamide To a solution of 1-phenyl-2-(1-(tetrahydro-2H-pyran-2-yl)-1H-indol-3-yl)ethan-1-amine (0.60 g, 1.87 mmol) and 2-bromothiazole-5-carboxylic acid (0.43 g, 2.06 mmol) in CH₃CN (8 mL) was added pyridine (0.44 g, 5.62 mmol) followed by addition of N-[(dimethylamino)-1H-1,2,3-triazolo-[4,5-b]pyridin-1-ylmethylene]-N-methylmethanaminium hexafluorophosphate N-oxide (HATU; 0.71 g, 1.87 mmol). The reaction mixture was heated at 80° C. for 16 h. The reaction mixture was concentrated in vacuo. The crude obtained was purified by column chromatography (silica 100-200 mesh, 2 to 3% MeOH in DCM) and triturating with pentane (2×5 mL) to afford 2-bromo-N-(1-phenyl-2-(1-(tetrahydro-2H-pyran-2-yl)-1H-indol-3-yl) ethyl)thiazole-5-carboxamide (0.40 g, 42%) as an off-white solid. ¹H NMR (400 MHz, DMSO-d₆) δ 1.44-1.60 (m, 2H), 1.68-1.84 (m, 2H), 1.86-1.98 (m, 2H), 3.14-3.22 (m, 2H), 3.62-3.74 (m, 1H), 3.80-3.94 (m, 1H), 5.20-5.28 (m, 1H), 5.52 (d, J=9.0 Hz, 1H), 7.00-7.22 (m, 2H), 7.36-7.23 (m, 4H), 7.44 (d, J=8.2 Hz, 3H), 7.63 (d, J=6.9 Hz, 1H), 8.28 (d, J=5.4 Hz, 1H), 9.12 (d, J=7.3 Hz, 1H).

Step 6: Synthesis of 2-(4-methylpiperazin-1-yl)-N-(1-phenyl-2-(1-(tetrahydro-2H-pyran-2-yl)-1H-indol-3-yl)ethyl)thiazole-5-carboxamide To a solution of 2-bromo-N-(1-phenyl-2-(1-(tetrahydro-2H-pyran-2-yl)-1H-indol-3-yl)ethyl)thiazole-5-carboxamide (0.39 g, 0.76 mmol) and N-methylpiperazine (0.09 g, 0.91 mmol) in CH₃CN (5 mL) was added K₂CO₃ (0.26 g, 1.90 mmol), and the reaction mixture was heated in a sealed tube at 80° C. for 16 h. The reaction mixture was concentrated in vacuo. The residue was diluted with H₂O (10 mL) and extracted with 10% MeOH in DCM (3×20 mL). The organic layer was separated, dried over anhydrous Na₂SO₄ and concentrated in vacuo. The crude obtained was purified by column chromatography (silica 100-200 mesh, 2 to 10% MeOH in DCM) and triturating with pentane (2×5 mL) to afford 2-(4-methylpiperazin-1-yl)-N-(1-phenyl-2-(1-(tetrahydro-2H-pyran-2-yl)-1H-indol-3-yl)ethyl)thiazole-5-carboxamide (0.30 g, 72%) as an off-white solid. MS (ESI) m/e [M+H]⁺/RT (min)/%: 530.00/3.21/98.1%. ¹H NMR (400 MHz, DMSO-d₆) δ 1.50-1.98 (m, 6H), 2.19 (s, 3H), 2.34-2.40 (m, 4H), 3.10-3.20 (m, 2H), 3.40-3.44 (m, 4H), 3.64-3.74 (m, 1H), 3.84-3.94 (m, 1H), 5.16-5.24 (m, 1H), 5.53 (d, J=9.4 Hz, 1H), 5.74 (s, 1H), 7.14-7.01 (m, 2H), 7.24-7.31 (m, 3H), 7.38-7.50 (m, 3H), 7.62 (s, 1H), 7.89 (s, 1H), 8.56 (s, 1H).

Step 7

To a solution of 2-(4-methylpiperazin-1-yl)-N-(1-phenyl-2-(1-(tetrahydro-2H-pyran-2-yl)-1H-indol-3-yl)ethyl)thiazole-5-carboxamide (0.25 g, 0.47 mmol) in MeOH (2.5 mL) and H₂O (2.5 mL) was added concentrated HCl (0.25 mL) at 0° C., and the reaction mixture was heated at 50° C. for 2 h. The reaction mixture was concentrated in vacuo. The residue was diluted with saturated NaHCO₃ (10 mL) solution and extracted with 10% MeOH in DCM (3×10 mL). The organic layer was separated, dried over anhydrous Na₂SO₄ and concentrated in vacuo. The crude obtained was purified by column chromatography (silica 100-200 mesh, 2 to 4% MeOH in DCM) and triturating with pentane (3×2.5 mL) to afford N-(2-(1H-indol-3-yl)-1-phenylethyl)-2-(4-methylpiperazin-1-yl)thiazole-5-carboxamide (0.10 g, 63%) as an off-white solid. HPLC Purity: 99.6%. MS (ESI) m/e [M+H]⁺/RT (min)/%: 446.00/2.56/99.0%. ¹H NMR (400 MHz, DMSO-d₆) δ 2.19 (s, 3H), 2.37-2.44 (m, 4H), 3.26-3.09 (m, 2H), 3.40-3.48 (m, 4H), 5.19-5.25 (m, 1H), 6.92-7.09 (m, 3H), 7.23 (d, J=6.8 Hz, 1H), 7.28-7.38 (m, 3H), 7.41 (d, J=6.9 Hz, 2H), 7.60 (d, J=7.4 Hz, 1H), 7.89 (s, 1H), 8.56 (d, J=8.0 Hz, 1H), 10.72 (s, 1H).

Example 21. N-(2-(1H-indol-3-yl)ethyl)-N-methyl-2-(4-methylpiperazin-1-yl)thiazole-5-carboxamide

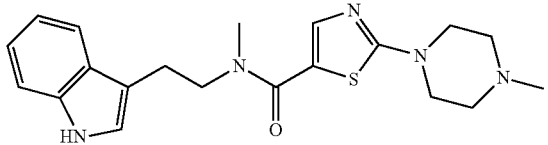 [SMILES: CN1CCN(c2ncc(C(=O)N(C)CCc3c[nH]c4ccccc34)s2)CC1]

Step 1. Synthesis of N-(2-(1H-indol-3-yl)ethyl)-2-bromo-N-methylthiazole-5-carboxamide To a solution of N-methyl-tryptamine (0.108 g, 0.47 mmol) and 2-bromothiazole-5-carboxylic acid (0.098 g, 0.47 mmol) in DMF (4.3 mL) was added HATU (0.182 g, 0.48 mmol) followed by addition of DIPEA (0.378 mL, 2.17 mmol). The reaction mixture was stirred at room temperature for 16 h. The reaction mixture was diluted with H₂O (20 mL) and extracted with DCM (3×20 mL). The organic layer was separated, dried over anhydrous Na₂SO₄ and concentrated in vacuo. The crude material was purified by column chromatography (silica, 0 to 10% methanol in dichloromethane) to give N-(2-(1H-indol-3-yl)ethyl)-2-bromo-N-methylthiazole-5-carboxamide (0.168 g, 98%) and used directly in the next reaction.

Step 2

To a solution of N-(2-(1H-indol-3-yl)ethyl)-2-bromo-N-methylthiazole-5-carboxamide (0.168 g, 0.46 mmol) and 1-methylpiperazine (0.102 mL, 0.92 mmol) in THF (1.8 mL) was added of DIPEA (0.161 mL, 0.92 mmol), and the reaction mixture was heated in a sealed tube at 170° C. for 45 min. The reaction mixture was concentrated in vacuo. The crude obtained was purified by column chromatography (silica, 0 to 5% methanol in dichloromethane) to give N-(2-(1H-indol-3-yl)ethyl)-N-methyl-2-(4-methylpiperazin-1-yl)thiazole-5-carboxamide (0.140 g, 79%) as a light yellow solid. ¹H NMR (500 MHz, CDCl₃) δ 8.09 (s, 1H), 7.62 (d, J=6.5 Hz, 1H), 7.42 (s, 1H), 7.36 (d, 1H, J=8.0 Hz), 7.19 (t, J=7.5 Hz, 1H), 7.11 (t, J=7.5 Hz, 1H), 7.03 (d, J=1.5 Hz, 1H), 3.83 (t, J=7.5 Hz, 2H), 3.54-3.62 (m, 4H), 3.14 (s, 3H), 3.19-3.09 (m, 2H), 2.52-2.50 (m, 4H), 2.35 (s, 3H). (ESMS⁺): 384.4, (ESMS⁻): 382.3.

Example 22. N-(1-(1H-indol-3-yl)hexan-2-yl)-2-(4-(2-(trifluoromethoxy)ethyl)piperazin-1-yl)thiazole-5-carboxamide

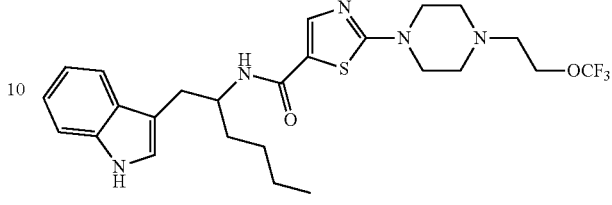

Step 1. Synthesis of 1-(4-benzylpiperazin-1-yl)-2-(trifluoromethoxy)ethan-1-one

To a solution of 2-(trifluoromethoxy)acetic acid (0.50 g, 3.47 mmol) in DMF (10 mL) was added HATU (1.71 g, 4.51 mmol). The reaction mixture was stirred at room temperature for 1 h followed by addition of 1-benzylpiperazine (0.67 g, 3.81 mmol) and TEA (1.70 g, 17.3 mmol). The reaction mixture was stirred at room temperature for 16 h. The reaction mixture was quenched with H₂O (100 mL) and extracted with Et₂O (2×100 mL). The organic layer was separated, washed with H₂O (3×50 mL), dried over anhydrous Na₂SO₄, and concentrated in vacuo. The crude obtained was purified by column chromatography (silica, 100-200 mesh, 0% to 0.5% MeOH in DCM) to afford 1-(4-benzylpiperazin-1-yl)-2-(trifluoromethoxy)ethan-1-one (0.65 g, 62%) as a light yellow solid. MS (ESI) m/e [M+H]⁺/Rt/%: 303.00/2.85/99.5%; 1H NMR (400 MHz, CDCl₃) δ 2.42-2.50 (m, 4H), 3.40-3.44 (m, 2H), 3.53 (s, 2H), 3.62-3.68 (m, 2H), 4.57 (s, 2H), 7.24-7.36 (m, 5H).

Step 2. Synthesis of 1-benzyl-4-(2-(trifluoromethoxy)ethyl)piperazine

To a solution of 1-(4-benzylpiperazin-1-yl)-2-(trifluoromethoxy)ethan-1-one (0.65 g, 2.15 mmol) in THF (7 mL) was added BH₃-DMS (1.02 mL, 10.7 mmol) at rt. The reaction mixture was heated at reflux for 2 h. The reaction mixture was concentrated in vacuo. The residue was diluted with H₂O (50 mL) and extracted with EtOAc (3×75 mL). The organic layer was separated, washed with brine (50 mL), dried over anhydrous Na₂SO₄, and concentrated in vacuo to afford 1-benzyl-4-(2-(trifluoromethoxy)ethyl)piperazine (0.50 g crude) as a colorless liquid. MS (ESI) m/e [M+H]⁺/Rt/%: 288.95/3.32/97.6%; ¹H NMR (400 MHz, CDCl₃) δ 2.40-2.60 (m, 8H), 2.69 (t, J=6.0 Hz, 2H), 3.48 (s, 2H), 4.06 (t, J=6.0 Hz, 2H), 7.22-7.38 (m, 5H).

Step 3. Synthesis of 1-(2-(trifluoromethoxy)ethyl)piperazine

To a solution of 1-benzyl-4-(2-(trifluoromethoxy)ethyl) piperazine (0.25 g, 0.86 mmol) in MeOH (5 mL) was added Pd/C (0.05 g) followed by addition of CH₃COOH (catalytic) at rt. The reaction mixture stirred at room temperature for 3 h under hydrogen pressure. The reaction mixture was filtered through diatomaceous earth, washing with 20% MeOH in DCM (100 mL), and the filtrate was concentrated in vacuo to afford 1-(2-(trifluoromethoxy)ethyl)piperazine (0.14 g crude) as a light yellow liquid. MS (ESI) m/e [M+H]⁺/Rt/%:

199.00/1.97/88.4%; ¹H NMR (400 MHz, CDCl₃) δ 2.50-2.64 (m, 4H), 2.73 (t, J=5.6 Hz, 2H), 2.98-3.06 (m, 4H), 4.10 (t, J=5.7 Hz, 2H).

Step 4

To a solution of 1-(2-(trifluoromethoxy)ethyl)piperazine (0.12 g, 0.46 mmol) and N-(1-(1H-indol-3-yl)hexan-2-yl)-2-bromothiazole-5-carboxamide (0.17 g, 0.41 mmol) in DMF (3 mL) was added DIPEA (0.54 g, 4.19 mmol). The reaction mixture was heated in sealed tube at 100° C. for 16 h. The reaction mixture was diluted with H₂O (50 mL) and extracted with EtOAc (3×50 mL). The combined organic layers were dried over anhydrous Na₂SO₄ and concentrated in vacuo. The crude obtained was purified by preparative HPLC to afford the title compound (0.007 g, 3%) as a yellow solid. HPLC Purity: 93.5%; MS (ESI) m/e [M+H]⁺/Rt/%: 524.00/2.98/92.8%; ¹H NMR (400 MHz, DMSO-d₆) δ 0.82 (t, J=7.3 Hz, 3H), 1.16-1.60 (m, 6H), 2.40-2.60 (m, 4H), 2.60-2.72 (m, 2H), 3.30 (s, 2H), 3.60-3.50 (m, 4H), 4.08-4.14 (m, 1H), 4.18-4.22 (m, 2H), 6.94-7.04 (m, 2H), 7.06 (s, 1H), 7.29 (d, J=7.8 Hz, 1H), 7.56 (d, J=7.3 Hz, 1H), 7.80 (s, 1H), 7.97 (d, J=7.8 Hz, 1H), 10.75 (s, 1H).

Example 23. N-(1-(1H-indol-3-yl)hexan-2-yl)-2-(4-methyl-3-(trifluoromethyl)piperazin-1-yl)thiazole-5-carboxamide

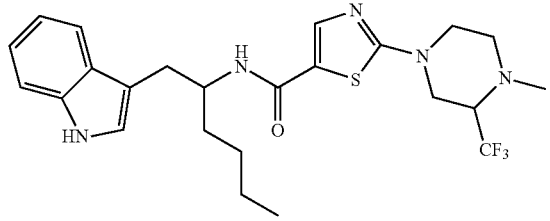 [SMILES: CCCCC(Cc1c[nH]c2ccccc12)NC(=O)c1cnc(N2CCN(C)C(C(F)(F)F)C2)s1]

Step 1. Synthesis of 1-benzyl-3-(trifluoromethyl)piperazine

To a solution of 3,3-dibromo-1,1,1-trifluoropropan-2-one (2.00 g, 7.43 mmol) in H₂O (5 mL) was added NaOAc (1.20 g, 82.1 mmol) and the resulting mixture was heated at 100° C. for 12 h. The reaction mixture was extracted with EtOAc (30 mL). The organic layer was separated, dried over anhydrous Na₂SO₄, and concentrated in vacuo. The residue was diluted with MeOH (10 mL) and treated with N-benzylethane-1,2-diamine (3.50 mL) and NaCNBH₃ (0.92 g, 14.8 mmol) portion wise. The reaction mixture was heated at 60° C. for 16 h. The reaction mixture was concentrated in vacuo. The crude obtained was purified by column chromatography (silica 100-200 mesh, 0.2 to 2% MeOH in DCM) to afford 1-benzyl-3-(trifluoromethyl)piperazine (1.10 g, 80%) as a brown liquid. MS (ESI) m/e [M+H]⁺/Rt/%: 245.00/2.86/86.0%; ¹H NMR (400 MHz, DMSO-d₆) δ 1.98-2.08 (m, 1H), 2.60-2.86 (m, 6H), 3.50 (s, 2H), 7.20-7.44 (m, 5H).

Step 2. Synthesis of 4-benzyl-1-methyl-2-(trifluoromethyl)piperazine

To a solution of 1-benzyl-3-(trifluoromethyl)piperazine (1.10 g, 4.50 mmol) in DCM (20 mL) was added HCHO (0.33 g, 11.2 mmol) dropwise at room temperature. The resulting mixture was stirred for 15 min, then was cooled to 0° C. and treated portionwise with Na(OAc)₃BH (2.38 g, 11.2 mmol). The reaction mixture was stirred at room temperature for 16 h. The reaction mixture was diluted with H₂O (10 mL) and extracted with 10% MeOH in DCM (3×20 mL). The organic layer was separated, dried over anhydrous Na₂SO₄, and concentrated in vacuo to afford 4-benzyl-1-methyl-2-(trifluoromethyl)piperazine (0.50 g crude) as an off-white solid. This compound was used as such for the next reaction without further purification. MS (ESI) m/e [M+H]⁺/Rt/%: 258.95/3.41/87.6%.

Step 3. Synthesis of 1-methyl-2-(trifluoromethyl)piperazine

To a solution of 4-benzyl-1-methyl-2-(trifluoromethyl)piperazine (0.50 g, 2.04 mmol) in MeOH (20 mL) was added Pd/C (0.20 g) and AcOH (0.50 mL). The reaction mixture was stirred at room temperature under hydrogen pressure for 16 h. The reaction mixture was filtered through diatomaceous earth, washing with MeOH (20 mL), and the filtrate was concentrated in vacuo. The crude obtained was purified by triturating with pentane (10 mL) to afford 1-methyl-2-(trifluoromethyl)piperazine (0.50 g crude) as a brown liquid. MS (ESI) m/e [M+H]⁺/Rt/%: 168.95/1.73/32.7%.

Step 4

To a solution of N-(1-(1H-indol-3-yl)hexan-2-yl)-2-bromothiazole-5-carboxamide (0.40 g, 0.98 mmol) and 1-methyl-2-(trifluoromethyl)piperazine (0.24 g, 1.47 mmol) in CH₃CN (8 mL) was added K₂CO₃ (0.54 g, 3.94 mmol) and tetrabutylammonium bromide (0.03 g, 0.09 mmol). The reaction mixture was heated at 80° C. for 48 h. The reaction mixture was concentrated in vacuo. The residue was diluted with H₂O (5 mL) and extracted with 5% MeOH in DCM (3×15 mL). The organic layer was separated, dried over anhydrous Na₂SO₄, and concentrated in vacuo. The crude obtained was purified by preparative HPLC to afford the title compound (0.08 g, 16%) as an off-white solid. HPLC Purity: 99.7%; MS (ESI) m/e [M+H]⁺/Rt/%: 494.00/3.02/99.9%; ¹H NMR (400 MHz, DMSO-d₆) δ 0.81 (t, J=6.7 Hz, 3H), 1.18-1.33 (m, 4H), 1.47-1.56 (m, 2H), 2.70 (dd, J=12.5, 5.9 Hz, 1H), 2.76-2.98 (m, 3H), 3.40-3.50 (m, 4H), 3.38-3.47 (m, 2H), 4.08-4.14 (m, 1H), 6.95 (t, J=7.3 Hz, 1H), 7.00-7.12 (m, 2H), 7.31 (d, J=8.0 Hz, 1H), 7.57 (d, J=7.8 Hz, 1H), 7.81 (s, 1H), 7.96 (d, J=8.5 Hz, 1H), 10.75 (s, 1H).

Example 24. N-(1-(1H-indol-3-yl)hexan-2-yl)-2-((3R,5R)-3,4,5-trimethylpiperazin-1-yl)thiazole-5-carboxamide

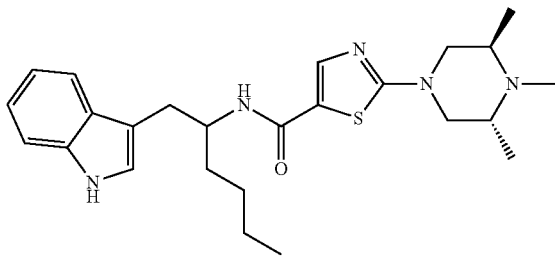 [SMILES: CCCCC(Cc1c[nH]c2ccccc12)NC(=O)c1cnc(N2C[C@@H](C)N(C)[C@H](C)C2)s1]

Step 1. Synthesis of tert-butyl (S)-(1-(dibenzylamino)-1-oxopropan-2-yl)carbamate To a −30° C. solution of (tert-butoxycarbonyl)-L-alanine (5.00 g, 26.0 mmol) in THF (100 mL) was added TEA (3.20 g, 31.0 mmol) and reaction mixture was added ClCO$_2$Bu-i (3.97 g, 29.0 mmol) dropwise. The reaction mixture was stirred at the same temperature for 30 min and then at room temperature for 5 h. The reaction mixture was cooled to 0° C. followed by dropwise addition of dibenzylamine (5.73 g, 29.0 mmol) and TEA (5.73 g, 33.0 mmol) solution in THF (25 mL). The reaction mixture was stirred at room temperature for 48 h. The reaction mixture was quenched with saturated NaHCO$_3$ (100 mL) and extracted with EtOAc (3×50 mL). The organic layer was separated, washed with brine (20 mL), dried over anhydrous Na$_2$SO$_4$, and concentrated in vacuo. The crude obtained was purified by column chromatography (silica 100-200 mesh, 1 to 10% EtOAc in hexanes) and then triturated with hexanes (5 mL) to afford tert-butyl (S)-(1-(dibenzylamino)-1-oxopropan-2-yl)carbamate (6.17 g, 63%) as a white solid. MS (ESI) m/e [M+H]$^+$/Rt/%: 369.00/3.66/97.2%.

Step 2. Synthesis of (S)—N1,N1-dibenzylpropane-1,2-diamine

To a 0° C. solution of tert-butyl (S)-(1-(dibenzylamino)-1-oxopropan-2-yl)carbamate (5.50 g, 14.9 mmol) in DCM (17.8 mL) was added TFA (17.8 mL) dropwise. The reaction mixture was stirred at room temperature for 18 h. The reaction mixture was concentrated in vacuo. The residue was diluted with DCM (75 mL) and washed with saturated NaHCO$_3$ solution (100 mL). The organic layer was separated, dried over anhydrous Na$_2$SO$_4$, and concentrated in vacuo. The crude obtained was dissolved in THF (120 mL) followed by dropwise addition of BH$_3$-DMS (18.0 mL, 23.6 mmol) and the reaction mixture was stirred at room temperature for 48 h. The reaction mixture was quenched with 10% HCl solution (20 mL) at 0° C. The reaction mixture was basified with 50% NaOH solution (20 mL) and KOH (34.5 g) and heated at reflux for 24 h. The reaction mixture was diluted with H$_2$O (50 mL) and extracted with EtOAc (3×50 mL). The organic layer was separated, dried over anhydrous Na$_2$SO$_4$, and concentrated in vacuo. The crude obtained was purified by column chromatography (silica, 100-200 mesh, 0 to 1% MeOH in DCM) to afford (S)—N1,N1-dibenzylpropane-1,2-diamine (3.00 g, 79%) as a white semi solid. $^1$H NMR (400 MHz, DMSO-d$_6$) δ 0.87 (d, J=6.3 Hz, 3H), 1.40 (brs, 2H), 2.18 (d, J=6.3 Hz, 2H), 2.96-3.02 (m, 1H), 3.46 (s, 2H), 3.56 (s, 2H), 7.19-7.38 (m, 10H).

Step 3. Synthesis of methyl ((S)-1-(dibenzylamino)propan-2-yl)-L-alaninate

To a 0° C. solution of (S)—N1,N1-dibenzylpropane-1,2-diamine (0.90 g, 3.54 mmol) in DCM (50 mL) was added TEA (1.00 g, 10.6 mmol) and the mixture was stirred at 0° C. for 10 min followed by addition of methyl (R)-2-(((trifluoromethyl)sulfonyl)oxy)propanoate (1.30 g, 5.50 mmol). The reaction mixture was stirred at room temperature for 2 h. The reaction mixture was quenched with saturated NaHCO$_3$ (20 mL) solution and extracted with DCM (3×20 mL). The organic layer was separated, dried over anhydrous Na$_2$SO$_4$, and concentrated in vacuo. The crude obtained was purified by column chromatography (silica, 100-200 mesh, 2 to 12% EtOAc in hexanes) to afford methyl ((S)-1-(dibenzylamino)propan-2-yl)-L-alaninate (1.15 g, 96%) as a colorless liquid. MS (ESI) m/e [M+H]$^+$/Rt/%: 341.00/3.95/98.8%; $^1$H NMR (400 MHz, CDCl$_3$) δ 0.94 (d, J=6.2 Hz, 3H), 1.22 (d, J=6.2 Hz, 3H), 2.24-2.32 (m, 1H), 2.42-2.50 (m, 1H), 2.72-2.80 (m, 1H), 3.40-3.44 (m, 1H), 3.50 (s, 2H), 3.59 (s, 2H), 3.71 (s, 3H), 7.21-7.36 (m, 10H).

Step 4. Synthesis of methyl N—((S)-1-(dibenzylamino)propan-2-yl)-N-methyl-L-alaninate A stirred solution of methyl ((S)-1-(dibenzylamino)propan-2-yl)-L-alaninate (0.50 g, 1.40 mmol) and HCOOH (2.50 mL) in HCHO (2.50 mL) was heated in sealed tube at 80° C. for 6 h. The reaction mixture was quenched with saturated NaHCO$_3$ (40 mL) solution and extracted with EtOAc (4×25 mL). The organic layer was separated, dried over anhydrous Na$_2$SO$_4$, and concentrated in vacuo to afford methyl N—((S)-1-(dibenzylamino)propan-2-yl)-N-methyl-L-alaninate (0.49 g crude) as a yellow liquid. This compound was used as such for the next reaction without further purification. MS (ESI) m/e [M+H]$^+$/Rt/%: 355.00/4.19/90.5%; $^1$H NMR (400 MHz, CDCl$_3$) δ 0.96 (d, J=6.5 Hz, 1H), 1.09 (d, 6.7 Hz, 3H), 2.15 (s, 3H), 2.30-2.38 (m, 1H), 2.48-2.54 (m, 1H), 2.98-3.08 (m, 1H), 3.40 (s, 2H), 3.44 (s, 2H), 3.72-3.37 (m, 1H), 3.64 (s, 3H), 3.66-3.70 (m, 2H), 7.18-7.39 (m, 10H).

Step 5. Synthesis of (3S,5S)-1-benzyl-3,4,5-trimethylpiperazin-2-one

To a solution of methyl N—((S)-1-(dibenzylamino)propan-2-yl)-N-methyl-L-alaninate (0.48 g, 1.35 mmol) in EtOH (25 mL) was added 10% Pd/C (0.19 g) and conc. HCl (0.25 mL). The reaction mixture was heated at 35° C. under hydrogen pressure (8 kg) for 16 h. The reaction mixture was filtered through diatomaceous earth, washing with EtOH (50 mL) and MeOH (50 mL). The filtrate was concentrated in vacuo to afford (3S,5S)-1-benzyl-3,4,5-trimethylpiperazin-2-one (0.35 g crude) as a green liquid. This compound was used as such for the next reaction without further purification. MS (ESI) m/e [M+H]$^+$/Rt/%: 232.95/2.39/85.0%.

Step 6. Synthesis of (2S,6S)-4-benzyl-1,2,6-trimethylpiperazine

To a solution of LAH (0.16 g, 4.19 mmol) in THF (20 mL) was added (3S,5S)-1-benzyl-3,4,5-trimethylpiperazin-2-one (0.32 g, 1.39 mmol) portion wise and the reaction mixture was stirred at room temperature for 1 h. The reaction mixture was heated at reflux for 6 h. The reaction mixture was quenched with H$_2$O (2 mL), 15% NaOH (0.20 mL), and H$_2$O (0.7 mL), and filtered, washing with excess THF. The organic layer was separated, dried over anhydrous Na$_2$SO$_4$, and concentrated in vacuo to afford (2S,6S)-4-benzyl-1,2,6-trimethylpiperazine (0.19 g crude) as a colorless liquid. This compound was used as such for the next reaction without further purification. MS (ESI) m/e [M+H]$^+$/Rt/%: 219.00/3.26/79.3%; $^1$H NMR (400 MHz, DMSO-d$_6$) δ 1.36 (d, J=6.4 Hz, 6H), 2.10 (s, 3H), 2.39-2.30 (m, 3H), 2.64-2.74 (m, 3H), 3.37 (s, 2H), 7.19-7.36 (m, 5H).

Step 7. Synthesis of (2S,6S)-1,2,6-trimethylpiperazine

To a solution of (2S,6S)-4-benzyl-1,2,6-trimethylpiperazine (0.19 g, 0.87 mmol) in MeOH (50 mL) was added Pd(OH)$_2$ (0.09 g) and the reaction mixture was heated at 40° C. under hydrogen pressure (8 kg) for 6 h. The reaction mixture was filtered through diatomaceous earth, washing with MeOH (20 mL). The filtrate was concentrated in vacuo to afford (2S,6S)-1,2,6-trimethylpiperazine (0.12 g crude) as a colorless liquid. MS (ESI) m/e [M+H]+/Rt/%: 129.00/1.98/24.7%.

Step 8

To a solution of (2S,6S)-1,2,6-trimethylpiperazine (0.11 g, 0.20 mmol) and N-(1-(1H-indol-3-yl)hexan-2-yl)-2-bromothiazole-5-carboxamide (0.09 g, 0.23 mmol) in CH$_3$CN (5 mL) was added K$_2$CO$_3$ (0.14 g, 1.00 mmol) and the reaction mixture was heated in a sealed tube at 85° C. for 16 h. The reaction mixture was concentrated in vacuo. The residue was diluted with H$_2$O (10 mL) and extracted with 10% MeOH in DCM (3×10 mL). The organic layer was separated, dried over anhydrous Na$_2$SO$_4$, and concentrated in vacuo. The crude obtained was purified by preparative HPLC to afford the title compound (0.015 g, 14%) as a white solid. HPLC Purity: 96.1%; MS (ESI) m/e [M+H]+/Rt/%: 454.00/2.66/98.4%; $^1$H NMR (400 MHz, DMSO-d$_6$) δ 0.80 (t, J=6.9 Hz, 3H), 0.95 (d, J=6.4 Hz, 6H), 1.16-1.60 (m, 6H), 2.22 (s, 3H), 2.78-2.94 (m, 4H), 3.15 (dd, J=12.4, 6.3 Hz, 2H), 3.52 (d, J=10.9 Hz, 2H), 4.10-4.16 (m, 1H), 6.95 (t, J=7.5 Hz, 1H), 6.99-7.12 (m, 2H), 7.31 (d, J=8.0 Hz, 1H), 7.57 (d, J=7.9 Hz, 1H), 7.76 (s, 1H), 7.91 (d, J=8.6 Hz, 1H), 10.75 (s, 1H).

Example 42. N-(1-cyclobutyl-2-(1H-indol-3-yl)ethyl)-2-(4-methylpiperazin-1-yl)thiazole-5-carboxamide

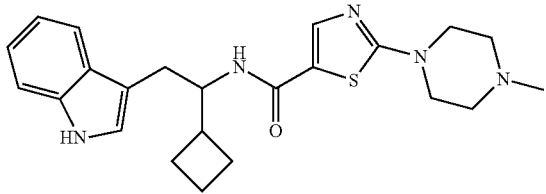 [SMILES: CN1CCN(c2ncc(C(=O)NC(Cc3c[nH]c4ccccc34)C3CCC3)s2)CC1]

Step 1. Synthesis of 1-cyclobutyl-2-(1H-indol-3-yl)ethan-1-one

To a 0° C. solution of 3-methyl-1H-indole (2.50 g, 19.0 mmol) in ethylene dichloride (25 mL) was added AlCl$_3$ (12.6 g, 95.4 mmol) and the reaction mixture was stirred at 0° C. for 10 min and then heated at 45° C. for 30 min. The reaction mixture was cooled at 0° C. and cyclobutanecarbonyl chloride (4.50 g, 38.1 mmol) was added dropwise. The reaction mixture was stirred at room temperature for 16 h. The reaction mixture was poured in to ice cold H$_2$O (200 mL) and extracted with DCM (3×100 mL). The organic layer was separated, dried over anhydrous Na$_2$SO$_4$ and concentrated in vacuo. The crude obtained was purified by column chromatography (silica, 100-200 mesh, 0 to 10% EtOAc in hexanes) to afford 1-cyclobutyl-2-(1H-indol-3-yl)ethan-1-one (2.01 g, 50%) as light green liquid. MS (ESI) m/e [M+H]+/Rt/%: 214.00/3.20/92.3%; $^1$H NMR (400 MHz, DMSO-d$_6$) δ 1.62-1.73 (m, 1H), 1.79-1.89 (m, 1H), 1.93-2.01 (m, 2H), 2.04-2.13 (m, 2H), 3.39 (t, J=8.3 Hz, 1H), 3.72 (s, 2H), 6.92-6.99 (m, 1H), 7.05 (t, J=7.6 Hz, 1H), 7.20 (s, 1H), 7.33 (d, J=7.8 Hz, 1H), 7.39 (d, J=7.8 Hz, 1H), 10.91 (brs, 1H).

Step 2. Synthesis of 1-Cyclobutyl-2-(1H-Indol-3-Yl)Ethan-1-Amine Hydrochloride

To a solution of 1-cyclobutyl-2-(1H-indol-3-yl)ethan-1-one (1.90 g, 8.92 mmol) in MeOH (50 mL) was added NH$_4$OAc (5.83 g, 75.8 mmol) and the reaction mixture was stirred at room temperature for 10 min. NaBH$_3$CN (0.84 g, 13.3 mmol) was added and the reaction mixture was stirred at room temperature for 10 min and then was heated at reflux for 16 h. The reaction mixture was concentrated in vacuo. The residue was acidified with 3 N HCl, decanted, and dried in vacuo. The crude obtained was purified by triturating with pentane (50 mL) to afford 1-cyclobutyl-2-(1H-indol-3-yl)ethan-1-amine hydrochloride (1.80 g crude) as a brown semi solid. MS (ESI) m/e [M+H]+/Rt/%: 215.00/3.21/96.0%; $^1$H NMR (400 MHz, DMSO-d$_6$) δ 1.66-2.01 (m, 6H), 2.40-2.46 (m, 1H), 2.91 (d, J=6.4 Hz, 2H), 6.97-7.03 (m, 1H), 7.07-7.13 (m, 1H), 7.22-7.29 (m, 1H), 7.37 (d, J=8.3 Hz, 1H), 7.57 (d, J=7.8 Hz, 1H), 7.88 (brs, 2H), 11.02 (brs, 1H).

Step 3

To a solution of 2-(4-methylpiperazin-1-yl)thiazole-5-carboxylic acid (0.24 g, 1.05 mmol) in DMF (10 mL), HATU (0.43 g, 1.14 mmol) and DIPEA (0.47 mL, 2.63 mmol) were added and the reaction mixture was stirred at room temperature for 10 min. 1-cyclobutyl-2-(1H-indol-3-yl)ethan-1-amine hydrochloride (0.25 g, 0.87 mmol) was added and the reaction mixture was stirred in sealed tube at room temperature for 16 h. The reaction mixture was diluted with H$_2$O (100 mL) and extracted with EtOAc (3×100 mL). The organic layer was separated, washed with H$_2$O (2×100 mL), brine (75 mL), dried over anhydrous Na$_2$SO$_4$, and concentrated in vacuo. The crude obtained was purified by column chromatography (silica, 230-400 mesh, 0 to 5% MeOH in DCM) to afford the title compound (0.16 g, 45%) as an off-white solid. HPLC Purity: 97.3%; MS (ESI) m/e [M+H]+/Rt/%: 424.00/2.59/96.9%; $^1$H NMR (400 MHz, DMSO-d$_6$) δ 0.86 (m, 1H), 1.23-1.33 (m, 1H), 1.67-1.97 (m, 5H), 2.22 (s, 3H), 2.40-2.46 (m, 4H), 2.71-2.88 (m, 2H), 3.39-3.48 (m, 4H), 4.06-4.22 (m, 1H), 6.91-6.98 (m, 1H), 7.01-7.08 (m, 2H), 7.30 (d, J=7.8 Hz, 1H), 7.51 (d, J=7.8 Hz, 1H), 7.79 (s, 1H), 7.84 (d, J=8.8 Hz, 1H), 10.72 (brs, 1H).

Example 43. N-(1-cyclohexyl-2-(1H-indol-3-yl)ethyl)-2-(4-methylpiperazin-1-yl)thiazole-5-carboxamide

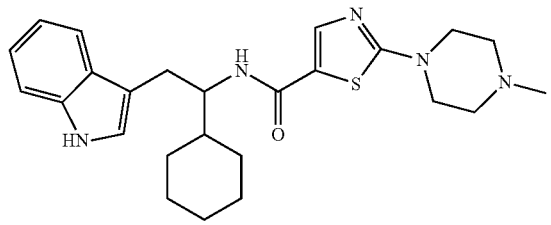 [SMILES: CN1CCN(c2ncc(C(=O)NC(Cc3c[nH]c4ccccc34)C3CCCCC3)s2)CC1]

Step 1. Synthesis of 1-cyclohexyl-2-(1H-indol-3-yl)ethan-1-one

To a solution of 3-methyl-1H-indole (5.00 g, 38.1 mmol) in EDC (50 mL), AlCl$_3$ (25.0 g, 190 mmol) was added at 0°

C. and the reaction mixture was stirred at 0° C. for 10 min and then was heated at 45° C. for 30 min. The reaction mixture was cooled at 0° C. followed by dropwise addition of cyclohexanecarbonyl chloride (8.30 g, 56.0 mmol). The reaction mixture was stirred at room temperature for 16 h. The reaction mixture was poured in to ice cold H$_2$O (300 mL) and extracted with DCM (3×150 mL). The organic layer was separated, dried over anhydrous Na$_2$SO$_4$ and concentrated in vacuo. The crude obtained was purified by column chromatography (silica, 100-200 mesh, 0 to 12% EtOAc in hexanes) to afford 1-cyclohexyl-2-(1H-indol-3-yl)ethan-1-one (2.20 g, 24%) as light brown liquid. MS (ESI) m/e [M+H]$^+$/Rt/%: 242.00/3.39/92.1%; $^1$H NMR (400 MHz, DMSO-d$_6$) δ 1.13-1.27 (m, 6H), 1.57 (d, J=9.8 Hz, 1H), 1.66 (d, J=5.9 Hz, 2H), 1.76 (d, J=9.8 Hz, 2H), 3.82 (s, 2H), 6.91-6.98 (m, 1H), 7.05 (t, J=7.3 Hz, 1H), 7.19 (s, 1H), 7.35 (dd, J=17.4, 8.1 Hz, 2H), 10.89 (brs, 1H).

Step 2. Synthesis of 1-Cyclohexyl-2-(1H-Indol-3-Yl)Ethan-1-Amine Hydrochloride

To a solution of 1-cyclohexyl-2-(1H-indol-3-yl)ethan-1-one (0.50 g, 2.07 mmol) in MeOH (20 mL), NH$_4$OAc (1.27 g, 16.5 mmol) was added and the reaction mixture was stirred at room temperature for 10 min. NaBH$_3$CN (0.19 g, 3.10 mmol) was added and the reaction mixture was stirred at room temperature for 10 min and then was heated at reflux for 16 h. The reaction mixture was concentrated in vacuo. The residue was acidified with 3 N HCl, decanted, and dried in vacuo. The crude obtained was purified by triturating with pentane (250 mL) to afford 1-cyclohexyl-2-(1H-indol-3-yl)ethan-1-amine hydrochloride (0.43 g crude) as a light brown solid. MS (ESI) m/e [M+H]$^+$/Rt/%: 243.00/3.78/82.6%; $^1$H NMR (400 MHz, DMSO-d$_6$) δ 1.10-1.33 (m, 6H), 1.56-1.81 (m, 5H), 2.92-2.99 (m, 1H), 2.99-3.07 (m, 1H), 3.20-3.26 (m, 1H), 6.98-7.05 (m, 1H), 7.07-7.13 (m, 1H), 7.27 (d, J=2.0 Hz, 1H), 7.37 (d, J=7.8 Hz, 1H), 7.55 (d, J=7.8 Hz, 1H), 7.86 (brs, 3H), 11.00 (brs, 1H).

Step 3

To a solution of 2-(4-methylpiperazin-1-yl)thiazole-5-carboxylic acid (0.26 g, 1.14 mmol) in DMF (10 mL), HATU (0.47 g, 2.85 mmol) and DIPEA (0.51 mL, 2.85 mmol) were added and the reaction mixture was stirred at room temperature for 10 min. 1-cyclohexyl-2-(1H-indol-3-yl)ethan-1-amine hydrochloride (0.30 g, 0.95 mmol) was added and the reaction mixture was stirred in sealed tube at room temperature for 16 h. The reaction mixture was diluted with H$_2$O (100 mL) and extracted with EtOAc (3×100 mL). The organic layer was separated, washed with H$_2$O (2×100 mL), brine (75 mL), dried over anhydrous Na$_2$SO$_4$, and concentrated in vacuo. The crude obtained was purified by column chromatography (silica, 230-400 mesh, 0 to 5% MeOH in DCM) to afford the title compound (0.12 g, 28%) as an off-white solid. HPLC Purity: 95.8%; MS (ESI) m/e [M+H]$^+$/Rt/%: 452.00/2.46/96.8%; $^1$H NMR (400 MHz, DMSO-d$_6$) δ 1.03-1.19 (m, 5H), 1.47-1.82 (m, 6H), 2.20 (s, 3H), 2.32-2.38 (m, 4H), 2.80 (dd, J=14.7, 9.8 Hz, 1H), 2.94-3.04 (m, 1H), 3.38-3.44 (m, 4H), 3.91-4.09 (m, 1H), 6.90-6.96 (m, 1H), 7.00-7.07 (m, 2H), 7.28 (d, J=7.8 Hz, 1H), 7.50 (d, J=7.8 Hz, 1H), 7.78-7.84 (m, 2H), 10.68 (brs, 1H).

Example 63. N-(1-(1H-indol-3-yl)propan-2-yl)-2-(4-methylpiperazin-1-yl)thiazole-5-carboxamide

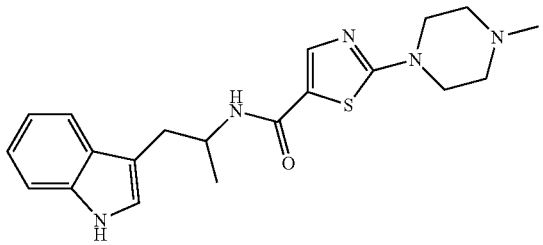 [SMILES: CC(Cc1c[nH]c2ccccc12)NC(=O)c1cnc(N2CCN(C)CC2)s1]

Step 1. Synthesis of 3-(2-nitroprop-1-en-1-yl)-1H-indole

To a solution of 1H-indole-3-carbaldehyde (3.00 g, 20.6 mmol) in CH$_3$COOH (20.6 mL) and nitroethane (50 mL) was added NH$_4$OAc (0.78 g, 1.00 mmol) and the reaction mixture was heated at 110° C. for 8 h. The reaction mixture was cooled to 0° C. and filtered. The crude obtained was purified by column chromatography (silica 100-200 mesh, 10 to 40% EtOAc in hexanes) to afford 3-(2-nitroprop-1-en-1-yl)-1H-indole (2.50 g, 60%) as a red solid. $^1$H NMR (400 MHz, DMSO-d$_6$) δ 2.54 (s, 3H), 7.22-7.40 (m, 2H), 7.44-7.50 (m, 1H), 7.73-7.88 (m, 2H), 7.52 (s, 1H), 8.70 (brs, 1H).

Step 2. Synthesis of 1-(1H-indol-3-yl)propan-2-amine

To a suspension of LAH (2.60 g, 69.3 mmol) in dry THF (25 mL) was added a solution of 3-(2-nitroprop-1-en-1-yl)-1H-indole (2.00 g, 9.90 mmol) in THF (10 mL) dropwise and the reaction mixture was heated at reflux for 6 h. The reaction mixture was diluted with EtOAc (200 mL). The reaction mixture was cooled to 0° C., quenched with saturated Na$_2$SO$_4$ (10 mL), and filtered. The organic layer was separated, dried over anhydrous Na$_2$SO$_4$, and concentrated in vacuo. The crude obtained was washed with pentane (10 mL) to afford 1-(1H-indol-3-yl)propan-2-amine (1.20 g, 70%) as an off-white solid. MS (ESI) m/e [M+H]$^+$/Rt/%: 175.00/2.78/39.6%.

Step 3. Synthesis of N-(1-(1H-indol-3-yl)propan-2-yl)-2-bromothiazole-5-carboxamide To a solution of 1-(1H-indol-3-yl)propan-2-amine (1.00 g, 4.80 mmol) and 2-bromothiazole-5-carboxylic acid (1.16 g, 8.72 mmol) in DMF (20 mL) was added 2-chloro-1-methylpyridinium iodide (Mukaiyama reagent; 1.83 g, 7.20 mmol) followed by addition of DIPEA (2.19 g, 16.8 mmol). The reaction mixture was stirred at room temperature for 16 h. The reaction mixture was diluted with H$_2$O (50 mL) and extracted with DCM (3×20 mL). The organic layer was separated, dried over anhydrous Na$_2$SO$_4$, and concentrated in vacuo. The crude obtained was purified by column chromatography (silica 1000-200 mesh, 0.1 to 0.4% MeOH in DCM) and triturating with pentane (10 mL) to afford N-(1-(1H-indol-3-yl)propan-2-yl)-2-bromothiazole-5-carboxamide (0.35 g, 20%) as a brown solid. MS (ESI) m/e [M+H+1]$^+$/Rt/%: 366.00/2.97/95.5%; $^1$H NMR (400 MHz, CDCl$_3$) δ 1.29 (d, J=6.9 Hz, 3H), 3.06 (d, J=5.7 Hz, 2H), 4.48-4.56 (m, 1H), 5.86 (d, J=7.4 Hz, 1H), 7.08 (d, J=2.1 Hz, 1H), 7.10-7.26 (m, 2H), 7.41 (d, J=8.1 Hz, 1H), 7.58 (s, 1H), 7.61-7.65 (m, 1H), 8.14 (s, 1H).

Step 4

To a solution of N-(1-(1H-indol-3-yl)propan-2-yl)-2-bromothiazole-5-carboxamide (0.15 g, 0.41 mmol) and 1-methylpiperazine (0.06 g, 0.61 mmol) in CH$_3$CN (5 mL) was added K$_2$CO$_3$ (0.17 g, 1.20 mmol) and the reaction mixture was heated in sealed tube at 100° C. for 16 h. The reaction mixture was concentrated in vacuo. The residue was diluted with H$_2$O (10 mL) and extracted with 10% MeOH in DCM (3×10 mL). The organic layer was separated, dried over anhydrous Na$_2$SO$_4$, and concentrated in vacuo. The crude obtained was purified by combi-flash column chromatography (0.1 to 1% MeOH in DCM) and triturating with DCM: pentane (1:10, 10 mL) to afford the title compound (0.068 g, 43%) as a white solid. HPLC Purity: 99.1%; MS (ESI) m/e [M+H]$^+$/Rt/%: 384.00/2.16/98.0%; $^1$H NMR (400 MHz, DMSO-d$_6$) δ 1.12 (d, J=6.5 Hz, 3H), 2.21 (s, 3H), 2.36-2.43 (m, 4H), 2.76 (dd, J=14.1, 7.3 Hz, 1H), 2.96 (dd, J=14.1, 6.2 Hz, 1H), 3.40-3.47 (m, 4H), 4.16-4.22 (m, 1H), 6.96 (t, J=7.4 Hz, 1H), 7.00-7.14 (m, 2H), 7.32 (d, J=8.0 Hz, 1H), 7.59 (d, J=7.8 Hz, 1H), 7.80 (s, 1H), 8.04 (d, J=7.9 Hz, 1H), 10.78 (s, 1H).

Example 64. N-(1-(1H-indol-3-yl)butan-2-yl)-2-(4-methylpiperazin-1-yl)thiazole-5-carboxamide

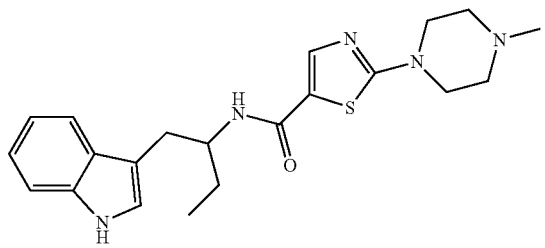 [SMILES: CCC(Cc1c[nH]c2ccccc12)NC(=O)c1cnc(N2CCN(C)CC2)s1]

Step 1. Synthesis of 3-(2-nitrobut-1-en-1-yl)-1H-indole

To a solution of 1H-indole-3-carbaldehyde (3.00 g, 20.0 mmol) in nitropropane (30 mL) was added NH$_4$OAc (1.84 g, 24.0 mmol) and the reaction mixture was heated at 100° C. for 18 h. The reaction mixture was concentrated in vacuo. The residue was diluted with H$_2$O (50 mL) and extracted with EtOAc (3×50 mL). The organic layer was separated, washed with brine (200 mL), dried over anhydrous Na$_2$SO$_4$, and concentrated in vacuo. The crude obtained was purified by washing with pentane (20 mL) to afford 3-(2-nitrobut-1-en-1-yl)-1H-indole (4.48 g, 62%) as an orange solid. $^1$H NMR (400 MHz, DMSO-d$_6$) δ 1.20 (t, J=7.3 Hz, 3H), 2.94 (q, J=7.3 Hz, 2H), 7.17-7.32 (m, 2H), 7.49-7.59 (m, 1H), 7.83 (d, J=7.8 Hz, 1H), 7.99 (s, 1H), 8.41 (s, 1H), 12.19 (brs, 1H).

Step 2. Synthesis of 1-(1H-indol-3-yl)butan-2-amine

To a solution of 3-(2-nitrobut-1-en-1-yl)-1H-indole (0.60 g, 2.77 mmol) in THF (60 mL) was added LAH (0.42 g, 11.1 mmol) and the reaction mixture was heated at 70° C. for 5 h. An additional portion of LAH (0.42 g, 11.1 mmol) was added and the reaction mixture was heated at 70° C. for a further 16 h. The reaction mixture was cooled to 0° C., quenched with saturated Na$_2$SO$_4$ (20 mL), and diluted with EtOAc (150 mL). The reaction mixture was stirred for 10 min, filtered through diatomaceous earth, and the filtrate was concentrated in vacuo. The crude obtained was purified by washing with pentane (10 mL) and dried in vacuo to afford 1-(1H-indol-3-yl)butan-2-amine (0.60 g crude) as a brown semisolid. MS (ESI) m/e [M+H]$^+$/Rt/%: 189.00/3.02/45.3%.

Step 3. Synthesis of N-(1-(1H-indol-3-yl)butan-2-yl)-2-bromothiazole-5-carboxamide To a solution of 1-(1H-indol-3-yl)butan-2-amine (0.60 g, 3.40 mmol) and 2-bromothiazole-5-carboxylic acid (0.79 g, 3.40 mmol) in DMF (10 mL) was added Mukaiyama reagent (1.21 g, 4.70 mmol) followed by addition of DIPEA (1.22 g, 9.50 mmol). The reaction mixture was stirred at room temperature for 16 h. The reaction mixture was diluted with H$_2$O (25 mL) and extracted with DCM (3×10 mL). The organic layer was separated, dried over anhydrous Na$_2$SO$_4$, and concentrated in vacuo. The crude obtained was purified by column chromatography (silica 100-200 mesh, 1 to 15% EtOAc in hexanes) to afford N-(1-(1H-indol-3-yl)butan-2-yl)-2-bromothiazole-5-carboxamide (0.26 g, 21%) as a brown solid. MS (ESI) m/e [M+H+1]/Rt/%: 380.00/3.09/77.1%; $^1$H NMR (400 MHz, DMSO-d$_6$) δ 0.85 (t, J=7.3 Hz, 3H), 1.42-1.53 (m, 1H), 1.57-1.66 (m, 1H), 2.85 (q, J=7.3 Hz, 2H), 3.96-4.10 (m, 1H), 6.89-6.97 (m, 1H), 7.03 (t, J=7.6 Hz, 1H), 7.10 (s, 1H), 7.30 (d, J=7.8 Hz, 1H), 7.55 (d, J=7.8 Hz, 1H), 8.20-8.24 (m, 1H), 8.49 (d, J=8.3 Hz, 1H), 10.77 (brs, 1H).

Step 4

To a solution of N-(1-(1H-indol-3-yl)butan-2-yl)-2-bromothiazole-5-carboxamide (0.25 g, 0.66 mmol) and 1-methylpiperazine (0.08 g, 0.79 mmol) in CH$_3$CN (6 mL) was added K$_2$CO$_3$ (0.27 g, 1.98 mmol) and the reaction mixture was heated at 100° C. for 16 h. The reaction mixture was concentrated in vacuo. The residue was diluted with H$_2$O (10 mL) and extracted with 5% MeOH in DCM (3×10 mL). The organic layer was separated, dried over anhydrous Na$_2$SO$_4$, and concentrated in vacuo. The crude obtained was purified by column chromatography (silica 230-400 mesh, 0.5 to 4% MeOH in DCM) and by preparative HPLC to afford the title compound (0.06 g, 22%) as a white solid. HPLC Purity: 99.8%; MS (ESI) m/e [M+H]$^+$/Rt/%: 398.00/2.32/99.2%; $^1$H NMR (400 MHz, DMSO-d$_6$) δ 0.85 (t, J=7.3 Hz, 3H), 1.42-1.48 (m, 1H), 1.54-1.64 (m, 1H), 2.21 (s, 3H), 2.44-2.54 (m, 4H), 2.78-2.94 (m, 2H), 3.41-3.49 (m, 4H), 4.00-4.08 (m, 1H), 6.92-6.99 (m, 1H), 7.04 (t, J=7.3 Hz, 1H), 7.10 (d, J=2.0 Hz, 1H), 7.31 (d, J=8.3 Hz, 1H), 7.56-7.61 (m, 1H), 7.81 (s, 1H), 7.93 (d, J=8.3 Hz, 1H), 10.76 (brs, 1H).

Example 65. N-(1-(1H-indol-3-yl)pentan-2-yl)-2-(4-methylpiperazin-1-yl)thiazole-5-carboxamide

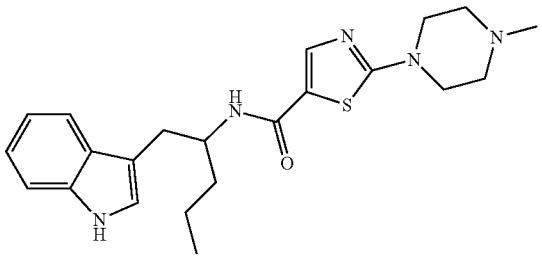 [SMILES: CCCC(Cc1c[nH]c2ccccc12)NC(=O)c1cnc(N2CCN(C)CC2)s1]

Step 1. Synthesis of 1-nitrobutane

To a solution of AgNO$_2$ (18.8 g, 122 mmol) in Et$_2$O (200 mL), 1-iodobutane (15.0 g, 81.0 mmol) was added and the reaction mixture was stirred in sealed tube at room temperature for 16 h. The reaction mixture was filtered through diatomaceous earth, washing with Et$_2$O (100 mL). The filtrate was concentrated in vacuo to afford 1-nitrobutane (9.00 g crude) as a light brown liquid. This compound was used as such for the next reaction without further purification. $^1$H NMR (400 MHz, CDCl$_3$) δ 0.98 (t, J=7.3 Hz, 3H), 1.38-1.48 (m, 2H), 1.98-2.08 (m, 2H), 4.39 (t, J=6.8 Hz, 2H).

Step 2. Synthesis of 3-(2-nitropent-1-en-1-yl)-1H-indole

To a solution of 1-nitrobutane (8.50 g, 82.5 mmol) and 1H-indole-3-carbaldehyde (2.00 g, 13.7 mmol) in CH$_3$COOH (5 mL), NH$_4$OAc (1.60 g, 20.6 mmol) was added and the reaction mixture was heated in sealed tube at 100° C. for 15 h. The reaction mixture was concentrated in vacuo. The residue was basified to pH 8 with saturated NaHCO$_3$ solution (30 mL) and extracted with EtOAc (2×200 mL). The organic layer was separated, dried over anhydrous Na$_2$SO$_4$, and concentrated in vacuo. The crude obtained was purified by column chromatography (silica, 100-200 mesh, 10 to 20% EtOAc in hexanes) to afford 3-(2-nitropent-1-en-1-yl)-1H-indole (0.80 g, 25%) as a yellow solid. MS (ESI) m/e [M+H]$^+$/Rt/%: 231.00/3.57/89.9%; $^1$H NMR (400 MHz, DMSO-d$_6$) δ 1.03 (t, J=7.6 Hz, 3H), 1.60-1.70 (m, 2H), 2.90-2.97 (m, 2H), 7.18-7.29 (m, 2H), 7.52 (d, J=7.8 Hz, 1H), 7.83 (d, J=7.3 Hz, 1H), 7.95 (s, 1H), 8.44 (s, 1H), 12.13 (brs, 1H).

Step 3. Synthesis of 1-(1H-indol-3-yl)pentan-2-amine

To a suspension of 3-(2-nitropent-1-en-1-yl)-1H-indole (0.80 g, 3.47 mmol) in THF (30 mL), LAH (0.66 g, 17.3 mmol) was added lot wise at 0° C. and the reaction mixture was stirred at room temperature for 1 h and then was heated at reflux for 6 h. The reaction mixture was quenched with saturated Na$_2$SO$_4$ (5 mL) and EtOAc (50 mL). The reaction mixture was filtered through diatomaceous earth, washing with EtOAc (20 mL). The filtrate was concentrated in vacuo to afford 1-(1H-indol-3-yl)pentan-2-amine (0.58 g crude) as a brown liquid. This compound was used as such for the next reaction without further purification. MS (ESI) m/e [M+H]$^+$/Rt/%: 203.00/3.16/65.1%.

Step 4

To a solution of 2-(4-methylpiperazin-1-yl)thiazole-5-carboxylic acid (0.30 g, 1.32 mmol) in DMF (8 mL), HATU (1.00 g, 2.64 mmol) was added followed by addition of DIPEA (0.70 mL, 3.96 mmol). The reaction mixture was stirred at room temperature for 10 min followed by addition of 1-(1H-indol-3-yl)pentan-2-amine (0.32 g, 1.58 mmol) solution in DMF (1.8 mL). The reaction mixture was stirred at room temperature for 5 h. The reaction mixture was diluted with H$_2$O (100 mL) and extracted with EtOAc (2×100 mL). The organic layer was separated, washed with H$_2$O (200 mL), brine (200 mL), dried over anhydrous Na$_2$SO$_4$, and concentrated in vacuo. The crude obtained was purified by column chromatography (silica, 100-200 mesh, 0 to 10% MeOH in DCM) and preparative HPLC to afford the title compound (0.13 g, 25%) as an off-white solid. HPLC Purity: 99.0%; MS (ESI) m/e [M+H]$^+$/Rt/%: 412.00/2.49/97.0%; $^1$H NMR (400 MHz, DMSO-d$_6$) δ 0.81 (t, J=7.3 Hz, 3H), 1.16-1.28 (m, 1H), 1.36-1.44 (m, 1H), 1.50-1.58 (m, 2H), 2.21 (s, 3H), 2.36-2.43 (m, 4H), 2.75-2.93 (m, 2H), 3.39-3.47 (m, 4H), 4.05-4.20 (m, 1H), 6.93-6.98 (m, 1H), 7.04 (t, J=7.6 Hz, 1H), 7.09 (d, J=2.0 Hz, 1H), 7.31 (d, J=7.8 Hz, 1H), 7.57 (d, J=7.8 Hz, 1H), 7.81 (s, 1H), 7.96 (d, J=8.3 Hz, 1H), 10.77 (brs, 1H).

Example 66. N-(1-(1H-indol-3-yl)-4-methylpentan-2-yl)-2-(4-methylpiperazin-1-yl)thiazole-5-carboxamide

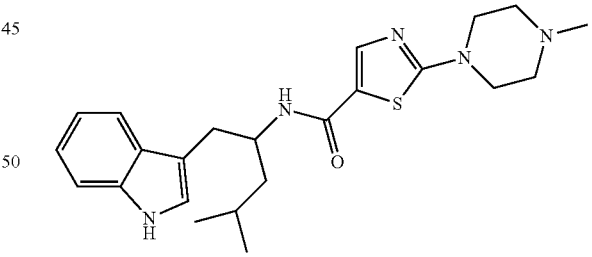

The title compound was prepared using a method analogous to that described for Example 65. HPLC Purity: 96.1%; MS (ESI) m/e [M+H]$^+$/Rt/%: 426.00/2.65/98.9%; $^1$H NMR (400 MHz, DMSO-d$_6$) δ 0.77 (d, J=6.4 Hz, 3H), 0.84 (d, J=6.8 Hz, 3H), 1.27-1.34 (m, 1H), 1.44-1.53 (m, 1H), 1.57-1.69 (m, 1H), 2.21 (s, 3H), 2.38-2.42 (m, 4H), 2.76-2.92 (m, 2H), 3.40-3.47 (m, 4H), 4.14-4.29 (m, 1H), 6.93-6.99 (m, 1H), 7.04 (t, J=7.6 Hz, 1H), 7.09 (d, J=1.5 Hz, 1H), 7.31 (d, J=7.8 Hz, 1H), 7.57 (d, J=7.8 Hz, 1H), 7.79 (s, 1H), 7.93 (d, J=8.8 Hz, 1H), 10.75 (brs, 1H).

Example 67. N-(1-cyclobutyl-3-(1H-indol-3-yl)propan-2-yl)-2-(4-methylpiperazin-1-yl)thiazole-5-carboxamide

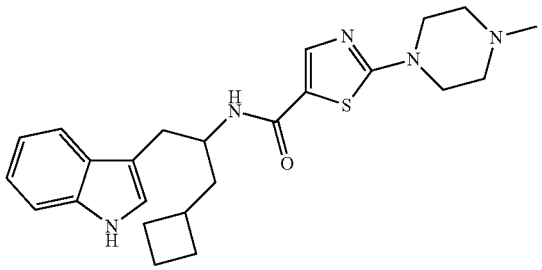 [SMILES: CN1CCN(c2ncc(C(=O)NC(Cc3c[nH]c4ccccc34)CC3CCC3)s2)CC1]

The title compound was prepared using methods analogous to those described in the preceding examples. HPLC Purity: 99.2%; MS (ESI) m/e [M+H]+/Rt/%: 438.00/2.66/98.9%; $^1$H NMR (400 MHz, DMSO-$d_6$) δ 1.41-1.50 (m, 1H), 1.60-1.62 (m, 2H), 1.63-1.81 (m, 3H), 1.89-1.98 (m, 2H), 2.23 (s, 3H), 2.28-2.36 (m, 1H), 2.38-2.44 (m, 4H), 2.74-2.93 (m, 2H), 3.42-3.46 (m, 4H), 4.03-4.15 (m, 1H), 6.93-6.98 (m, 1H), 7.04 (t, J=7.6 Hz, 1H), 7.08 (s, 1H), 7.31 (d, J=8.3 Hz, 1H), 7.56 (d, J=7.8 Hz, 1H), 7.78 (s, 1H), 7.90 (d, J=8.8 Hz, 1H), 10.76 (brs, 1H).

Example 68. N-(1-(1H-indol-3-yl)hexan-2-yl)-2-(4-methyl-2-oxopiperazin-1-yl)thiazole-5-carboxamide

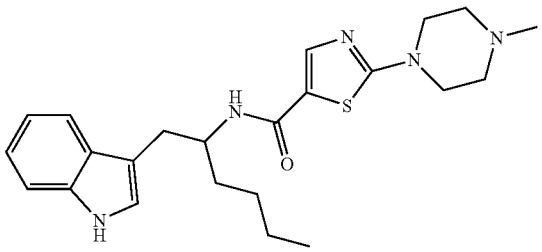 [SMILES: CCCCC(Cc1c[nH]c2ccccc12)NC(=O)c1cnc(N2CCN(C)CC2)s1]

Step 1

To a solution of N-(1-(1H-indol-3-yl)hexan-2-yl)-2-bromothiazole-5-carboxamide (0.10 g, 0.24 mmol) and 4-methylpiperazin-2-one (0.03 g, 0.29 mmol) in dioxane (7 mL), Cs$_2$CO$_3$ (0.23 g, 0.72 mmol) and 2-(dicyclohexylphosphino) 3,6-dimethoxy-2',4',6'-triisopropyl-1,1'-biphenyl (BrettPhos precatalyst; 0.02 g, 0.02 mmol) were added. The reaction vessel was purged with argon for 20 min and the mixture was then heated at 110° C. for 16 h. The reaction mixture was filtered through diatomaceous earth, washing with 5% MeOH in DCM (2×10 mL). The filtrate was concentrated, and the crude obtained was purified by column chromatography (silica, 100-200 mesh, 1 to 4% MeOH in DCM) and preparative HPLC to afford the title compound (0.03 g, 14%) as a white solid. HPLC Purity: 99.4%; MS (ESI) m/e [M+H]+/Rt/%: 440.00/2.69/98.0%; $^1$H NMR (400 MHz, DMSO-$d_6$) δ 0.81 (t, J=6.8 Hz, 3H), 1.19-1.35 (m, 4H), 1.47-1.63 (m, 2H), 2.31 (s, 3H), 2.81 (t, J=5.4 Hz, 2H), 2.85-2.97 (m, 2H), 3.34 (s, 2H), 4.03 (t, J=5.6 Hz, 2H), 4.16 (m, 1H), 6.92-6.98 (m, 1H), 7.04 (t, J=7.6 Hz, 1H), 7.11 (d, J=1.5 Hz, 1H), 7.31 (d, J=8.3 Hz, 1H), 7.58 (d, J=7.8 Hz, 1H), 8.13 (s, 1H), 8.24 (d, J=8.8 Hz, 1H), 10.75 (brs, 1H).

Example 69. N-(1-(5-methyl-1H-indol-3-yl)hexan-2-yl)-2-(4-methylpiperazin-1-yl)thiazole-5-carboxamide

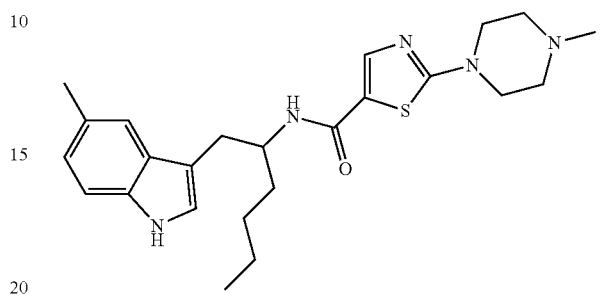

The title compound was prepared starting from 1-nitropentane (prepared from 1-iodopentane as described above) and 5-methyl-1H-indole-3-carbaldehyde using methods analogous to those described herein. HPLC Purity: 99.8%; MS (ESI) m/e [M+H]+/Rt/%: 440.00/2.78/96.0%; $^1$H NMR (400 MHz, DMSO-$d_6$) δ 0.83 (d, J=6.4 Hz, 3H), 1.21-1.34 (m, 4H), 1.46-1.55 (m, 2H), 2.21 (s, 3H), 2.32 (s, 3H), 2.32-2.42 (m, 4H), 2.78-2.90 (m, 2H), 3.40-3.48 (m, 4H), 4.05-4.11 (m, 1H), 6.86 (d, J=8.2 Hz, 1H), 7.03 (s, 1H), 7.18 (d, J=8.2 Hz, 1H), 7.33 (s, 1H), 7.80 (s, 1H), 7.91 (d, J=8.5 Hz, 1H), 10.61 (s, 1H).

Example 70. N-(1-(5,7-dibromo-1H-indol-3-yl)hexan-2-yl)-2-(4-methylpiperazin-1-yl)thiazole-5-carboxamide

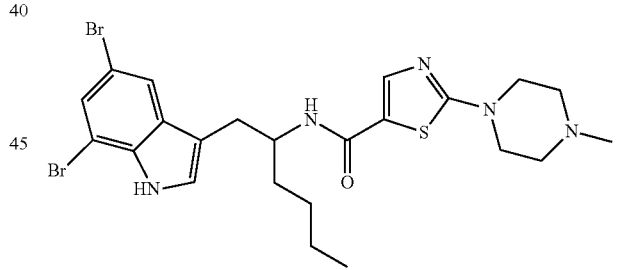

Step 1. Synthesis of 5,7-dibromo-1H-indole

To a solution of 2,4-dibromo-1-nitrobenzene (15.0 g, 53.3 mmol) in THF (150 mL), vinylmagnesium bromide (21.0 g, 160 mmol) was added at −40° C. and the reaction mixture was stirred at −40° C. for 30 min. The reaction mixture was poured into saturated solution of NH$_4$Cl (300 mL) and extracted with EtOAc (3×300 mL). The organic layer was separated, washed with brine (200 mL), dried over anhydrous Na$_2$SO$_4$, and concentrated in vacuo. The crude obtained was purified by column chromatography (silica, 100-200 mesh, 0 to 8% EtOAc in hexanes) to afford 5,7-dibromo-1H-indole (5.90 g, 41%) as a brown solid. $^1$H NMR (400 MHz, DMSO-$d_6$) δ 6.56 (d, J=2.4 Hz, 1H), 7.43-7.52 (m, 2H), 7.78 (s, 1H), 11.57 (brs, 1H).

Step 2. Synthesis of 5,7-dibromo-1H-indole-3-carbaldehyde

POCl$_3$ (4.90 mL, 50.9 mmol) was added dropwise to a stirred solution of DMF (24 mL) at 0° C. and the reaction mixture was stirred at same temperature for 10 min. 5,7-dibromo-1H-indole (5.60 g, 20.3 mmol) solution in DMF (56 mL) was added dropwise at 0° C. and the reaction mixture was stirred at 0° C. for 10 min and then at room temperature for 3 h. The reaction mixture was diluted with 3.8 M KOH solution (11.4 g, 203 mmol) dropwise and the reaction mixture was heated at reflux for 16 h. The reaction mixture was poured in to saturated solution of NaHCO$_3$ (300 mL) and extracted with EtOAc (3×150 mL). The organic layer was separated, washed with H$_2$O, dried over anhydrous Na$_2$SO$_4$, and concentrated in vacuo. The crude obtained was washed with pentane (2×60 mL) and dried in vacuo to afford 5,7-dibromo-1H-indole-3-carbaldehyde (5.92 g, 97%) as a brown solid. This compound was used as such for the next reaction without further purification. $^1$H NMR (400 MHz, DMSO-d$_6$) δ 7.69 (d, J=0.98 Hz, 1H), 8.23 (d, J=0.98 Hz, 1H), 8.42 (s, 1H), 9.95 (s, 1H), 12.60 (brs, 1H).

Step 3. Synthesis of (E)-5,7-dibromo-3-(2-nitrohex-1-en-1-yl)-1H-indole

The title compound (0.69 g, 35%) was obtained as a yellow solid from 5,7-dibromo-1H-indole-3-carbaldehyde (1.50 g, 4.98 mmol) and 1-nitropentane (4.37 g, 37.3 mmol) as described in the preceding examples. $^1$H NMR (400 MHz, DMSO-d$_6$) δ 0.93 (t, J=7.1 Hz, 3H), 1.39-1.47 (m, 2H), 1.55 (m, 2H), 2.86-2.97 (m, 2H), 7.65 (s, 1H), 7.87 (s, 1H), 8.17 (s, 1H), 8.32 (s, 1H), 12.55 (brs, 1H).

Step 4. Synthesis of 5,7-dibromo-3-(2-nitrohexyl)-1H-indole

To a solution of (E)-5,7-dibromo-3-(2-nitrohex-1-en-1-yl)-1H-indole (0.41 g, 1.02 mmol) in toluene (13 mL), was added diethyl 2,6-dimethyl-1,4-dihydropyridine-3,5-dicarboxylate (0.77 g, 3.07 mmol) followed by addition of silica (0.77 g) and the reaction mixture was heated in sealed tube at 120° C. for 16 h. The reaction mixture was concentrated in vacuo. The crude obtained was purified by column chromatography (silica, 100-200 mesh, 0 to 10% EtOAc in hexanes) to afford 5,7-dibromo-3-(2-nitrohexyl)-1H-indole (0.89 g crude) as a yellow semi solid. MS (ESI) m/e [M+H]$^+$/Rt/%: 405.00/3.96/42.5%.

Step 5. Synthesis of 1-(5,7-dibromo-1H-indol-3-yl)hexan-2-amine

To a solution of 5,7-dibromo-3-(2-nitrohexyl)-1H-indole (0.89 g, 2.21 mmol) in MeOH (10 mL), Zn (0.72 g, 11.0 mmol) was added followed by NH$_4$Cl (0.59 g, 11.0 mmol) and the reaction mixture was stirred at room temperature for 2 h. Additional Zn (0.29 g, 4.42 mmol) and NH$_4$Cl (0.23 g, 11.0 mmol) were added and the reaction mixture was stirred at room temperature for 30 min. The reaction mixture was filtered through diatomaceous earth, washing with MeOH (3×30 mL), and the filtrate was concentrated in vacuo. The residue was diluted with H$_2$O (50 mL) and extracted with EtOAc (3×75 mL). The organic layer was separated, washed with brine (50 mL), dried over anhydrous Na$_2$SO$_4$, and concentrated in vacuo. The crude obtained was dissolved in DCM (5 mL), recrystallized with pentane (20 mL), filtered, and dried in vacuo to afford 1-(5,7-dibromo-1H-indol-3-yl)hexan-2-amine (0.28 g crude) as an off-white solid. The product was used in the following step without further purification.

Step 6

The title compound was prepared from 2-(4-methylpiperazin-1-yl)thiazole-5-carboxylic acid (0.20 g, 0.90 mmol) and 1-(5,7-dibromo-1H-indol-3-yl)hexan-2-amine (0.28 g, 0.75 mmol) as described in the preceding examples. The crude product was purified to an off-white solid by column chromatography (silica, 230-400 mesh, 0 to 4% MeOH in DCM) and by preparative HPLC (0.33 g, 34%). HPLC Purity: 99.7%; MS (ESI) m/e [M+H]$^+$/Rt/%: 582.00/3.10/99.5%; $^1$H NMR (400 MHz, DMSO-d$_6$) δ 0.86 (t, J=6.6 Hz, 3H), 1.19-1.35 (m, 4H), 1.40-1.52 (m, 2H), 2.20 (s, 3H), 2.32-2.38 (m, 4H), 2.82 (d, J=6.4 Hz, 2H), 3.40-3.51 (m, 4H), 3.96-4.02 (m, 1H), 7.22 (s, 1H), 7.40 (s, 1H), 7.75 (s, 1H), 7.81 (s, 1H), 7.90 (d, J=8.3 Hz, 1H), 11.24 (brs, 1H).

The remaining examples may be prepared using methods analogous to those described herein.

Biological Example 1: In-Vitro Fluorescence Polarization Assay with Alpha-Synuclein Peptide Fragment (4F)

The fluorescence polarization assay tests the ability of compounds to inhibit the self-aggregation of α-synuclein peptide fragments. Peptides were incubated for 120 min at room temperature in the presence or absence of test compounds (compound concentrations were 33.3 to 0.015 μM). Samples were read on a Beckman Coulter DTX 880 plate reader in fluorescence polarization mode using excitation at 485 nm and emission at 520 nm. Data was analyzed using a four-parameter logistic fit (XLFit, IDBS Software). Peptide 4F (CTGFVKKDQLGK (SEQ ID NO: 1)) was prepared by American Peptide. Fresh peptide samples were reconstituted in purified water at 5 mM and diluted into 50 mM HEPES pH 7.4 with 50 mM NaCl to 100 nM final concentration. Solid compounds were dissolved in DMSO (10 mM), and then diluted serially in DMSO (300×) followed by dilution in buffer (1×) to provide solutions with a consistent final DMSO concentration of 0.33%. Data for compounds tested are presented in Table 1.

TABLE 1

| Ex. | IC$_{50}$ (μM) |
|---|---|
| 1 | 1.4 |
| 2 | 1.2 |
| 3 | 1.1 |
| 4 | 1.5 |
| 5 | 0.9 |
| 6 | 1.1 |
| 7 | 1.2 |
| 8 | 1.2 |
| 9 | 1.0 |
| 10 | 1.0 |
| 11 | 1.6 |
| 12 | 1.5 |
| 13 | 1.2 |
| 14 | 1.4 |
| 15 | 2.2 |
| 16 | 1.2 |
| 18 | 1.4 |
| 19 | 2.4 |
| 20 | 2.0 |
| 22 | 1.7 |
| 23 | 1.4 |

TABLE 1-continued

| Ex. | IC$_{50}$ (µM) |
|---|---|
| 24 | 1.1 |
| 63 | 5.0 |
| 64 | 4.6 |
| 66 | 2.4 |

Biological Example 2: NMR Assay for Effect of Test Compounds on Alpha-Synuclein Interaction with Lipid Membranes To measure the interaction of test compounds with full-length ASYN in the presence of lipid membranes, an NMR assay is conducted. NMR measurements are made in 20 mM Phosphate, pH=7.4, 100 mM NaCl on Varian Direct Drive 600 MHz and Varian Inova 800 MHz spectrometers with 10% D$_2$O as lock solvent. Spectra are processed using NMRPipe (see F. Delaglio, S. Grzesiek, G. W. Vuister, G. Zhu, J. Pfeifer, A. Bax, *J Biomol NMR* 1995, 6, 277-293). α-Synuclein is used at 0.12 mM while 1-palmitoyl-2-oleoyl-sn-glycero-3-phosphoglycerol (POPG)-liposomes are added at 0.8 mg/ml where present. All $^1$H-$^{15}$N correlation spectra are recorded with a SOFAST pulse sequence (see P. Schanda, E. Kupce, B. Brutscher, *J Biomol NMR* 2005, 33, 199-211). Resonance assignment at near physiological conditions are readily available from a previous publication (BMRB ID 16300; see J. N. Rao, Y. E. Kim, L. S. Park, T. S. Ulmer, *J Mol Biol* 2009, 390, 516-529). For ligand titration, the test compounds are added stepwise to the liposome/ASYN mixture. $^{15}$N-$^1$H correlation spectra are recorded for each step, and the signal intensities are referenced to the free form of ASYN while accounting for dilution effects. To reduce noise in the available data, the intensity ratio for several amide positions of ASYN are averaged for two regions chosen to correspond to the SL1 and SL2 binding modes observed previously (see C. R. Bodner, A. S. Maltsev, C. M. Dobson, A. Bax, *Biochemistry* 2010, 49, 862-871).

The heteronuclear single quantum coherence (HSQC) spectroscopy signal intensity for ASYN is attenuated when ASYN is embedded in lipid membranes. Reversal of lipid-induced attenuation of the HSQC signal by test compounds indicates the ability of the test compound to disrupt the association of ASYN with lipid membrane. Test compounds may reverse the interaction of ASYN with 1-palmitoyl-2-oleoyl-sn-glycero-3-phosphoglycerol (POPG) (0.8 mg/mL) liposomes in a concentration-dependent manner. Results for ASYN residues 66-76 are also analyzed.

Biological Example 3: Effect of Test Compounds on Annular Oligomers in Lipid Membranes Electron microscopy is used to directly visualize the effect of test compounds on the formation of ASYN oligomers in lipid membranes. Formvar grids with the lipid monolayer are counterstained with a saturated uranyl acetate solution in 50% EtOH for 25 minutes. The grids are then floated on a droplet of 2% bismuth subnitrate for 10 min, and again carefully rinsed with double distilled water three times and allowed to completely dry. Grids are imaged using a Zeiss EM10 transmission electron microscope Electron Microscope. From each sample grid, 5-10 electron micrographs at 10,000× magnification and 5-10 images at 40,000× are obtained. The best negatives are scanned and analyzed with the ImageJ 1.43 program to estimate the numbers of annular oligomers per higher power field (100×100 nm) (Rasband, W. S., ImageJ, U. S. National Institutes of Health, Bethesda, Md., USA, http://imagej.nih.gov/ij/, 1997-2014).

Test compounds that interact with oligomeric and lipid-bound forms of ASYN may do so in a way that reduces the affinity of ASYN oligomers for the lipid membrane. Compounds can interfere with ASYN oligomerization, the binding of ASYN to lipid membranes, and the formation of annular ring-like oligomers ("pores") in these membranes, which may alter the aggregation of ASYN and prevent the formation of specific oligomeric structures believed to contribute to the neurotoxicity of misfolded, oligomerized ASYN in Parkinson's disease.

Biological Example 4: Effect of Test Compounds on Alpha-Synuclein in Cells

The effect of test compounds on the accumulation of ASYN in B103 neuroblastoma cells overexpressing human ASYN is studied. A lentiviral expression system is used to express GFP-tagged ASYN in these cells. Forty-eight hours after expression is initiated, vehicle or test compound is added for an additional 24 hours. The amount of accumulated GFP-ASYN is then visualized to determine the reduction in concentration of ASYN-GFP in the ASYN-overexpressing cells.

Biological Example 5: In Vivo Efficacy Studies

Parkinson's disease (PD) is characterized by aberrant accumulation of oligomeric forms of alpha-synuclein (ASYN). It is hypothesized that these toxic forms of ASYN contribute to the neuronal dysfunction and cell death observed in PD and other synucleinopathies, in part, though the formation of pore-like structures in cell membranes. The compounds described herein were designed to ameliorate PD-related symptoms and pathology by selectively blocking the formation and accumulation of these toxic species of ASYN.

A) Transgenic Mouse Model of Parkinson's Disease. Test compounds are evaluated in a transgenic mouse model of PD overexpressing human wild-type ASYN under the Thy-1 promoter (also referred to as the Line 61 ASYN transgenic mouse), by administering test compounds at 0, 1, or 5 mg/kg (i.p.) once daily (five days per week) for three months and then assessing PD-relevant sensorimotor performance, biochemical alterations, and neuropathological changes in ASYN and related proteins.

The Round Beam Task is used to assess sensorimotor impairments, using number of slips as the primary outcome measure. ASYN transgenic and non-transgenic mice are tested, and the statistical significance in the increase in number of slips for vehicle-treated transgenic subjects as compared to vehicle-treated non-transgenic control subjects is calculated.

Western Blot analysis of cerebral cortical and hippocampal brain homogenates is performed, and the statistical significance of the reduction in transgenic ASYN protein levels is calculated. Biochemical evaluations of oligomeric proteins using A11 antibody dot blot methods (including ASYN) in cortical homogenates are performed.

B) Line 61 ASYN Transgenic Mouse Models. Previous immunolabeling studies by Masliah and colleagues have demonstrated statistically significant increases in ASYN immunolabeling in cortical neuropil in the Line 61 ASYN transgenic mouse (Masliah E. et al., Science, 2000, 287 (5456):1265-9). These neuropathological findings can be reconfirmed in the current study using the methods described by Masliah and colleagues. Neurodegeneration-related markers including tyrosine hydroxylase, NeuN, and GFAP are monitored.

The effect of test compounds at various dosages on sensorimotor impairment in Line 61 ASYN transgenic mice is studied, using the Round Beam Motor Performance assay described above, and the statistical significance in the increase in the number of slips in vehicle-treated ASYN transgenic control mice as compared to vehicle-treated non-transgenic control subjects is calculated. These studies evaluate improvement in sensorimotor, biochemical, behavioral, and neuropathological outcomes in a transgenic mouse model Parkinson's disease/Dementia with Lewy bodies (PD/DLB).

The invention claimed is:
1. A compound of Formula (IA):

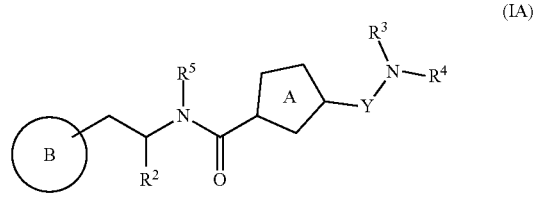

(IA)

wherein
B is indole, indazole, pyrrolopyridine, benzisoxazole, benzofuran, benzothiophene, quinolone, imidazopyridine, quinolinone, or pyrrolidine, each of which is unsubstituted or substituted with —($R^1$)$_m$;
wherein m is 0, 1, or 2; and
each $R^1$ is independently $C_{1-4}$alkyl (optionally substituted with one or more halo or —$OC_{1-4}$alkyl groups), halo, —OH, or $OC_{1-4}$alkyl;
$R^2$ is H, $C_{1-5}$alkyl (unsubstituted or substituted with one or more halo substituents), —$OC_{1-4}$alkyl, or —$SC_{1-4}$alkyl, or an aryl, monocyclic cycloalkyl, or —$C_{1-4}$alkyl-(monocyclic cycloalkyl) group, wherein each aryl or cycloalkyl is unsubstituted or substituted with halo, $C_{1-4}$alkyl, or halo-$C_{1-4}$alkyl;
A is a 5-membered heteroaryl ring;
Y is absent or is $C_{1-4}$alkylene; and
where when Y is absent, $R^3$ and $R^4$ taken together with the nitrogen to which they are attached form a monocyclic or bicyclic heterocycloalkyl or

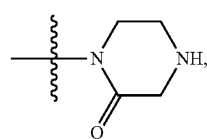 [SMILES: *N1CCNCC1=O]

each unsubstituted or substituted with one or more $R^g$ substituents; and
when Y is $C_{1-4}$alkylene, $R^3$ and Y taken together with the nitrogen to which $R^3$ is attached form a monocyclic or bicyclic heterocycloalkyl ring, which ring is unsubstituted or substituted with $C_{1-4}$alkyl or halo; and $R^4$ is H or $C_{1-4}$alkyl;
wherein each $R^g$ substituent is independently $C_{1-4}$alkyl (unsubstituted or substituted with one or more $C_{1-4}$alkoxy, halo-$C_{1-4}$alkoxy, or halo groups), $C_{3-7}$cycloalkyl, $C_{1-4}$alkoxy, halo-$C_{1-4}$alkoxy, or halo; and $R^5$ is H or $C_{1-4}$alkyl;
or a pharmaceutically acceptable salt thereof,
provided that the compound is not:

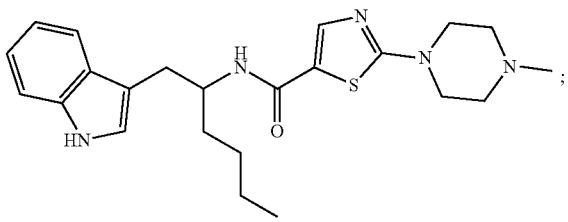

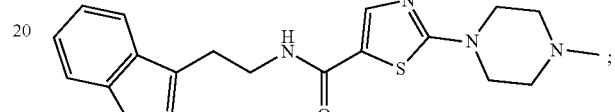

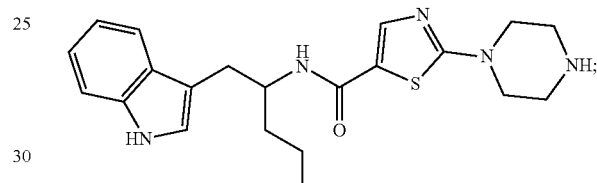

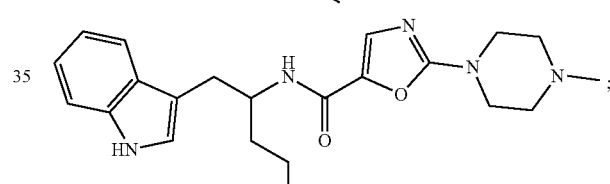

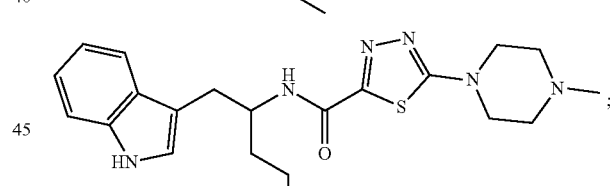

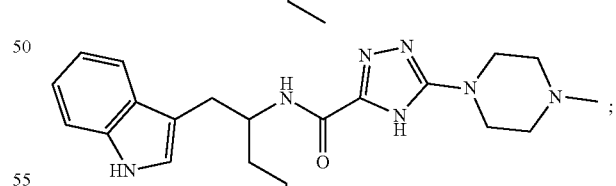

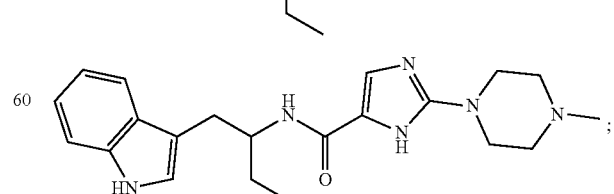

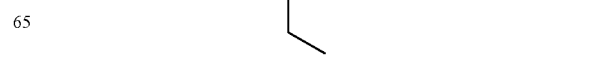

181
-continued

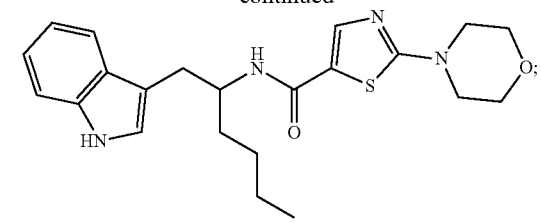
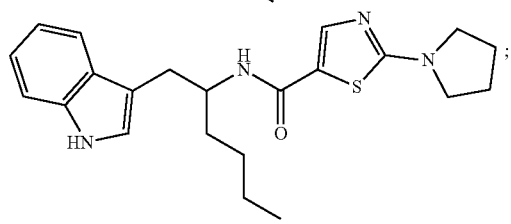
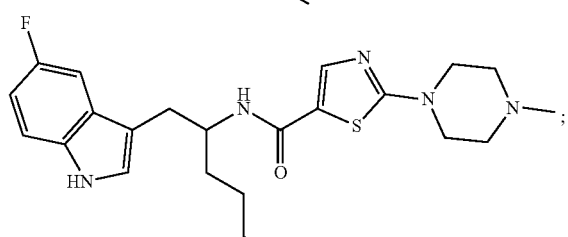
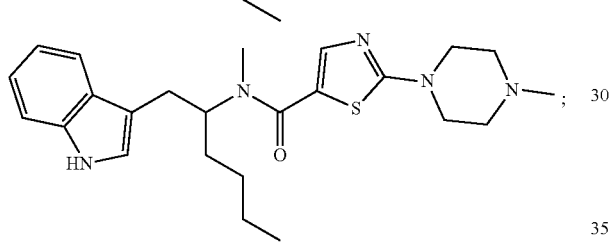
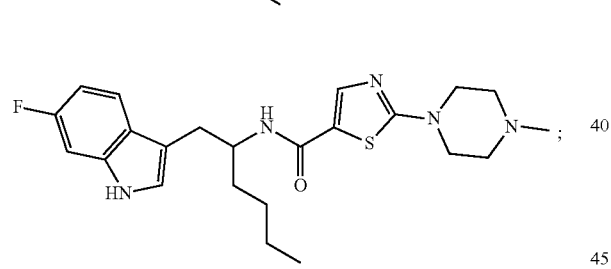
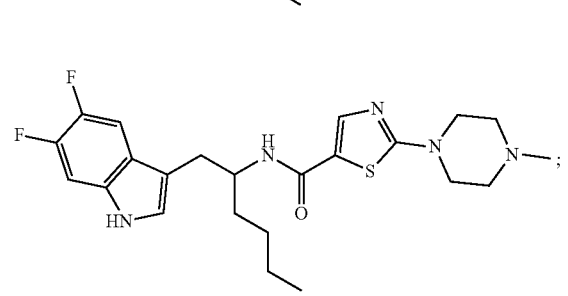
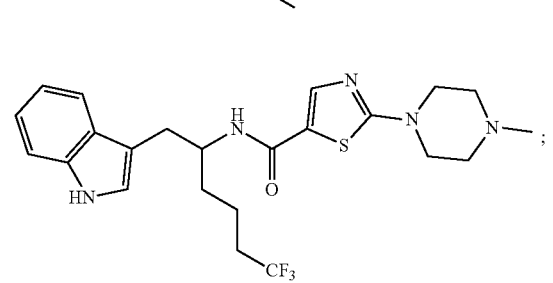

182
-continued

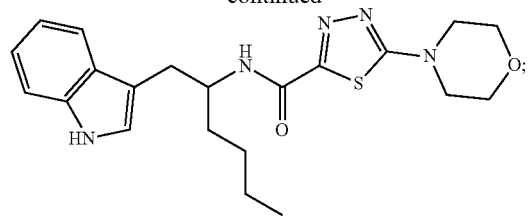
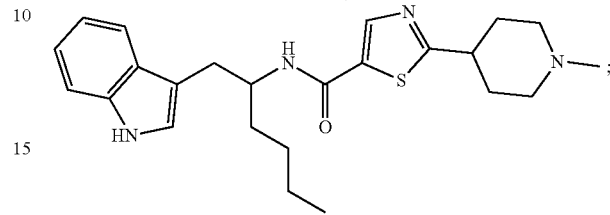
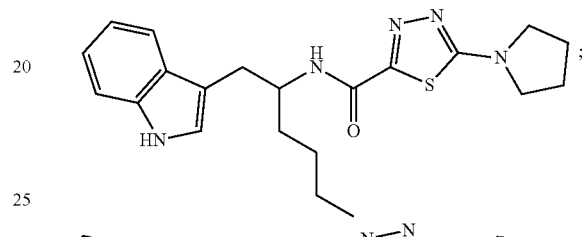
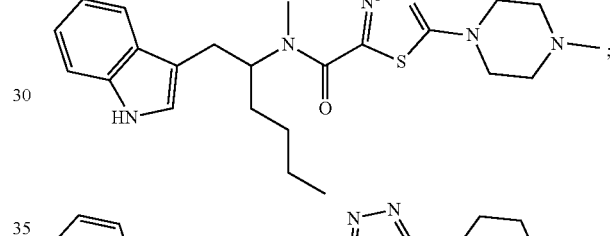
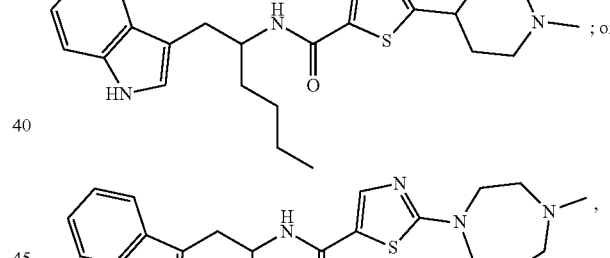
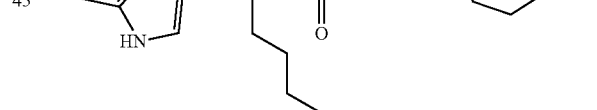

or a pharmaceutically acceptable salt thereof.

2. The compound of claim 1, or a pharmaceutically acceptable salt thereof, wherein one or more of the following limitations applies:
  (a1) m is 1 or 2; or
  (a2) m is 1 or 2, and $R^1$ is as defined herein, wherein at least one $R^1$ is $C_{1-4}$alkyl (substituted with one or two halo groups, or with —$OC_{1-4}$alkyl), $C_{1-3}$alkyl (substituted with —$CF_3$), —OH, or —$OC_{1-4}$alkyl;
  (b) $R^2$ is $C_{1-5}$alkyl substituted with two halo groups, —$OC_{1-4}$alkyl, or —$SC_{1-4}$alkyl, or is monocyclic cycloalkyl substituted with halo, $C_{1-4}$alkyl, or halo-$C_{1-4}$alkyl, or is —$C_{1-4}$alkyl-(monocyclic cycloalkyl), wherein the cycloalkyl is unsubstituted or substituted with halo, $C_{1-4}$alkyl, or halo-$C_{1-4}$alkyl, or is aryl substituted with halo, $C_{1-4}$alkyl, or halo-$C_{1-4}$alkyl; and (c) when $R^3$ and $R^4$ taken together with the nitrogen to which they are attached form a monocyclic heterocycloalkyl, said heterocycloalkyl is substituted with one or more $R^g$ substituents and $R^g$ is as defined herein; and at least one $R^g$ substituent is $C_{1-4}$alkyl (substituted with one or more $C_{1-4}$alkoxy, halo-$C_{1-4}$alkoxy, or halo groups), $C_{1-4}$alkoxy, halo-$C_{1-4}$alkoxy, or halo.

3. The compound of claim 1, or a pharmaceutically acceptable salt thereof, wherein B is optionally substituted indole, benzofuran, benzothiophene, indazole, benzisoxazole, imidazopyridine, or pyrrolopyridine.

4. The compound of claim 1, or a pharmaceutically acceptable salt thereof, wherein $R^2$ is unsubstituted or substituted $C_{1-5}$alkyl; or is unsubstituted or substituted $C_{3-5}$alkyl.

5. The compound of claim 1, or a pharmaceutically acceptable salt thereof, wherein $R^2$ is monocyclic cycloalkyl or —$C_{1-4}$alkyl-(monocyclic cycloalkyl), wherein each cycloalkyl is unsubstituted or substituted with halo, $C_{1-4}$alkyl, or halo-$C_{1-4}$alkyl.

6. The compound of claim 1, or a pharmaceutically acceptable salt thereof, wherein $R^2$ is optionally substituted aryl.

7. The compound of claim 1, or a pharmaceutically acceptable salt thereof, wherein $R^2$ is substituted $C_{1-5}$alkyl, or substituted monocyclic cycloalkyl, or substituted —$C_{1-4}$alkyl-(monocyclic cycloalkyl), or substituted phenyl.

8. The compound of claim 1, or a pharmaceutically acceptable salt thereof, wherein A is pyrrole, furan, thiophene, pyrazole, imidazole, oxazole, isoxazole, thiazole, triazole, oxadiazole, thiadiazole, or tetrazole.

9. The compound of claim 1, or a pharmaceutically acceptable salt thereof, wherein Y is absent and $R^3$ and $R^4$ taken together with the nitrogen to which they are attached form a monocyclic or bicyclic heterocycloalkyl ring, unsubstituted or substituted with one or more $R^g$ substituents.

10. The compound of claim 9, or a pharmaceutically acceptable salt thereof, wherein $R^3$ and $R^4$ taken together with the nitrogen to which they are attached form azetidine, pyrrolidine, piperidine, piperazine, morpholine, thiomorpholine, 1,1-dioxo-thiomorpholine, azepine, or diazepine, each unsubstituted or substituted with one or more $R^g$ substituents.

11. The compound of claim 9, or a pharmaceutically acceptable salt thereof, wherein $R^3$ and $R^4$ taken together with the nitrogen to which they are attached form piperazine substituted with one, two, or three $R^g$ substituents.

12. The compound of claim 9, or a pharmaceutically acceptable salt thereof, wherein $R^3$ and $R^4$ taken together with the nitrogen to which they are attached form a monocyclic heterocycloalkyl ring, unsubstituted or substituted with one or more $R^g$ substituents, and Y is absent.

13. The compound of claim 1, or a pharmaceutically acceptable salt thereof, wherein Y is $C_{1-4}$alkylene, and $R^3$ and Y are taken together with the nitrogen to which $R^3$ is attached form a monocyclic heterocycloalkyl ring, which ring is unsubstituted or substituted with $C_{1-4}$alkyl or halo; and $R^4$ is H or $C_{1-4}$alkyl.

14. The compound of claim 1, which is a compound of Formula (II):

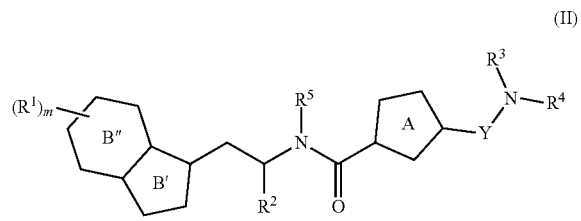

(II)

wherein

B' and B" together form indole, indazole, pyrrolopyridine, benzisoxazole, benzofuran, benzothiophene, or imidazopyridine; and R', $R^2$, $R^3$, $R^4$, $R^5$, m, A, and Y are as defined in any one of the preceding claims;

or a pharmaceutically acceptable salt thereof.

15. The compound of claim 1, which is a compound of Formula (III):

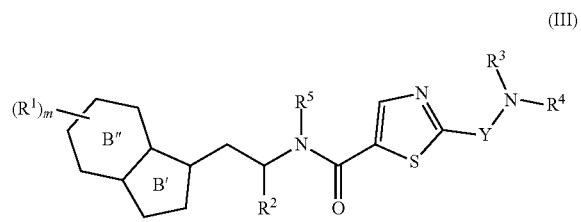

(III)

wherein

B' and B" together form indole, indazole, pyrrolopyridine, benzisoxazole, benzofuran, benzothiophene, or imidazopyridine; and R', $R^2$, $R^3$, $R^4$, $R^5$, m, and Y are as defined in any one of the preceding claims;

or a pharmaceutically acceptable salt thereof.

16. A compound selected from the group consisting of:

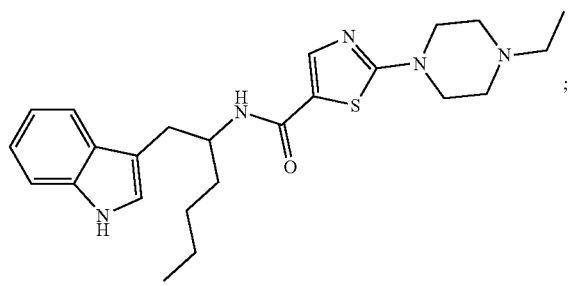

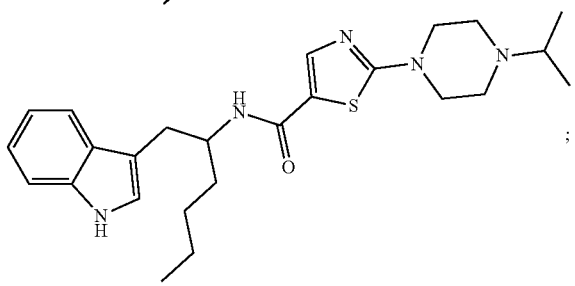

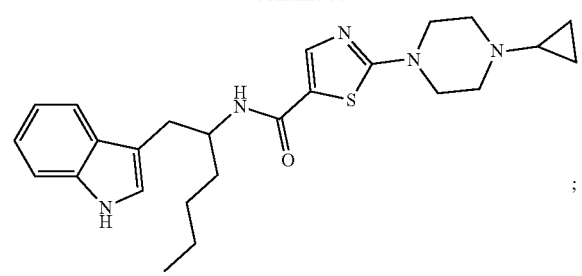
;
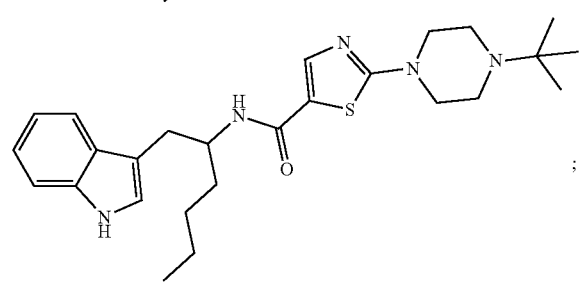
;
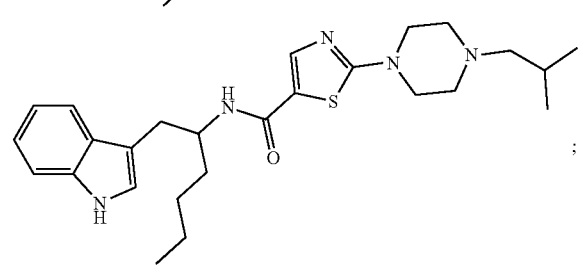
;
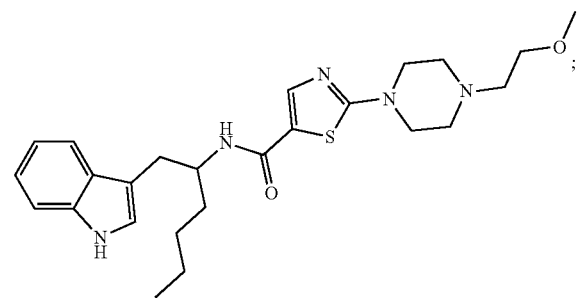
;
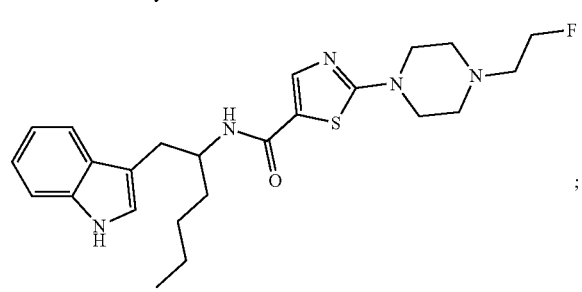
;
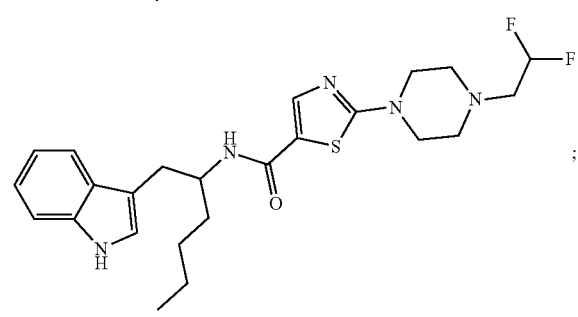
;
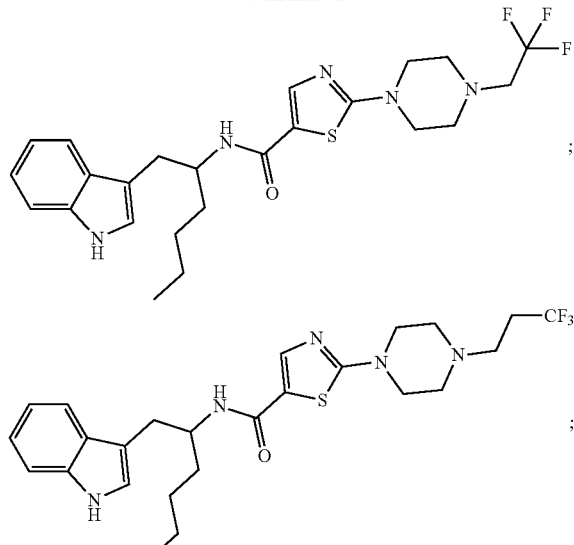
;
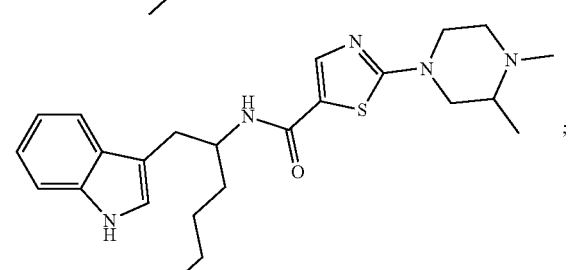
;
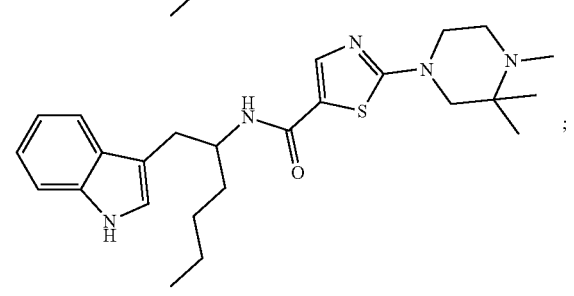
;
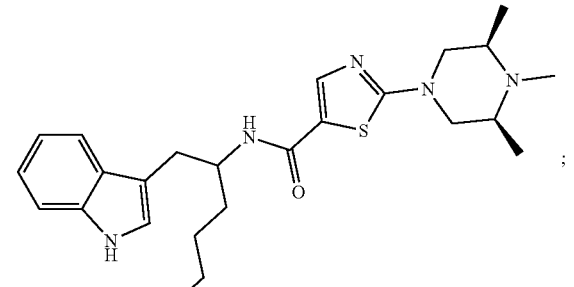
(cis)
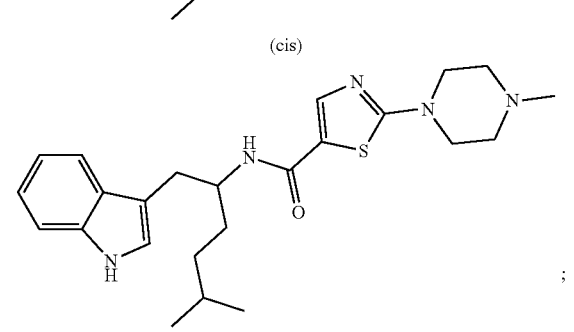
;

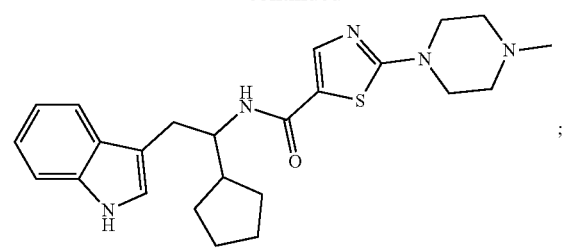
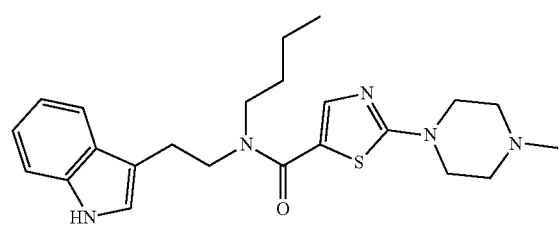
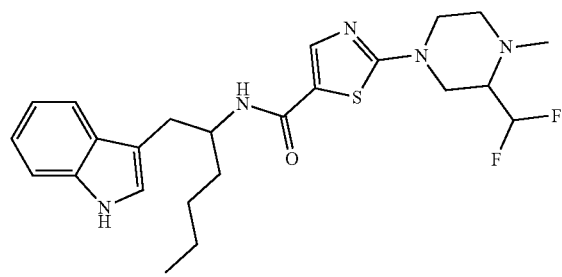
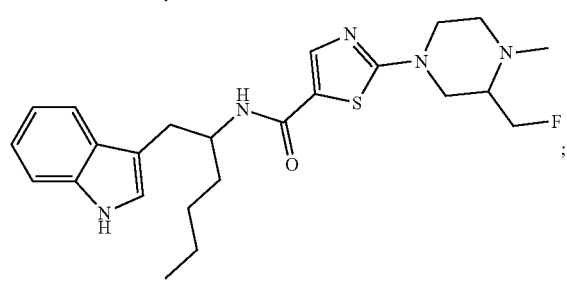
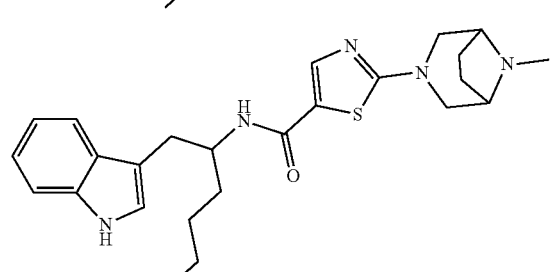
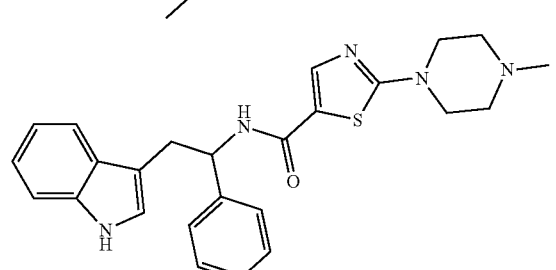
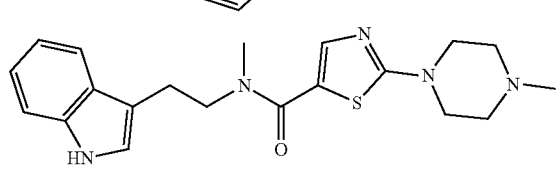
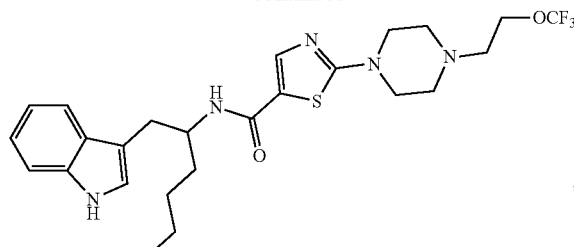
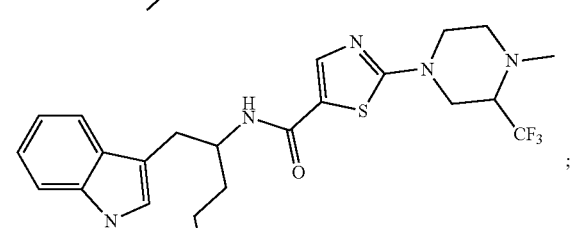
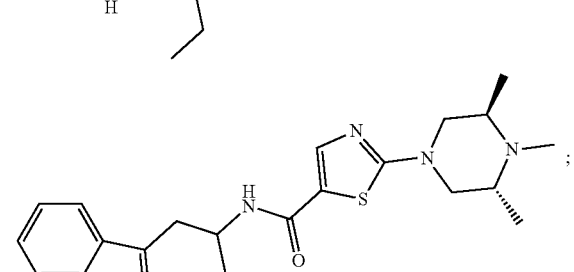
(trans)
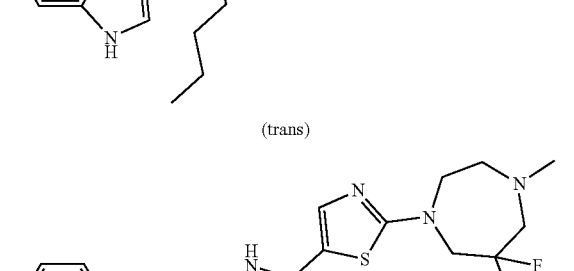
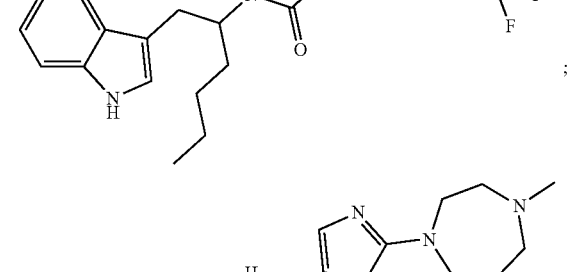
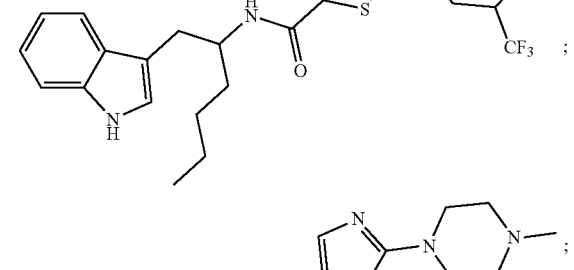
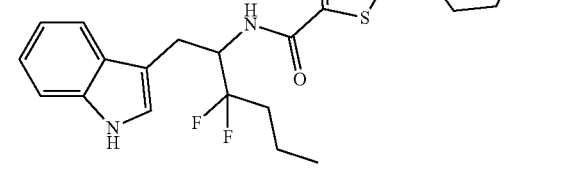

189
-continued
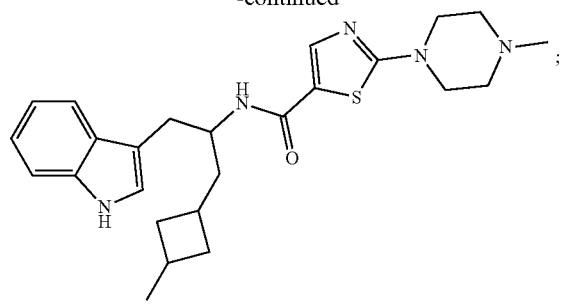
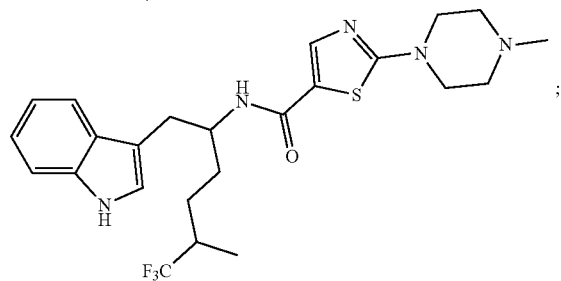
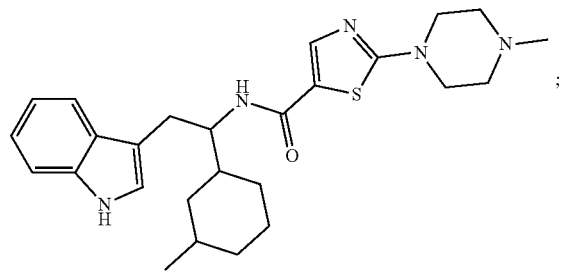
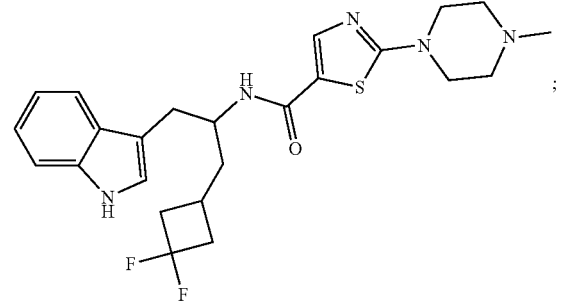
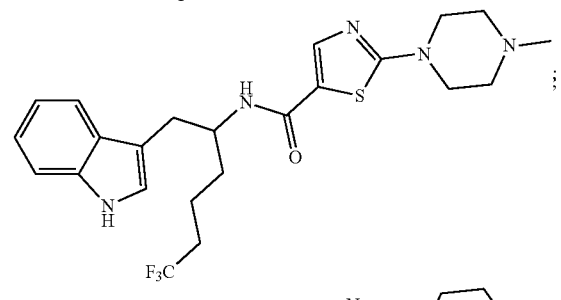
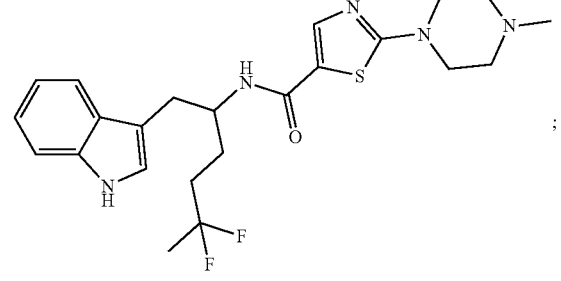
190
-continued
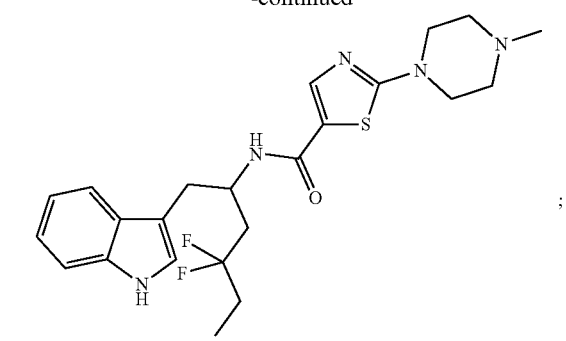
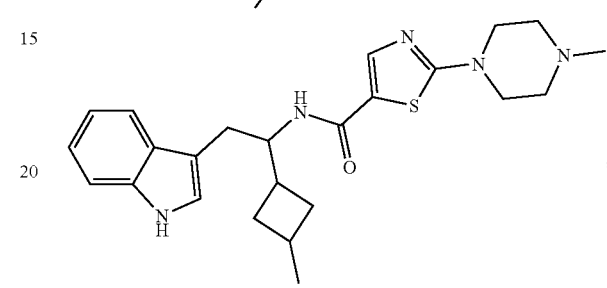
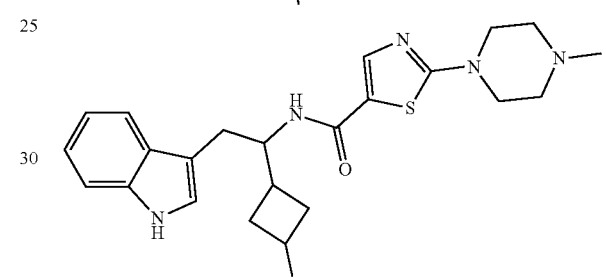
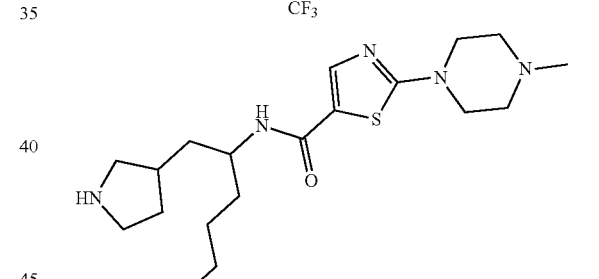
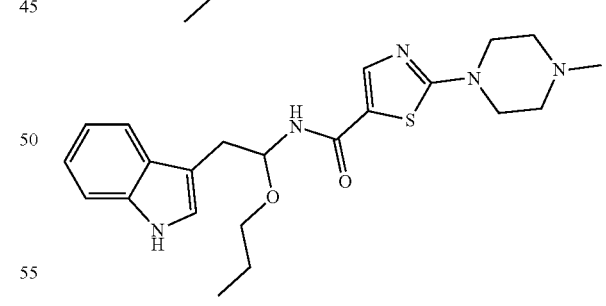
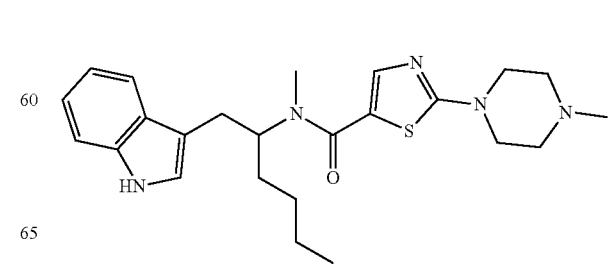

191
-continued
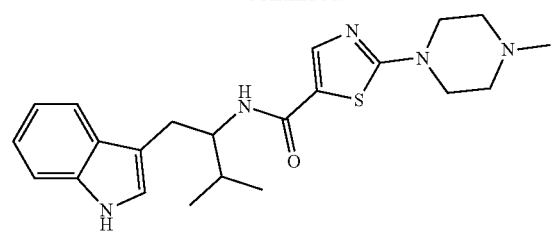
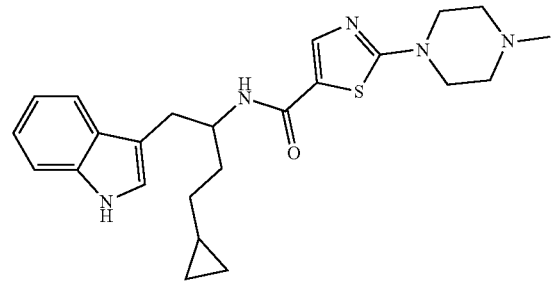
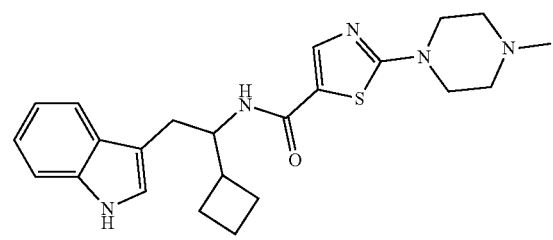
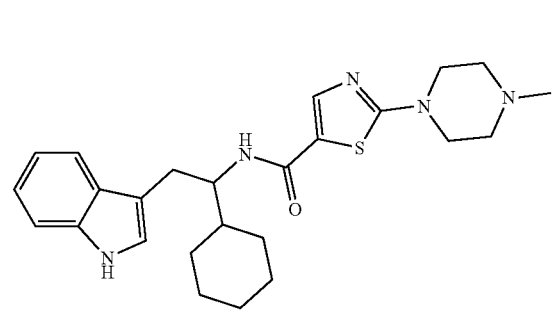
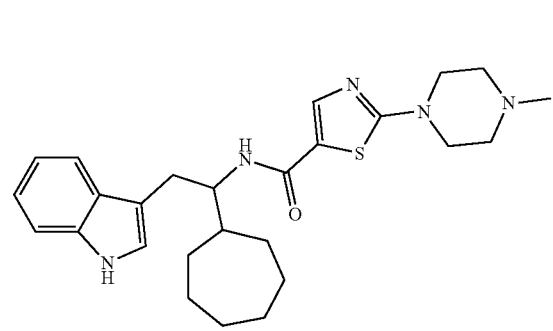
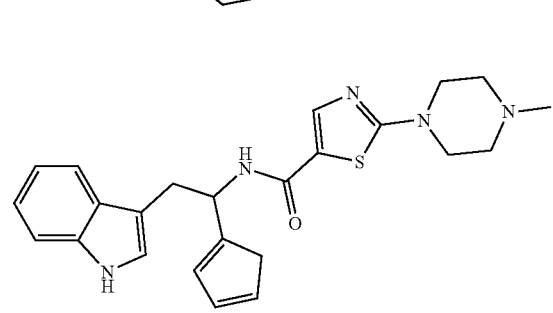
192
-continued
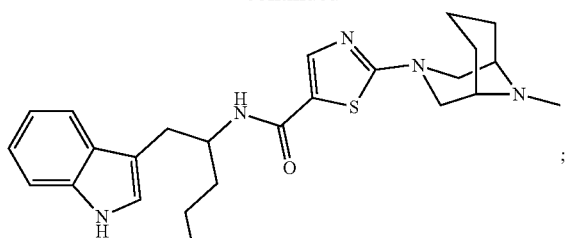
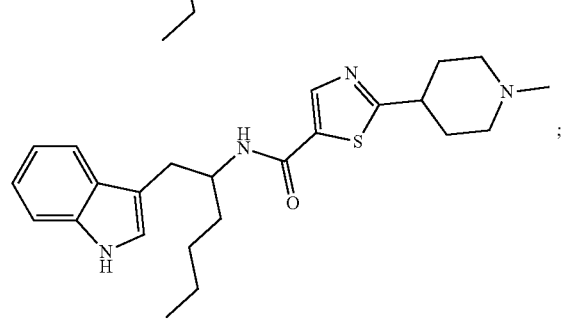
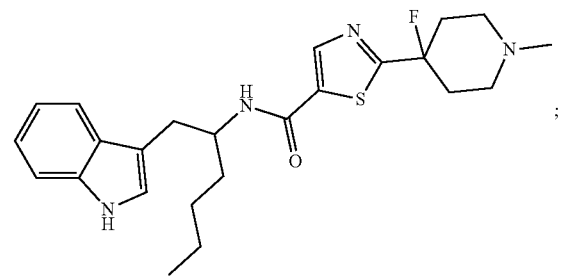
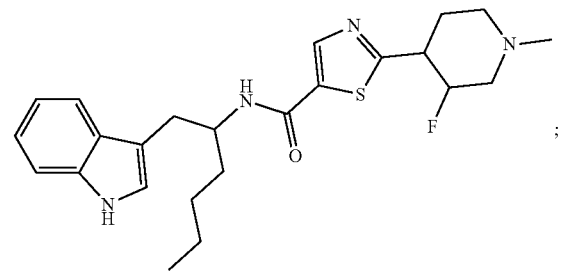
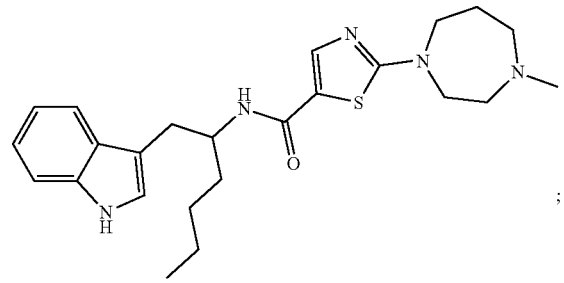
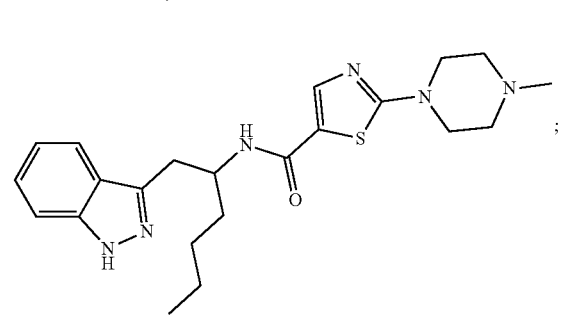

193
-continued
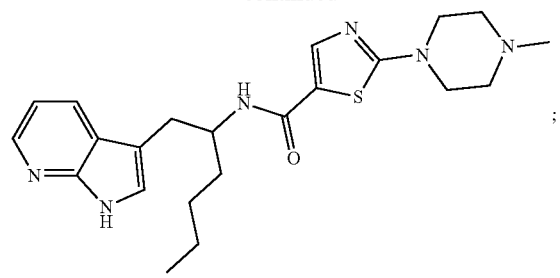
;
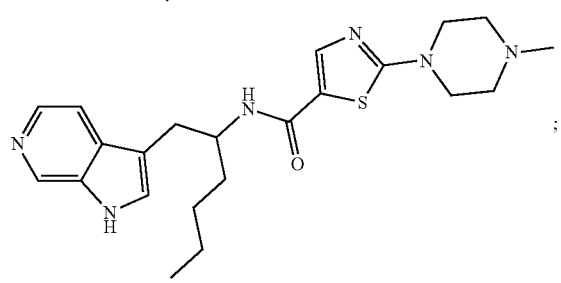
;
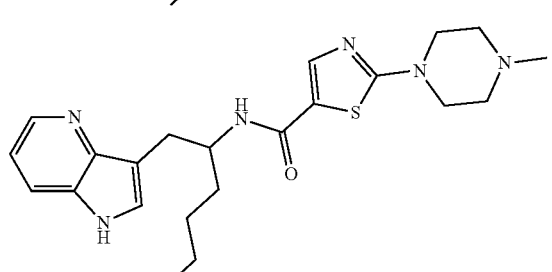
;
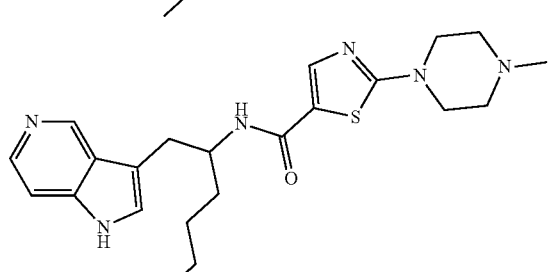
;
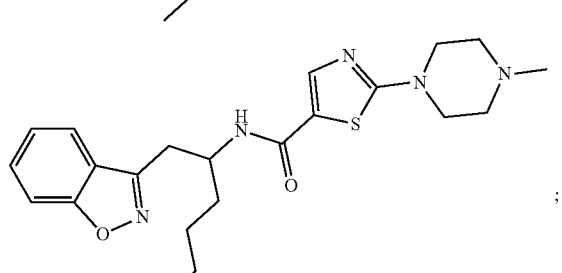
;
;
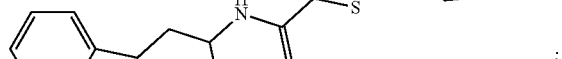
194
-continued
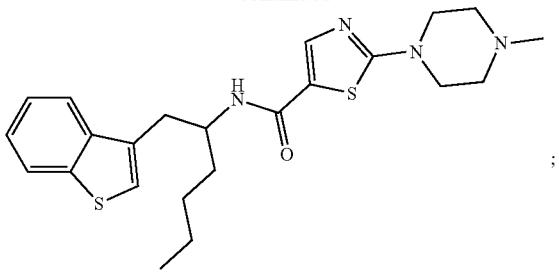
;
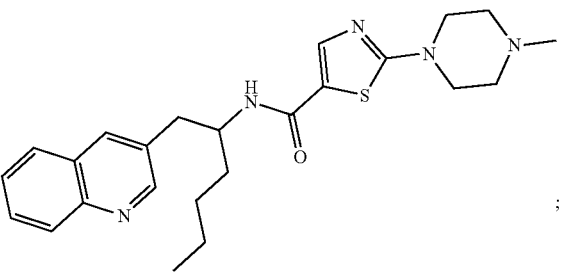
;
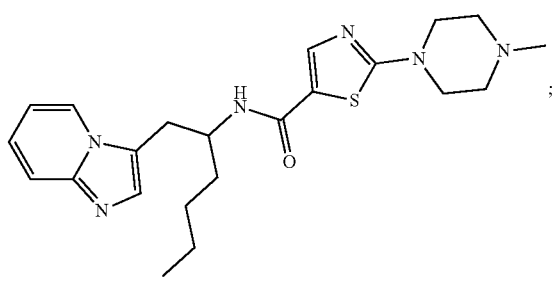
;
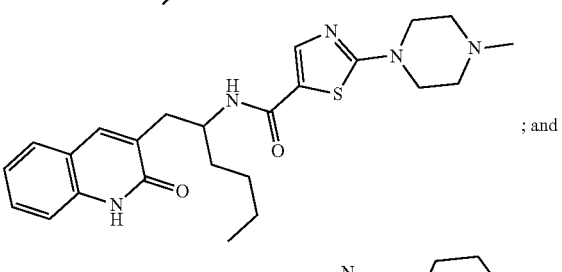
; and
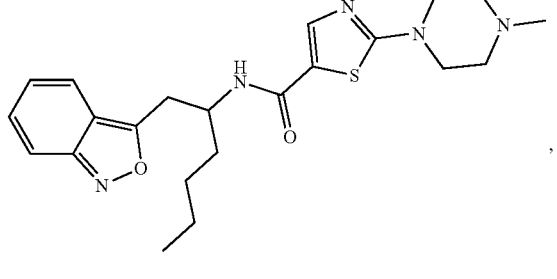
,
or a pharmaceutically acceptable salt thereof.
17. A compound selected from the group consisting of:
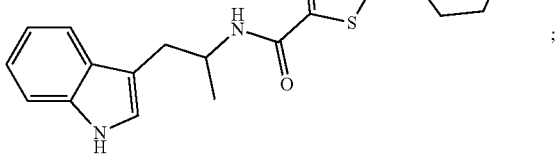
;

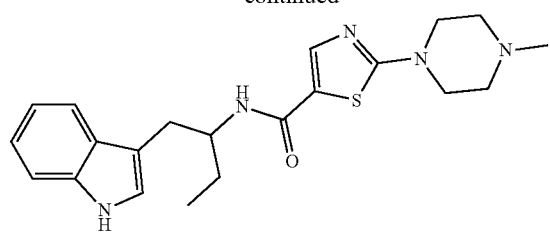
;
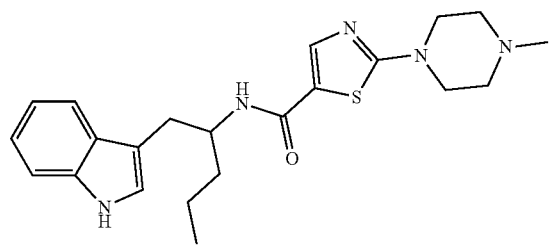
;
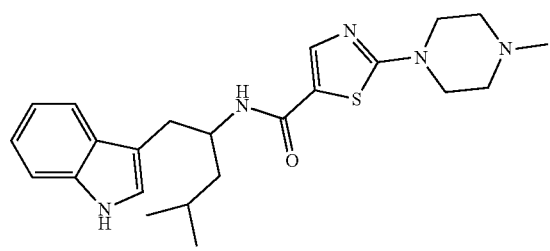
;
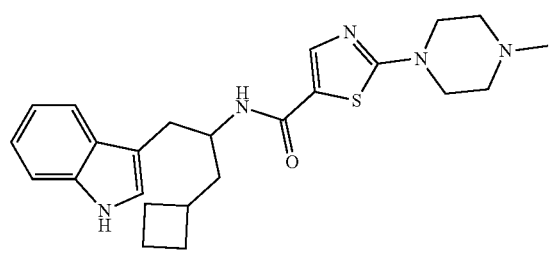
;
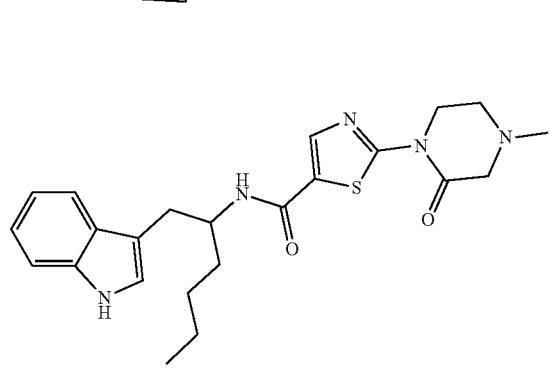
;
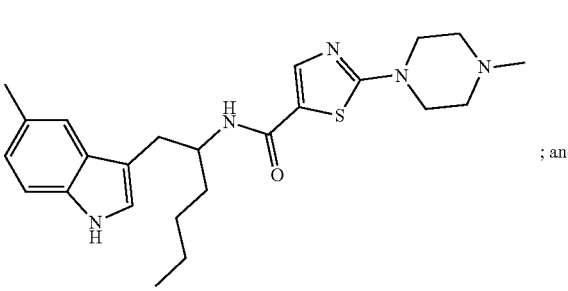
; and
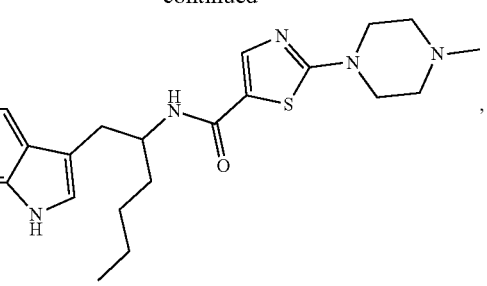
,
or a pharmaceutically acceptable salt thereof.
18. A compound selected from the group consisting of
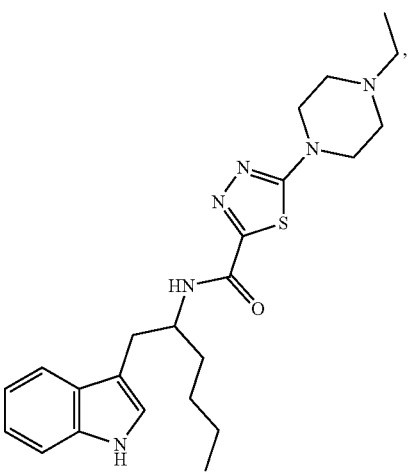
,
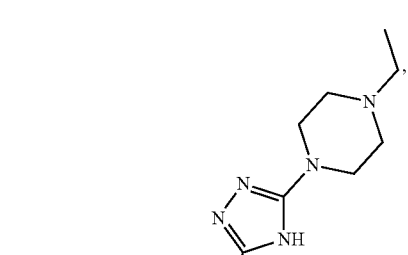
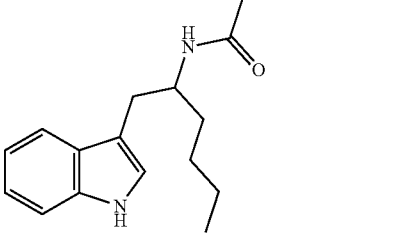

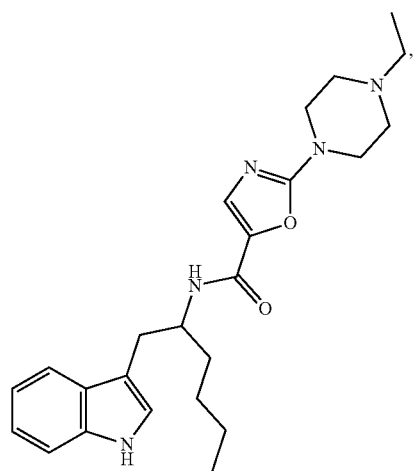
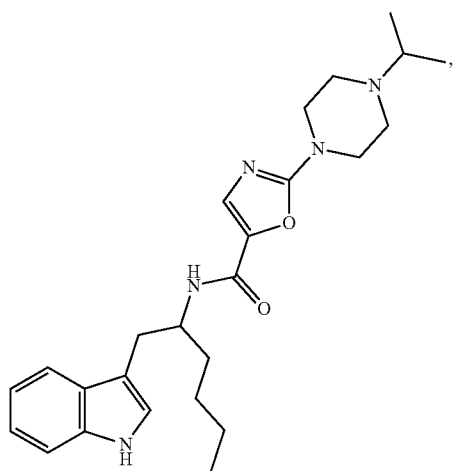
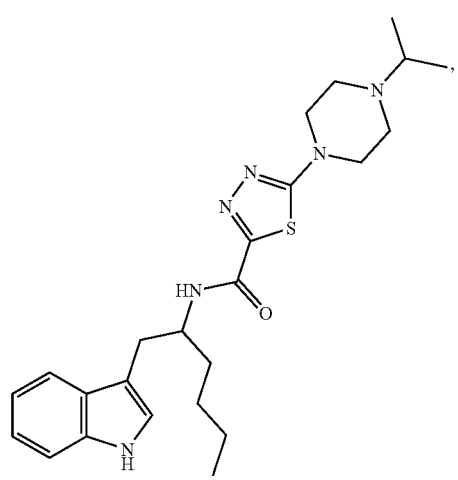
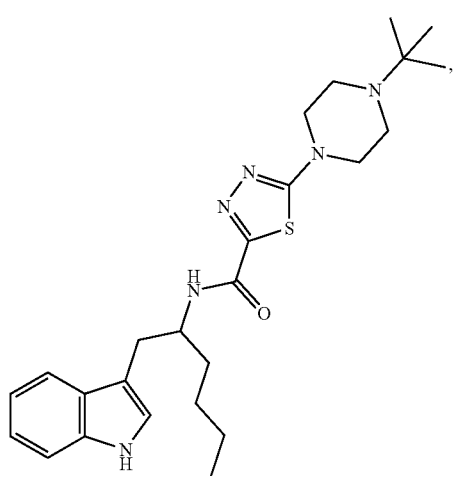
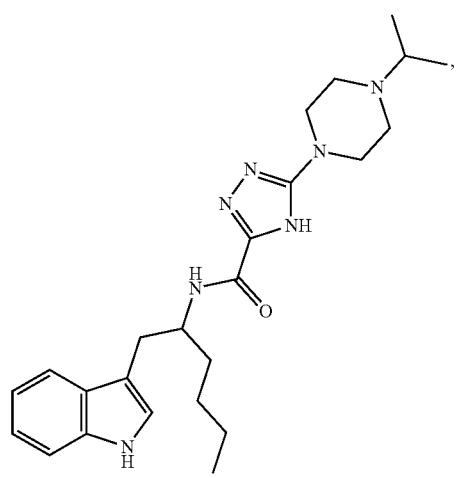
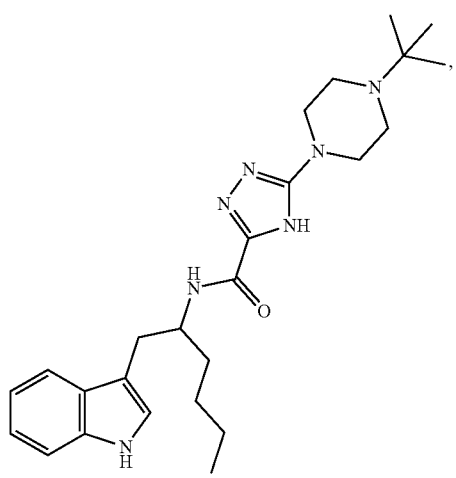

199
-continued
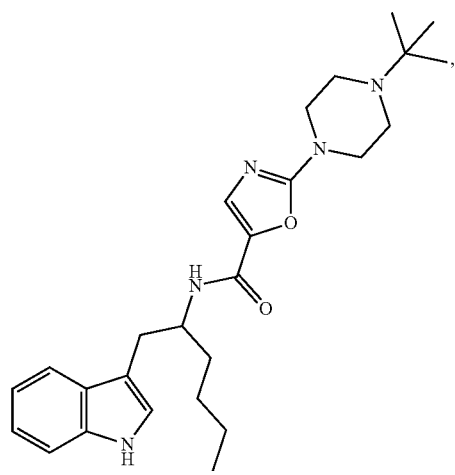
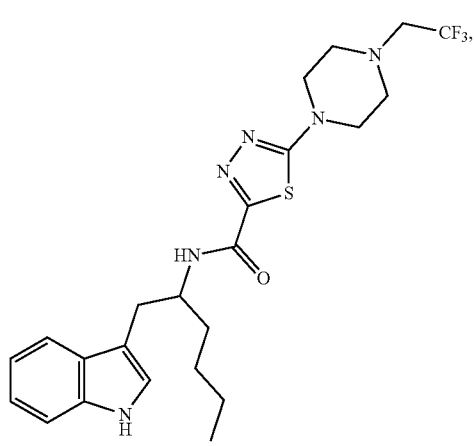
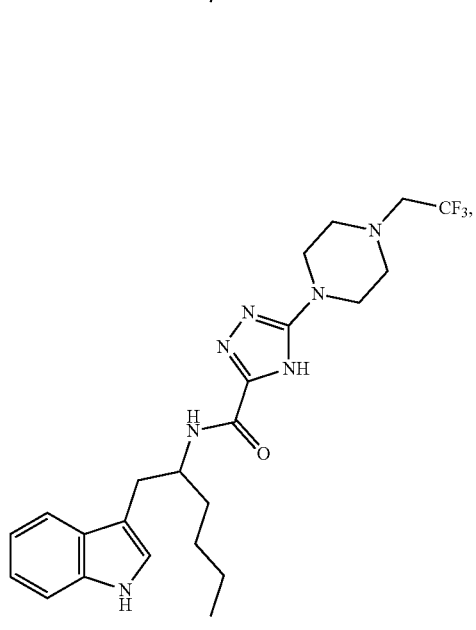
200
-continued
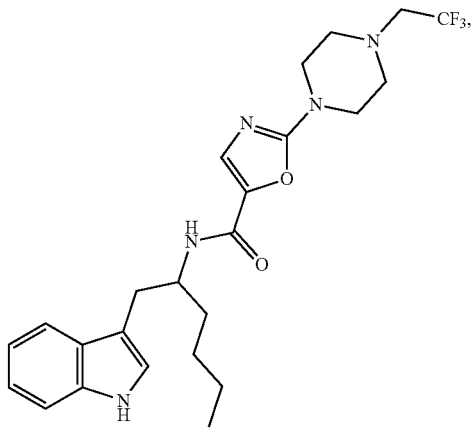
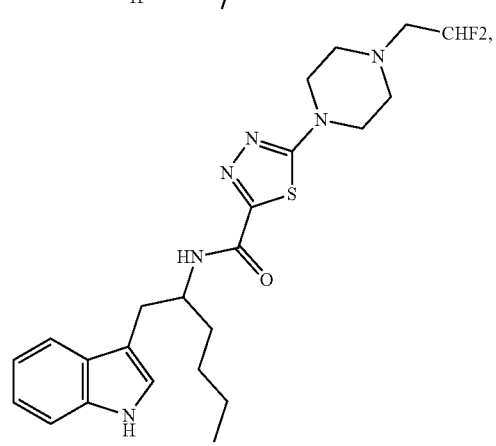
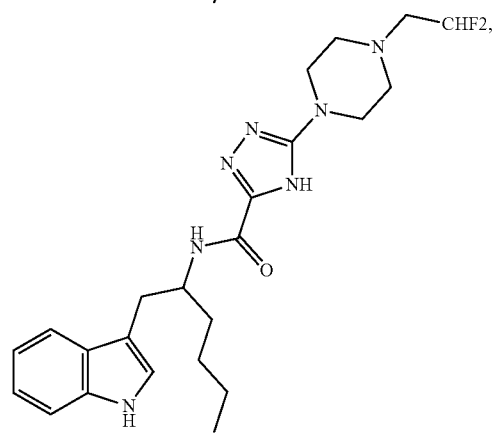
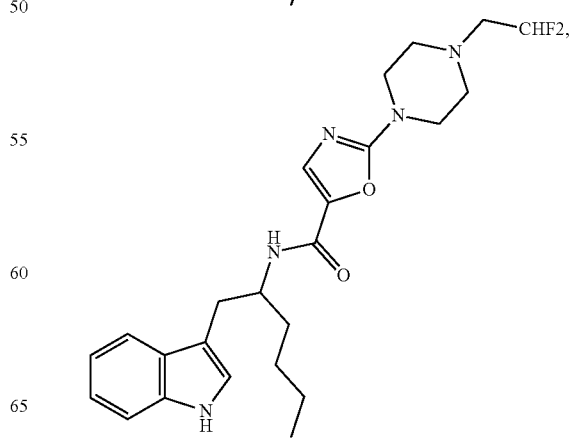

201 -continued 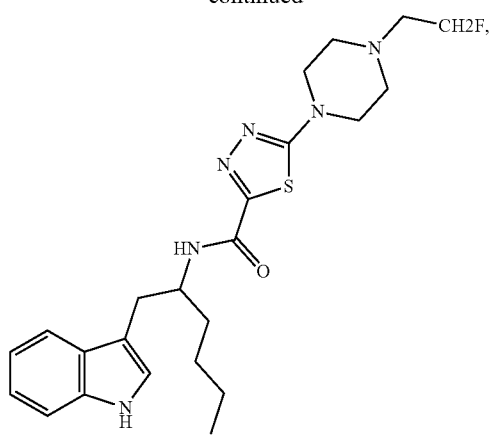
202 -continued 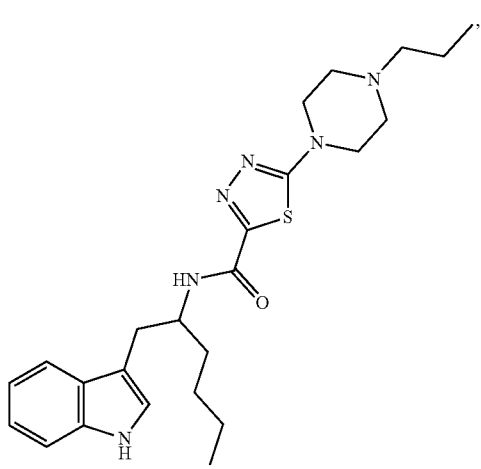

203
-continued
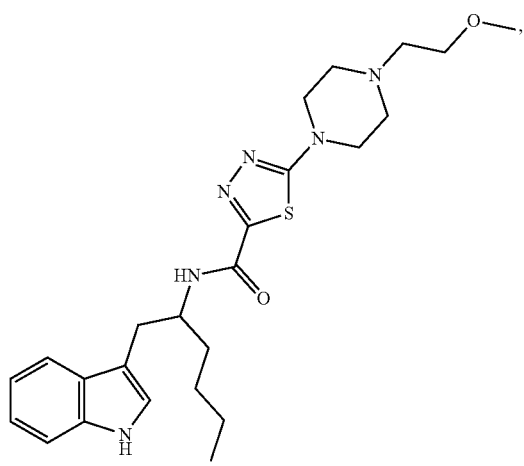
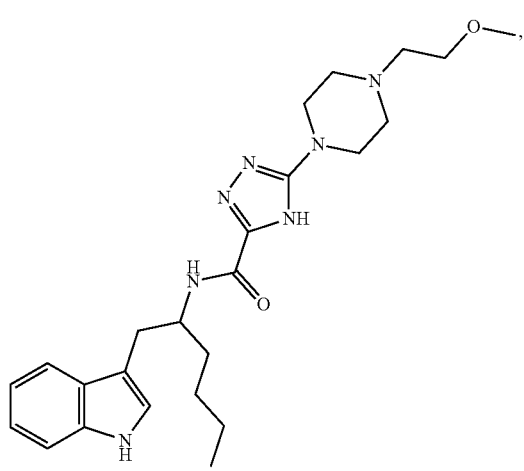
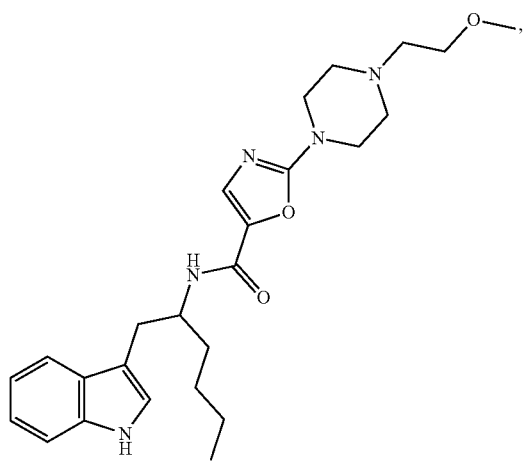
204
-continued
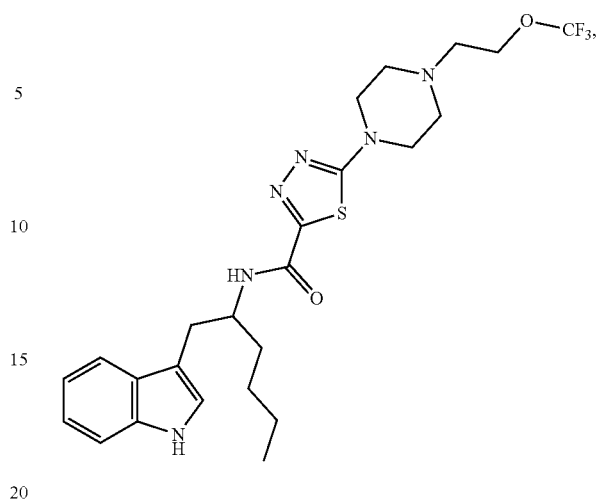
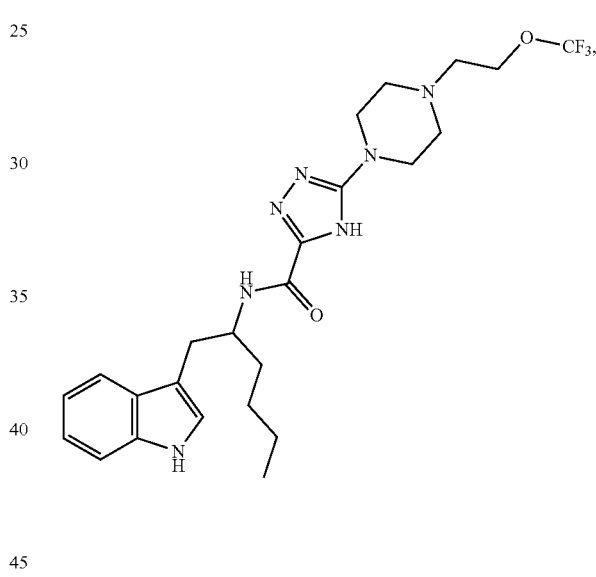
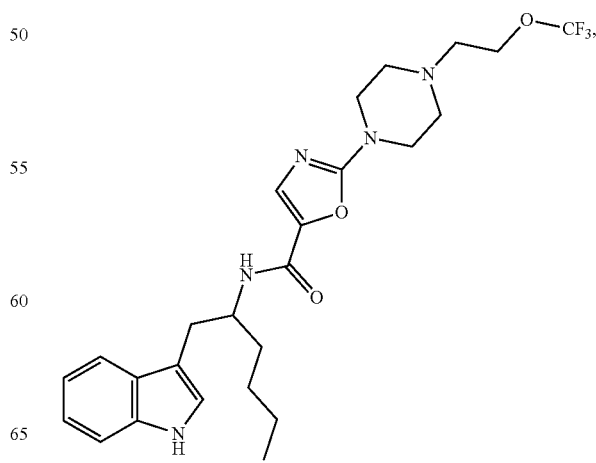

205
-continued
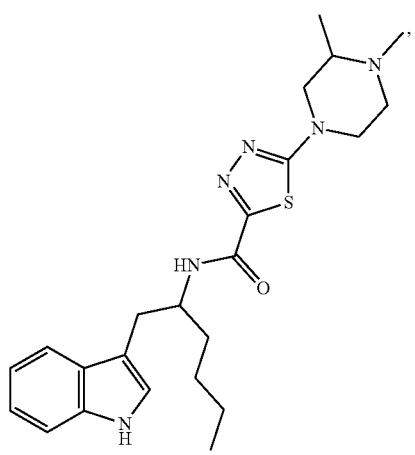
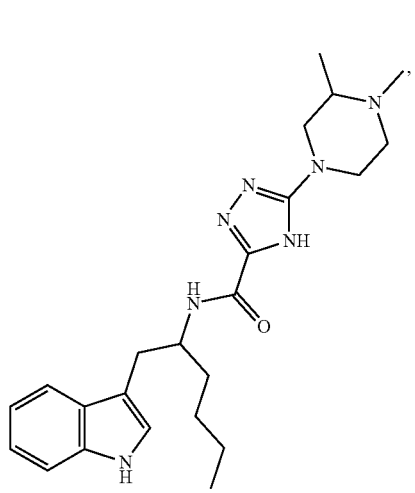
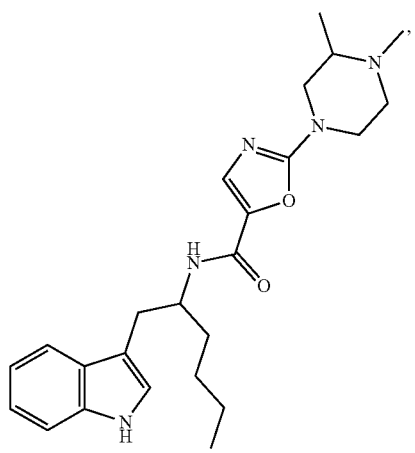
206
-continued
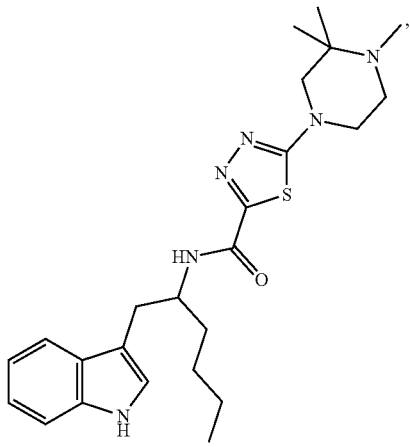
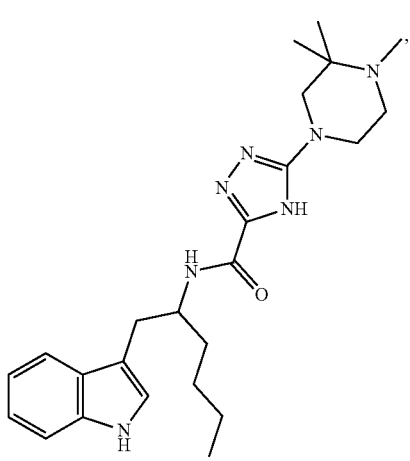
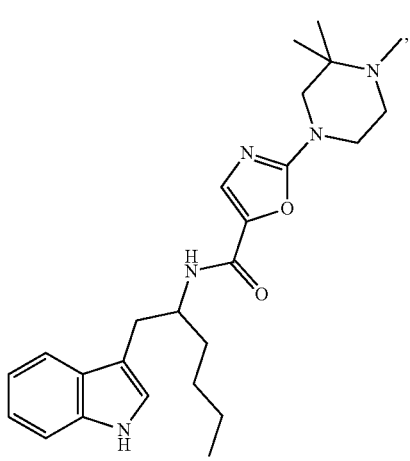

207
-continued
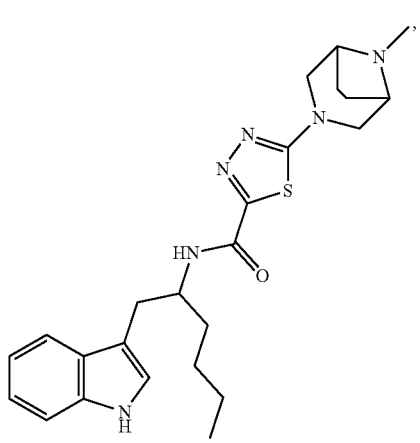
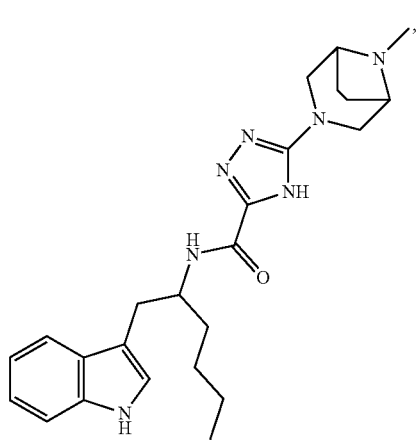
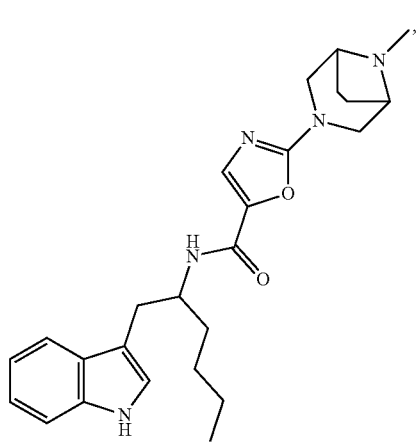
208
-continued
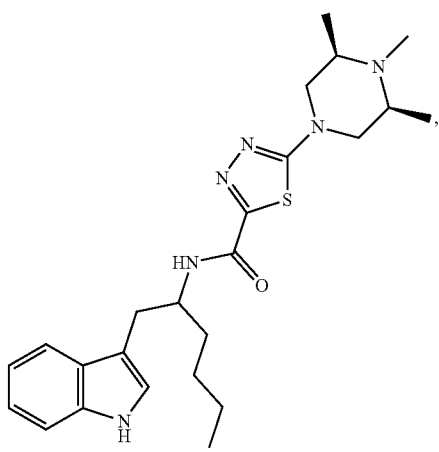
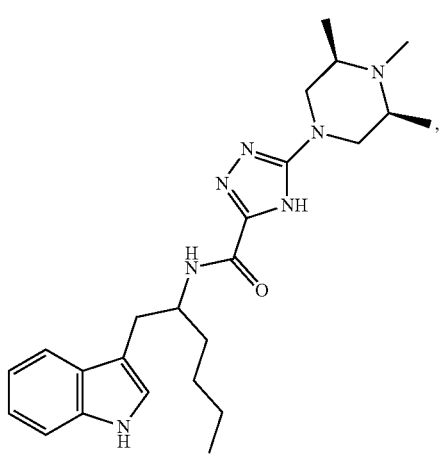
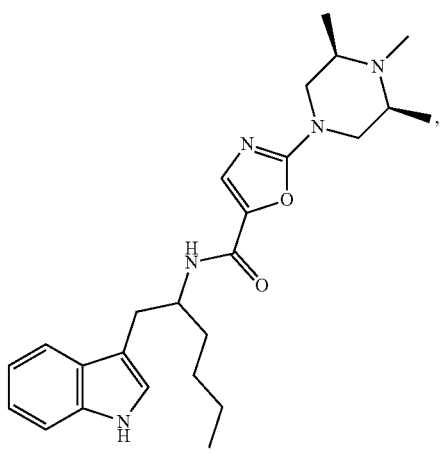

209
-continued
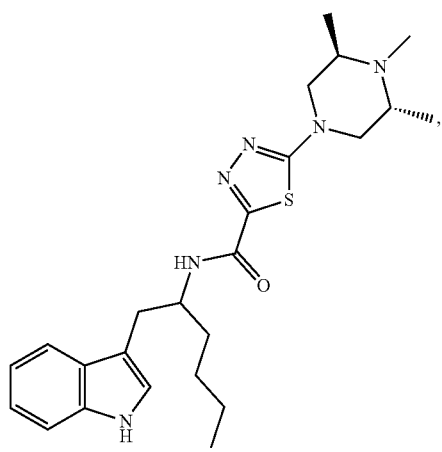
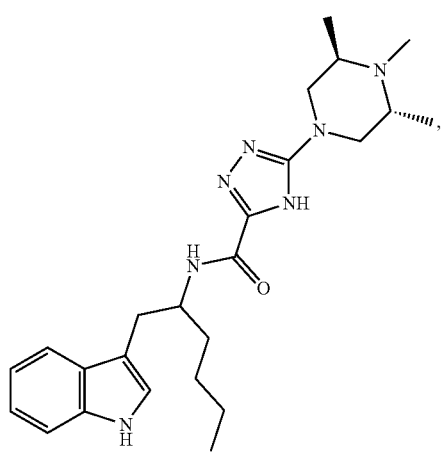
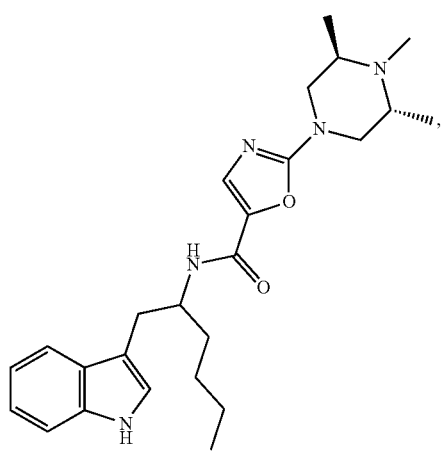
210
-continued
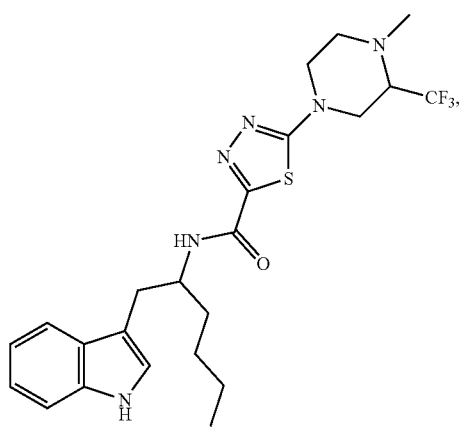
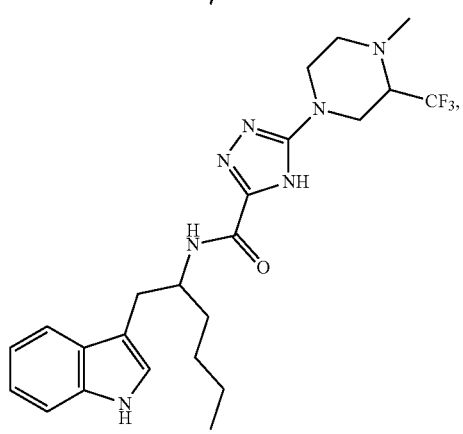
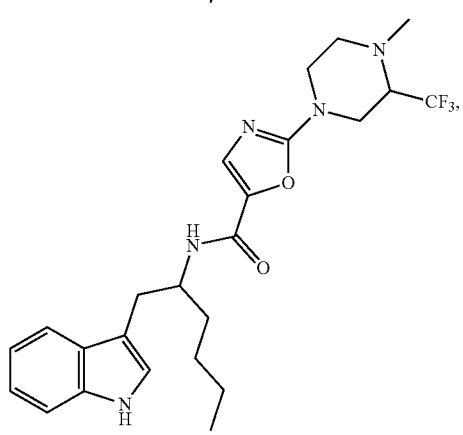

211
-continued
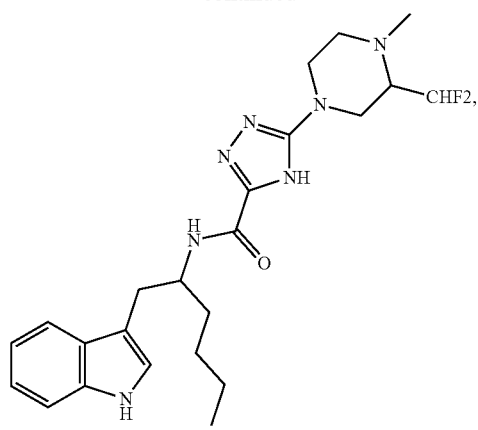
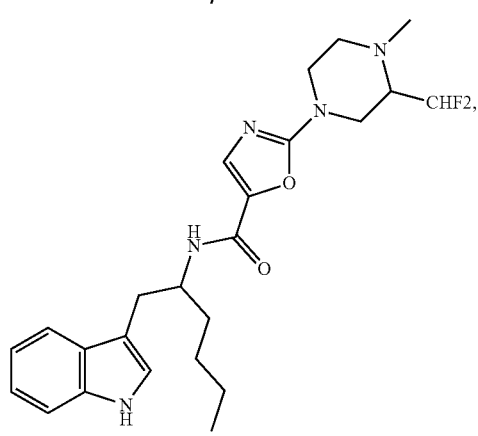
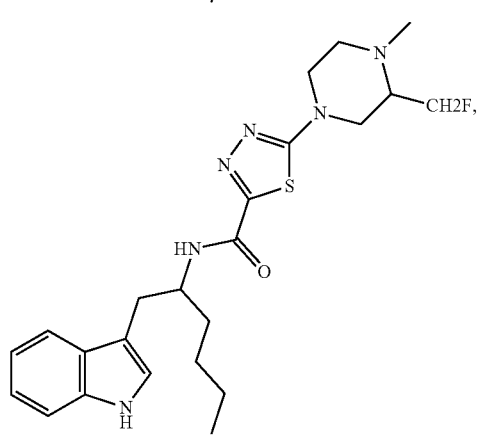
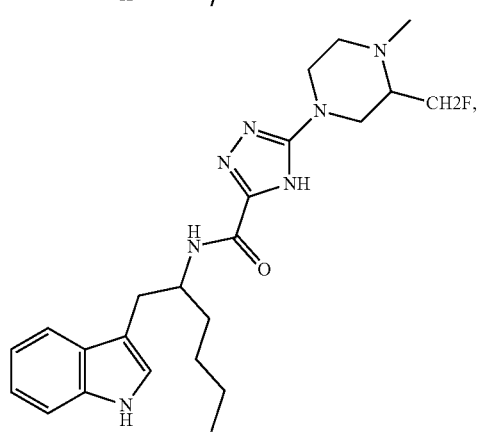
212
-continued
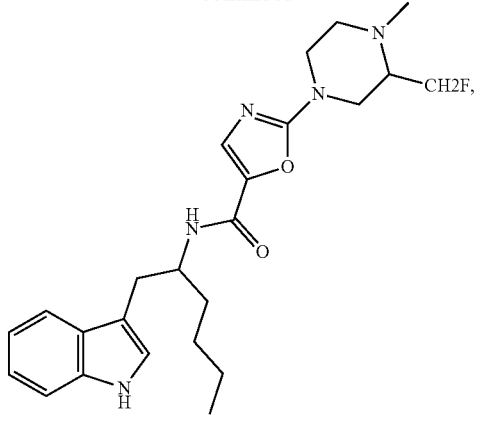
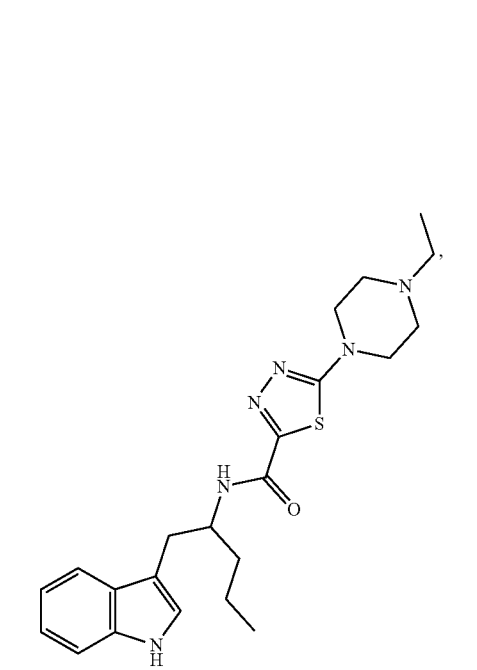
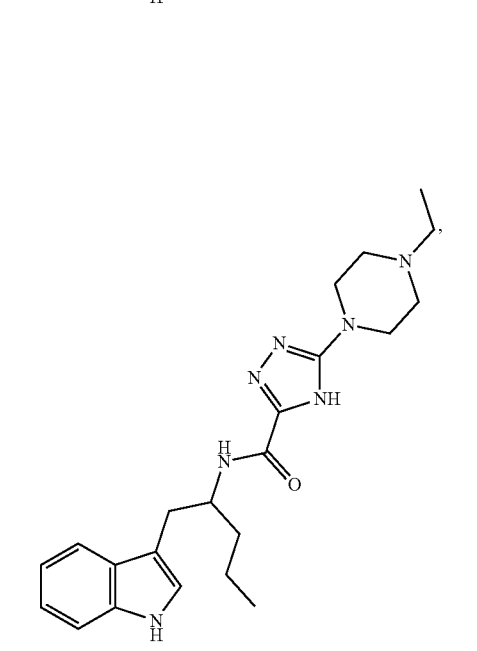

213
-continued
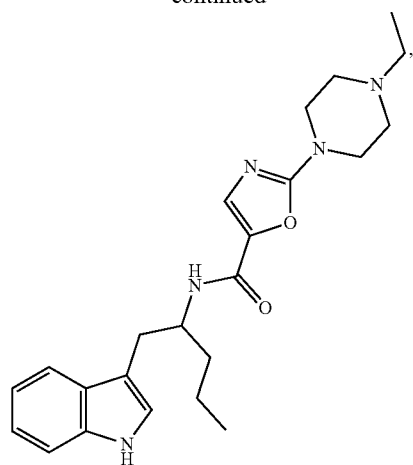
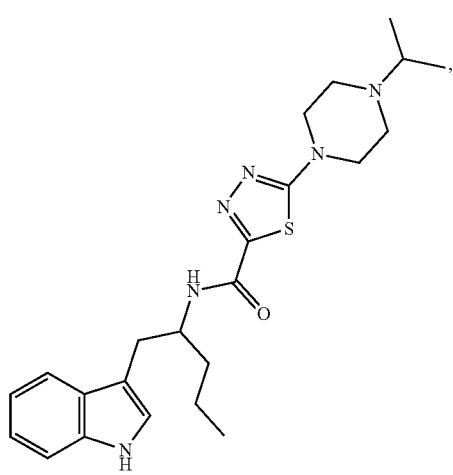
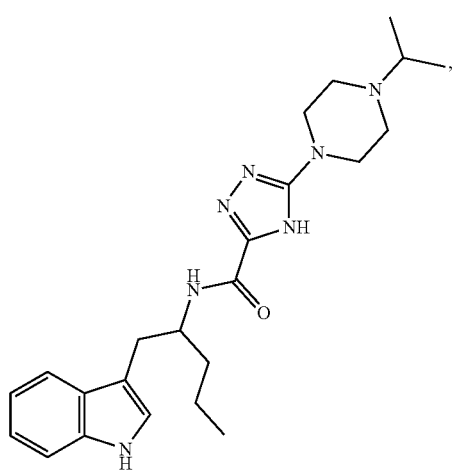
214
-continued
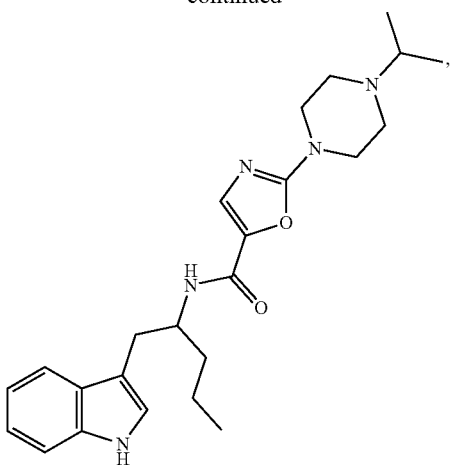
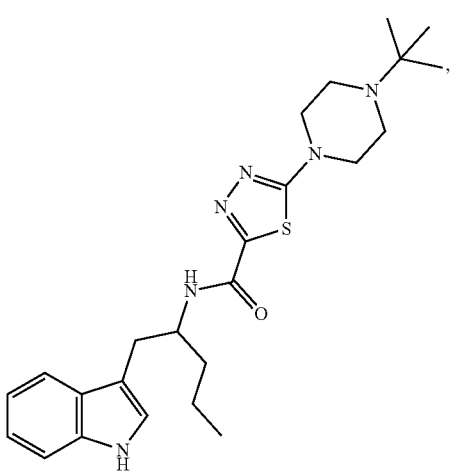
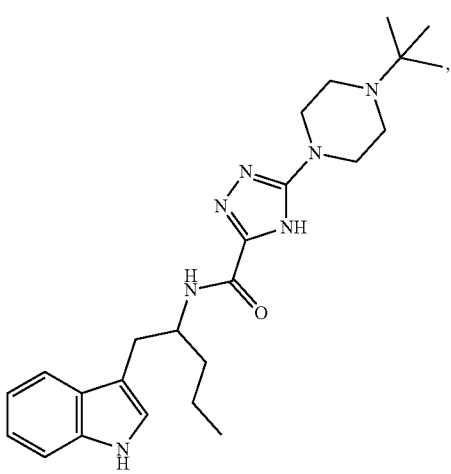

215
-continued
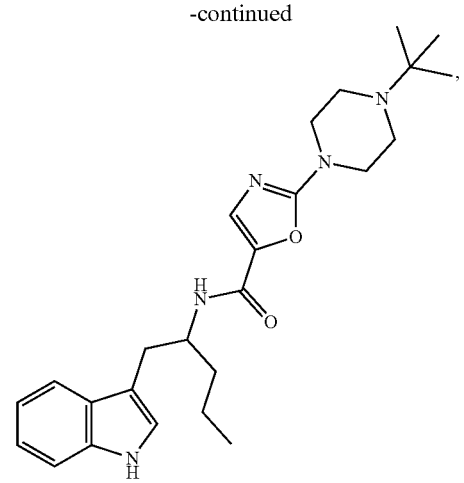
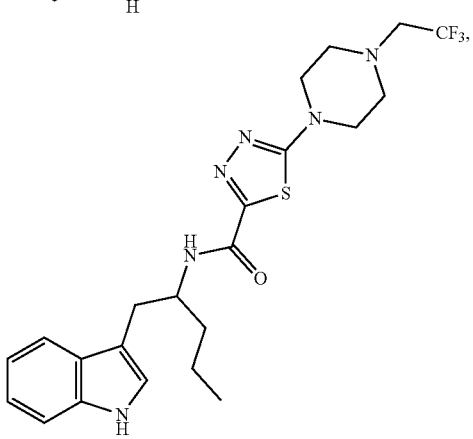
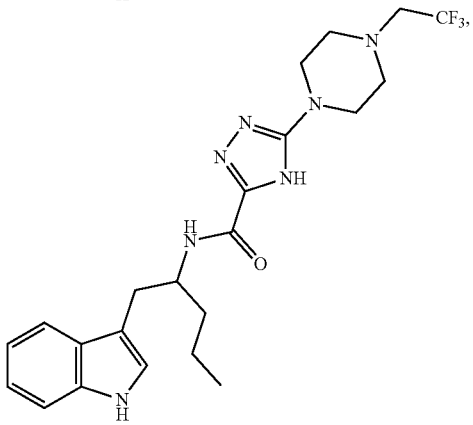
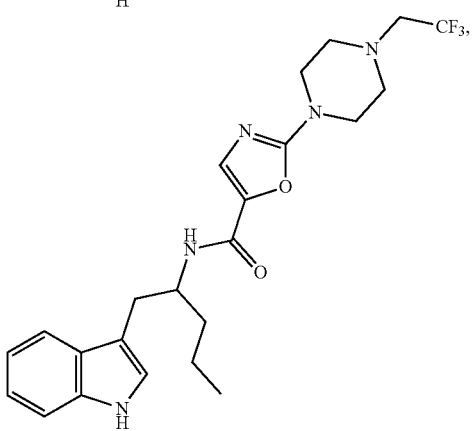
216
-continued
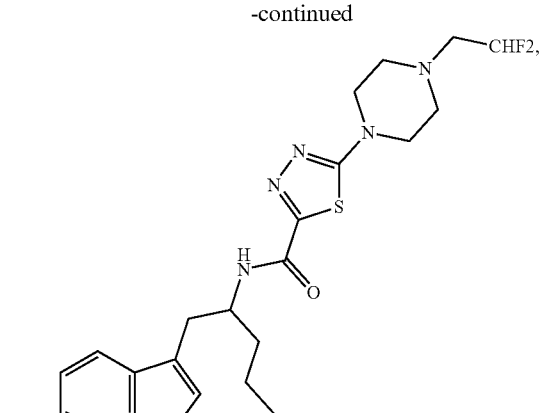
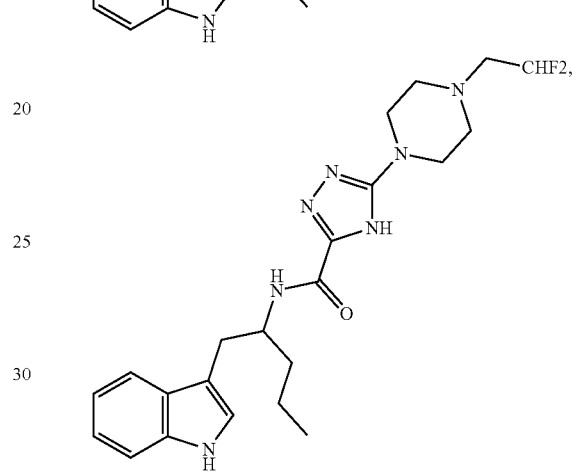
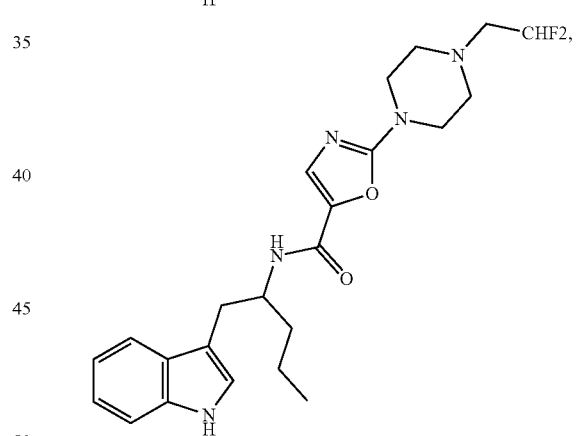
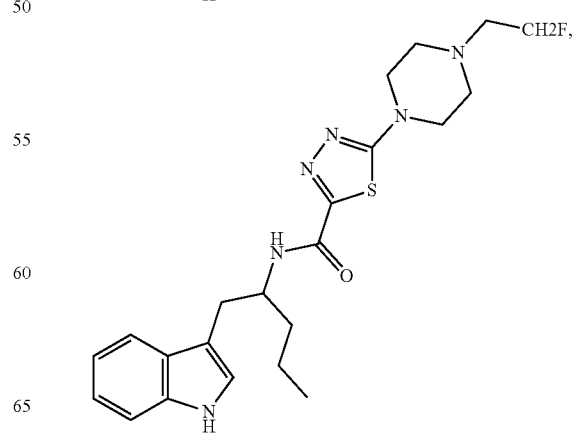

-continued
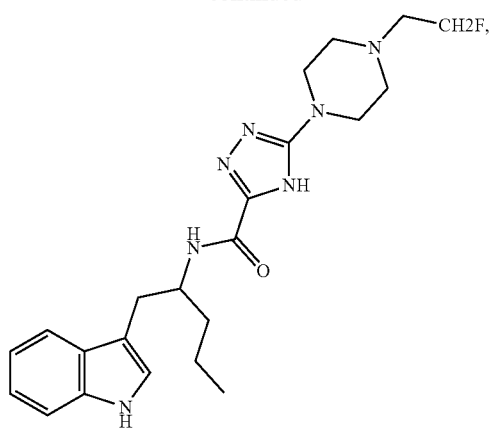
-continued
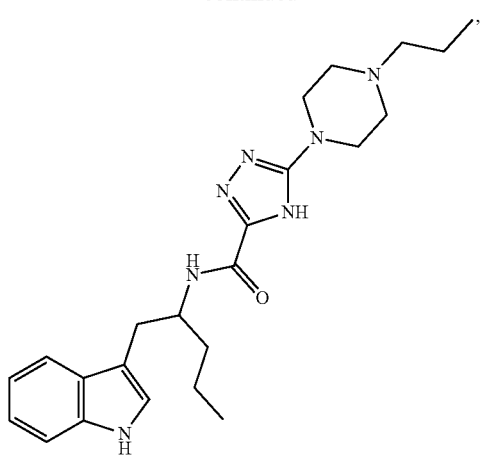
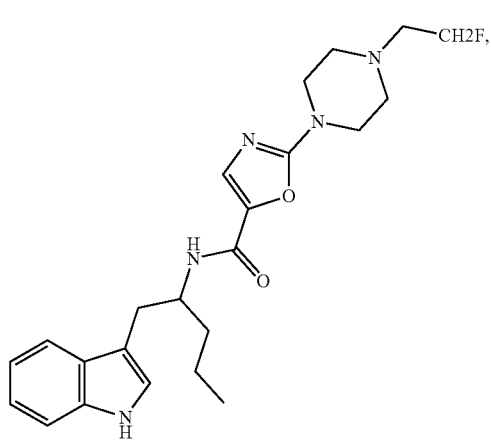
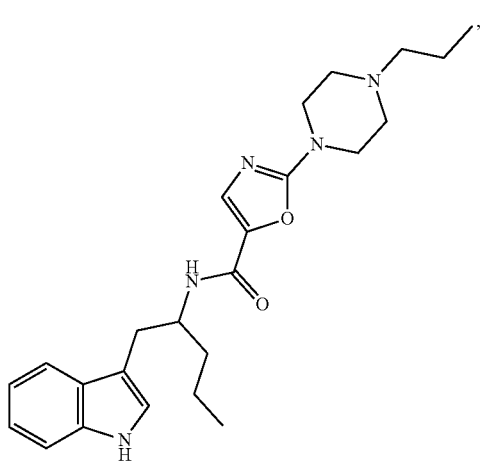
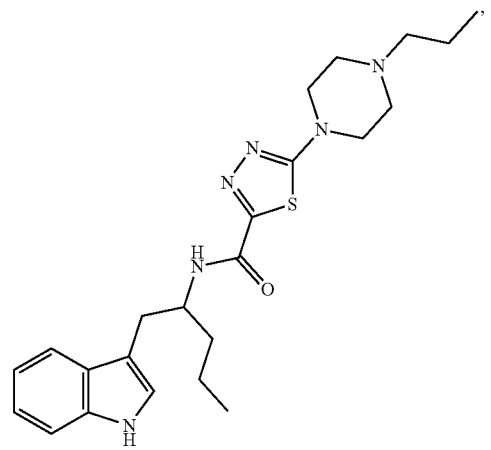
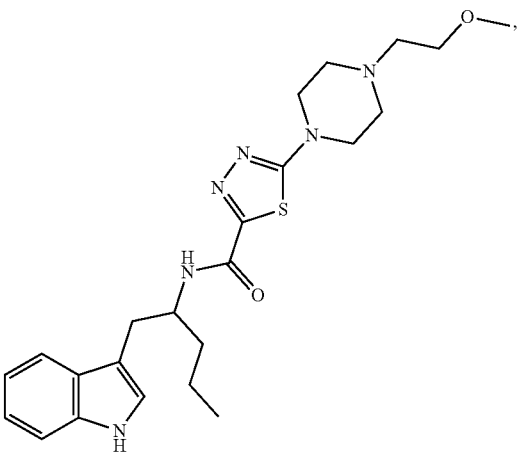

219
-continued
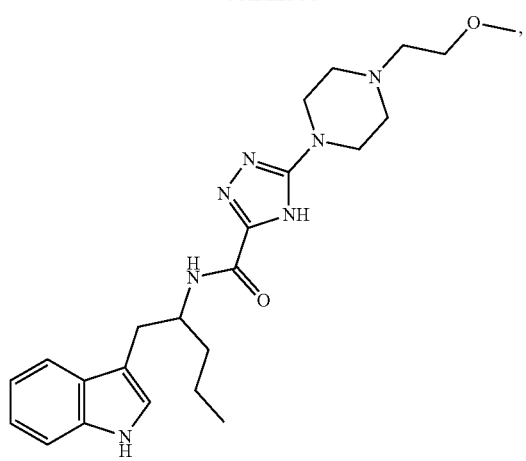
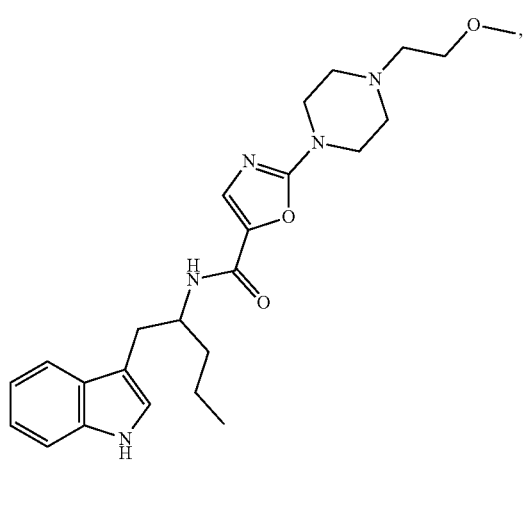
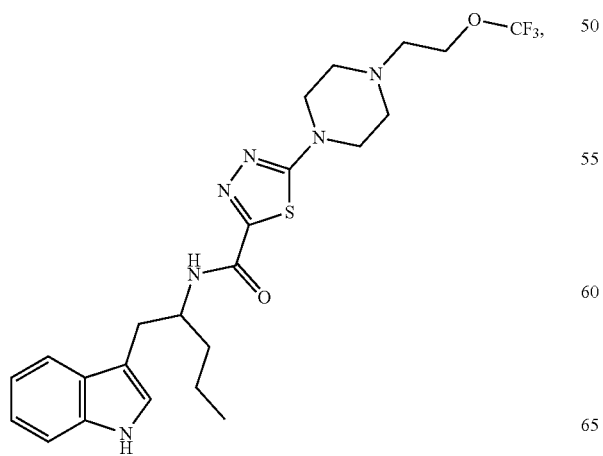
220
-continued
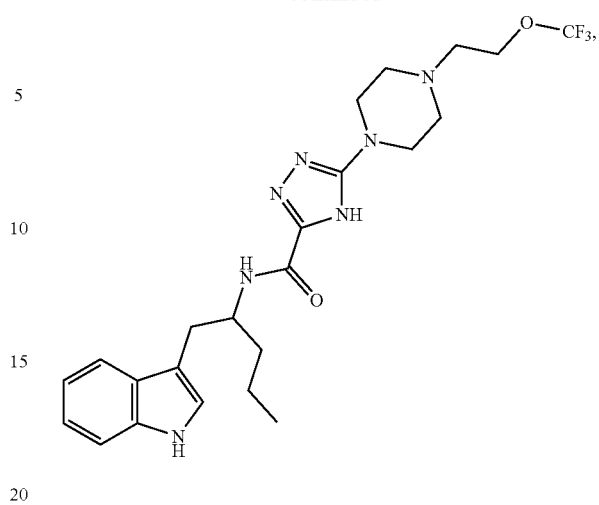
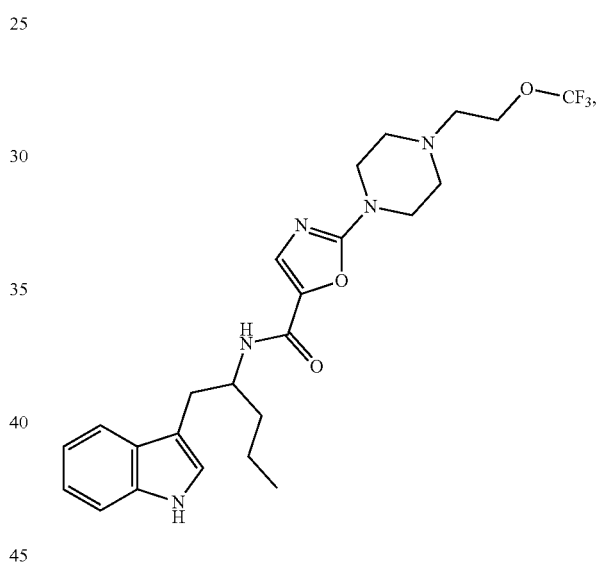
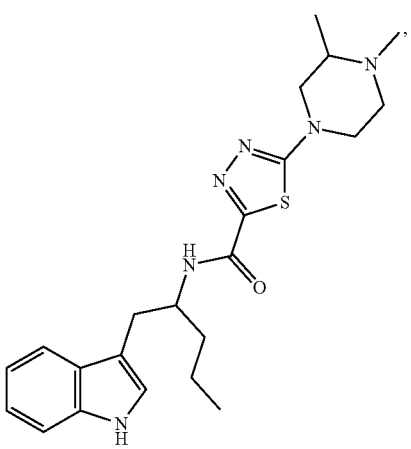

221
-continued
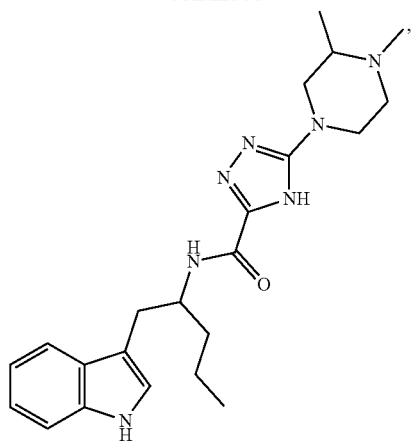
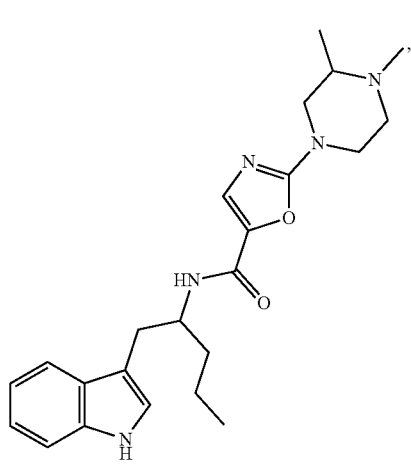
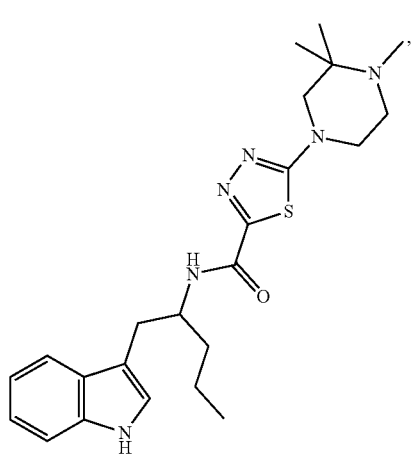
222
-continued
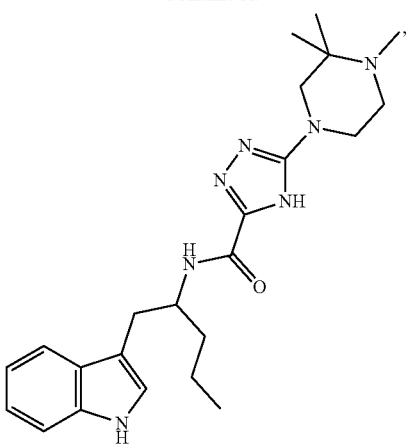
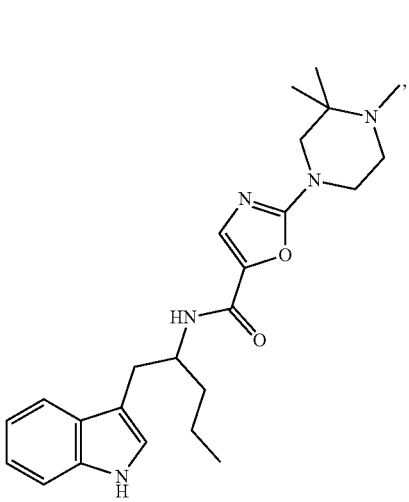
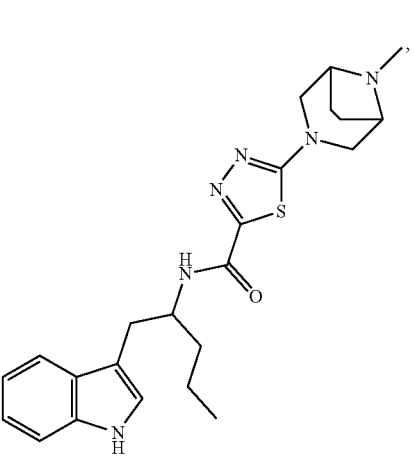

223
-continued

224
-continued

225
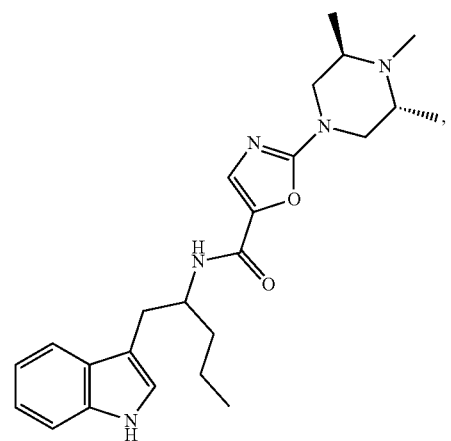
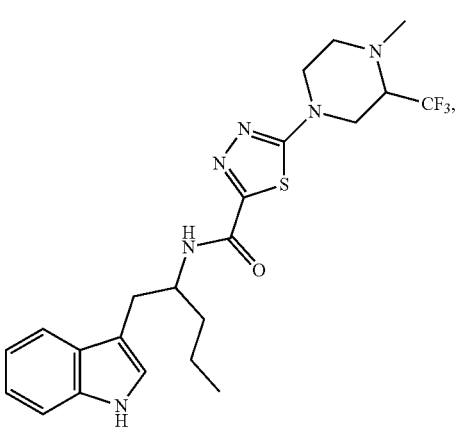
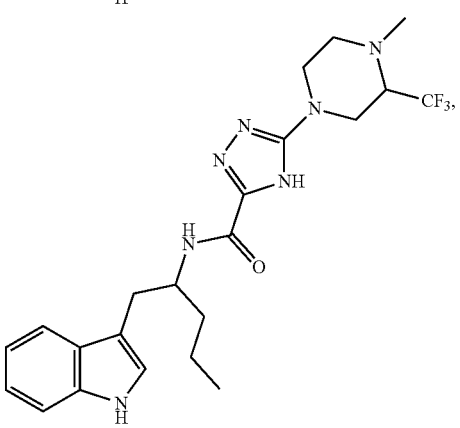
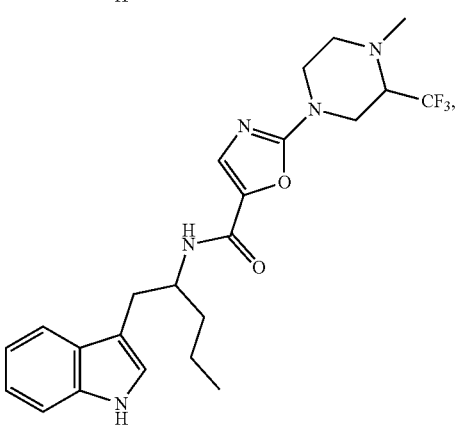
226
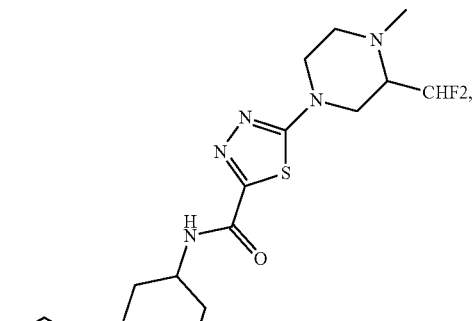
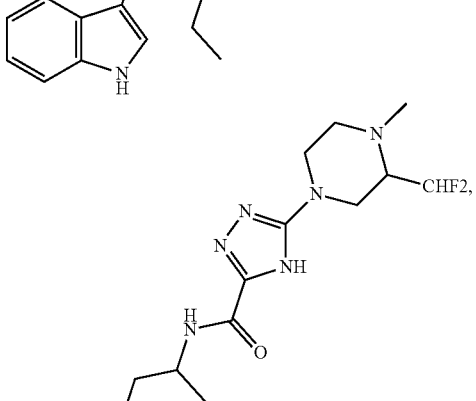
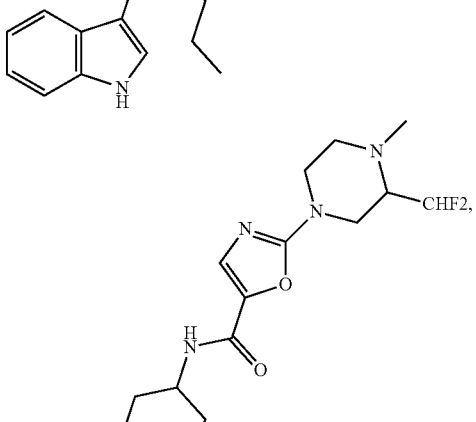
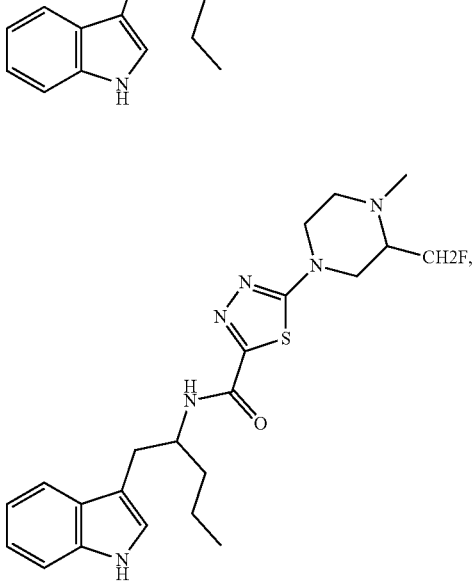

227
-continued
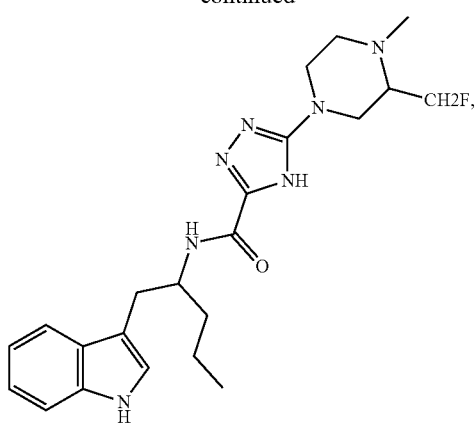
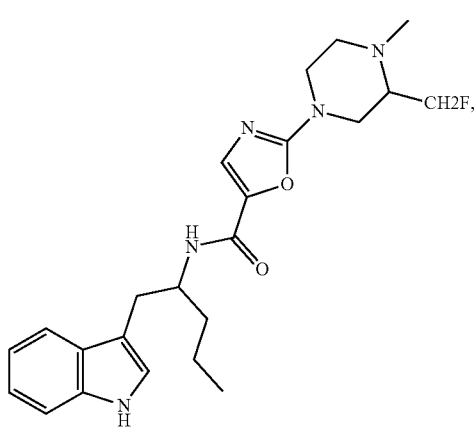
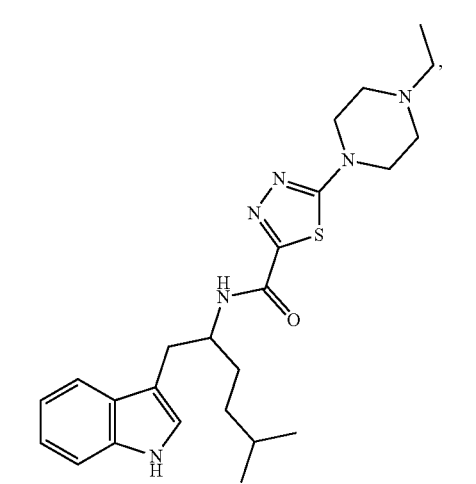
228
-continued
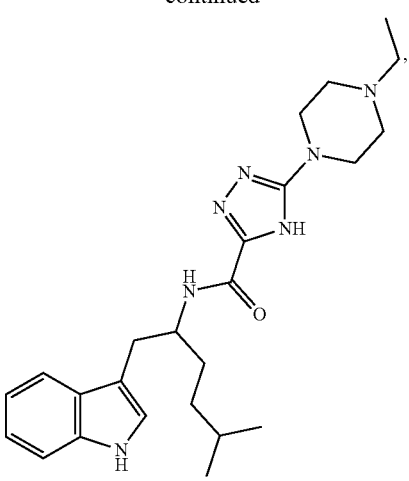
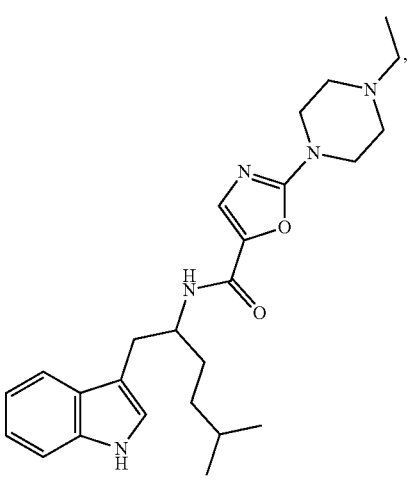
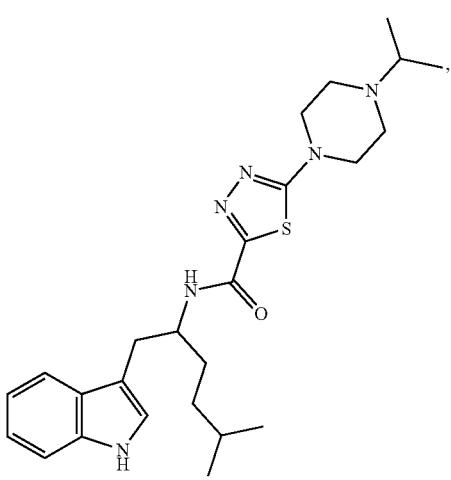

229
-continued
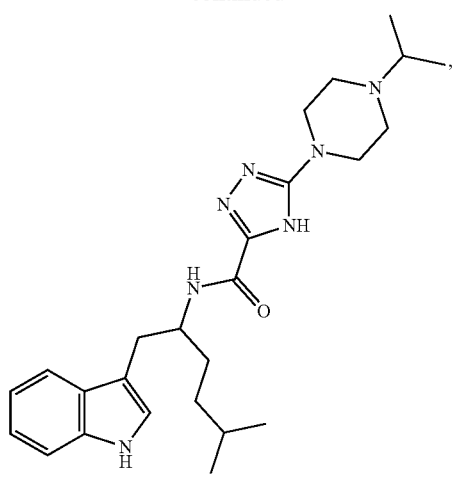
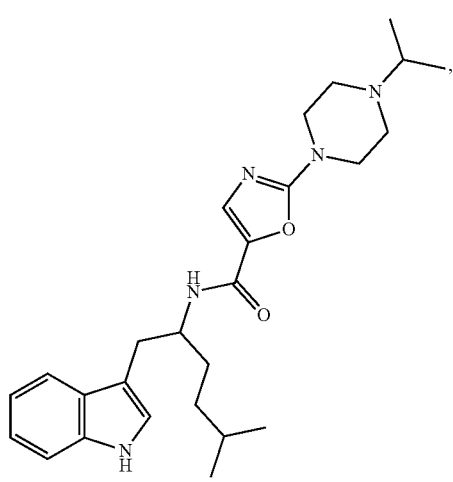
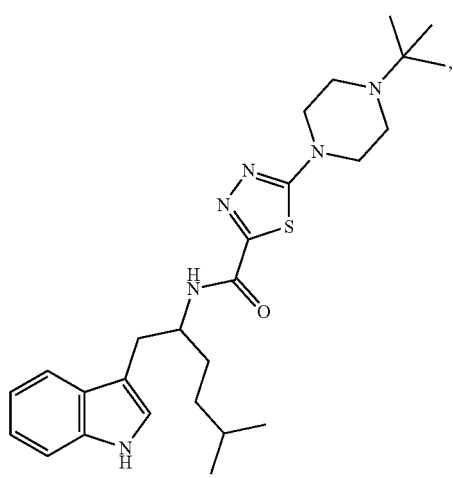
230
-continued
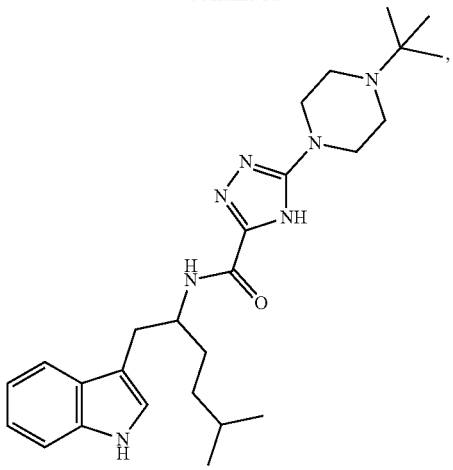
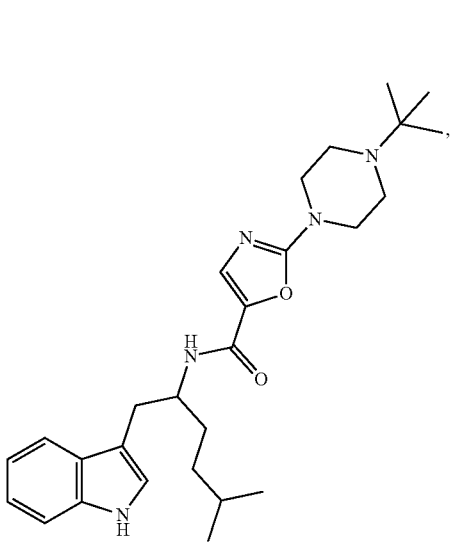
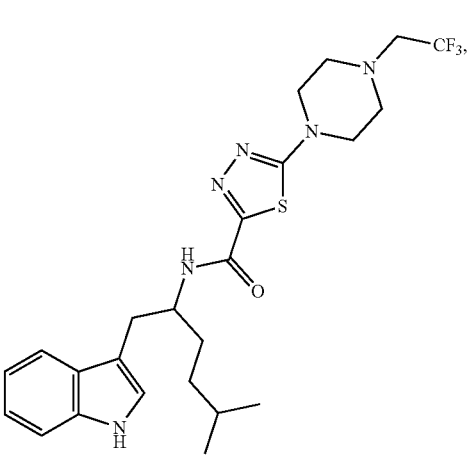

231
-continued
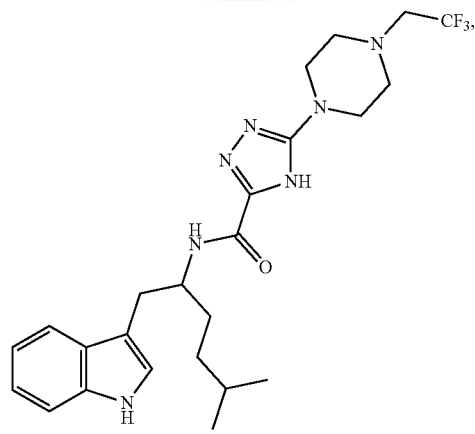
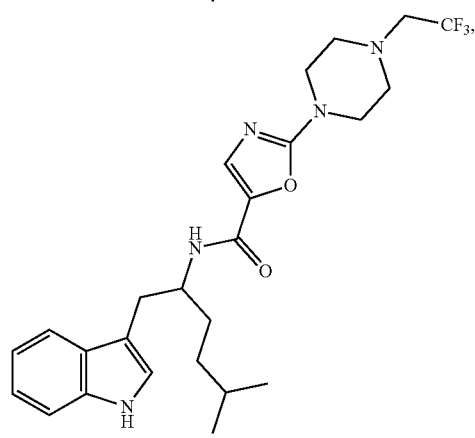
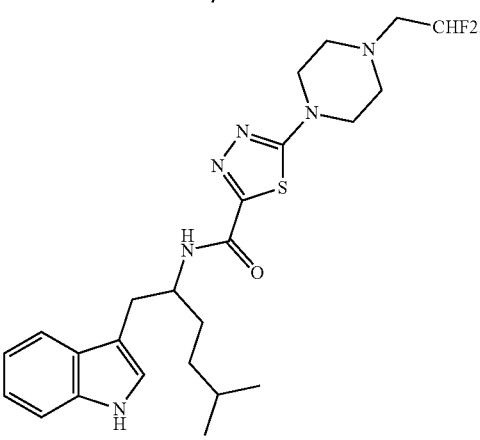
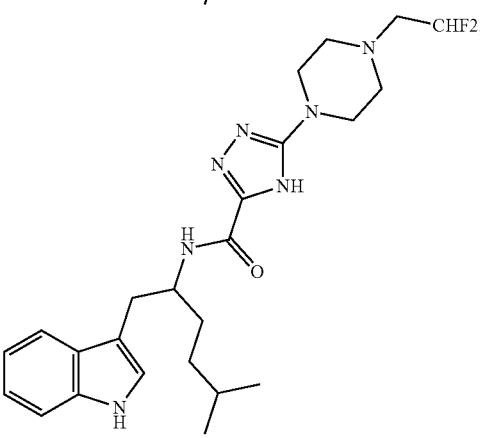
232
-continued
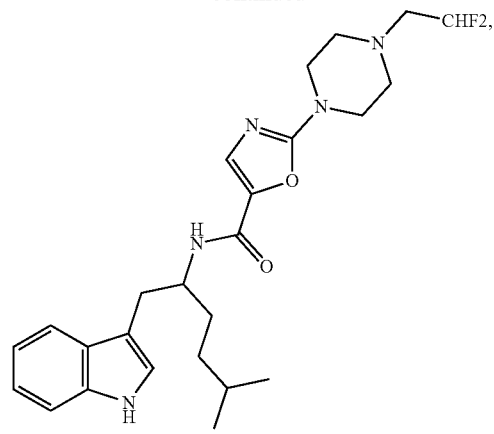
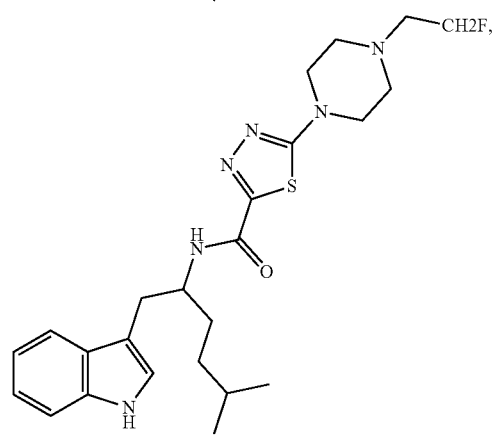
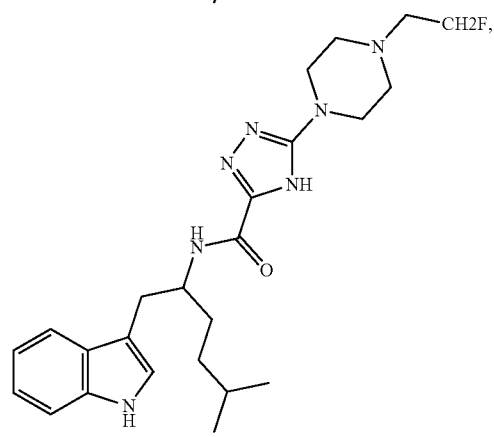
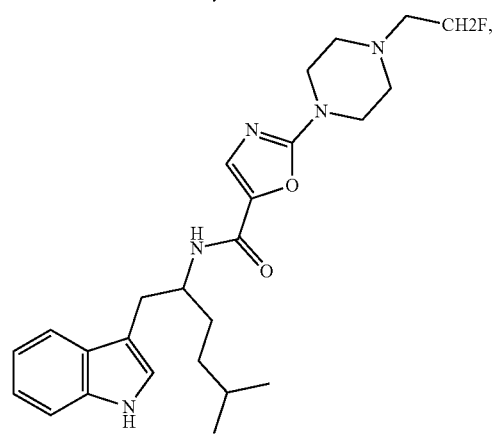

233
-continued
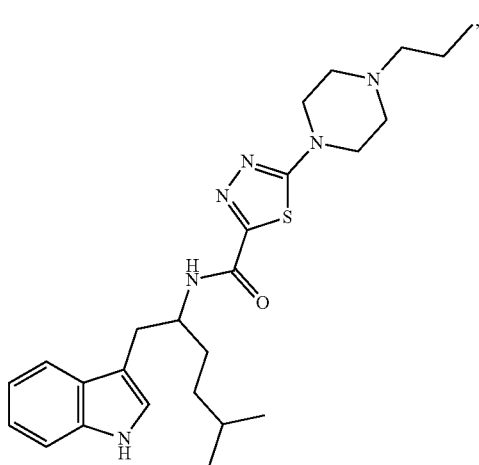
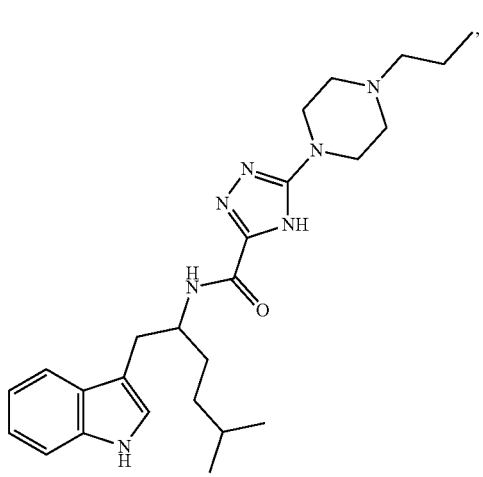
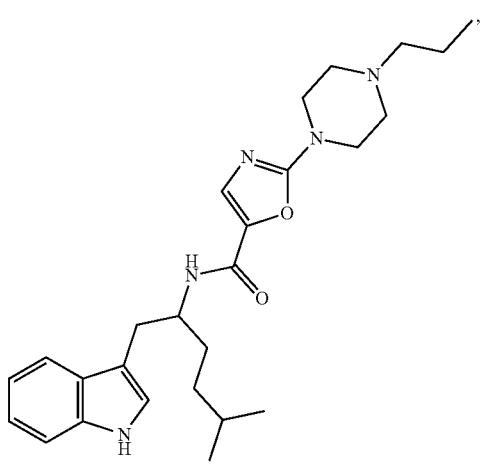
234
-continued
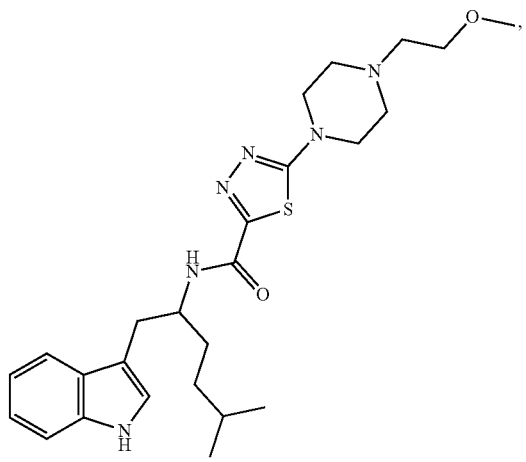
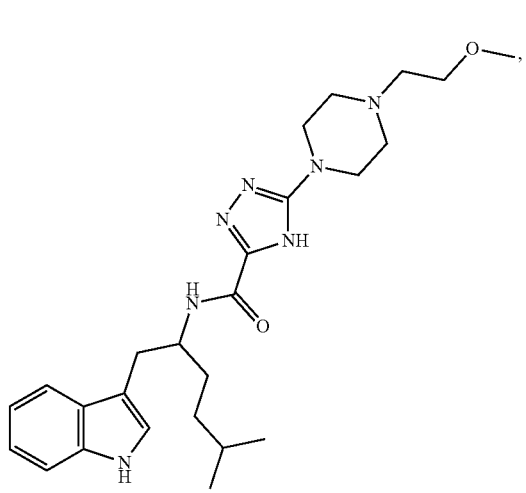
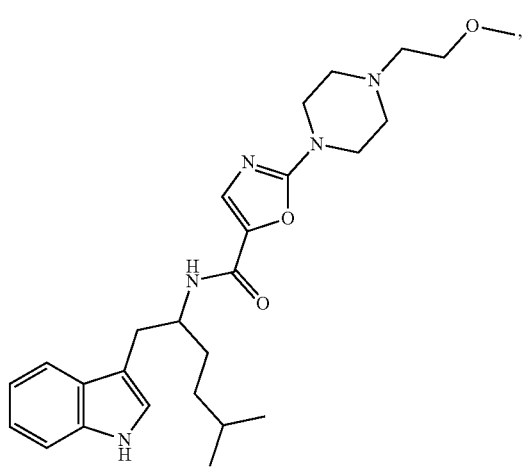

235
-continued
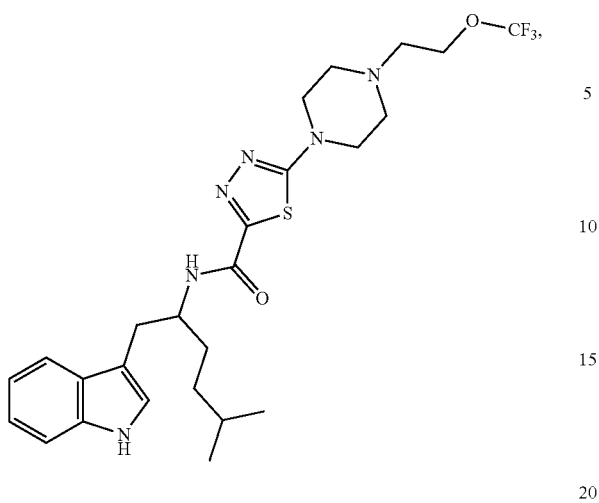
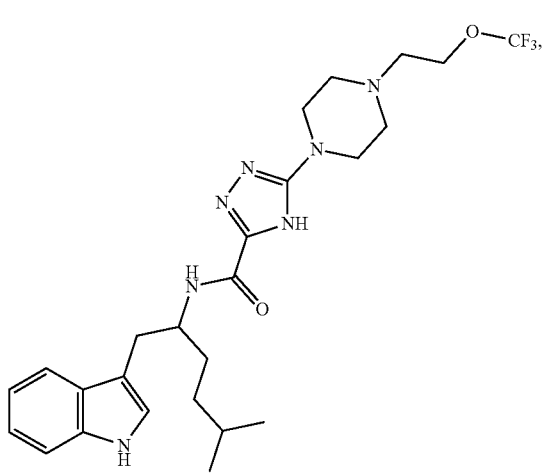
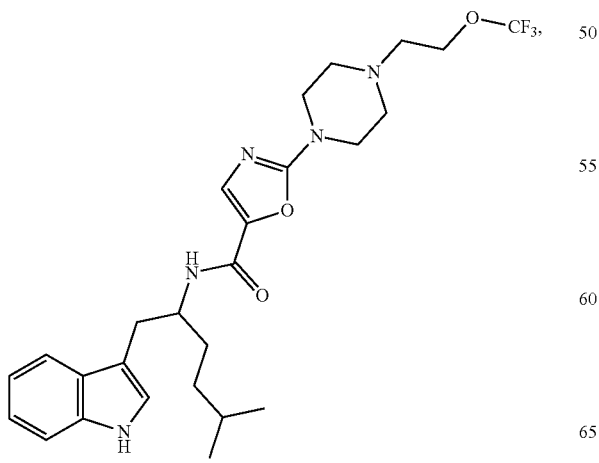
236
-continued
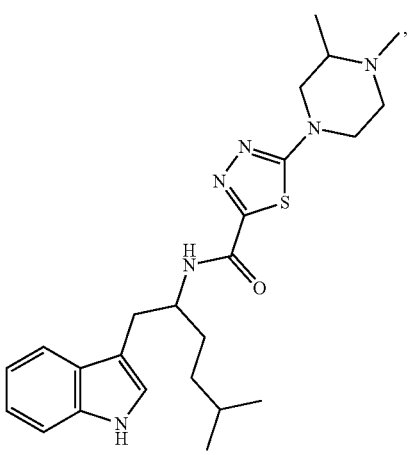
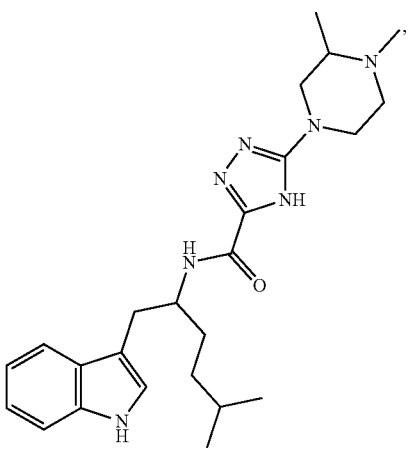
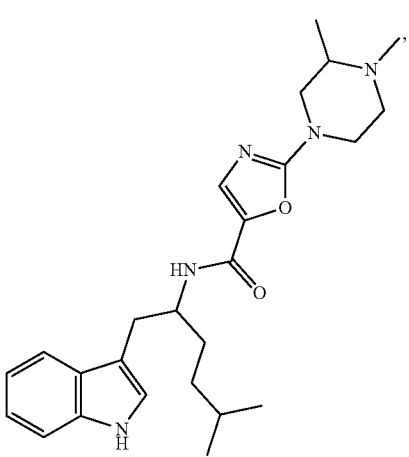

237
-continued
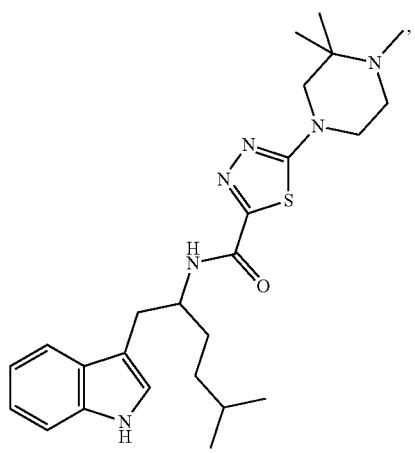
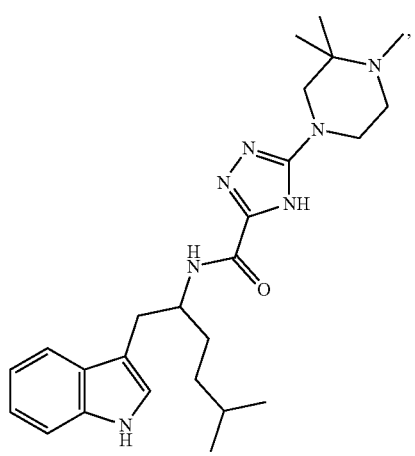
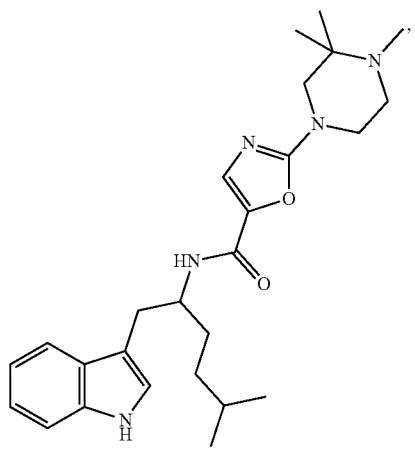
238
-continued
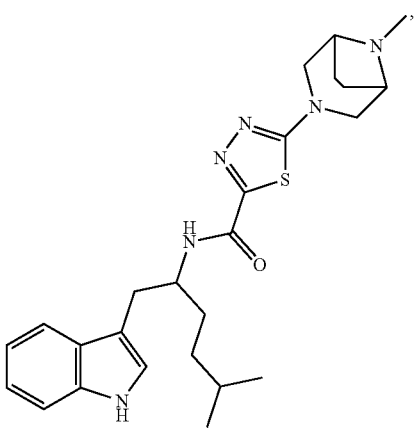
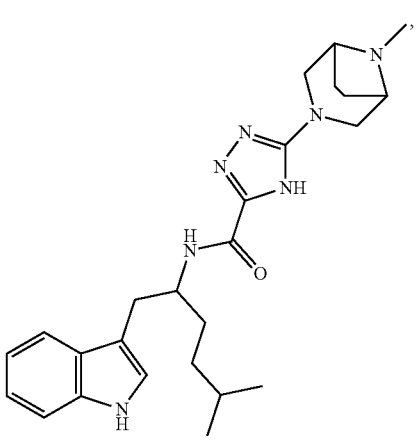
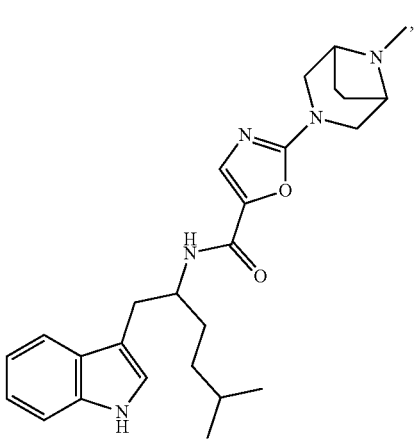

239
-continued
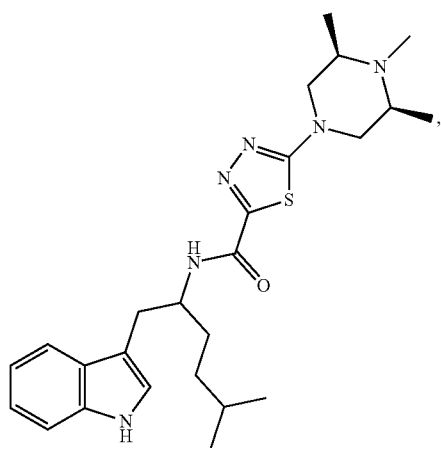
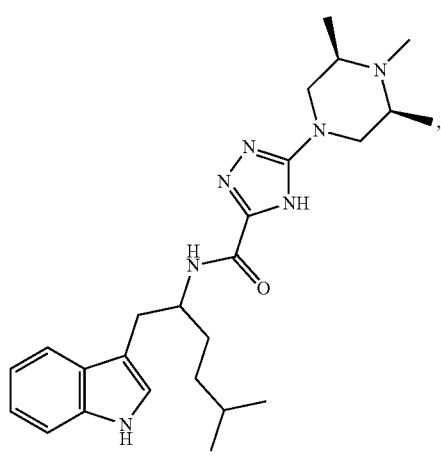
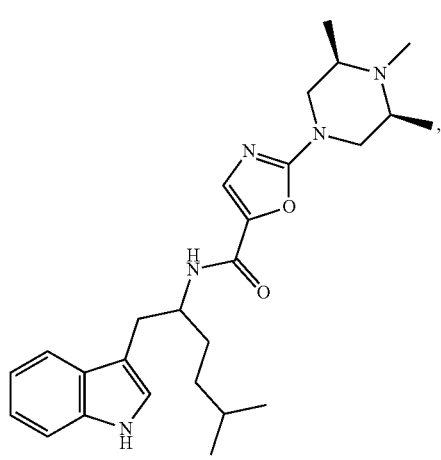
240
-continued
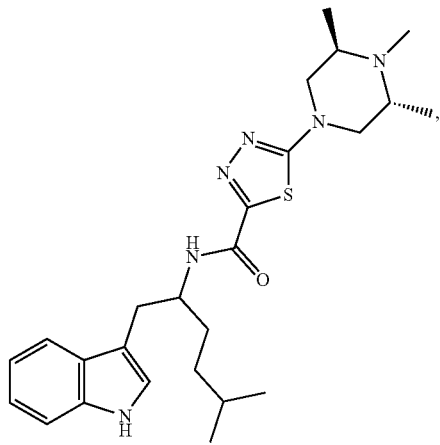
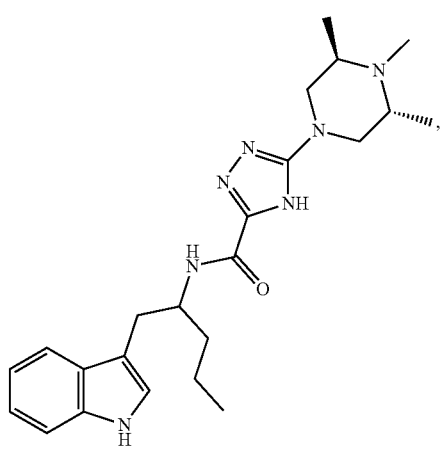
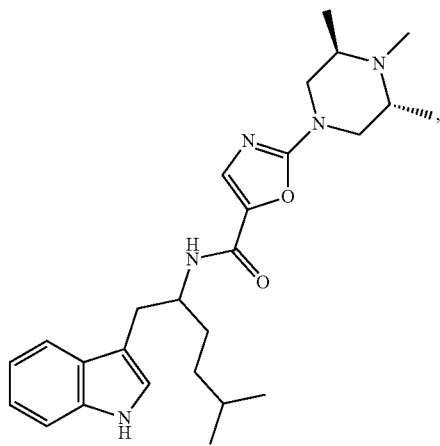

241
-continued
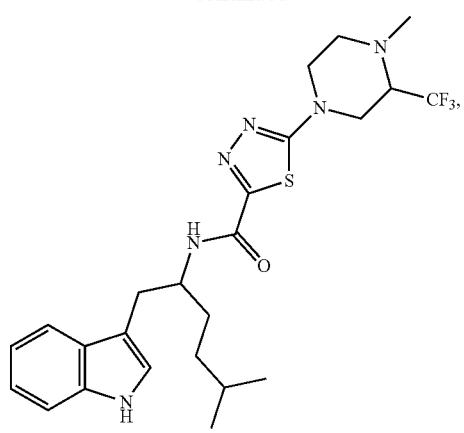
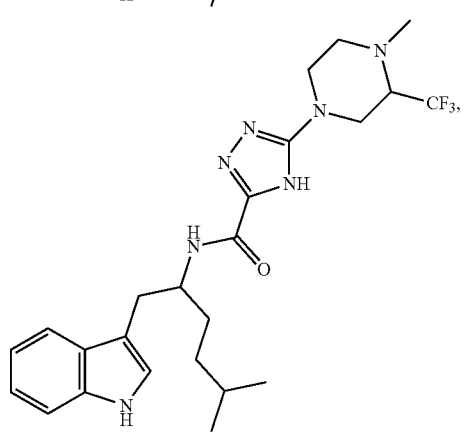
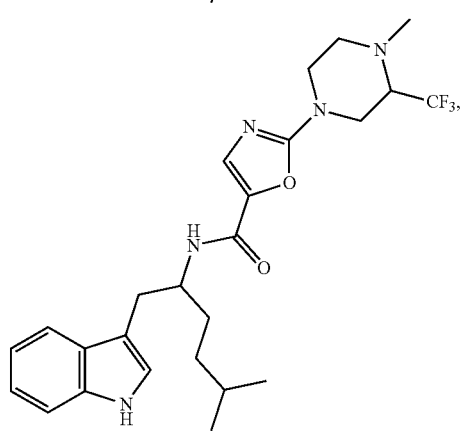
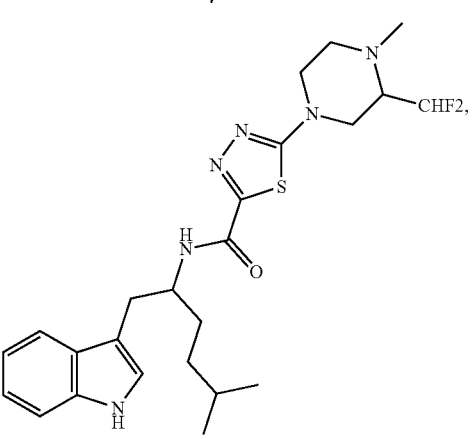
242
-continued
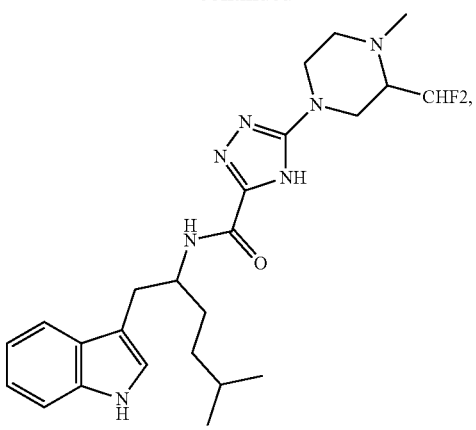
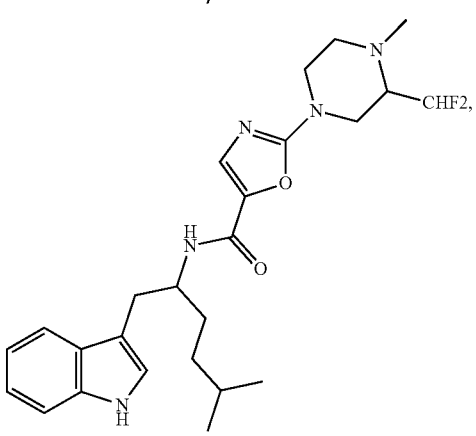
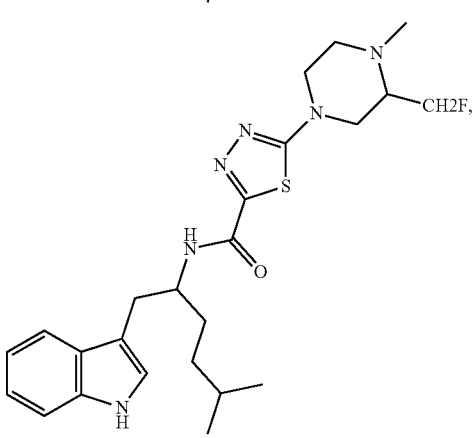
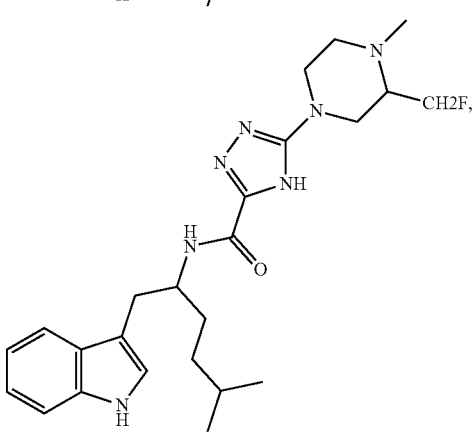

243
-continued
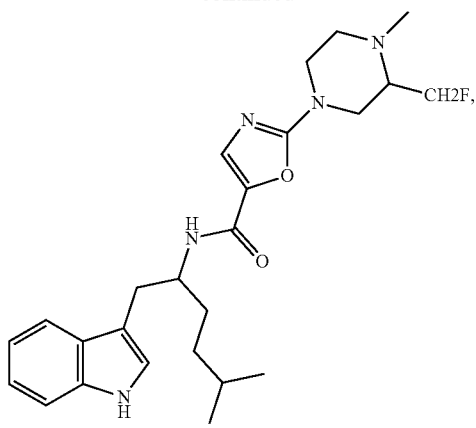
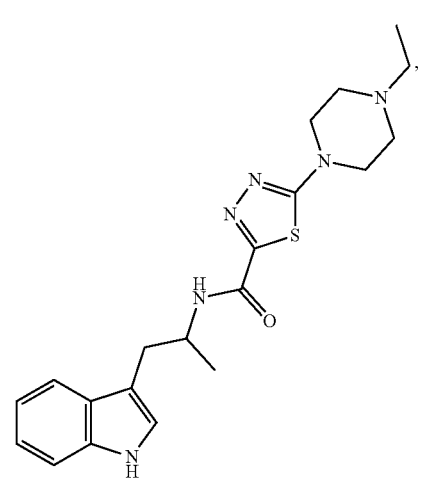
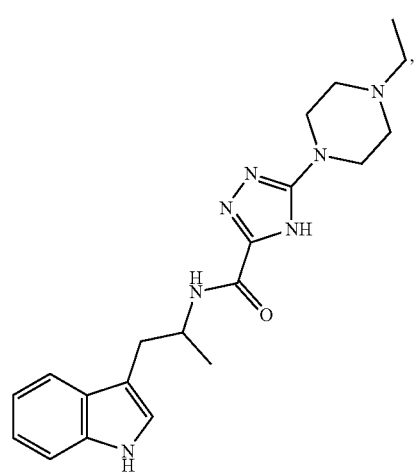
244
-continued
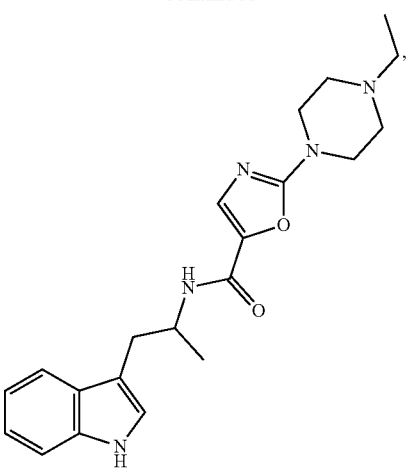
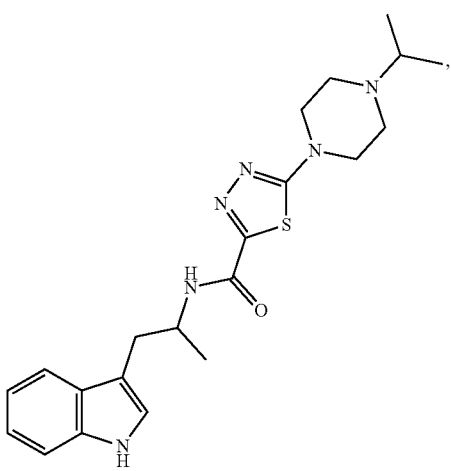
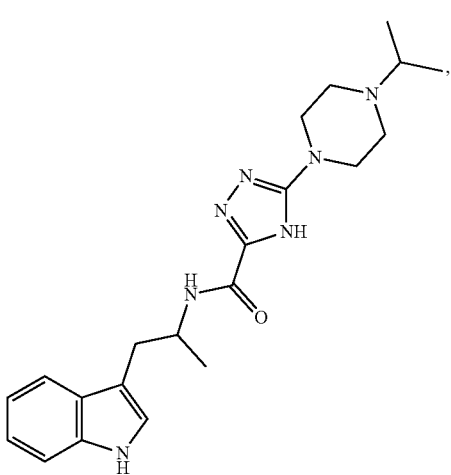

245
-continued
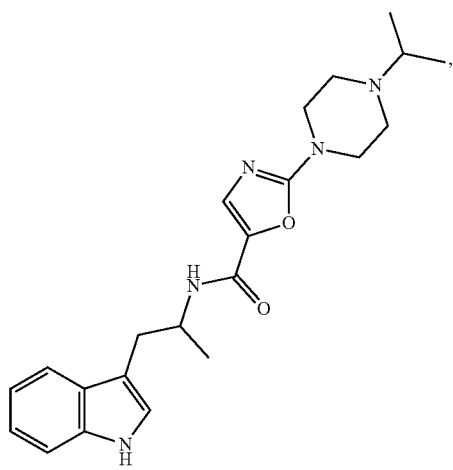
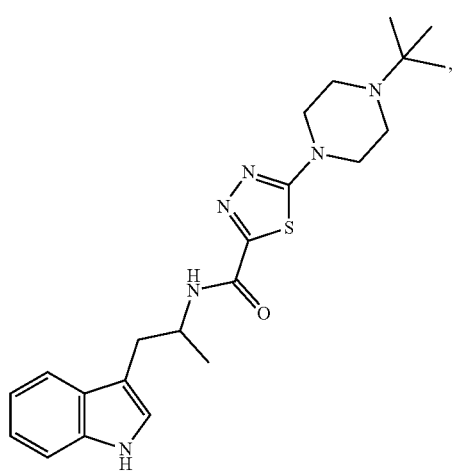
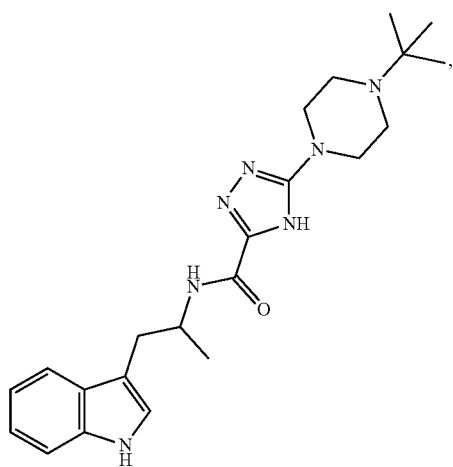
246
-continued
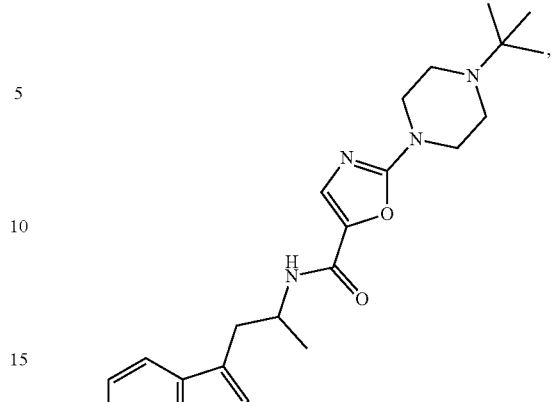
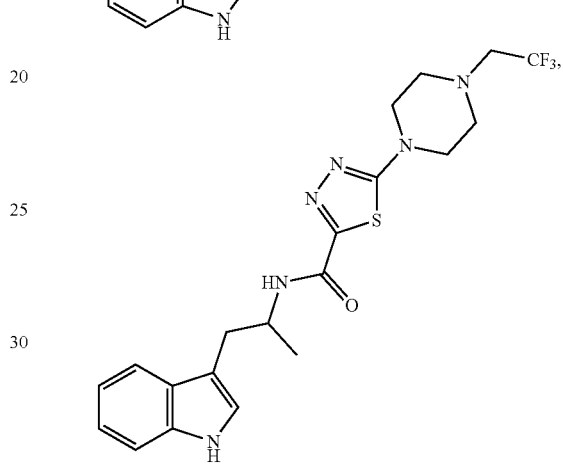
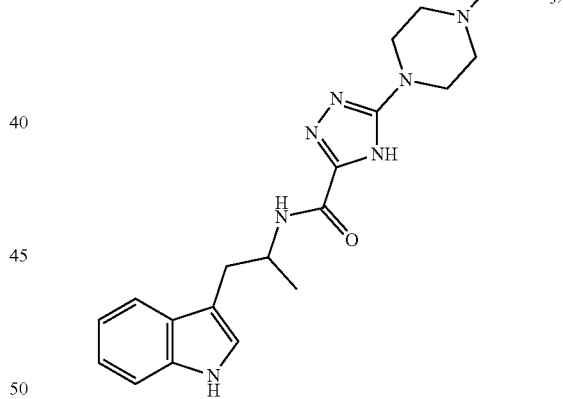
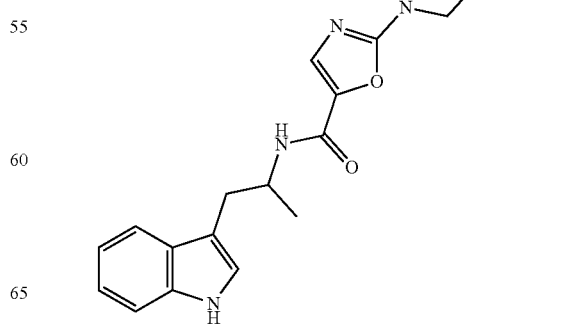

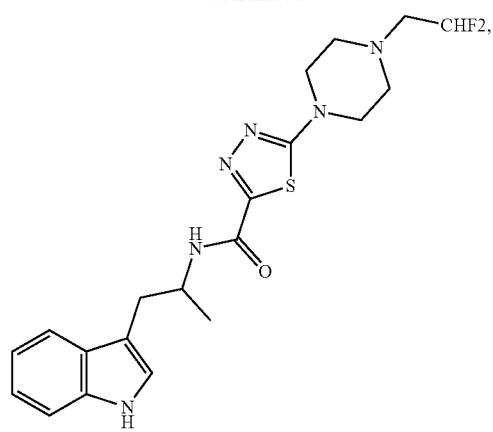
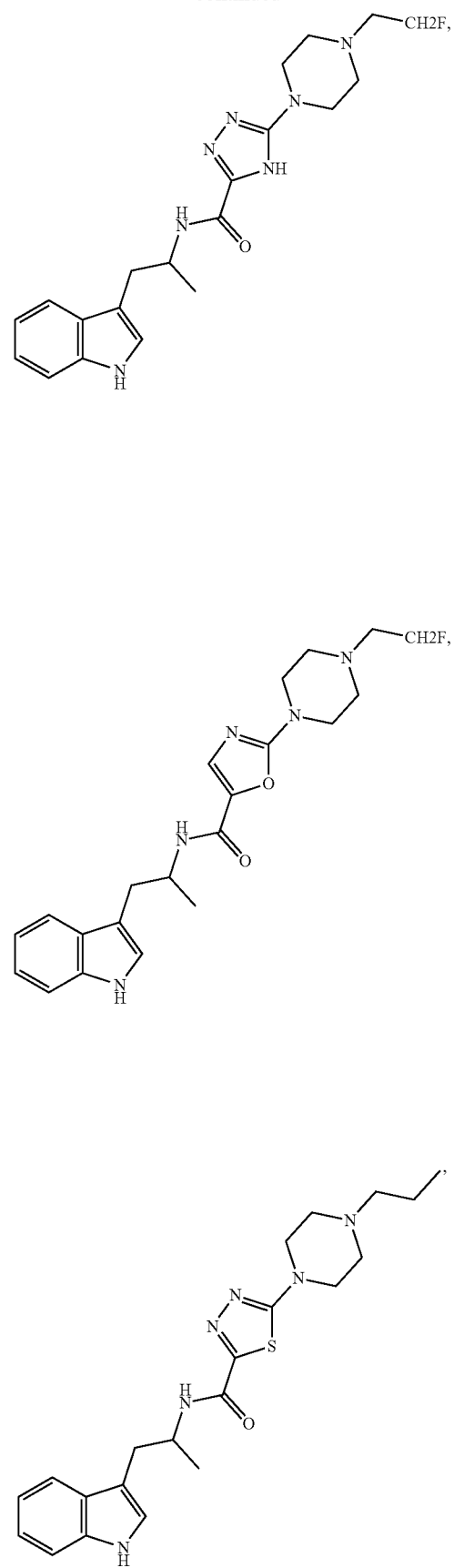

249
-continued
250
-continued
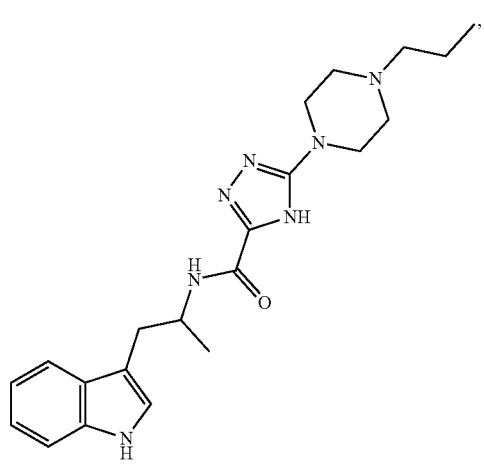
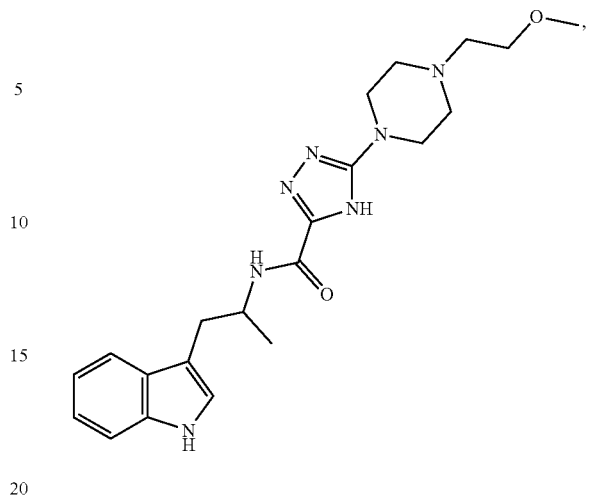
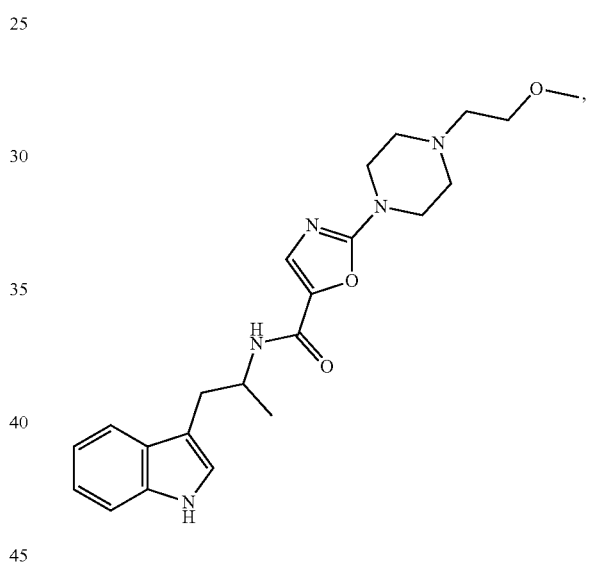
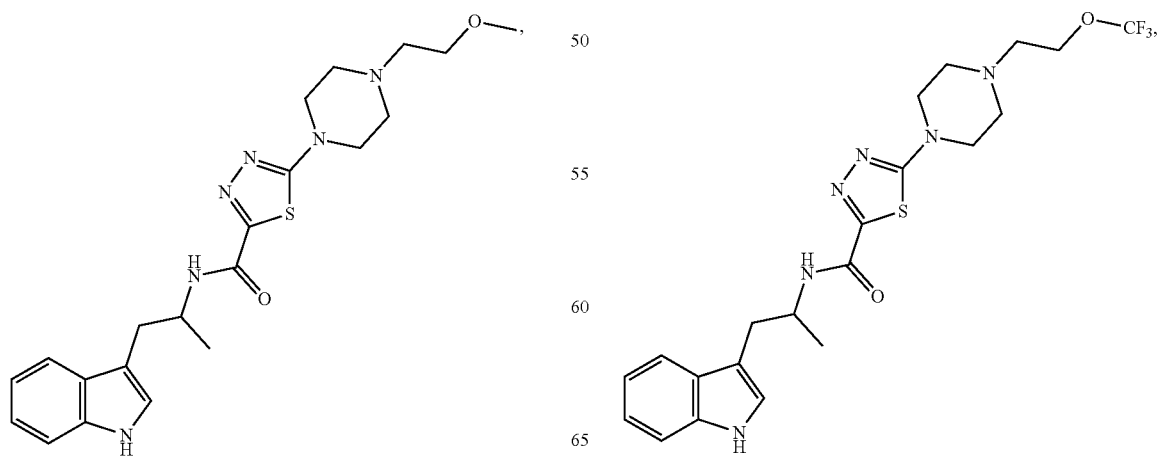

251
-continued
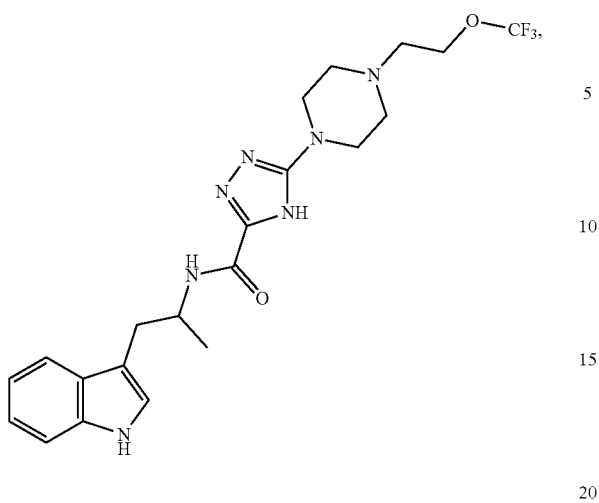
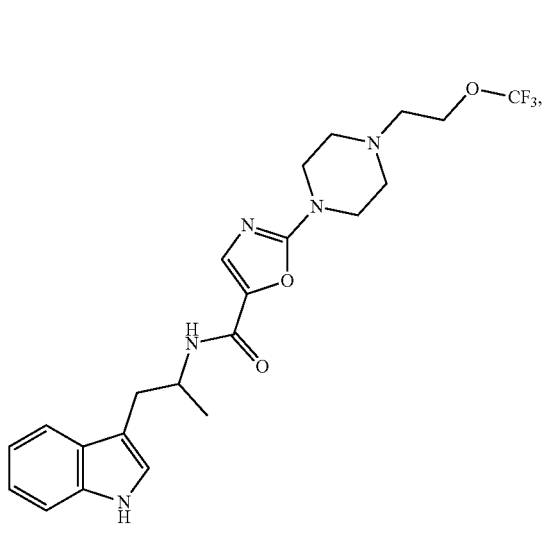
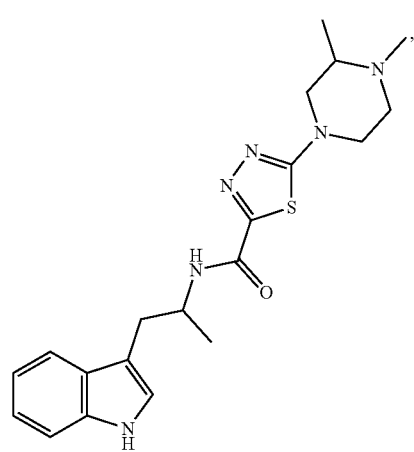
252
-continued
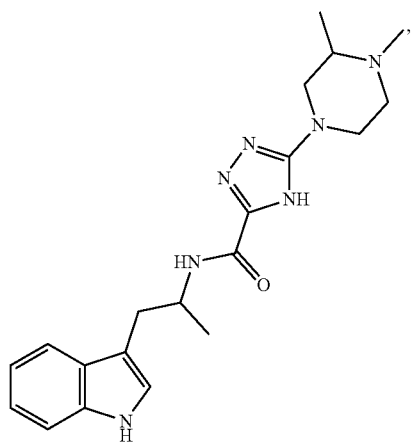
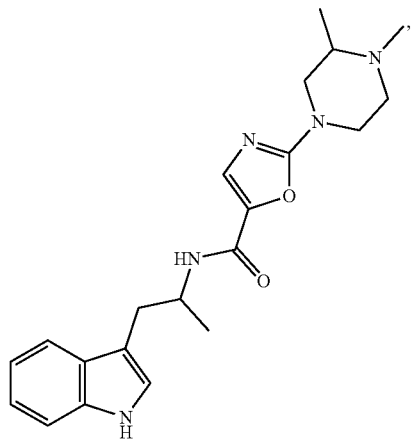
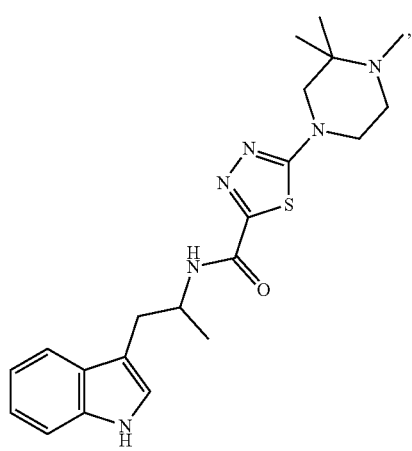

253
-continued
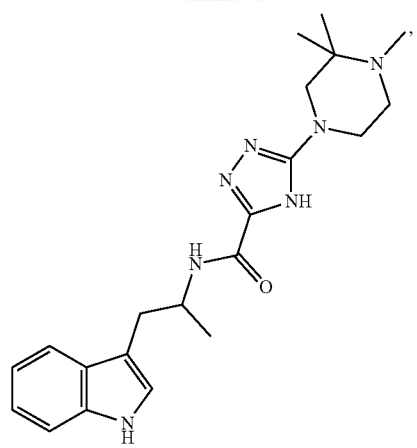
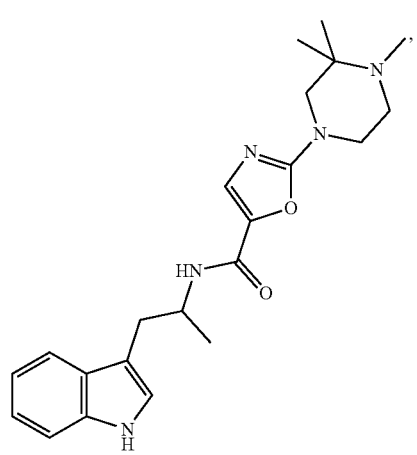
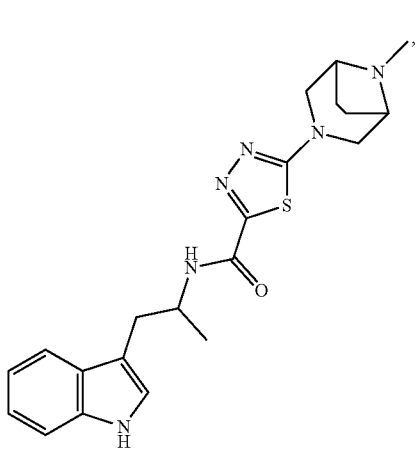
254
-continued
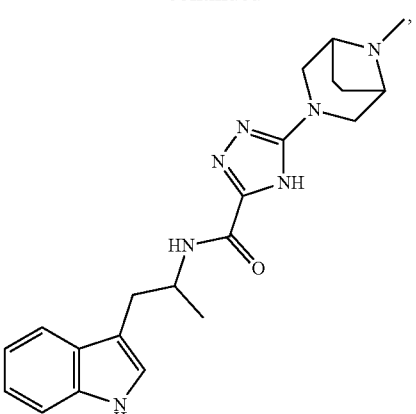
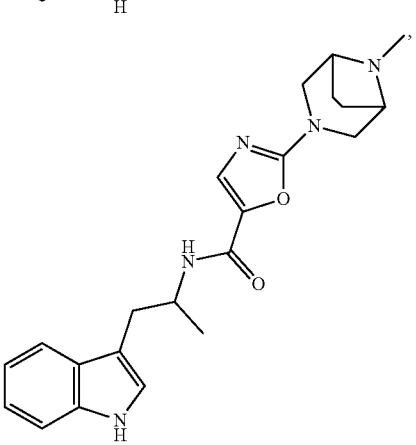
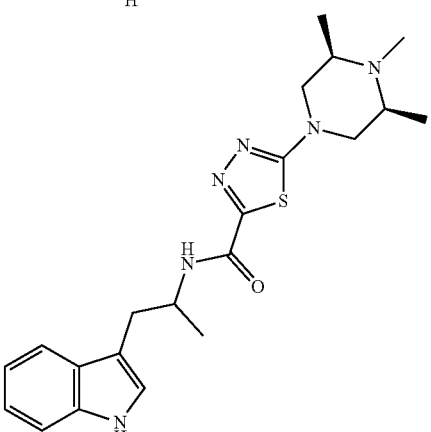
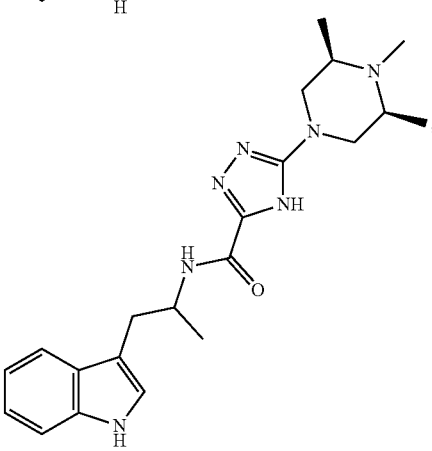

255
-continued
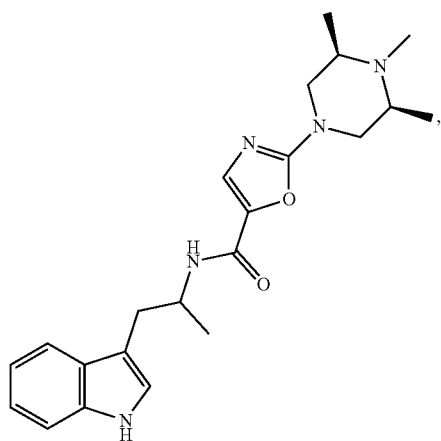
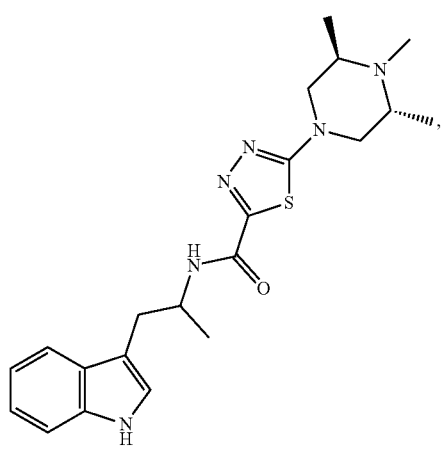
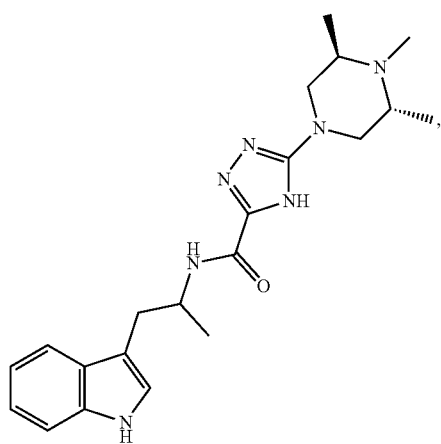
256
-continued
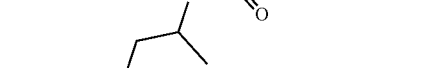
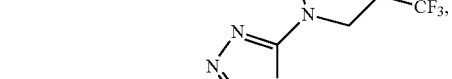

-continued
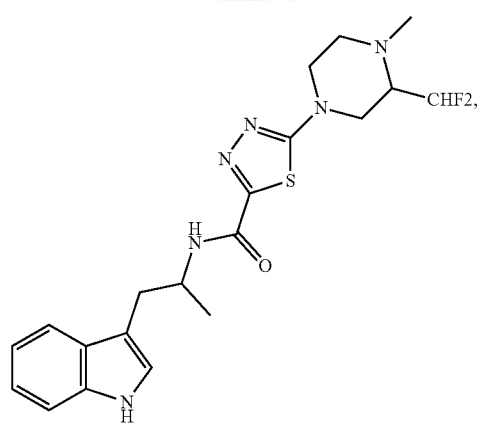
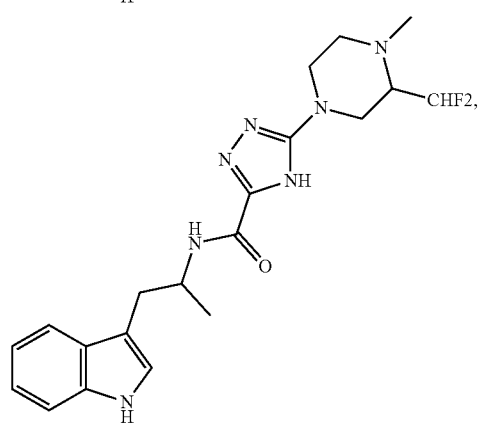
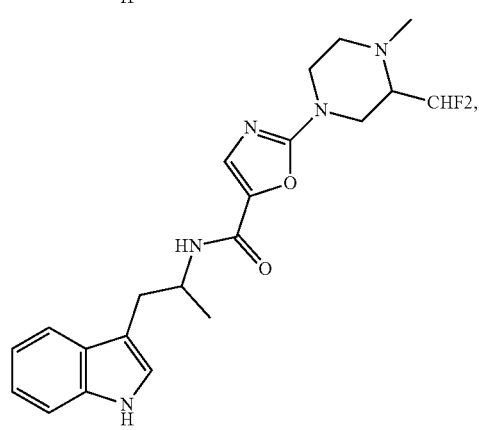
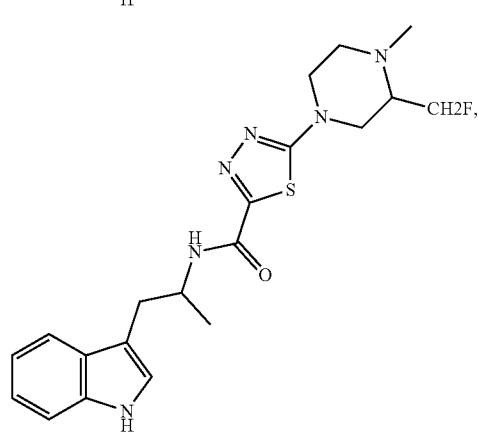
-continued
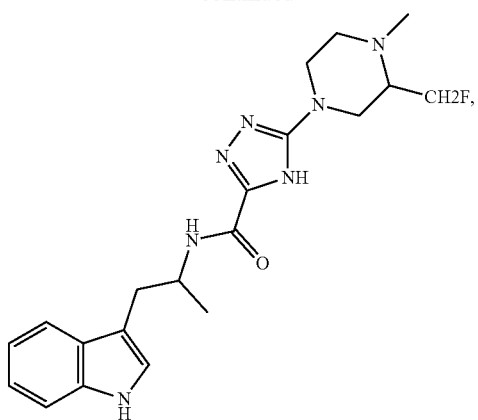
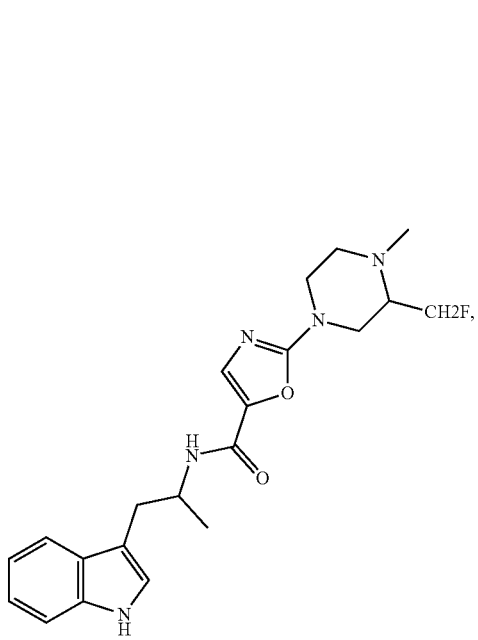
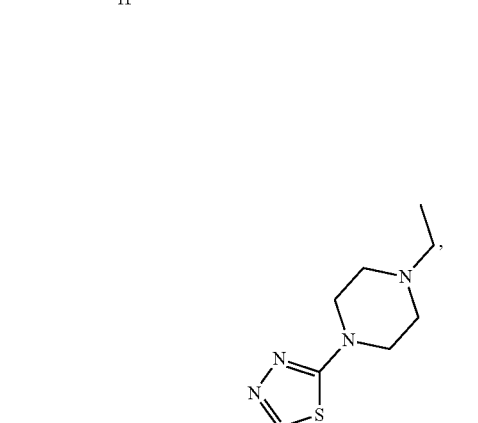
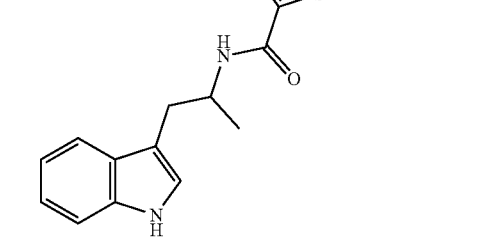

259
-continued
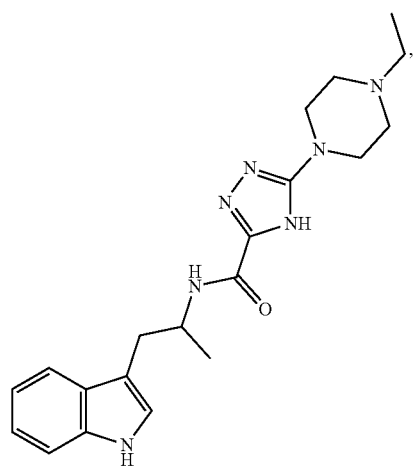
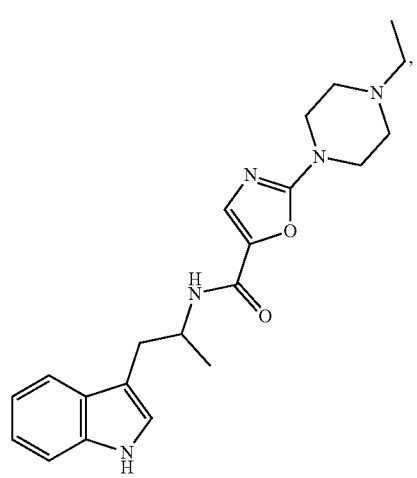
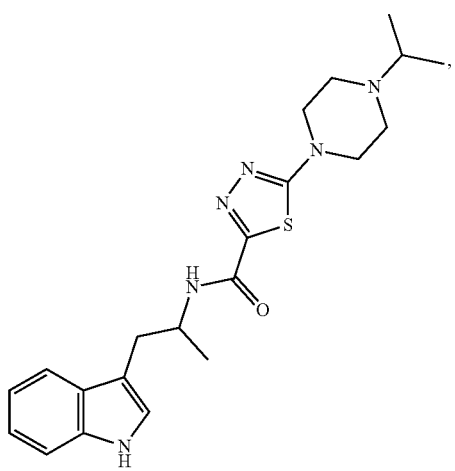
260
-continued
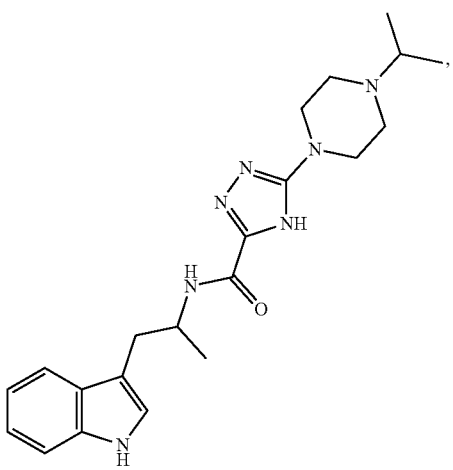
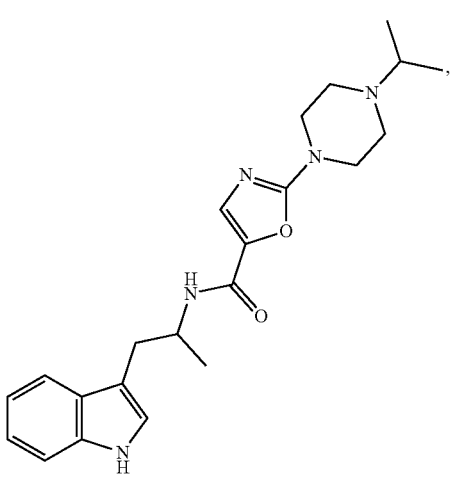
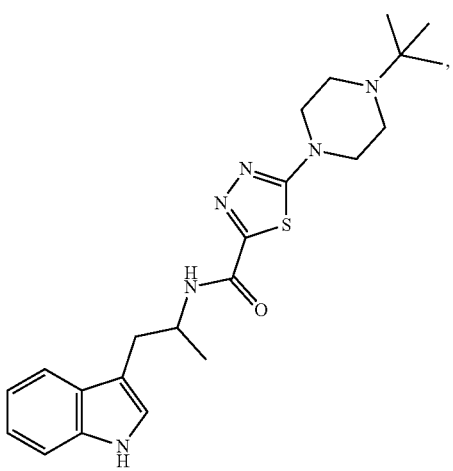

261
-continued
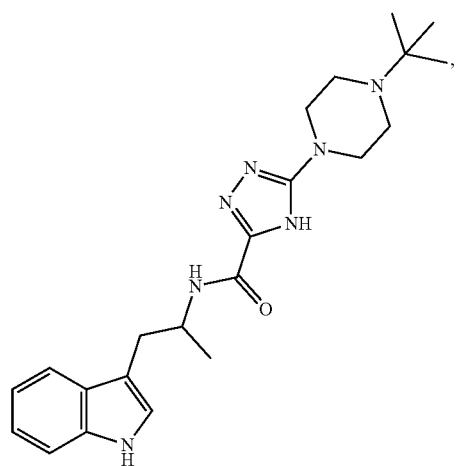
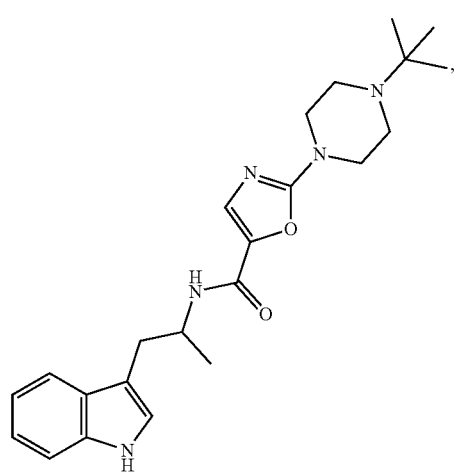
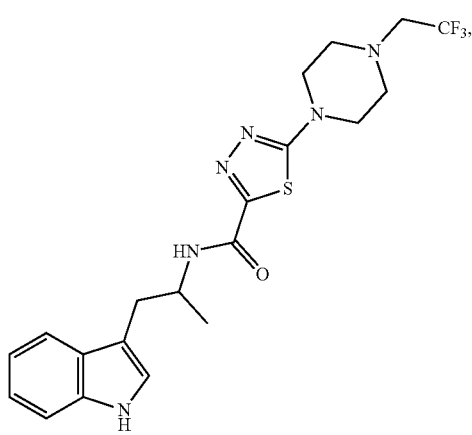
262
-continued
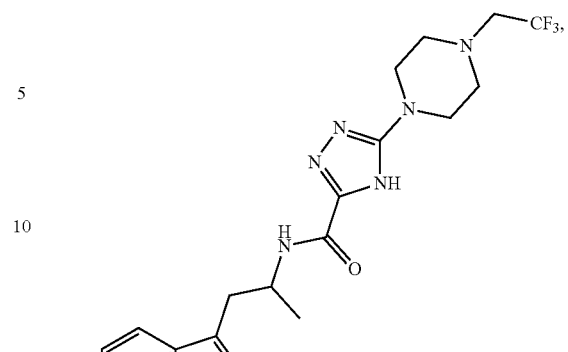
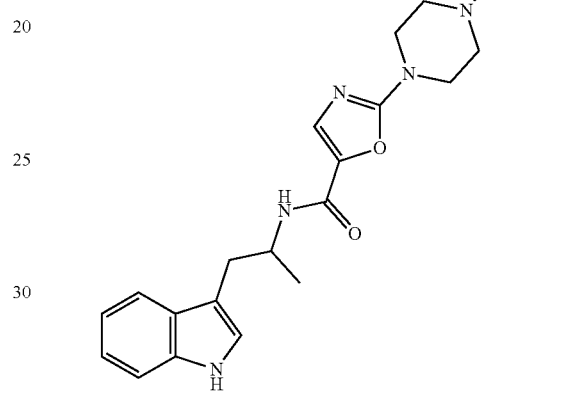
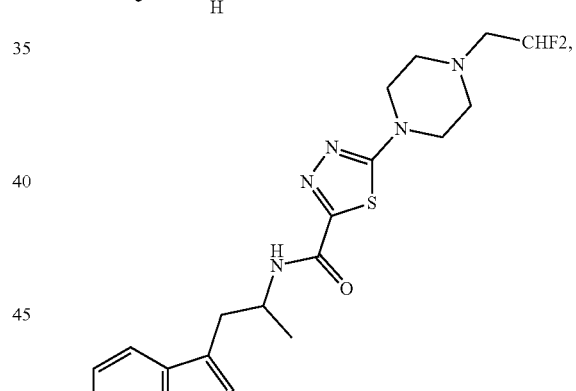
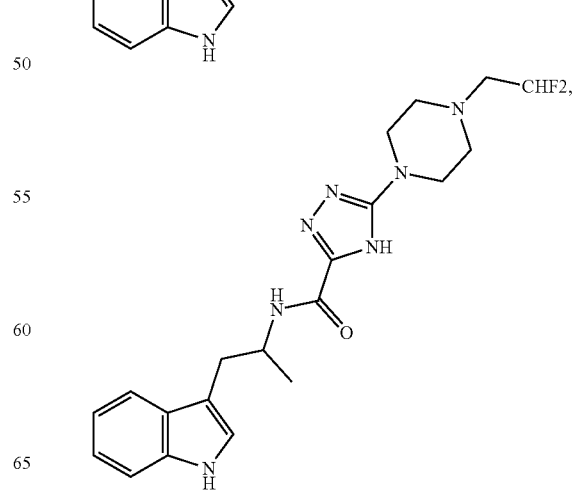

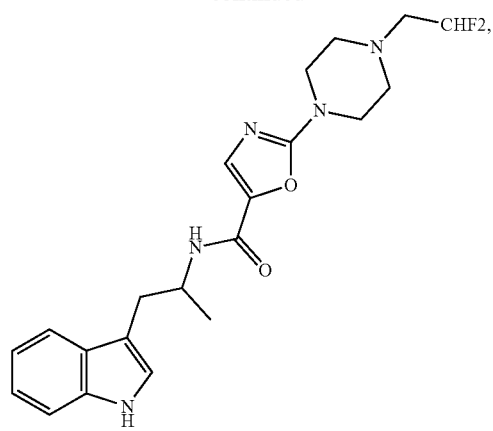
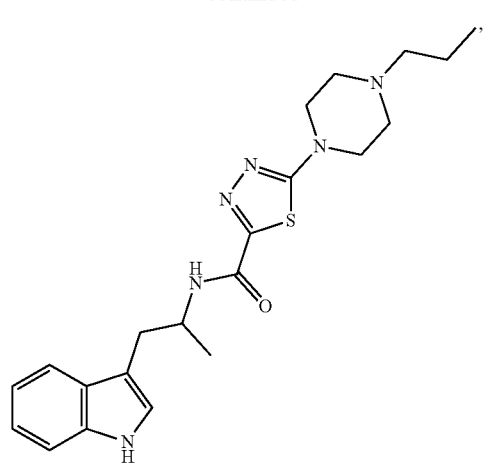
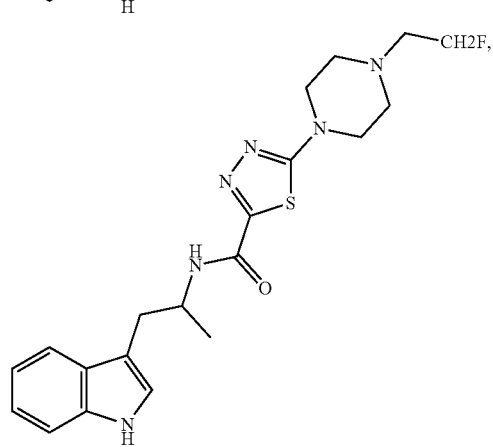
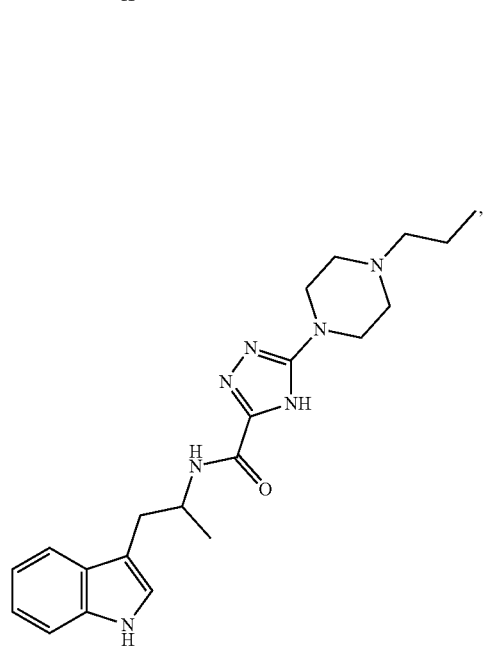
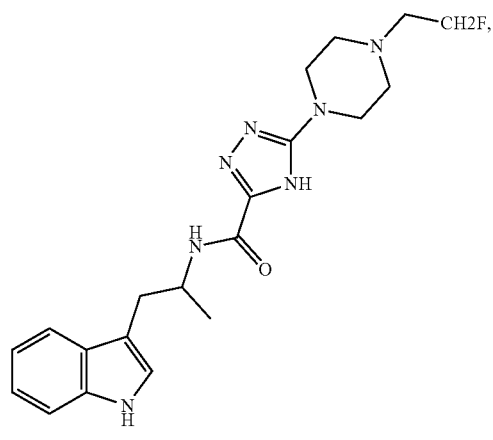
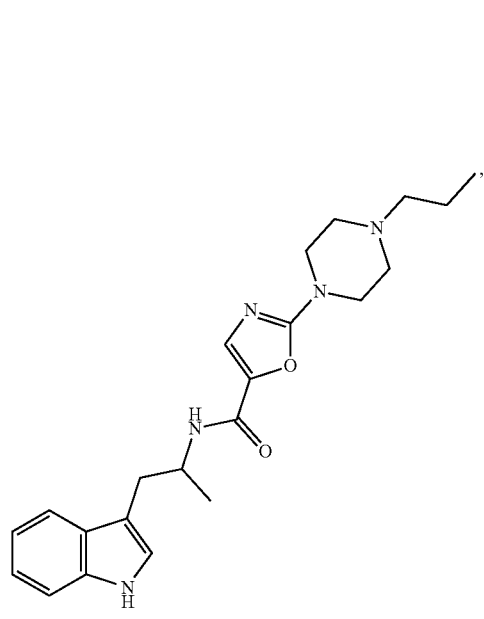
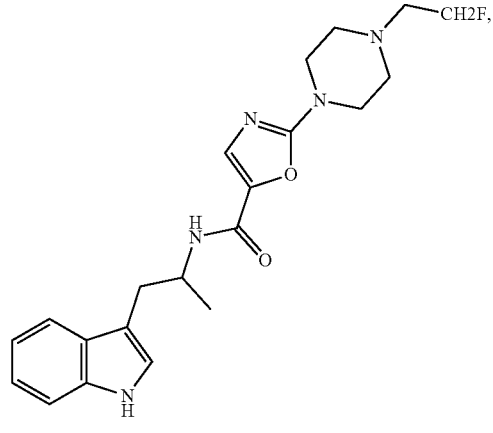

265
-continued
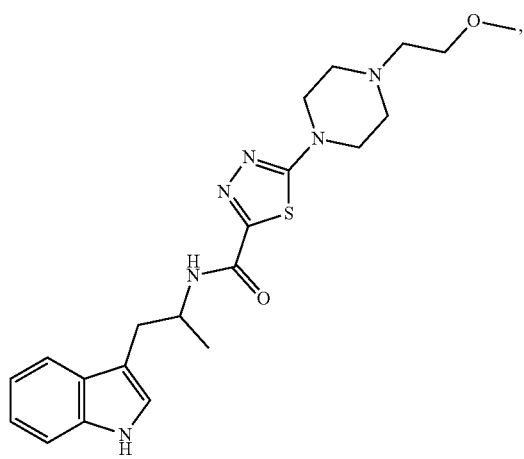
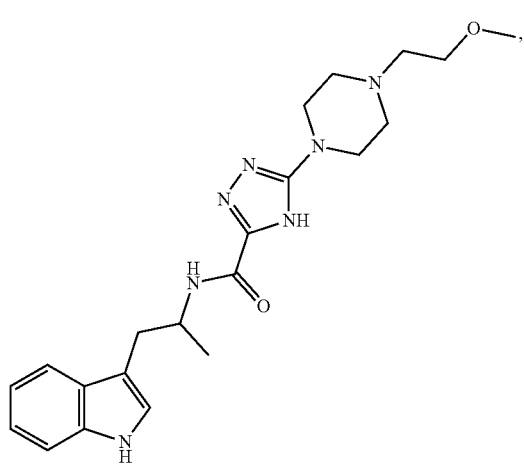
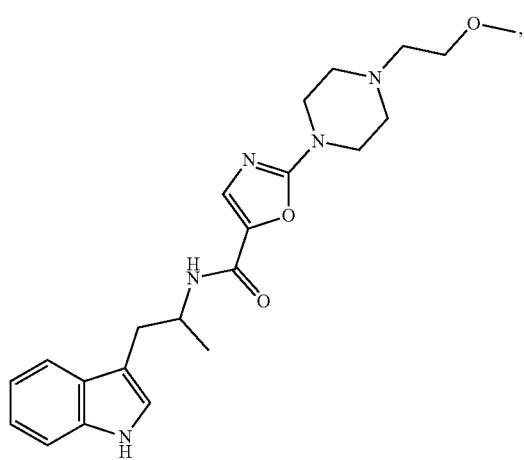
266
-continued
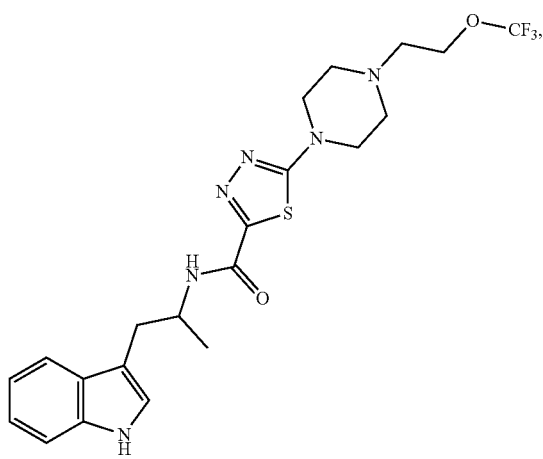

267
-continued
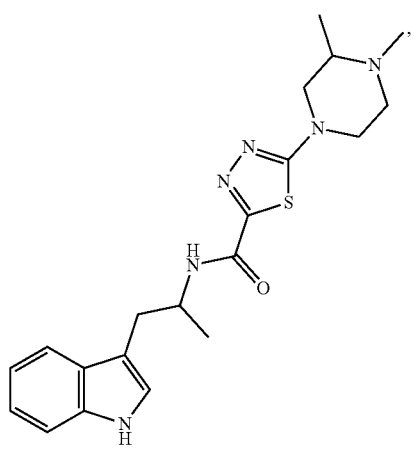
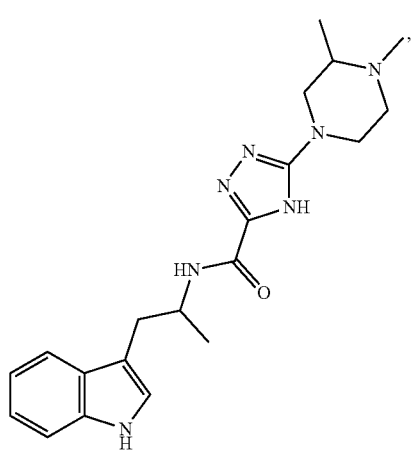
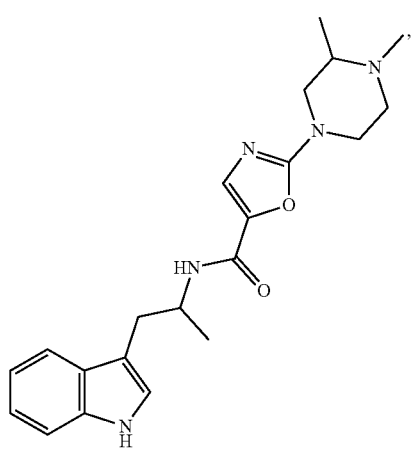
268
-continued
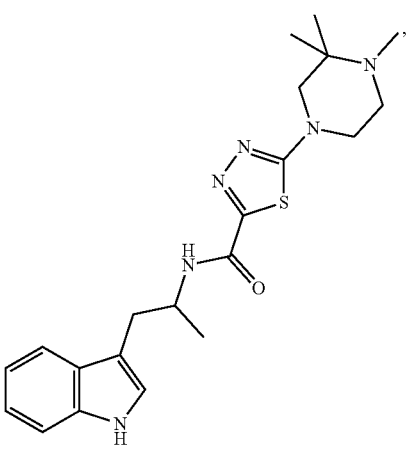
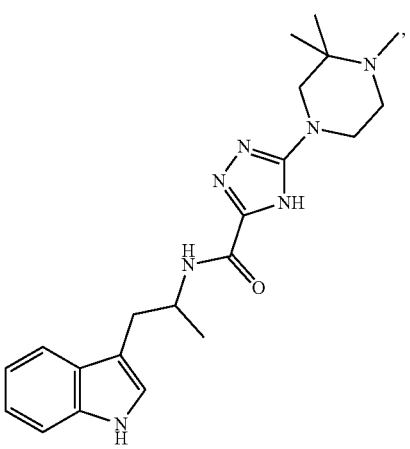
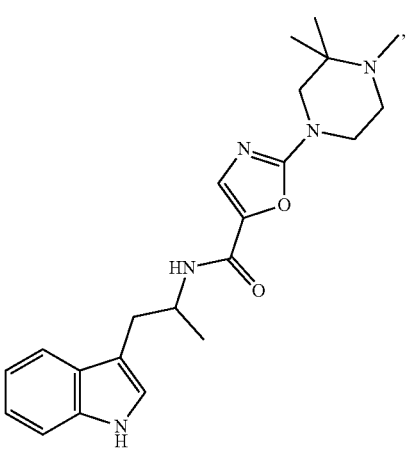

269
-continued
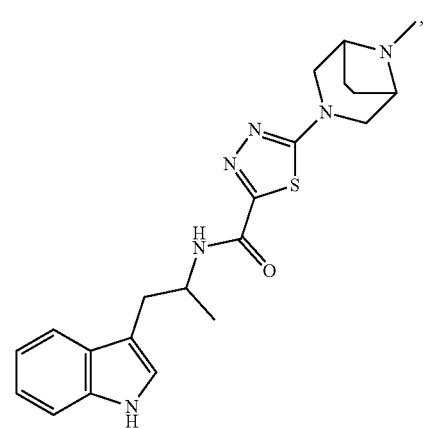
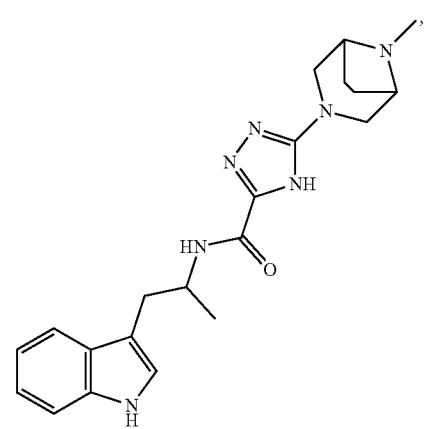
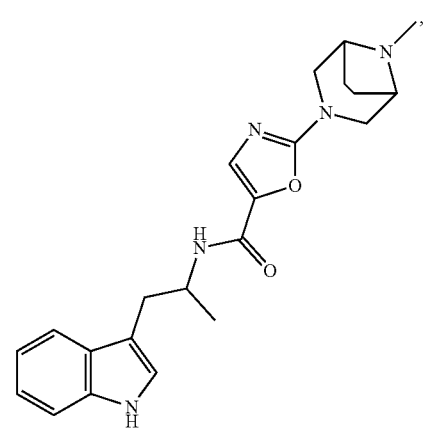
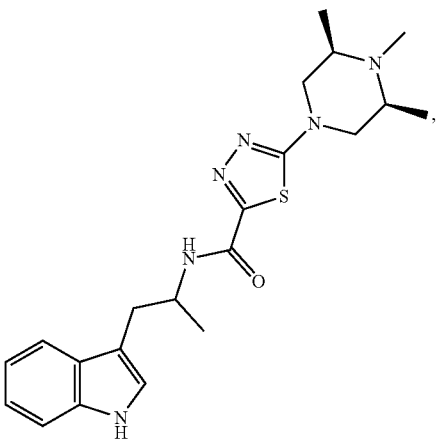
270
-continued
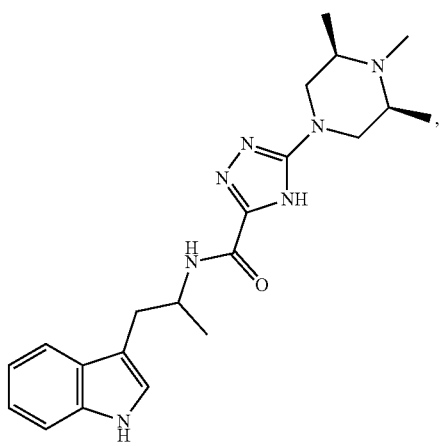
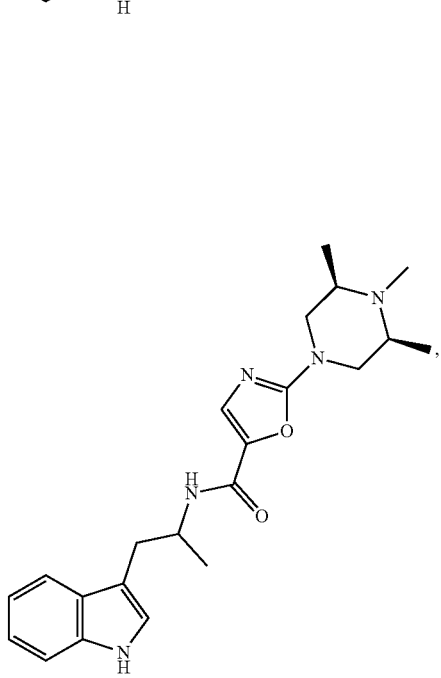
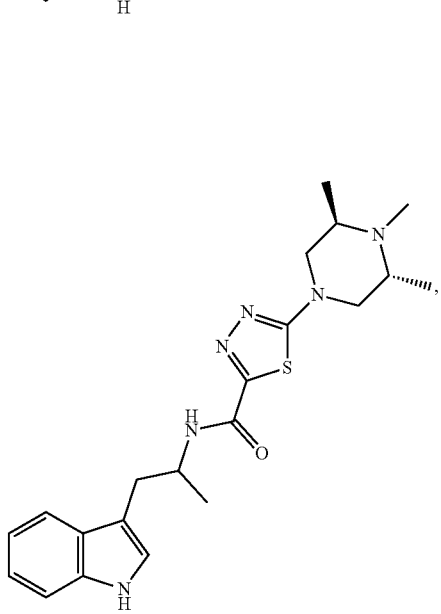

271
-continued
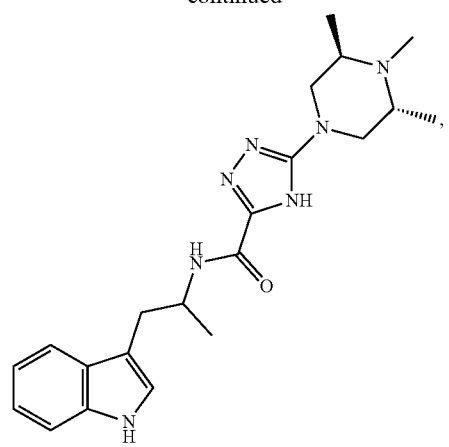
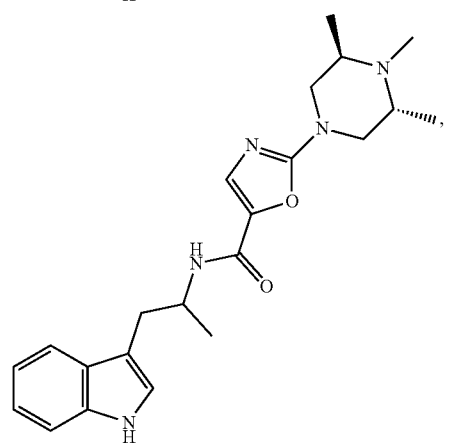
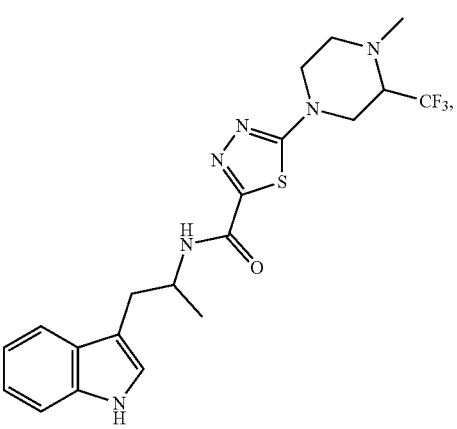
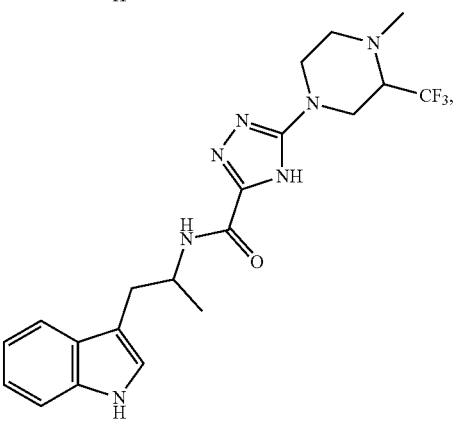
272
-continued
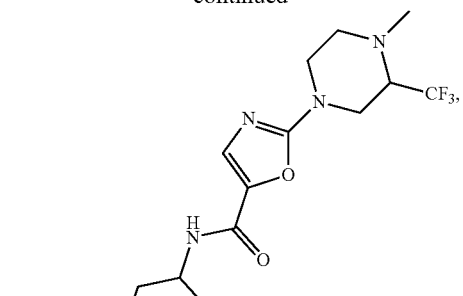
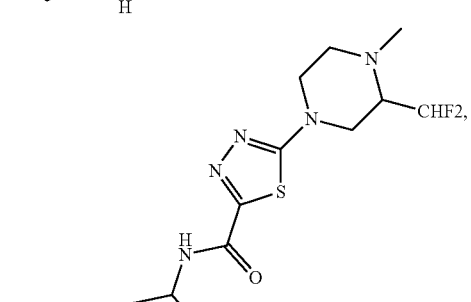
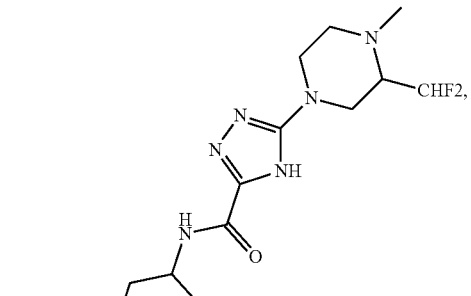
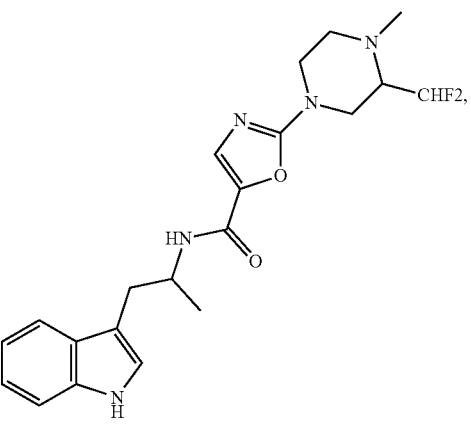

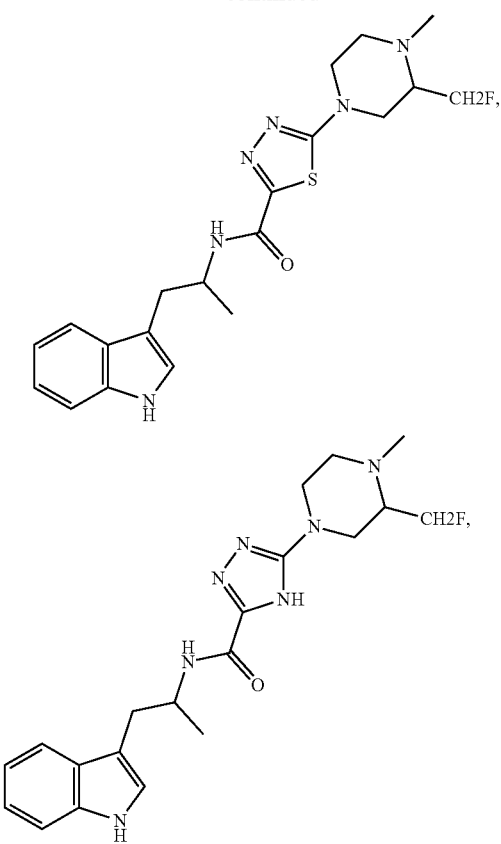

or a pharmaceutically acceptable salt thereof.

19. A pharmaceutical composition comprising at least one compound of claim 1, or a pharmaceutically acceptable salt thereof, and a pharmaceutically acceptable excipient.

20. A method of treating a neurodegenerative disease or condition associated with protein or peptide aggregation, comprising administering to a subject in need of such treatment an effective amount of at least one compound of claim 1, or a pharmaceutically acceptable salt thereof.

21. A method of interfering with the accumulation of protein or peptide aggregates in a cell, or preventing, slowing, reversing, or inhibiting protein or peptide aggregation in a cell, comprising contacting the cell with an effective amount of at least one compound of claim 1, or a pharmaceutically acceptable salt thereof, wherein the contacting is in vitro, ex vivo, or in vivo.

* * * * *